US011753663B2

(12) United States Patent
Burgard et al.

(10) Patent No.: US 11,753,663 B2
(45) Date of Patent: *Sep. 12, 2023

(54) MICROORGANISMS AND METHODS FOR ENHANCING THE AVAILABILITY OF REDUCING EQUIVALENTS IN THE PRESENCE OF METHANOL, AND FOR PRODUCING ADIPATE, 6-AMINOCAPROATE, HEXAMETHYLENEDIAMINE OR CAPROLACTAM RELATED THERETO

(71) Applicant: Genomatica, Inc., San Diego, CA (US)

(72) Inventors: Anthony P. Burgard, Bellefonte, PA (US); Robin E. Osterhout, San Diego, CA (US); Stephen J. Van Dien, Encinitas, CA (US); Cara Ann Tracewell, Solana Beach, CA (US); Priti Pharkya, San Diego, CA (US); Stefan Andrae, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/652,727

(22) PCT Filed: Dec. 16, 2013

(86) PCT No.: PCT/US2013/075287
§ 371 (c)(1),
(2) Date: Jun. 16, 2015

(87) PCT Pub. No.: WO2014/099725
PCT Pub. Date: Jun. 26, 2014

(65) Prior Publication Data
US 2015/0329885 A1 Nov. 19, 2015

Related U.S. Application Data

(60) Provisional application No. 61/738,306, filed on Dec. 17, 2012, provisional application No. 61/766,620, filed on Feb. 19, 2013.

(51) Int. Cl.
| | | |
|---|---|---|
| *C12P 17/10* | (2006.01) | |
| *C12P 13/02* | (2006.01) | |
| *C12P 7/24* | (2006.01) | |
| *C12P 19/02* | (2006.01) | |
| *C12P 7/44* | (2006.01) | |
| *C12P 13/00* | (2006.01) | |
| *C12N 9/04* | (2006.01) | |
| *C08G 63/78* | (2006.01) | |
| *C08G 73/02* | (2006.01) | |
| *C08G 69/16* | (2006.01) | |
| *C08G 69/08* | (2006.01) | |
| *C12N 15/52* | (2006.01) | |
| *A23L 29/00* | (2016.01) | |

(52) U.S. Cl.
CPC ............ *C12P 17/10* (2013.01); *A23L 29/065* (2016.08); *C08G 63/78* (2013.01); *C08G 69/08* (2013.01); *C08G 69/16* (2013.01); *C08G 73/0213* (2013.01); *C12N 9/0006* (2013.01); *C12N 15/52* (2013.01); *C12P 7/24* (2013.01); *C12P 7/44* (2013.01); *C12P 13/001* (2013.01); *C12P 13/005* (2013.01); *C12Y 101/01244* (2013.01)

(58) Field of Classification Search
CPC .......... C12P 17/10; C12P 13/005; C12P 7/44; C12P 7/24; C08G 63/78; C08G 69/08; C08G 69/16; C08G 73/0213; C12N 9/0006; C12N 15/52; C12Y 101/01244
See application file for complete search history.

(56) References Cited

U.S. PATENT DOCUMENTS

| | | | |
|---|---|---|---|
| 7,127,379 B2 | 10/2006 | Palsson et al. | |
| 8,445,244 B2 * | 5/2013 | Burgard | C12N 9/0008 435/183 |
| 10,150,976 B2 | 12/2018 | Burgard et al. | |
| 10,563,180 B2 | 2/2020 | Andrae et al. | |
| 2002/0012939 A1 | 1/2002 | Palsson et al. | |
| 2002/0168654 A1 | 11/2002 | Clow et al. | |
| 2003/0059792 A1 | 3/2003 | Negin et al. | |

(Continued)

FOREIGN PATENT DOCUMENTS

| | | |
|---|---|---|
| CA | 2654133 A1 | 12/2007 |
| CN | 101978042 A | 2/2011 |

(Continued)

OTHER PUBLICATIONS

Al-Taho et al., Molecular Cloning of the Methanol Dehydrogenase Structural Gene from Methylosinus trichosporium OB3b., Current Microbiology (1990), vol. 20, pp. 153-157.*

(Continued)

*Primary Examiner* — Marsha Tsay
(74) *Attorney, Agent, or Firm* — Greenberg Traurig LLP

(57) ABSTRACT

Provided herein is a non-naturally occurring microbial organism having a methanol metabolic pathway that can enhance the availability of reducing equivalents in the presence of methanol. Such reducing equivalents can be used to increase the product yield of organic compounds produced by the microbial organism, such as adipate, 6-aminocaproate, hexamethylenediamine or caprolactam. Also provided herein are methods for using such an organism to produce adipate, 6-aminocaproate, hexamethylenediamine or caprolactam.

20 Claims, 5 Drawing Sheets

(56) References Cited

U.S. PATENT DOCUMENTS

| | | | |
|---|---|---|---|
| 2003/0224363 | A1 | 12/2003 | Park et al. |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2009/0047719 | A1 | 2/2009 | Burgard et al. |
| 2009/0305364 | A1* | 12/2009 | Burgard ............... C12P 7/44 435/121 |
| 2010/0317069 | A1 | 12/2010 | Burk et al. |
| 2010/0330626 | A1 | 12/2010 | Burgard et al. |
| 2011/0003344 | A1 | 1/2011 | Burk et al. |
| 2011/0195461 | A1 | 8/2011 | Butk et al. |
| 2011/0207189 | A1* | 8/2011 | Burgard ............ C12N 9/0008 435/158 |
| 2012/0003652 | A1 | 1/2012 | Reeves et al. |
| 2012/0309026 | A1 | 12/2012 | Perez et al. |
| 2012/0309062 | A1 | 12/2012 | Burgard et al. |
| 2014/0329916 | A1* | 11/2014 | Burgard ............... C12P 17/10 514/784 |
| 2016/0083752 | A1* | 3/2016 | Burgard ............... C07C 55/10 523/222 |
| 2016/0237410 | A1* | 8/2016 | Andrae ............... C12N 9/0006 |

FOREIGN PATENT DOCUMENTS

| | | |
|---|---|---|
| CN | 102066551 A | 5/2011 |
| CN | 102575270 A | 7/2012 |
| WO | WO 2002/055995 A2 | 7/2002 |
| WO | WO 2007/141208 A2 | 12/2007 |
| WO | WO 2008/027742 A1 | 3/2008 |
| WO | WO 2009/151728 A2 | 12/2009 |
| WO | WO 2011031146 A2 | 3/2011 |
| WO | WO 2012135789 A2 | 10/2012 |
| WO | WO 2014/099725 A1 | 6/2014 |

OTHER PUBLICATIONS

UniProtKB POC7L2 (last viewed on Jul. 28, 2016).*
Synonyms of formate dehydrogenase (last viewed on Apr. 20, 2017).*
UniProtKB—P24186 (FOLD_ECOLI), last viewed on Apr. 25, 2017.*
UniProtKB—P37051 (PURU_ECOLI), last viewed on Apr. 25, 2017.*
UniProtKB—P00864 (CAPP_ECOLI), last viewed on Apr. 25, 2017.*
Diekert, G., et al. 1994 Antonie van Leeuwenhoek 66: 209-221. (Year: 1994).*
MetaCyc Pathway: formaldehyde assimilation II (assimilatory RuMP Cycle), created by Caspi R, SRI International on Sep. 7, 2004 , retrieved from the internet on Jan. 5, 2018: 7 pages total. (Year: 2004).*
Bouwer et al., "Bioremediation of organic compounds—putting microbial metabolism to work", Trends Biotechnol, 11(8):360-367 (1993).
International Search Report and Written Opinion and corresponding PCT Application PCT/US2013/075287 (8 pages).
Chica et al., "Semi-rational approaches to engineering enzyme activity: combining the benefits of directed evolution and rational design," *Curr. Opin. Biotechnol.*, 16(4):378-384 (2005).
Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.
Kizer et al., "Application of functional genomics to pathway optimization for increased isoprenoid production," *Appl. Environ. Microbiol.*, 74(10):3229-3241 (2008).
Prather et al., "De novo biosynthetic pathways: rational design of microbial chemical factories," *Curr. Opin. Biotechnol.*, 19(5):468-474 (2008).
Sen et al., "Developments in directed evolution for improving enzyme functions," *Appl. Biochem. Biotechnol.*, 143(3):212-223 (2007).
Vorholt et al., "Cofactor-dependent pathways of formaldehyde oxidation in methylotrophic bacteria," *Arch. Microbiol.*, 178:239-249 (2002).
Abe et al., "Discovery of amide (peptide) bond synthetic activity in Acyl-CoA synthetase," *J. Biol. Chem.*, 283(17):11312-11321 (2008).
Alber et al., "Malonyl-coenzyme A reductase in the modified 3-hydroxypropionate cycle for autotrophic carbon fixation in archaeal *Metallosphaera* and *Sulfolobus* spp.," *J. Bacteriol.*, 188:8551-8559 (2006).
Alber et al., "Study of an alternate glyoxylate cycle for acetate assimilation by Rhodobacter sphaeroides," *Mol. Microbiol.*, 61(2):297-309 (2006).
Andersen et al., "A gene duplication led to specialized gamma-aminobutyrate and beta-alaine aminotransferase in yeast," *FEBS J.*, 274(7):1804-1817 (2007).
Andreesen et al., "Formate Dehydrogenase of Clostridium thermoaceticum: Incorporation of Selenium-75, and the Effects of Selenite, Molybate, and Tungstate on the Enzyme," *J. Bacteriol.*, 116(2):867-873 (1973).
Ansorge et al., "Production of Recombinant L-Leucine Dehydrogenase from Bacillus cereus in Pilot Scale Using the Runaway Replication System *E. coli* [pIET98]," *Biotechnol. Bioeng.*, 68(5):557-562 (2000).
Atsumi et al., "Metabolic engineering of *Escherichia coli* for 1-butanol production," *Metab. Eng.*, 10(6):305-311 (2007).
Bachmann et al., "β-Lactam synthetase: a new biosynthetic enzyme," *Proc. Natl. Acad. Sci. U.S.A.*, 95(16):9082-9086 (1998).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.*, 172:7035-7042 (1990).
Berg et al., "A 3-Hydroxypropionate/4-Hydroxybutyrate Autotrophic Carbon Dioxide Assimilation Pathway in Archaea," *Science*, 318:1782-1786 (2007).
Bergquist et al., "Degenerate oligonucleotide gene shuffling (DOGS) and random drift mutagenesis (RNDN): two complementary techniques for enzyme evolution," *Biomol. Eng.*, 22:63-72 (2005).
Bergquist et al., "Degenerate oligonucleotide gene shuffling," *Methods Mol. Biol.*, 352:191-204 (2007).
Bernhard et al., "Functional and structural role of the cytochrome b subunit of the membrane-bound hydrogenase complex of Alcaligenes eutrophus H16," *Eur. J. Biochem.*, 248:179-186 (1997).
Binstock et al., "Fatty acid oxidation complex from *Escherichia coli*," *Methods Enzymol.*, 71 Pt C:403-411 (1981).
Blaschkowski et al., "Routes of Flavodoxin and Ferredoxin Reduction in *Escherichia coli*," *Eur. J. Biochem.*, 123:563-569 (1982).
Bonner et al., "Purification and Properties of Fatty Acyl Thiesterase I from *Escherichia coli*," *J. Biol. Chem.*, 247(10):3123-3133 (1972).
Bose et al., "Genetic analysis of the methanol- and methylamine-specific methyltransferase 2 genes of Methanosarcina acetivorans C2A," *J. Bacteriol.*, 190(11):4017-4026 (2008).
Bower et al., "Cloning, Sequencing, and Characterization of the Bacillus subtilis Biotin Biosynthetic Operon," *J. Bacteriol.*, 178(14):4122-4130 (1996).
Boynton et al., "Cloning, sequencing, and expression of clustered genes encoding beta- hydroxybutyryl-coenzyme A (CoA) dehydrogenase, crotonase, and butyryl-CoA dehydrogenase from Clostridium acetobutylicum ATCC 824," *J. Bateriol.*, 178(11):3015-3024 (1996).
Brasen et al., "Unusual ADP-forming acetyl-coenzyme A synthetases from the mesophilic halophilic eurarchacon Haloarcula marismortui and from the hyperthermophilic crenarchaeon Pyrobaculum aerophilum," *Arch. Microbiol.*, 182:277-287 (2004).
Buck et al., "Primary Structure of the Succinyl-CoA Synthetase of *Escherichia coli*," *Biochemistry*, 24:6245-6252 (1985).
Buckel et al., "Glutaconate CoA-Transferase from Acidaminococcus fermentans," *Eur. J. Biochem.*, 118:315-321 (1981).

(56) References Cited

OTHER PUBLICATIONS

Burgard et al., "Minimal Reaction Sets for *Escherichia coli* Metabolism under Different Growth Requirements and Uptake Environments," *Biotechnol. Prog.*, 17:791-797 (2001).
Burgard et al., "Optknock: a bilevel programming framework for identifying gene knockout strategies for microbial strain optimization," *Biotechnol. Bioeng.*, 84(6):647-657 (2003).
Burgdorf, "The Soluble NAD-Reducing [NiFe]-Hydrogenase from Ralstonia eutropha H16 Consists of Six Subunits and Can Be Specifically Activated by NADPH," *J. Bact.*, 187(9):3122-3132 (2005).
Campbell et al., "A new *Escherichia coli* metabolic competency: growth on fatty acids by a novel anaerobic β-oxidation pathway," *Mol. Microbiol.*, 47(3):793-805 (2003).
Campbell et al., "The enigmatic *Escherichia coli* fadE gene is yafH," *J. Bacteriol.*, 184(13):3759-3764 (2002).
Cary et al., "Cloning and expression of Clostridium acetobutylicum ATCC 824 acetoacetyl-coenzyme A: acetate/butyrate:coenzyme A-transferase in *Escherichia coli*," *Appl. Environ. Microbiol.*, 56(6):1576-1583 (1990).
Clark et al., "Purification and Properties of 5,10-Methylenetetrahydrofolate Reductase, an Iron-sulfur Flavoprotein from Clostridium formicoaceticum," *J. Biol. Chem.*, 259(17):10845-10849 (1984).
Coco et al., "DNA shuffling method for generating highly recombined genes and evolved enzymes," *Nat. Biotechnol.*, 19(4):354-359 (2001).
Colonna et al., "Synthesis and radiocarbon evidence of terephthalate polyesters completely prepared from renewable resources," *Green Chemistry*, 13:2543-2548 (2011).
Cooper, "Glutamate-γ-aminobutyrate transaminase," *Methods Enzymol.*, 113:80-82 (1985).
Coppi, "The hydrogenases of Geobacter sulfurreducens: a comparative genomic perspective," *Microbiology*, 151:1239-1254 (2005).
Corthesy-Theulaz et al., "Cloning and characterization of Helicobacter pylori succinyl CoA:acetoacetate CoA-transferase, a novel prokaryotic member of the CoA-transferase family," *J. Biol. Chem.*, 272(41):25659-25667 (1997).
Cracknell et al., "A kinetic and thermodynamic understanding of O2 tolerance in [NiFe]-ydrogenases," *Proc Nat Acad Sci*, 106(49):20681-20686 (2009).
Currie et al., "Authentication and dating of biomass components of industrial materials; links to sustainable technology," *Nuclear Instruments and Methods in Physics Research B*, 172:281-287 (2000).
Daniel et al., "Biochemical and molecular characterization of the oxidative branch of glycerol utilization by Citrobacter freundii," *J.Bac.*, 177(15):4392-4401 (1995).
D'Ari et al., "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli*," *J. Biol. Chem.*, 266(35):23953-23958 (1991).
Das et al., "Characterization of a corrinoid protein involved in the C1 metabolism of strict anaerobic bacterium Moorella thermoacetica," *Proteins*, 67(1):167-176 (2007).
De Bok et al., "Two W-containing formate dehydrogenases (CO2-reductases) involving syntrophic propionate oxidation by Syntrophobacter fumaroxidans," *Eur. J. Biochem.*, 270:2476-2485 (2003).
Deana, "Substrate specificity of a dicarboxyl-CoA: dicarboxylic acid coenzyme A transferase from rat liver mitochondria," *Biochem. Int.*, 26(4):767-773 (1992).
Di Gennaro, "Styrene lower catabolic pathway in Pseudomonas fluorescens ST: identification and characterization of genes for phenylacetic acid degradation," *Arch. Microbiol.*, 188(2):117-125 (2007).
Drake et al., "Physiology of the thermophilic acetogen Moorella thermoacetica," *Res. Microbiol.*, 155:869-883 (2004).

Drake, H. L., "Demonstration of Hydrogenase in Extracts of the Homoacetate-Fermenting Bacterium Clostridium thermoaceticum," *J. Bacteriol.*, 150:702-709 (1982).
Duncan et al., "Acetate utilization and butyryl coenzyme A (CoA):acetate-CoA transferase in butyrate-producing bacteria from the human large intestine," *Appl. Environ. Microbiol.*, 68(10):5186-5190 (2002).
Fonknechten et al., "A Conserved Gene Cluster Rules Anaerobic Oxidative Degradation of L-Ornithine," *J. Bacteriol*, 191(9):3162-3167 (2009).
Fox et al., "Characterization of the Region Encoding the CO-Induced Hydrogenase of Rhodospirillum rubrum," *J Bacteriol.*, 178:6200-6208 (1996).
Fuchs, "Alternative pathways of carbon dioxide fixation: insights into the early evolution of life?," *Annu. Rev. Microbiol.*, 65:631-658 (2011).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Fujinaga et al., "Cloning and Expression in *Escherichia coli* of The Gene Encoding the [2Fe—2S] Ferredoxin from Clostridium Pasteurianum," *Biochemical and Biophysical Research Communications*, 192(3):1115-1122 (1993).
Galagan et al., "The genome of M. acetivorans reveals extensive metabolic and physiological diversity," *Genome Res.*, 12(4):532-542 (2002).
Garcia-Alles et al., "Phosphoenolpyruvate- and ATP-dependent dihydroxyacetone kinases: covalent substrate-binding and kinetic mechanism.," *Biochemistry*, 43(41):13037-13045 (2004).
Germer, "Overexpression, Isolation, and Spectroscopic Characterization of the Bidirectional [NiFe] Hydrogenase from Synechocystis sp. PCC 6803," *J. Biol. Chem.*, 284(52):36462-36472 (2009).
Gibbs et al., "Degenerate oligonucleotide gene shuffling (DOGS): a method for enhancing the frequency of recombination with family shuffling," *Gene*, 271:13-20 (2001).
Goenrich et al., "A glutathione-dependent formaldehyde-activating enzyme (Gfa) from Paracoccus denitrificans detected and purified via two-dimensional proton exchange NMR spectroscopy," *J Biol Chem.*, 277(5):3069-3072 (2002).
Gutknecht et al., "The dihydroxyacetone kinase of *Escherichia coli* utilizes a phosphoprotein instead of ATP as phosphoryl donor," *EMBO J.*, 20(10):2480-2486 (2001).
Hagemeier et al., "Insight into the mechanism of biological methanol activation based on the crystal structure of the methanol-cobalamin methyltransferase complex," *Proc. Natl. Acad. Sci. U.S. A.*, 103(50):18917-18922 (2006).
Harms et al., "Methylcobalamin: Coenzyme M methyltransferase isoenzymes MtaA and MtbA from Methanosarcina barkeri. Cloning, sequencing and differential transcription of the encoding genes, and functional overexpression of the mtaA gene in *Escherichia coli*," *Eur. J. Biochem.*, 235(3):653-659 (1996).
Hasegawa et al., "Transcriptional regulation of ketone body-utilizing enzyme, acetoacetyl-CoA synthetase, by C/EBPα during adipocyte differentiation," *Biochim. Biophys. Acta*, 1779:414-419 (2008).
Hashimoto et al., "Activation of L-Lysine ε-Dehydrogenase from Agrobacterium tumefaciens by Several Amino Acids and Monocarboxylates," *J. Biochem.*, 106:76-80 (1989).
Hayes et al., "Combining computational and experimental screening for rapid optimization of protein properties," *Proc. Natl. Acad. Sci. U.S.A.*, 99(25):15926-15931 (2002).
Heggeset et al., "Genome sequence of thermotolerant Bacillus methanolicus: features and regulation related to methylotrophy and production of L-lysine and L-glutamate from methanol," *Applied and Environmental Microbiology*, 78(15):5170-5181 (2012).
Herrmann et al., "Energy Conservation via Electron-Transferring Flavoprotein in Anaerobic Bacteria," *J. Bacteriol.*, 190(3):784-791 (2008).
Heydari et al., "Highly Stable L-Lysine 6-Dehydrogenase from the Thermophile Geobacillus stearothemophilus Isolated from a Japanese Hot Spring: Characterization, gene Cloning and Sequencing, and Expression," *Appl. Environ. Microbiol.*, 70:937-942 (2004).

(56) References Cited

OTHER PUBLICATIONS

Hibbert et al. "Directed evolution of biocatalytic processes," *Biomol. Eng.*, 22:11-19 (2005).
Hillmer et al., "Particulate Nature of Enzymes Involved in the Fermentation of Ethanol and Acetate by Clostridium Kluyveri," *FEBS Lett.*, 21(3):351-354 (1972).
Hoffmeister et al., "Mitochondrial trans-2-enoyl-COA reductase of wax ester fermentation from Euglena gracilis defines a new family of enzymes involved in lipid synthesis," *J. Biol. Chem.*, 280:4329-4338 (2005).
Huang et al., "Identification and Characterization of a Second Butyrate Kinase from Clostridium acetobutylicum ATCC 824, " *J. Mol. Microbiol. Biotechnol.*, 2(1):33-38 (2000).
Hugler et al., "Malonyl-coenzyme A reductase from Chloroflexus aurantiacus, a key enzyme of the 3-hydroxypropionate cycle for autotrophic CO(2) fixation," *J. Bacteriol.*, 184:2404-2410 (2002).
Huisman et al., "Ch. 30: Enzyme Evolution for Chemical Process Applications," In R N. Patel (ed.), *Biocatalysis in the pharmaceutical and biotechnology industries*, CRC Press, Boca Raton, FL, p. 717-742 (2007).
Ingoldsby et al., "The discovery of four distinct glutamate dehydrogenase genes in a strain of Halobacterium salinarum," *Gene*, 349:237-244 (2005).
Ishige et al., "Wax ester production from n-alkanes by *Acinetobacter* sp. strain M-1: ultrastructure of cellular inclusions and role of acyl coenzyme A reductase," *Appl. Environ. Microbiol.*, 68(3):1192-1195 (2002).
Ismail et al., "Functional genomics by NMR spectroscopy Phenylacetate catabolism in *Escherichia coli*," *Eur. J. Biochem.*, 270:3047-3054 (2003).
Ito et al., "Cloning and high-level expression of the glutathione-independent formaldehyde dehydrogenase gene from Pseudomonas putida," *J Bacteriol.*, 176:2483-2491 (1994).
Jacobi et al., "The hyp operon gene products are required for the maturation of catalytically active hydrogenase isoenzymes in *Escherichia coli*," *Arch. Microbiol.*, 158(6):444-451 (1992).
Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," *Biochemistry*, 13(14):2898-2903 (1974).
Jerome et al., "Development of a fed-batch process for the production of a dye-linked formaldehyde dehydrogenase in Hyphomicrobium zavarzinii ZV 580," *Appl Microbiol Biotechnol.*, 77:779-788 (2007).
Johnson et al. Purification and properties of dihydroxyacetone kinase from Klebsiella pneumoniae. *J. Bacteriol.*, 160(1):55-60 (1984).
Karlen et al., "Absolute determination of the activity of two $C^{14}$ dating standards," *Arkiv Geofysik* 4:465-471 (1968).
Kaschabek et al., "Degradation of chloroaromatics: purification and characterization of maleylacetate reductase from *Pseudomonas* sp. Strain B13," *J. Bacteriol.*, 175:6075-6081 (1993).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.*, 184(1):207-215 (2002).
Kato et al., "The physiological role of the ribulose monophosphate pathway in bacteria and archaea," *BioSci Biotechnol Biochem.*, 70(1):10-21 (2006).
Kazahaya et al., "Aerobic Dissimilation of Glucose by Heterolactic Bacteria," *J. Gen. Appl. Microbiol.*, 18(1):43-55 (1972).
Kellum et al., "Effects of cultivation gas phase on hydrogenase of the acetogen Clostridium thermoaceticum," *J. Bacteriol.*, 160(1):466-469 (1984).
Kenklies et al., "Proline biosynthesis from L-ornithine in Clostridium sticklandii: purification of Δ1-pyrroline-5-carboxylate reductase, and sequence and expression of encoding gene, proC," *Microbiology*, 145(Pt 4):819-826 (1999).
Kim, "Purification and Propertis of a mine α-Ketoglutarate Transaminase from *Escherichia coli*," *J. Biol. Chem.*, 239:783-786 (1964).

Kloosterman et al., "Molecular, biochemical, and functional characterization of a Nudix hydrolase protein that stimulates the activity of a nicotinoprotein alcohol dehydrogenase," *J Biol Chem.*, 277:34785-34792 (2002).
Koo et al., "Cloning and characterization of the bifunctional alcohol/acetaldehyde dehydrogenase gene (adhE) in Leuconostoc mesenteroides isolated from kimchi," *Biotechnol. Lett.*, 27(7):505-510 (2005).
Korber et al., "Crystallization of the NADP+-dependent Glutamate Dehydrogenase from *Escherichia coli*," *J. Mol. Biol.*, 234:1270-1273 (1993).
Korolev et al., "Autotracing of *Escherichia coli* acetate CoA-transferase α-subunit structure using 3.4 Å MAD and 1.9 Å native data," *Acta. Cryst.*, D58:2116-2121 (2002).
Kort et al., "Glutamate dehydrogenase from the hyperthermophilic bacterium Thermotoga maritima: molecular characterization and phylogenetic implications," *Extremophiles*, 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.*, 71:58-68 (2007).
Kowalchuk et al., "Contrasting patterns of evolutionary divergence within the Acinetobacter calcoaceticus pca operon," *Gene*, 146:23-30 (1994).
Kretz et al., "Gene site saturation mutagenesis: a comprehensive mutagenesis approach," *Methods Enzymol.*, 388:3-11 (2004).
Kurihara et al., "A Novel Putrescine Utilization Pathway Involves γ-Glutamylated Intermediates of *Escherichia coli* K-12," *J. Biol. Chem.*, 280(6):4602-4608 (2005).
Kurihara et al., "β-Glutamyputrescine synthetase in the putrescine utilization pathway of *Escherichia coli* K-12," *J. Biol. Chem.*, 283(29):19981-19990 (2008).
Kuznetsova et al., "Enzyme genomics: Application of general enzymatic screens to discover new enzymes," *FEMS Microbiol. Rev.*, 29:263-279 (2005).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.*, 395:147-155 (2006).
Lebbink et al., "Engineering activity and stability of *Thermotoga maritima* Glutamate Dydrogenase. I. Introduction of a Six-residue Ion-pair Network in the Hinge Region, " *J. Mol. Biol.*, 280:287-296 (1998).
Lebbink et al., "Engineering activity and stability of *Thermotoga maritima* glutamate dehydrogenase. II: construction of a 16-residue ion-pair network at the subunit interface," *J. Mol. Biol.*, 289(2):357-369 (1999).
Leduc et al., "The Hotdog Thiesterase EntH (YbdB) Plays a Role in Vivo in Optimal Enterobactin biosynthesis by Interacting with the ArCP Domain of EntB," *J. Bacteriol.*, 189(19):7112-7126 (2007).
Lee et al., "A new approach to directed gene evolution by recombined extension on truncated templates (RETT)," *J. Molec. Catalysis*, 26:119-129 (2003).
Li et al., "Properties of Nicotinamide Adenine Dinucleotide Phosphate-Dependent Formate Dehydrogenase from Clostridium thermoaceticum," *J. Bacteriol.*, 92(2):405-412 (1966).
Lin et al., "Fed-batch culture of a metabolically engineered *Escherichia coli* strain designed for high-level succinate production and yield under aerobic conditions," *Biotechnol. Bioeng.*, 90(6):775-779 (2005).
Lovell et al., "Cloning and expression in *Escherichia coli* of the Clostridium thermoaceticum gene encoding thermostable formyltetrahydrofolate synthetase," *Arch. Microbiol.*, 149(4):280-285 (1988).
Lovell, et al., "Primary structure of the thermostable formyltetrahydrofolate synthetase from Clostridium thermoaceticum," *Biochemistry*, 20(29):5687-5694 (1990).
Low et al., "Mimicking somatic hypermutation: affinity maturation of antibodies displayed on baceriophage using a bacterial mutator strain," *J. Mol. Biol.*, 260(3):359-368 (1996).
Lu et al., "Functional analysis and regulation of the divergent spuABCDEFG-spuI operons for polyamine uptake and utilization in Pseudomonas aeruginosa PA01," *J. Bacteriol.*, 184:3765-3773 (2002).

(56) References Cited

OTHER PUBLICATIONS

Lutz et al., "Creating multiple-crossover DNA libraries independent of sequence identity," *Proc. Natl. Acad. Sci. U.S.A.*, 98(20):11248-11253 (2001).
Lutz et al., "Rapid generation of incremental truncation libraries for protein engineering using α-phosphothioate nucleotides," *Nucleic Acids Res.*, 15:29(4):e16 (2001).
Mack et al., "Conversion of glutaconate CoA-transferase from Acidaminococcus fermentas into an acyl-CoA hydrolase by site-directed mutagenesis," *FEBS Lett.*, 405:209-212 (1997).
Mack et al., "Location of the two genes encoding glutaconate coenzyme A-transferase at the beginning of the hydroxyglutarate operon in Acidaminococcus fermentans," *Eur. J. Biochem.*, 226:41-51 (1994).
Maeda et al., "Enhanced hydrogen production from glucose by metabolically engineered *Escherichia coli*," *Appl. Microbiol. Biotechnol.*, 77:879-890 (2007).
Maeder et al., "The Methanosarcina barkeri genome: comparative analysis with Methanosarcina acetivorans and Methanosarcina mazei reveals extensive rearrangement within methanosarcinal genomes," *J. Bacteriol.*, 188(22):7922-7931 (2006).
Mann, "An International Reference Material for Radiocarbon Dating," *Radiocarbon*, 25(2):519-527 (1983).
Martinez-Blanco et al., "Purification and Biochemical Characterization of Phenylacetyl-CoA Ligase from Pseudomonas putida," *J. Biol. Chem.*, 265(12):7084-7090 (1990).
Matthies et al., "Reciprocal Isomerization of Butyrate and Isobutyrate by the Strictly Anaerobic Bacterium Strain WoG13 and Methanogenic Isobutyrate Degradation by a Devined Triculture," *Appl. Environ. Microbiol.*, 58(5):1435-1439 (1992).
McPherson et al., "Complete nucleotide sequence of the *Escherichia coli* gdhA gene," *Nucleic Acids Res.*, 11(15):5257-5266 (1983).
Miller et al., "Structure of beta-lactam synthetase reveals how to synthesize antibiotics instead of asparagine," *Nat Struct. Biol*, 8:684-689 (2001).
Miller et al., "The catalytic cycle of beta-lactam synthetase observed by x-ray crystallographic snapshots," *Proc Natl Acad Sci USA*, 99:14752-14757 (2002).
Misono et al., "Occurrence of L-Lysine ε-Dehydrogenase in Agrobacterium tumefaciens," *J. Bacteriol.*, 150(1):398-401 (1982).
Mitsui et al., "Formaldehyde fixation contributes to detoxification for growth of a nonmethylotroph, Burkholderia cepacia TM1, on vanillic acid," *Appl. Environ. Microbiol.*, 69(10):6128-6132 (2003).
Mizugaki et al. "Studies on the metabolism of unsaturated fatty acids. IX. Stereochemical studies of the reaction catalyzed by trans-2-enoyl-Coenzyme A reductase of *Escherichia coli*," *J. Biochem.*, 92(5):1649-1654 (1982).
Molin et al., "Dihydroxyacetone kinases in *Saccharomyces cerevisiae* are involved in detoxification of dihydroxyacetone," *J Biol Chem.*, 17; 278(3):1415-1423(2003).
Muller et al., "Nucleotide exchange and excision technology (NExT) DNA shuffling: a robust method for DNA fragmentation and directed evolution," *Nucleic Acids Res.*, 33(13):e117 (2005).
Musfeldt et al., "Novel Type of ADP-Forming Acetyl Coenzyme A Synthetase in Hyperthermophilic Archaea: Heterologous Expression and Characterization of Isoenzymes from the Sulfate Reducer Archaeoglobus fulgidus and the Methanogen Methanococcus jannaschii," *J. Bacteriol.*, 184(3):636-644 (2002).
Myronova et al., "Three-dimensional structure determination of a protein supercomplex that oxidizes methane to formaldehyde in Methylococcus capsulatus (Bath)," *Biochem*, 45:11905-11914 (2006).
Naggert et al., "Cloning, Sequencing, and Characterization of *Escherichia coli* thioesteraseII," *J. Biol. Chem.*, 266(17):11044-11050 (1991).
Nagy et al., "Formyltetrahydrofolate hydrolase, a regulatory enzyme that functions to balance pools of tetrahydrofolate and one-carbon tetrahydrofolate adducts in *Escherichia coli*," *J. Bacteriol.*, 3:1292-1298 (1995).

Naidu et al., "Characterization of a three-component vanillate O-demethylase from Moorella thermoacetica," *J. Bacteriol.*, 183(11):3276-3281 (2001).
Nakahigashi et al., "Nucleotide sequence of the fadA and fadB genes from *Escherichia coli*," *Nucleic Acids Res.*, 18(16):4937 (1990).
Ness et al., "Synthetic shuffling expands functional protein diversity by allowing amino acids to recombine independently," *Nat. Biotechnol.*, 20(12):1251-1255 (2002).
Nishimaki et al., "Studies on the Metabolism of Unsaturated Fatty Acids. XIV. Purification and Properties of NADPH-Dependent trans-2-Enoyl-COA Reductase of *Escherichia coli* K-12," *J. Biochem.*, 95(5):1315-1321 (1984).
Nogales et al., "Characterization of the last step of the aerobic phenylacetic acid degradation pathway," *Microbiology*, 153(Pt 2):357-365 (2007).
Nunn et al., "The nucleotide sequence and deduced amino acid sequence of the genes for cytochrome cL and a hypothetical second subunit of the methanol dehydrogenase of Methylobacterium AM1," *Nucl Acid Res.*, 16:7722 (1988).
O'Brien et al., "Chemical, physical and enzymatic comparisons of formyltetrahydrofolate synthetases from thermo- and mesophilic clostridia," *Experientia. Suppl.*, 26:249-262 (1976).
Ohgami et al., "Expression of acetoacetyl-CoA synthetase, a novel cytosolic ketone body-utilizing enzyme, in human brain," *Biochem. Pharmacol.*, 65:989-994 (2003).
Ohsugi et al., "Metabolism of L-β-Lysine by a Pseudomonas, Purification and Properties of a Deacetylase-Thiolesterase utilizing 4-Acetamidobutyrl CoA and Related Compounds," *J. Biol. Chem.*, 256:7642-7651 (1981).
Olivera et al., "Molecular characterization of the phenylacetic acid catabolic pathway in Pseudomonas putida U: The phenylacetyl-CoA catabolon," *Proc. Natl. Acad. Sci. U.S.A.*, 95:6419-6424 (1998).
Orita et al., "Bifunctional enzyme fusion of 3-hexulose-6-phosphate synthase and 6-phospho-3- hexuloisomerase," *Appl Microbiol Biotechnol.*, 76:439-445 (2007).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. U.S.A.*, 96(7):3562-3567 (1999).
Otten et al., "Directed evolution: selecting today's biocatalysts," *Biomol. Eng.*, (22):1-9 (2005).
Park et al., "Biosynthesis of poly(3-hydroxybutyrate- co-3-hydroxyalkanoates) by metabolically engineered *Escherichia coli* strains," *Appl. Biochem. Biotechnol.*, (113-116):335-346 (2004).
Park et al., "Identification and Characterization of a New Enoyl coenzyme A Hydratase involved in biosynthesis of Medium-Chain-Length Polyhdroxyalkanoates in recombinant *Escherichia coli*," *J. Bacteriol.*, 185(18):5391-5397 (2003).
Park et al., "New FadB homologous enzymes and their use in enhanced biosynthesis of medium-chain-length polyhydroxyalkanoates in FadB mutant *Escherichia coli*," *Biotechnol. Bioeng.*, 86:681-686 (2004).
Park et al., "Growth of mycobacteria on carbon monoxide and methanol," *J. Bact.*, 185(1):142-147 (2003).
Parkin et al., "Rapid and Efficient Electrocatalytic CO2/CO Interconversions by Carboxydothermus hydrogenoformans CO Dehydrogenase I on an Electrode," *J Am. Chem. Soc.*, 129:10328-10329 (2007).
Peoples et al., "Fine structural analysis of the Zoogloea ramigera phhA-phhB locus encoding beta-ketothiolase and acetoacetyl-CoA reductase: nucleotide sequence of phbB," *Mol. Microbiol.*, 3:349-357 (1989).
Pierce et al., "The Complete Genome Sequence of Moorella thermoacetia (f. Clostridum thermoaceticum)," *Environ. Microbiol.*, 10(10):2550-2573 (2008).
Ploux et al., "The NADPH-linked acetoacetyl-COA reductase from Zoogloea ramigera, Characterization and mechanistic studies of the cloned enzyme over-produced in *Escherichia coli*," *Eur. J. Biochem.*, 174:177-182 (1988).

(56) References Cited

OTHER PUBLICATIONS

Poehlein et al., "An ancient pathway combining carbon dioxide fixation with the generation and utilization of a sodium ion gradient for ATP synthesis," *PLOS One*, 7:e33439 (2012).
Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.*, 175:377-385 (1993).
Pritchard et al., "A general model of error-prone Pcr," *J. Theor. Biol.*, 234:497-509 (2005).
Pritchett et al., "Genetic, physiological and biochemical characterization of multiple methanol methyltransferase isozymes in Methanosarcina acetivorans C2A," *Mol. Microbiol.*, 56(5):1183-1194 (2005).
Ragsdale, "Life with carbon monoxide," *Crit. Rev. Biochem. Mol. Biol.*, 39(3):165-195 (2004).
Rajpal et al., "A general method for greatly improving the affinity of antibodies by using combinatorial libraries," *Proc. Natl. Acad. Sci. U.S.A.*, 102(24):8466-8471 (2005).
Rakhely, "Cyanobacterial-Type, Heteropentameric, NAD-Reducing NiFe Hydrogenase in the Purple Sulfur Photosynthetic Bacterium Thiocapsa roseopersicina," *Appl. Environ. Microbiol.*, 70(2):722-728 (2004).
Ramos et al., "Mutations affecting the enzymes involved in the utilization of 4-aminobutyric acid as nitrogen source by the yeast Saccharomyces cerevisiae," *Eur. J. Biochem.*, 149:401-404 (1985).
Rangarajan et al., "Structure of [NiFe] hydrogenase maturation protein HypE from *Escherichia coli* and its interaction with HypF," *J. Bacteriol.*, 190(4):1447-1458 (2008).
Reda et al., "Reversible interconversion of carbon dioxide and formate by an electroactive enzyme," *Proc. Natl. Acad. Sci. U.S.A.*, 105:10654-10658 (2008).
Reetz et al., "Directed Evolution of an Enantioselective Enzyme through Combinatorial Multiple-Cassette Mutagenesis," *Agnew. Chem. Int. Ed. Engl.*, 40:3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative Saturation Mutagenesis on the Basis of B Factors as a Strategy for Increasing Protein Thermostability," *Agnew. Chem. Int. Ed. Engl.*, 45:7745-7751 (2006).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Reiser et al., "Isolation of mutants of Acinetobacter calcoaceticus deficient in wax ester synthesis and complementation of one mutation with a gene encoding a fatty acyl coenzyme A reductase," *J. Bacteriol.*, 179(9):2969-2975 (1997).
Ro et al., "Dihydroxyacetone synthase from a methanol-utilizing carboxydobacterium, *Acinetobacter* sp. strain JC1 DSM 3803," *J. Bact.*, 179(19):6041-6047 (1997).
Ruldeekulthamrong et al., "Molecular characterization of lysine 6-dehydrogenase from Achromobacter denitrificans," *BMB Rep.*, 41:790-795 (2008).
Samsonova et al., "Molecular cloning and characterization of *Escherichia coli* K12 ygjG gene," *BMC Microbiol.*, 3:2 (2003).
Sato et al., "Poly[(R)-3-Hydroxybutyrate] Formation in *Escherichia coli* from Glucose through an Enoyl-CoA Hydratase-Mediated Pathway," *J. Biosci. Bioeng.*, 103(1):38-44 (2007).
Sauer et al., "Methanol:Coenzyme M methyltransferase from Methanosarcina barkeri. Purification, properties and encoding genes of the corrinoid protein MT1," *Eur. J. Biochem.*, 243(3):670-677 (1997).
Sawers et al., "Characterization and physiological roles of membrane-bound hydrogenase isoenzymes from Salmonella typhimurium," *J. Bacteriol.*, 168(1):398-404 (1986).

Sawers et al., "Differential expression of hydrogenase isoenzymes in *Escherichia coli* K-12: evidence for a third isoenzyme," *J. Bacteriol.*, 164(3):1324-1331 (1985).
Sawers et al., "Purification and properties of membrane-bound hydrogenase isoenzyme 1 from anaerobically grown *Escherichia coli* K12," *Eur. J. Biochem.*, 156(2):265-275 (1986).
Sawers, "The hydrogenases and formate dehydrogenases of *Escherichia coli*," Antonie Van Leeuwenhoek, 66(1-3):57-88 (1994).
Schink et al., "The membrane-bound hydrogenase of Alcaligenes eutrophus. I. Solubilization, purification, and biochemical properties," *Biochim. Biophys. Acta*, 567:315-324 (1979).
Schwarzer et al., "Nonribosomal peptides: from genes to products," *Nat. Prod. Rep.*, 20:275-287 (2003).
Scott et al., "Soluble γ-Aminobutyric-Glutamic Transaminase from Pseudomonas fluorescens," *J. Biol. Chem.*, 234:932-936 (1959).
Seedorf et al., "The genome of Clostridium kluyveri, a strict anaerobe with unique metabolic features," *Proc. Natl. Acad. Sci. U.S.A.*, 105(6):2128-2133 (2008).
Selifonova et al., "Rapid evolution of novel traits in microorganisms," *Appl. Environ. Microbiol.*, 67(8):3645-3649 (2001).
Shao et al., "Random-priming in vitro recombination: an effective tool for directed evolution," *Nucleic Acids Res.*, 26(2):681-683 (1998).
Sheppard et al., "Purification and properties of NADH-dependent 5, 10-methylenetetrahydrofolate reductase (MetF) from *Escherichia coli*," *J. Bacteriol.*, 181:718-725 (1999).
Sieber et al., "Libraries of hybrid proteins from distantly related sequences," *Nat. Biotechnol.*, 19(5):456-460 (2001).
Siebold et al., "A mechanism of covalent substrate binding in the x-ray structure of subunit K of the *Escherichia coli* dihydroxyacetone kinase," *Proc. Natl. Acad. Sci. USA*, 100(14):8188-8192 (2003).
Slater et al., "Multiple β-ketothiolases mediate poly(β-hydroxyalkanoate) copolymer synthesis in Ralstonia eutropha," *J. Bacteriol.*, 180(8):1979-1987 (1998).
Sohling et al., "Molecular analysis of the anaerobic succinate degradation pathway in Clostridium kluyveri.," *J. Bacteriol.*, 178(3):871-880 (1996).
Söhling et al., "Purification and characterization of a Coenzyme-A-dependent succinate-semialdehyde dehydrogenase from Clostridium kluyveri," *Eur. J. Biochem.*, 212:121-127 (1993).
Soini et al., "High cell density media for *Escherichia coli* are generally designed for aerobic cultivations—consequences for large-scale bioprocesses and shake flask cultures," *Microb. Cell. Fact.*, 7:26 (2008).
Song et al., "Structure, Function, and Mechanism of the Phenylacetate Pathway Hot Dog-fold Thioesterase PaaI," *J. Biol. Chem.*, 281(16):11028-11038 (2006).
St. Maurice et al., "Flavodoxin:quinone reductase (FqrB): a redox partner of pyruvate:ferredoxin oxidoreductase that reversibly couples pyruvate oxidation to NADPH production in Helicobacter pylori and Campylobacter jejuni," *J. Bacteriol.*, 189:4764-4773 (2007).
Stemmer, "DNA Shuffling by random fragmentation and reassembly: in vitro recombination for molecular evolution," *Proc. Natl. Acad. Sci. U.S.A.*, 91(22):10747-10751 (1994).
Stemmer, "Rapid evolution of a protein in vitro by DNA shuffling," *Nature*, 370:389-391 (1994).
Stols et al., "New vectors for co-expression of proteins: Structure of Bacillus subtilis ScoAB obtained by high-throughput protocols," *Protein Expr. Purif.*, 53:396-403 (2007).
Stoyan et al., "Cloning, sequencing and overexpression of the leucine dehydrogenase gene from *Bacillus cereus*," *J. Biotechnol.*, 54:77-80 (1997).
Sunga et al., "The Pichia pastoris formaldehyde dehydrogenase gene (FLD1) as a marker for selection of multicopy expression strains of P. pastoris," *Gene*, 330:39-47 (2004).
Suzuki, et al., "*Corynebacterium* sp. U-96 contains a cluster of genes of enzymes for the catabolismof sarcosine to pyruvate," *Biosci. Biotechnol. Biochem.*, 69(5):952-956 (2005).
Tahlan et al., "Two Sets of Paralogous Genes Encode the Enzymes Involved in the Early Stages of Clavulanic Acid and Clavam Metabolite Biosynthesis in Streptomyces clavuligerus," *Antimicrob. Agents. Chemother.*, 48:930-939 (2004).

(56) References Cited

OTHER PUBLICATIONS

Takacs et al., "Formate hydrogenlyase in the hyperthermophilic archaeon, Thermococcus litoralis," *BMC Microbiol.*, 8:88 (2008).

Takahashi et al., "Metabolic Pathways for Cytoxic End Product Formation from Glutamate- and Aspartate-Containing Peptides by Porphyromonas gingivalis," *J. Bacteriol.*, 182(17):4704-4710 (2000).

Tallant et al., "Coenzyme M methylase activity of the 480-kilodalton corrinoid protein from Methanosarcina barkeri," *J. Bacteriol.*, 178(5):1295-1301 (1996).

Tallant et al., "The MtsA subunit of the methylthiol:Coenzyme M methyltransferase of Methanosarcina barkeri catalyses both half-reactions of corrinoid-dependent dimethylsulfide: Coenzyme M methyl transfer," *J. Biol. Chem.*, 276(6):4485-4493 (2001).

Tamaki et al., "Purification, Properties, and Sequencing of Aminisobutyrate Aminotransferases from Rat Liver," *Meth. Enzymol.*, 324:376-389 (2000).

Thauer, "Microbiology. A fifth pathway of carbon fixation," *Science*, 318:1732-1733 (2007).

Toth et al., "The ald gene, encoding a coenzyme A-acylating aldehyde dehydrogenase, distinguishes Clostridium beijerinckii and two other solvent-producing clostridia from Clostridium acetobutylicum," *Appl. Environ. Microbiol.*, 65(11):4973-4980 (1999).

Tucci et al., "A novel prokaryotic trans-2-enoyl-COA reductase from the spirochete Treponema denticola," *FEBS Lett.*, 581:1561-1566 (2007).

Vamecq et al., "The microsomal dicarboxylyl-CoA synthetase," *Biochem. J.*, 230:683-693 (1985).

Vanderwinkel et al., "Growth of *Escherichia coli* on Fatty Acids: Requirement for Coenzyme a Transferase Activity," *Biochem. Biophys. Res. Commun.*, 33:902-908 (1968).

Vardar-Schara et al., "Metabolically engineered bacteria for producing hydrogen via fermentation," *Microbio. Biotechnol.*, 1:107-125 (2008).

Volkov et al., "Random chimeragenesis by heteroduplex recombination," *Methods Enzymol.*, 328:456-463 (2000).

Volkov et al., "Recombination and chimeragenesis by in vitro heteroduplex formation and in vivo repair," *Nucleic Acids Res.*, 27(18):e18 (1999).

Vorholt, et al., "Novel formaldehyde-activating enzyme in Methylobacterium extorquens AM1 required for growth on methanol," *J. Bacteriol.*, 182(23):6645-6650 (2000).

Wakil et al., "Studies on the Fatty Acid Oxidizing System of Animal Tissues," *J. Biol. Chem.*, 207:631-638 (1954).

Walter et al., "Sequence and arrangement of two genes of the butyrate-synthesis pathway of Clostridium acetobutylicum ATCC 824," *Gene*, 134:107-111 (1993).

Wang et al., "Molecular cloning and functional identification of a novel phenylacetyl-CoA ligase gene from Penicillium chrysogenum," *Biochem. Biophys. Res. Commun.*, 360(2):453-458 (2007).

Wang et al., "NADP Reduction with Reduced Ferredoxin and NADP Reduction with NADH Are Coupled via an Electron-Bifurcating Enzyme Complex in Clostridium kluyveri," *J Bacteriol.*, 192:5115-5123 (2010).

Westin et al., "The Identification of Succinyl-CoA Thioesterase Suggests a Novel Pathway for Succinate Production in Peroxisomes," *J. Biol. Chem.*, 280(46):38125-38132 (2005).

Whitehead et al., "Cloning and expression in *Escherichia coli* of the gene for 10-formyltetrahydrofolate synthetase from Clostridium acidiurici ("Clostridium acidi-urici")," *J. Bacteriol.*, 167:205-209 (1986).

Whitehead et al., "Nucleotide Sequence of the Clostridium acidi-urici ("Clostridium acidi-urici") Gene for 10-Formyltetrahydrofolate Synthetase Shows Extensive Amino Acid Homology with the Trifunctional Enzyme C1-Tetrahydrofolate Synthase from *Saccharomyces cerevisiae*," *J. Bacteriol.*, 170(7):3255-3261 (1988).

Winzer et al., "Differential regulation of two thiolase genes from Clostridium acetobutylicum DSM 792," *J. Mol. Microbiol. Biotechnol.*, 2:531-541 (2000).

Wong et al., "Sequence satruation mutagenesis with tunable mutation frequencies," *Anal. Biochem.*, 341:187-189 (2005).

Wong et al., "Sequence saturation mutagenesis (SeSaM): a novel method for directed evolution," *Nucleic Acids Res.*, 32(3):e26 (2004).

Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3:74-82 (2008).

Wu et al., "Life in hot carbon monoxide: the complete genome sequence of Carboxydothermus hydrogenoformans Z-2901," *Plos Genet.*, 1:e65 (2005).

Yamamoto et al., "Carboxylation reaction catalyzed by 2-oxoglutarate:ferredoxin oxidoreductases from Hydrogenobacter thermophilus," *Extremophiles*, 14:79-85 (2010).

Yamamoto et al., "Purification and properties of NADP-dependent formate dehydrogenase from Clostridium thermoaceticum, a tungsten-selenium-iron protein," *J. Biol. Chem.*, 258(3):1826-1832 (1983).

Yang et al, "Nucleotide Sequence of the fadA Gene. Primary structure of 3-ketoacyl-coenzyme A thiolase from *Escherichia coli* and the structural organization of the fadAB operon," *J. Biol. Chem.* 265(18):10424-10429 (1990) with correction in *J. Biol. Chem.* 266(24):16255 (1991).

Yang et al., "Aspartate Dehydrogenase, a Novel Enszyme Idnetified from Structural and Functional Studies of TM16343," *J. Biol. Chem.*, 278:8804-8808 (2003).

Yang et al., "Nucleotide sequence of the promoter and fadB gene of the fadBA operon and primary structure of the multifunctional fatty acid oxidation protein from *Escherichia coli*," *Biochemistry*, 30(27):6788-6795 (1991).

Yasueda et al., "Bacillus subtilis yckG and yckF encode two key enzymes of the ribulose monophosphate pathway used by methylotrophs, and yckH is required for their expression," *J Bac*, 181(23):7154-7160 (1999).

Youngleson et al., "Homology between hydroxybutyryl and hydroxyacyl coenzyme A dehydrogenase enzymes from Clostridium acetobutylicum fermentation and vertebrate fatty acid beta-oxidation pathways," *J. Bacteriol.*, 171(12):6800-6807 (1989).

Zhao et al., "Molecular evolution by staggered extension process (StEP) in vitro recombination," *Nat. Biotechnol.*, 16(3):258-261 (1998).

Zhou et al., "Isolation, crystallization and preliminary X-ray analysis of a methanol-induced corrinoid protein from Moorella thermoacetica," *Acta Crystallogr. Sect. F. Struct. Biol. Cyrst. Commun.*, 61:537-540 (2005).

Zhuang et al., "The YbgC protein encoded by the ybgC gene of the tol-pal gene cluster of Haemophilus influenzae catalyzes acyl-coenzyme A thioester hydrolysis," *FEBS Lett.*, 516:161-163 (2002).

U.S. Appl. No. 14/107,832, 2014/0329916, filed Dec. 16, 2013, Microorganisms and Methods for Enhancing the Availability of Reducing Equivalents in the Presence of Methanol, and for Producing Adipate, 6-Aminocaproate, Hexamethylenediamine or Caprolactam Related Thereto, Issued U.S. Pat. No. 10,150,976.

U.S. Appl. No. 16/178,432, 2019/0300919, filed Nov. 1, 2018, Producing Adipate, 6-Aminocaproate, Hexamethylenediamine or Caprolactam in the Presence of Methanol Using a Microorganism Having Increased Availability of Reducing Equivalents, Issued U.S. Pat. No. 11,447,804.

U.S. Appl. No. 18/158,680, Not Yet Published, filed Jan. 24, 2023, Microorganisms and Methods for Enhancing the Availability of Reducing Equivalents in the Presence of Methanol, and for Producing Adipate, 6-Aminocaproate, Hexamethylenediamine or Caprolactam Related Thereto, Pending.

* cited by examiner

MICROORGANISMS AND METHODS FOR ENHANCING THE AVAILABILITY OF REDUCING EQUIVALENTS IN THE PRESENCE OF METHANOL, AND FOR PRODUCING ADIPATE, 6-AMINOCAPROATE, HEXAMETHYLENEDIAMINE OR CAPROLACTAM RELATED THERETO

CROSS-REFERENCE TO RELATED APPLICATIONS

This application is a 371 national stage application of international application Serial No. PCT/US2013/075287 filed Dec. 16, 2013, which claims the benefit of U.S. Ser. No. 61/766,620 filed Feb. 19, 2013, and U.S. Ser. No. 61/738,306 filed Dec. 17, 2012, each of which is incorporated herein by reference in its entirety.

1. SUMMARY

Provided herein are methods generally relating to metabolic and biosynthetic processes and microbial organisms capable of producing organic compounds. Specifically, provided herein is a non-naturally occurring microbial organism (NNOMO) having a methanol metabolic pathway (MMP) that can enhance the availability of reducing equivalents in the presence of methanol and/or convert methanol to formaldehyde. Such NNOMOs and reducing equivalents can be used to increase the product yield of organic compounds produced by the microbial organism, such as adipate, 6-aminocaproate (6-ACA), hexamethylenediamine (HMDA) and/or caprolactam. Also provided herein are NNOMOs and methods thereof to produce optimal yields of adipate, 6-ACA, HMDA and/or caprolactam.

In a first aspect, provided herein is a NNOMO having a methanol metabolic pathway (MMP), wherein said organism comprises at least one exogenous nucleic acid encoding a MMP enzyme (MMPE) expressed in a sufficient amount to enhance the availability of reducing equivalents in the presence of methanol and/or convert methanol to formaldehyde. In certain embodiments, the MMP comprises one or more enzymes selected from the group consisting of a methanol methyltransferase (EM1); a methylenetetrahydrofolate reductase (EM2); a methylenetetrahydrofolate dehydrogenase (EM3); a methenyltetrahydrofolate cyclohydrolase (EM4); a formyltetrahydrofolate deformylase (EM5); a formyltetrahydrofolate synthetase (EM6); a formate hydrogen lyase (EM15); a hydrogenase (EM16); a formate dehydrogenase (EM8); a methanol dehydrogenase (EM9); a formaldehyde activating enzyme (EM10); a formaldehyde dehydrogenase (EM11); a S-(hydroxymethyl)glutathione synthase (EM12); a glutathione-dependent formaldehyde dehydrogenase (EM13); and an S-formylglutathione hydrolase (EM14). Such organisms, in certain embodiments, advantageously allow for the production of reducing equivalents, which can then be used by the organism for the production of adipate, 6-ACA, HMDA or caprolactam using any one of the AdiPs, 6-ACAPs, HMDAPs or CapPs provided herein.

In one embodiment, the MMP comprises an EM9. In another embodiment, the MMP comprises an EM9 and an EM10. In other embodiments, the MMP comprises an EM1 and an EM2. In one embodiment, the MMP comprises an EM9, an EM3, an EM4 and an EM5. In another embodiment, the MMP comprises an EM9, an EM3, an EM4 and an EM6. In other embodiments, the MMP comprises an EM9 and an EM11. In another embodiment, the MMP comprises an EM9, an EM12, an EM13 and an EM14. In other embodiments, the MMP comprises an EM9, an EM13 and an EM14. In an embodiment, the MMP comprises an EM9, an EM10, an EM3, an EM4 and an EM5. In another embodiment, the MMP comprises an EM9, an EM10, an EM3, an EM4 and an EM6. In other embodiments, the MMP comprises an EM1, an EM2, an EM3, and EM4, and EM5. In one embodiment, the MMP comprises an EM1, an EM2, an EM3, an EM4 and EM6. In certain of the above embodiments, the MMP further comprises an EM8. In other of the above embodiments, the MMP further comprises and a formate hydrogen lyase (EM15). In yet other of the above embodiments, the MMP further comprises a hydrogenase (EM16). In certain embodiments, the organism comprises two, three, four, five, six or seven exogenous nucleic acids, each encoding a MMPE.

In a second aspect, provided herein is a NNOMO having (1) a MMP, wherein said organism comprises at least one exogenous nucleic acid encoding a MMPE expressed in a sufficient amount to enhance the availability of reducing equivalents in the presence of methanol; and (2) an adipate pathway (AdiP), wherein said organism comprises at least one exogenous nucleic acid encoding an AdiP enzyme (AdiPE) expressed in a sufficient amount to produce adipate. In certain embodiments, the AdiP enzyme is selected from the group consisting of 3-oxoadipyl-CoA thiolase (EA1), 3-oxoadipyl-CoA reductase (EA2), 3-hydroxyadipyl-CoA dehydratase (EA3), 5-carboxy-2-pentenoyl-CoA reductase (EA4), adipyl-CoA hydrolase (EA11A), adipyl-CoA ligase (EA11B), adipyl-CoA transferase (EA11C) and phosphotransadipylase/adipate kinase (EA11D).

In a third aspect, provided herein is a NNOMO having (1) a MMP, wherein said organism comprises at least one exogenous nucleic acid encoding a MMPE expressed in a sufficient amount to enhance the availability of reducing equivalents in the presence of methanol; and (2) a 6-ACA pathway (6-ACAP), wherein said organism comprises at least one exogenous nucleic acid encoding a 6-ACAP enzyme (6-ACAPE) expressed in a sufficient amount to produce 6-ACA. In certain embodiments, the 6-ACAPE is selected from the group consisting of EA1, EA2, EA3, EA4, adipyl-CoA reductase (aldehyde forming) (EA5), 6-ACA transaminase (EA6A) and 6-ACA dehydrogenase (EA6B).

In a fourth aspect, provided herein is a NNOMO having (1) a MMP, wherein said organism comprises at least one exogenous nucleic acid encoding a MMPE expressed in a sufficient amount to enhance the availability of reducing equivalents in the presence of methanol; and (2) a HMDA pathway (HMDAP), wherein said organism comprises at least one exogenous nucleic acid encoding a HMDAP enzyme (HMDAPE) expressed in a sufficient amount to produce HMDA. In certain embodiments, the HMDAPE is selected from the group consisting of EA1, EA2, EA3, EA4, EA5, EA6A, EA6B, 6-aminocaproyl-CoA/acyl-CoA transferase (EA7A), 6-aminocaproyl-CoA synthase (EA7B), 6-aminocaproyl-CoA reductase (aldehyde forming) (EA9), HMDA transaminase (EA10A), and HMDA dehydrogenase (EA10B).

In a fifth aspect, provided herein is a NNOMO having (1) a MMP, wherein said organism comprises at least one exogenous nucleic acid encoding a MMPE expressed in a sufficient amount to enhance the availability of reducing equivalents in the presence of methanol; and (2) a caprolactam pathway (CapP), wherein said organism comprises at least one exogenous nucleic acid encoding a CapP enzyme (CapPE) expressed in a sufficient amount to produce caprolactam. In certain embodiments, the CapPE is selected from the group consisting of EA1, EA2, EA3, EA4, EA5, EA6A, EA6B, EA7A, and EA7B. In other embodiments, the CapPE is selected from the group consisting of EA1, EA2, EA3, EA4, EA5, EA6A, EA6B, and amidohydrolase (EA8).

In other embodiments, the organism having a MMP, either alone or in combination with an adipate, 6-ACA, HMDA or caprolactam pathway, as provided herein, further comprises a formaldehyde assimilation pathway (FAP) that utilizes formaldehyde, e.g., obtained from the oxidation of methanol, in the formation of intermediates of certain central metabolic pathways that can be used, for example, in the formation of biomass. In certain embodiments, the organism further comprises a FAP, wherein said organism comprises at least one exogenous nucleic acid encoding a formaldehyde assimilation pathway enzyme (FAPE) expressed in a sufficient amount to produce an intermediate of glycolysis and/or a metabolic pathway that can be used in the formation of biomass. In one embodiment, the FAPE is expressed in a sufficient amount to produce an intermediate of glycolysis. In another embodiment, the FAPE is expressed in a sufficient amount to produce an intermediate of a metabolic pathway that can be used in the formation of biomass. In some of the embodiments, the FAP comprises a hexulose-6-phosphate (H6P) synthase (EF1), a 6-phospho-3-hexuloisomerase (EF2), a dihydroxyacetone (DHA) synthase (EF3) or a DHA kinase (EF4). In one embodiment, the FAP comprises an EF1 and an EF2. In one embodiment, the intermediate is a H6P, a fructose-6-phosphate (F6P), or a combination thereof. In other embodiments, the FAP comprises an EF3 or an EF4. In one embodiment, the intermediate is a DHA, a DHA phosphate (DHAP), or a combination thereof. In certain embodiments, the organism comprises two exogenous nucleic acids, each encoding a FAPE.

In certain embodiments, provided herein is a NNOMO having a MMP, wherein said organism comprises at least one exogenous nucleic acid encoding an EM9 expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis. In certain embodiments, the FAPE is selected from the group consisting of an EF1, an EF2, an EF3 and an EF4.

In some embodiments, provided herein is a NNOMO having a MMP, either alone or in combination with an AdiP, 6-ACAP, HMDAP, CapP and/or a FAP as provided herein, wherein said organism further comprises a formate reutilization pathway (FRP). In certain embodiments the organism comprises at least one exogenous nucleic acid encoding a FRP enzyme (FRPE) expressed in a sufficient amount to produce formaldehyde, pyruvate or acetyl-CoA. In some embodiments, the FRP comprises: (1) a formate reductase (EFR1); (2) (i) a formate ligase (EFR2A), a formate transferase (EFR2B), or a formate synthetase (EFR2C), and (ii) a formyl-CoA reductase (EFR3); (3) (i) a formyltetrahydrofolate synthetase (EFR4), (ii) a methenyltetrahydrofolate cyclohydrolase (EFR5), (iii) a methylenetetrahydrofolate dehydrogenase (EFR6) and (iv) a formaldehyde-forming enzyme (EFR7) or spontaneous; (6) (i) an EFR4, (ii) an EFR5, (iii) an EFR6, (iv) a glycine cleavage system (EFR8), (v) a serine hydroxymethyltransferase (EFR9), and (vi) a serine deaminase (EFR10); (7) (i) an EFR1, (ii) an EFR4, (iii) an EFR5, (iv) an EFR6, (v) an EFR8, (vi) an EFR9, and (vii) an EFR10; (8) (i) an EFR2A, an EFR2B or an EFR2C, (ii) an EFR3, (iii) an EFR4, (iv) an EFR5, (v) an EFR6, (vi) an EFR8, (vii) an EFR9, and (viii) an EFR10; (9) (i) an EFR7 or spontaneous, (ii) an EFR4, (iii) an EFR5, (iv) an EFR6, (v) an EFR8, (vi) an EFR9, and (vii) an EFR10; and (10) (i) an EFR4, (ii) an EFR5, (iii) an EFR6, (iv) a methylenetetrahydrofolate reductase (EFR11), and (v) an acetyl-CoA synthase (EFR12). In some embodiments, the organism comprises two, three, four, five, six, seven or eight exogenous nucleic acids, each encoding a FRPE. In other embodiments, the at least one exogenous nucleic acid encoding a FRPE is a heterologous nucleic acid. In some embodiments, the FRP further comprises (i) a pyruvate formate lyase (EFR13); (ii) a pyruvate dehydrogenase (EFR14A), a pyruvate ferredoxin oxidoreductase (EFR14B), or a pyruvate:NADP+ oxidoreductase (EFR14C); (iii) a formate dehydrogenase (EFR15); or (iv) an EFR14A, EFR14B, or EFR14C; and an EFR15.

In certain embodiments, the AdiP, 6-ACAP, HMDAP or CapP further comprises a PEP carboxylase (EFR16A), a PEP carboxykinase (EFR16B), a pyruvate carboxylase (EFR17), a malate dehydrogenase (EFR18), a malic enzyme (EFR19), a fumarase (EFR20A), a fumarate reductase (EFR20B), a succinyl-CoA synthetase (EFR20C), a succinyl-CoA ligase (EFR20D), or a succinyl-CoA transferase (EFR20E).

In certain embodiments, at least one exogenous nucleic acid is a heterologous nucleic acid. In some embodiments, the organism is in a substantially anaerobic culture medium. In some embodiments, the microbial organism is a species of bacteria, yeast, or fungus.

In some embodiments, the organism further comprises one or more gene disruptions, occurring in one or more endogenous genes encoding protein(s) or enzyme(s) involved in native production of ethanol, glycerol, acetate, lactate, formate, $CO_2$, and/or amino acids by said microbial organism, wherein said one or more gene disruptions confer increased production of adipate, 6-ACA, HMDA or caprolactam in said microbial organism. In some embodiments, one or more endogenous enzymes involved in native production of ethanol, glycerol, acetate, lactate, formate, $CO_2$ and/or amino acids by the microbial organism, has attenuated enzyme activity or expression levels. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In another aspect, provided herein is a method of producing formaldehyde, comprising culturing a NNOMO provided herein under conditions and for a sufficient period of time to produce formaldehyde. In certain embodiments, the NNOMO comprises an exogenous nucleic acid encoding an EM9. In certain embodiments, the formaldehyde is consumed to provide a reducing equivalent. In other embodiments, the formaldehyde is consumed to incorporate into adipate, 6-ACA, HMDA or caprolactam or another target product.

In another aspect, provided herein is a method of producing an intermediate of glycolysis and/or a metabolic pathway that can be used in the formation of biomass, comprising culturing a NNOMO provided herein under conditions and for a sufficient period of time to produce the intermediate. In certain embodiments, the NNOMO comprises an exogenous nucleic acid encoding an EM9. In certain embodiments, the formaldehyde is consumed to provide a reducing equivalent. In other embodiments, the formaldehyde is consumed to incorporate into adipate, 6-ACA, HMDA or caprolactam or another target product.

In other aspects, provided herein are methods for producing adipate, 6-ACA, HMDA or caprolactam, comprising culturing any one of the NNOMOs comprising a MMP and an adipate, 6-ACA, HMDA or caprolactam pathway provided herein under conditions and for a sufficient period of time to produce adipate, 6-ACA, HMDA or caprolactam. In one embodiment, provided herein is a method for producing adipate, comprising culturing any one of the NNOMOs comprising a MMP and an AdiP provided herein under conditions and for a sufficient period of time to produce adipate. In another embodiment, provided herein is a method for producing 6-ACA, comprising culturing any one of the NNOMOs comprising a 6-ACAP provided herein under conditions and for a sufficient period of time to produce 6-ACA. In another embodiment, provided herein is a method for producing HMDA, comprising culturing any one of the NNOMOs comprising a MMP and a HMDAP provided herein under conditions and for a sufficient period of time to produce HMDA. In yet another embodiment, provided herein is a method for producing caprolactam, comprising culturing any one of the NNOMOs comprising a MMP and a CapP provided herein under conditions and for a sufficient period of time to produce caprolactam. In certain embodiments, the organism is cultured in a substantially anaerobic culture medium. In some embodiments, the NNOMO further comprises a FAP, FRP or a combination thereof, as provided herein.

2. BRIEF DESCRIPTION OF THE DRAWINGS

FIG. 1 shows exemplary metabolic pathways enabling the extraction of reducing equivalents from methanol. The enzymatic transformations shown are carried out by the following enzymes: 1A) a methanol methyltransferase (EM1), 1B) a methylenetetrahydrofolate reductase (EM2), 1C) a methylenetetrahydrofolate dehydrogenase (EM3), 1D) a methenyltetrahydrofolate cyclohydrolase (EM4), 1E) a formyltetrahydrofolate deformylase (EM5), 1F) a formyltetrahydrofolate synthetase (EM6), 1G) a formate hydrogen lyase (EM15), 1H) a hydrogenase (EM16), 1I) a formate dehydrogenase (EM8), 1J) a methanol dehydrogenase (EM9), 1K) a formaldehyde activating enzyme (EM10), 1L) a formaldehyde dehydrogenase (EM11), 1M) a S-(hydroxymethyl)glutathione synthase (EM12), 1N) a glutathione-dependent formaldehyde dehydrogenase (EM13), and 1O) a S-formylglutathione hydrolase (EM14). In certain embodiments, steps K and/or M are spontaneous.

FIG. 2 shows exemplary AdiPs, 6-ACAPs, HMDAPs and CapPs, which can be used to increase adipate, 6-ACA, HMDA or caprolactam yields from carbohydrates when reducing equivalents produced by a MMP provided herein are available. The enzymatic transformations shown are carried out by the following enzymes: 2A) 3-oxoadipyl-CoA thiolase (EA1); 2B) 3-oxoadipyl-CoA reductase (EA2); 2C) 3-hydroxyadipyl-CoA dehydratase (EA3); 2D) 5-carboxy-2-pentenoyl-CoA reductase (EA4), 2E) adipyl-CoA reductase (aldehyde forming) (EA5), 2F) 6-ACA transaminase (EA6A) or 6-ACA dehydrogenase (EA6B); 2G) 6-aminocaproyl-CoA/acyl-CoA transferase (EA7A) or 6-aminocaproyl-CoA synthase (EA7B); 2H) amidohydrolase (EA8); 2J) 6-aminocaproyl-CoA reductase (aldehyde forming) (EA9), 2K) HMDA transaminase (EA10A) or HMDA dehydrogenase (EA10B), 2L) adipyl-CoA hydrolase (EA11A), adipyl-CoA ligase (EA11B), adipyl-CoA transferase (EA11C) or phosphotransadipylase/adipate kinase (EA11D). In certain embodiments, step 2I reflects spontaneous cyclization (EA12). Adipate production can be carried out by 2A, 2B, 2C, 2D and 2L. 6-ACA production can be carried out by 2A, 2B, 2C, 2D, 2E and 2F. HMDA production can be carried out by 2A, 2B, 2C, 2D, 2E, 2F, 2G, 2J and 2K. Caprolactam production can be carried out by 2A, 2B, 2C, 2D, 2E, 2F, 2G and spontaneous cyclization (2I); or 2A, 2B, 2C, 2D, 2E, 2F and 2H.

Figure 4:
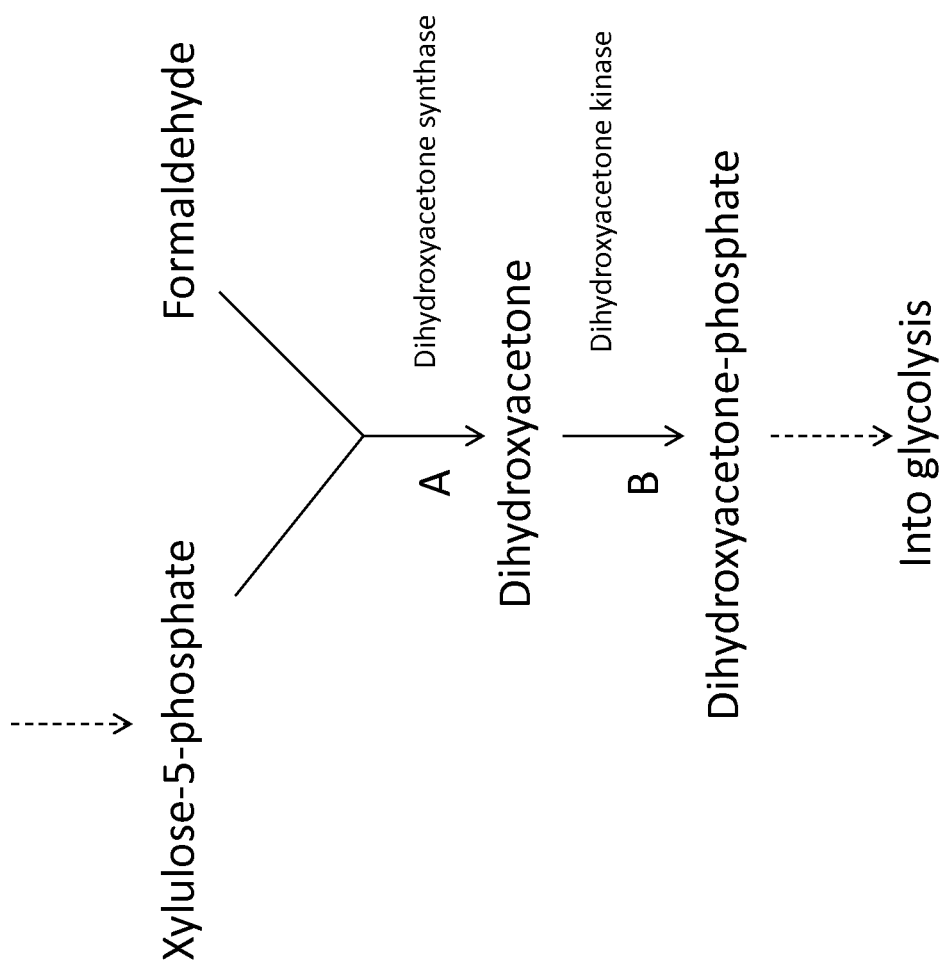
FIG. 4 shows an exemplary FAP. The enzymatic transformations are carried out by the following enzymes: 4A) a DHA synthase (EF3), and 4B) a DHA kinase (EF4).
Figure 5:
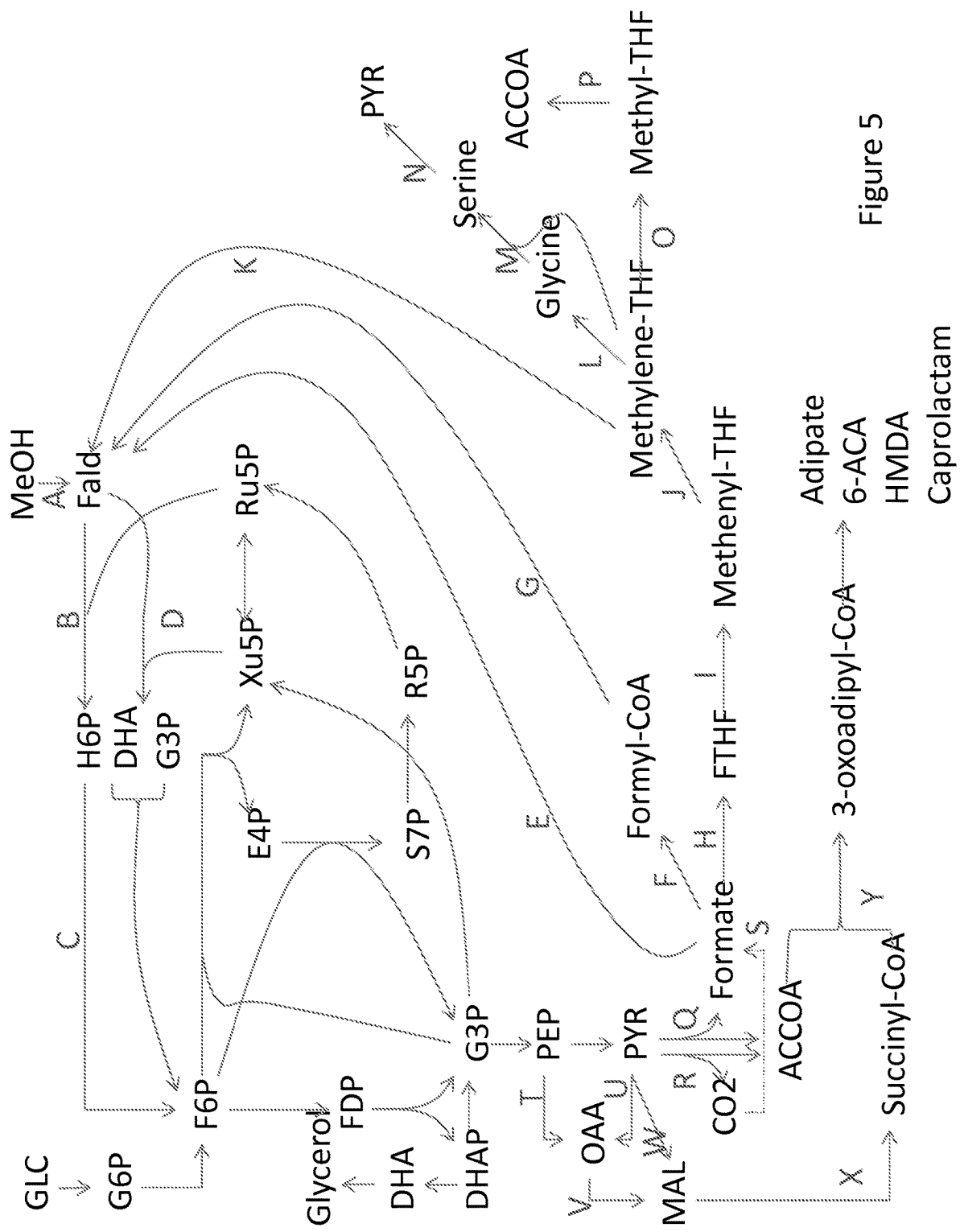

FIG. 5 shows exemplary metabolic pathways enabling the conversion of $CO_2$, formate, formaldehyde, MeOH, glycerol, and glucose to adipate, 6-ACA, HMDA and/or caprolactam. The enzymatic transformations shown are carried out by the following enzymes: A) methanol dehydrogenase (EM9) (see also FIG. 1, step J); B) 3-hexulose-6-phosphate synthase (EF1) (see also FIG. 3, step A); C) 6-phospho-3-hexuloisomerase (EF2) (see also FIG. 3, step B); D) DHA synthase (EF3) (see also FIG. 4, step A); E) a formate reductase (EFR1); F) a formate ligase (EFR2A), formate transferase (EFR2B), or formate synthetase (EFR2C); G) a formyl-CoA reductase (EFR3); H) a formyltetrahydrofolate synthetase (EFR4); I) a methenyltetrahydrofolate cyclohydrolase (EFR5); J) a methylenetetrahydrofolate dehydrogenase (EFR6); K) a formaldehyde-forming enzyme (EFR7); L) a glycine cleavage system (EFR8); M) a serine hydroxymethyltransferase (EFR9); N) a serine deaminase (EFR10); O) a methylenetetrahydrofolate reductase (EFR11); P) an acetyl-CoA synthase (EFR12); Q) a pyruvate formate lyase (EFR13); R) a pyruvate dehydrogenase (EFR14A), pyruvate ferredoxin oxidoreductase (EFR14B), or pyruvate:NADP+ oxidoreductase (EFR14C); S) a formate dehydrogenase (EFR15); T) a PEP carboxylase (EFR16A) or PEP carboxykinase (EFR16B), U) a pyruvate carboxylase (EFR17); V) a malate dehydrogenase (EFR18); W) a malic enzyme (EFR19); X) a fumarase (EFR20A), fumarate reductase (EFR20B), succinyl-CoA synthetase (EFR20C), succinyl-CoA ligase (EFR20D), or succinyl-CoA transferase (EFR20E); and Y) a 3-oxoadipyl-CoA thiolase (EA1: see FIG. 2, step A). In some embodiments, step K is spontaneous. Exemplary pathways for the conversion of succinyl-CoA to adipate, 6-ACA, HMDA and/or caprolactam can be found in FIG. 2.

3. DETAILED DESCRIPTION

3.1 Definitions

As used herein, the term "non-naturally occurring" when used in reference to a microbial organism or microorganism provided herein is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within an adipate, 6-ACA, HMDA or caprolactam biosynthetic pathway.

As used herein, "adipate," having the chemical formula —OOC—(CH$_2$)$_4$—COO— (IUPAC name hexanedioate), is the ionized form of adipic acid (IUPAC name hexanedioic acid), and it is understood that adipate and adipic acid can be used interchangeably throughout to refer to the compound in any of its neutral or ionized forms, including any salt forms thereof. It is understood by those skilled understand that the specific form will depend on the pH. The chemical structure of adipic acid is shown below:

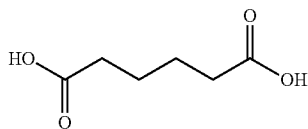

As used herein, "6-aminocaproate" or "6-ACA" having the chemical formula —OOC—(CH$_2$)$_5$—NH$_2$ is the ionized form of 6-aminocaproic acid (IUPAC name 6-aminohexanoic acid), and it is understood that 6-aminocaproate and 6-aminocaproic acid can be used interchangeably throughout to refer to the compound in any of its neutral or ionized forms, including any salt forms thereof. It is understood by those skilled understand that the specific form will depend on the pH. The chemical structure of aminocaproic acid is shown below:

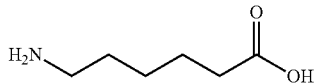

As used herein, "hexamethylenediamine" or "HMDA" (IUPAC name Hexane-1,6-diamine) has the formula H$_2$N(CH$_2$)$_6$NH$_2$. The chemical structure of HMDA is shown below:

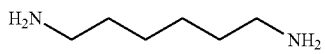

As used herein, "caprolactam" (IUPAC name azepan-2-one) is a lactam of 6-aminohexanoic acid. The chemical structure of caprolactam is shown below:

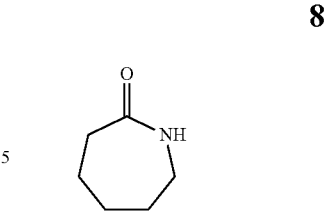

A metabolic modification refers to a biochemical reaction that is altered from its naturally occurring state. Therefore, NNOMOs can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the NNOMOs provided herein. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosolmal segments. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism. The term "growth-coupled" when used in reference to the consumption of a biochemical is intended to mean that the referenced biochemical is consumed during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product provided herein, but the remaining activity or amount of enzyme or protein can still be sufficient to maintain other pathways, such as a pathway that is critical for the host microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid product provided herein, but does not necessarily mimic complete disruption of the enzyme or protein.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid provided herein can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The NNOMOs provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the NNOMO. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the NNOMOs provided herein having adipate, 6-ACA, HMDA or caprolactam biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Feedstock refers to a substance used as a raw material for the growth of an organism, including an industrial growth process. When used in reference to a culture of microbial organisms such as a fermentation process with cells, the term refers to the raw material used to supply a carbon or other energy source for the cells. A "renewable" feedstock refers to a renewable energy source such as material derived from living organisms or their metabolic byproducts including material derived from biomass, often consisting of underutilized components like chaff. Agricultural products specifically grown for use as renewable feedstocks include, for example, corn, soybeans and cotton, primarily in the United States; flaxseed and rapeseed, primarily in Europe; sugar cane in Brazil and palm oil in South-East Asia. Therefore, the term includes the array of carbohydrates, fats and proteins derived from agricultural or animal products across the planet.

Biomass refers to any plant-derived organic matter. In the context of post-fermentation processing, biomass can be used to refer to the microbial cell mass produced during fermentation. Biomass available for energy on a sustainable basis includes herbaceous and woody energy crops, agricultural food and feed crops, agricultural crop wastes and residues, wood wastes and residues, aquatic plants, and other waste materials including some municipal wastes. Biomass feedstock compositions, uses, analytical procedures and theoretical yields are readily available from the U.S. Department of Energy and can be found described, for example, at the URL 1.eere.energy.gov/biomass/information_resources.html, which includes a database describing more than 150 exemplary kinds of biomass sources. Exemplary types of biomasses that can be used as feedstocks in the methods provided herein include cellulosic biomass, hemicellulosic biomass and lignin feedstocks or portions of feedstocks. Such biomass feedstocks contain, for example, carbohydrate substrates useful as carbon sources such as glucose, xylose, galactose, mannose, fructose, starch and the like.

The following is a list of abbreviations and their corresponding compound or composition names used herein. These abbreviations, which are used throughout the disclosure and the figures. It is understood that one of ordinary skill in the art can readily identify these compounds/compositions by such nomenclature. MeOH or MEOH=methanol; Fald=formaldehyde; GLC=glucose; G6P=glucose-6-phosphate; H6P=hexulose-6-phosphate; F6P=fructose-6-phosphate; FDP=fructose diphosphate or fructose-1,6-diphosphate; DHA=dihydroxyacetone; DHAP=dihydroxyacetone phosphate; G3P=and glyceraldehyde-3-phosphate; PYR=pyruvate; Sugar 3=arabinose; ACCOA=acetyl-CoA; AACOA=acetoacetyl-CoA; FTHF=formyltetrahydrofolate; THF=tetrahydrofolate; E4P=erythrose-4-phosphate: Xu5P=xyulose-5-phosphate; Ru5P=ribulose-5-phosphate; S7P=sedoheptulose-7-phosphate: R5P=ribose-5-phosphate; OAA=oxaloacetate; MAL=malate, 6-ACA=6-aminocaproate, HMDA=hexamethylenediamine.

It is also understood that association of multiple steps in a pathway can be indicated by linking their step identifiers with or without spaces or punctuation; for example, the following are equivalent to describe the 4-step pathway comprising Step W, Step X, Step Y and Step Z: steps WXYZ or W,X,Y,Z or W;X;Y;Z or W-X-Y-Z.

3.2 Microbial Organisms that Utilize Reducing Equivalents Produced by the Metabolism of Methanol Provided herein are NNOMOs and MMPs engineered to improve the availability of reducing equivalents, which can be used for the production of product molecules. Exemplary product molecules include, without limitation, adipate, 6-ACA, HMDA or caprolactam, although given the teachings and guidance provided herein, it will be recognized by one skilled in the art that any product molecule that utilizes reducing equivalents in its production can exhibit enhanced production through the biosynthetic pathways provided herein.

Adipic acid, a dicarboxylic acid, with molecular weight of 146.14, is a compound of commercial significance. Its major use is to produce nylon 6,6, a linear polyamide made by condensing adipic acid with HMDA that is primarily employed for manufacturing different kinds of fibers. Other uses of adipic acid include its use in plasticizers, unsaturated polyesters, and polyester polyols. Additional uses include for production of polyurethane, lubricant components, and as a food ingredient as a flavorant and gelling aid.

Historically, adipic acid was prepared from various fats using oxidation. The current commercial processes for adipic acid synthesis rely on the oxidation of KA oil, a mixture of cyclohexanone, the ketone or K component, and cyclohexanol, the alcohol or A component, or of pure cyclohexanol using an excess of strong nitric acid. There are several variations of this theme which differ in the routes for production of KA or cyclohexanol. For example, phenol is an alternative raw material in KA oil production, and the process for the synthesis of adipic acid from phenol has been described. The other versions of this process tend to use oxidizing agents other than nitric acid, such as hydrogen peroxide, air or oxygen.

Caprolactam is an organic compound which is a lactam of 6-aminohexanoic acid (ε-aminohexanoic acid, aminocaproic acid). It can alternatively be considered cyclic amide of caproic acid. The primary industrial use of caprolactam is as a monomer in the production of nylon-6. Most of the caprolactam is synthesized from cyclohexanone via an oximation process using hydroxylammonium sulfate followed by catalytic rearrangement using the Beckmann rearrangement process step.

There exists a need for the development of methods for effectively producing commercial quantities of compounds, such as adipate and caprolactam, as well as 6-ACA and HMDA.

Accordingly, provided herein is bioderived adipate produced according to the methods described herein and biobased products comprising or obtained using the bioderived adipate. The biobased product can comprise at least 5%, at least 10%, at least 20%, at least 30%, at least 40% or at least 50% bioderived adipate. The biobased product can comprises a portion of said bioderived adipate as a repeating unit. The biobased product can be a molded product obtained by molding the biobased product.

Also provided herein is bioderived caprolactam produced according to the methods described herein and biobased products comprising or obtained using the bioderived caprolactam. The biobased product can comprise at least 5%, at least 10%, at least 20%, at least 30%, at least 40% or at least 50% bioderived caprolactam. The biobased product can comprises a portion of said bioderived caprolactam as a repeating unit. The biobased product can be a molded product obtained by molding the biobased product.

Also provided herein is bioderived 6-ACA produced according to the methods described herein and biobased products comprising or obtained using the bioderived 6-ACA. The biobased product can comprise at least 5%, at least 10%, at least 20%, at least 30%, at least 40% or at least 50% bioderived 6-ACA. The biobased product can comprises a portion of said bioderived 6-ACA as a repeating unit. The biobased product can be a molded product obtained by molding the biobased product.

Also provided herein is bioderived HMDA produced according to the methods described herein and biobased products comprising or obtained using the bioderived HMDA. The biobased product can comprise at least 5%, at least 10%, at least 20%, at least 30%, at least 40% or at least 50% bioderived HMDA. The biobased product can comprises a portion of said bioderived HMDA as a repeating unit. The biobased product can be a molded product obtained by molding the biobased product.

Methanol is a relatively inexpensive organic feedstock that can be derived from synthesis gas components, CO and $H_2$, via catalysis. Methanol can be used as a source of reducing equivalents to increase the molar yield of product molecules from carbohydrates.

Methanol can be used as a redox, energy, and carbon source for the production of chemicals such as adipate, 6-ACA, HMDA or caprolactam, and their intermediates, by employing one or more methanol metabolic enzymes as described herein, for example as shown in FIGS. 1-5. Methanol can enter central metabolism in most production hosts by employing methanol dehydrogenase (FIG. 5, step A (see also FIG. 1, step J)) along with a pathway for formaldehyde assimilation. One exemplary FAP that can utilize formaldehyde produced from the oxidation of methanol is shown in FIG. 5, which involves condensation of formaldehyde and D-ribulose-5-phosphate to form H6P by H6P synthase (FIG. 5, step B (see also, FIG. 3, step A)). The enzyme can use $Mg^{2+}$ or $Mn^{2+}$ for maximal activity, although other metal ions are useful, and even non-metal-ion-dependent mechanisms are contemplated. H6P is converted into F6P by 6-phospho-3-hexuloisomerase (FIG. 5, step C (see also FIG. 3, step B)). Another exemplary pathway that involves the detoxification and assimilation of formaldehyde produced from the oxidation of methanol proceeds through DHA. DHA synthase (FIG. 5, step D (see also FIG. 4, step A)) is a transketolase that first transfers a glycoaldehyde group from xylulose-5-phosphate to formaldehyde, resulting in the formation of DHA and glyceraldehyde-3-phosphate (G3P), which is an intermediate in glycolysis. The DHA obtained from DHA synthase can be then further phosphorylated to form DHAP by a DHA kinase. DHAP can be assimilated into glycolysis, e.g., via isomerization to G3P, and several other pathways. Alternatively, DHA and G3P can be converted by F6P aldolase to form F6P.

By combining the pathways for methanol oxidation (FIG. 5, step A (see also FIG. 1, step J)) and formaldehyde assimilation (also called formaldehyde fixation herein) (FIG. 5, steps B and C (see also FIG. 3, steps A and B) or FIG. 5, step D (see also FIG. 4, step A)) improved molar yields of product/mol methanol can be achieved for adipate, 6-ACA, HMDA or caprolactam and their intermediates.

The yield on several substrates, including methanol, can be further increased by capturing some of the carbon lost from the conversion of pathway intermediates, e.g., pyruvate to acetyl-CoA, using one of the formate reutilization (also called formate assimilation herein) pathways shown in FIG. 5. For example, the $CO_2$ generated by conversion of pyruvate to acetyl-CoA (FIG. 5, step R) can be converted to formate via formate dehydrogenase (FIG. 5, step S). Alternatively, pyruvate formate lyase, which forms formate directly instead of $CO_2$, can be used to convert pyruvate to acetyl-CoA (FIG. 5, step Q). Formate can be converted to formaldehyde by using: 1) formate reductase (FIG. 5, step E), 2) a formyl-CoA synthetase, transferase, or ligase along with formyl-CoA reductase (FIG. 5, steps F-G), or 3) formyltetrahydrofolate synthetase, methenyltetrahydrofolate cyclohydrolase, methylenetetrahydrofolate dehydrogenase, and formaldehyde-forming enzyme (FIG. 5, steps H-I-J-K). Conversion of methylene-THF to formaldehyde alternatively will occur spontaneously. Alternatively, formate can be reutilized by converting it to pyruvate or acetyl-CoA using FIG. 5, steps H-I-J-L-M-N or FIG. 5, steps H-I-J-O-P, respectively. Formate reutilization is also useful when formate is an external carbon source. For example, formate can be obtained from organocatalytic, electrochemical, or photoelectrochemical conversion of $CO_2$ to formate. An alternative source of methanol for use in the present methods is organocatalytic, electrochemical, or photoelectrochemical conversion of $CO_2$ to methanol. By combining the pathways for methanol oxidation (FIG. 5, step A), formaldehyde assimilation (FIG. 5, Steps B and C or Step D), and formate reutilization, even higher molar yields mol product/mol methanol can be achieved for adipate, 6-ACA, HMDA or caprolactam. By combining pathways for formaldehyde assimilation and formate reutilization, yield increases on additional substrates are also available including but not limited to glucose, glycerol, sucrose, fructose, xylose, arabinose and galactose.

Figure 1:
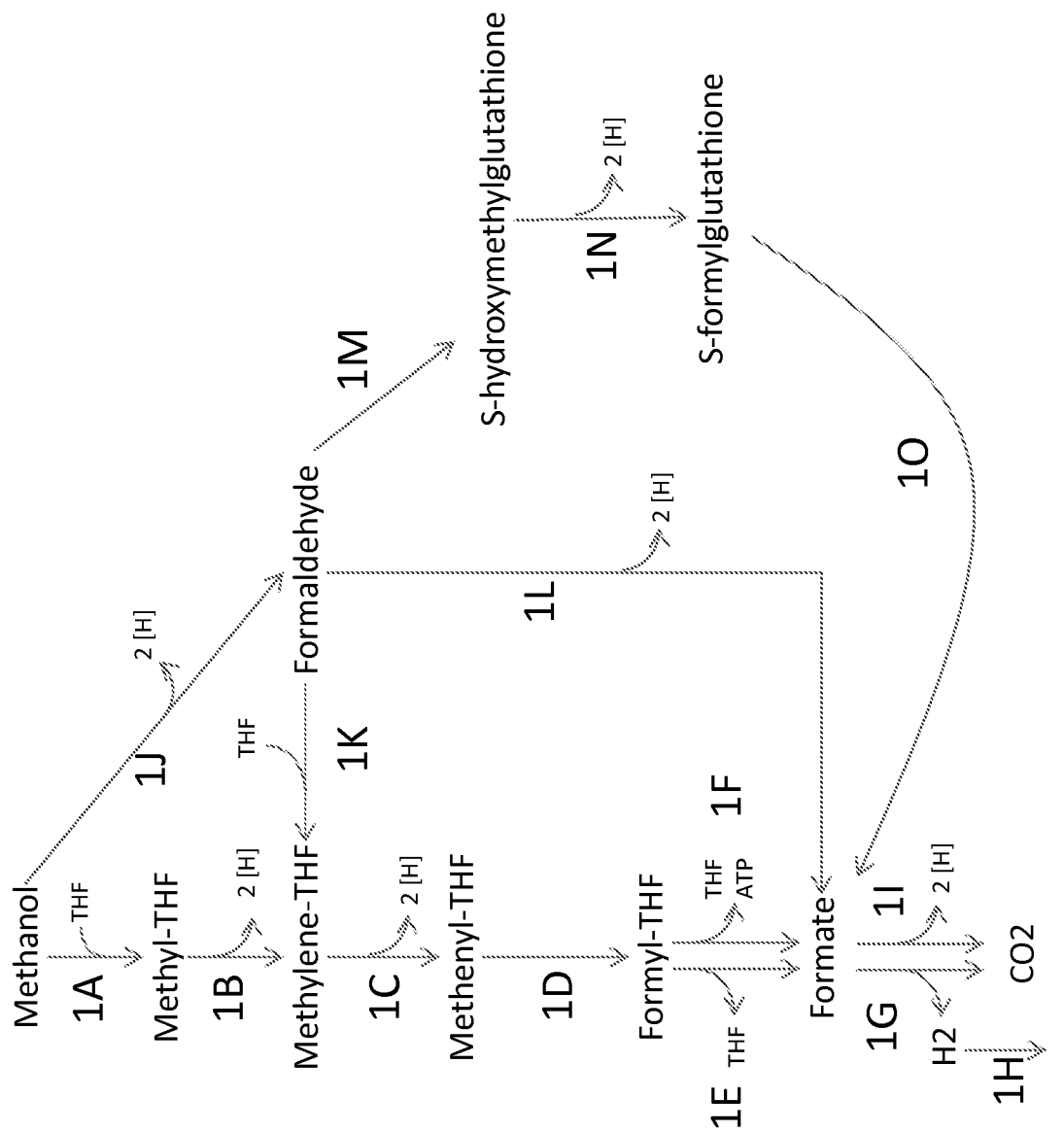

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 1. Reducing equivalents can also be extracted from hydrogen and carbon monoxide by employing hydrogenase and carbon monoxide dehydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes. The reducing equivalents produced by the metabolism of methanol, hydrogen, and carbon monoxide can be used to power several adipate, 6-ACA, HMDA or caprolactam pathways. In some embodiments, the reducing equivalents produced by the metabolism of methanol by one or more of the MMPs can then be used to power the glucose to adipate, 6-ACA, HMDA and caprolactam production pathways, for example, as shown in FIG. 2.

The product yields per C-mol of substrate of microbial cells synthesizing reduced fermentation products such as adipate, 6-ACA, HMDA and caprolactam are limited by insufficient reducing equivalents in the carbohydrate feedstock. Reducing equivalents, or electrons, can be extracted from methanol using one or more of the enzymes described in FIG. 1. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

Specific examples of how additional redox availability from methanol can improve the yield of reduced products such as adipate, 6-ACA, HMDA or caprolactam are shown.

Figure 2:
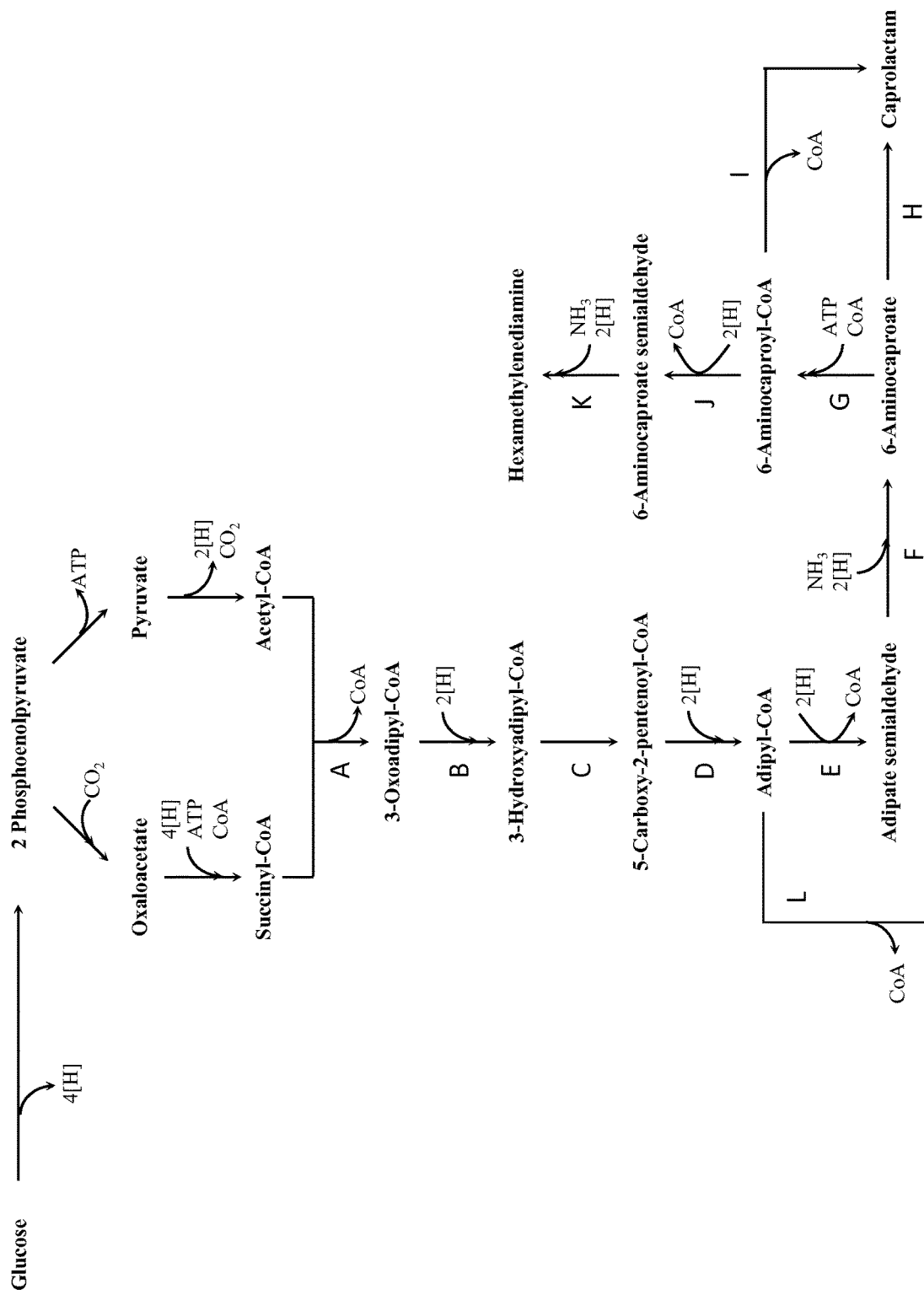

The maximum theoretical yield of adipate, 6-ACA, HMDA or caprolactam via the pathway shown in FIG. 2 supplemented with the reactions of the oxidative TCA cycle (e.g., citrate synthase, aconitase, isocitrate dehydrogenase, alpha-ketoglutarate dehydrogenase) is 1.09 mol/mol.

$$1\ C_6H_{12}O_6 \rightarrow 1.09\ C_4H_{10}O_2 + 1.64\ CO_2 + 0.55\ H_2O$$

When both feedstocks of sugar and methanol are available, the methanol can be utilized to generate reducing equivalents by employing one or more of the enzymes shown in FIG. 1. The reducing equivalents generated from methanol can be utilized to power the glucose to adipate, 6-ACA, HMDA or caprolactam production pathways, e.g., as shown in FIG. 2. Theoretically, all carbons in glucose will be conserved, thus resulting in a maximal theoretical yield to produce adipate from glucose at 2 mol adipate per mol of glucose under either aerobic or anaerobic conditions as shown in FIG. 2:

$$10CH_3OH + 3C_6H_{12}O_6 = 6C_4H_{10}O_2 + 8H_2O + 4CO_2$$

In a similar manner, the maximum theoretical yields of 6-ACA, HMDA or caprolactam can reach 2 mol/mol glucose using the reactions shown in FIGS. 1 and 2.

$$C_6H_{12}O_6 + 0.667CH_3OH + 1.333CO_2 \rightarrow 2C_4H_6O_4 + 1.333H_2O$$

$$C_6H_{12}O_6 + 2CH_3OH \rightarrow 2C_4H_8O_3 + 2H_2O$$

Exemplary flux distributions can demonstrate how the maximum theoretical yield of adipate, 6-ACA, HMDA or caprolactam from glucose and glycerol can be increased by enabling assimilation of formaldehyde, formate reutilization, and extraction of reducing equivalents from an external source such as hydrogen. By combining pathways for formaldehyde assimilation, formate reutilization, reducing equivalent extraction, and product synthesis, maximum theoretical yield stoichiometries for adipate, 6-ACA, HMDA or caprolactam on glucose and glycerol are made possible. In certain embodiments, achieving such maximum yield stoichiometries may require some oxidation of reducing equivalents (e.g., $H_2 + \frac{1}{2}O_2 \rightarrow H_2O$, $CO + \frac{1}{2}O_2 \rightarrow CO_2$, $CH_4O + 1.5\ O_2 \rightarrow CO_2 + 2\ H_2O$, $C_6H_{12}O_6 + 6\ O_2 \rightarrow CO_2 + 6\ H_2O$) to provide sufficient energy for the substrate to product pathways to operate. Nevertheless, if sufficient reducing equivalents are available, enabling pathways for assimilation of formaldehyde, formate reutilization, extraction of reducing equivalents, and product synthesis can even lead to production of adipate, 6-ACA, HMDA or caprolactam and their intermediates, directly from $CO_2$.

Pathways provided herein, and particularly pathways exemplified in specific combinations presented herein, are superior over other pathways based in part on the applicant's ranking of pathways based on attributes including maximum theoretical adipate, 6-ACA, HMDA or caprolactam yield, maximal carbon flux, maximal production of reducing equivalents, minimal production of $CO_2$, pathway length, number of non-native steps, thermodynamic feasibility, number of enzymes active on pathway substrates or structurally similar substrates, and having steps with currently characterized enzymes, and furthermore, the latter pathways are even more favored by having in addition at least the fewest number of non-native steps required, the most enzymes known active on pathway substrates or structurally similar substrates, and the fewest total number of steps from central metabolism.

In a first aspect, provided herein is a NNOMO having a MMP, wherein said organism comprises at least one exogenous nucleic acid encoding a MMPE expressed in a sufficient amount to enhance the availability of reducing equivalents in the presence of methanol. In other embodiments, the MMPE is expressed in a sufficient amount to convert methanol to formaldehyde. In certain embodiments, the MMP comprises one or more enzymes selected from the group consisting of an EM1; an EM2; an EM3; an EM4; an EM5; an EM6; an EM15; an EM16; an EM8; an EM9; an EM10; an EM11; an EM12; an EM13; and an EM14. Such organisms, in certain embodiments, advantageously allow for the production of reducing equivalents, which can then be used by the organism for the production of adipate, 6-ACA, HMDA or caprolactam using any one of the AdiPs, 6-ACAPs, HMDAPs or CapPs provided herein.

In certain embodiments, the MMP comprises 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, and 1O, thereof, wherein 1A is an EM1; 1B is an EM2; 1C is an EM3; 1D is an EM4; 1E is an EM5; 1F is an EM6; 1G is an EM15; 1H is an EM16; 1I is an EM8; 1J is an EM9; 1K is an EM10; 1L is an EM11; 1M is an EM12; 1N is EM13; and 1O is EM14. In some embodiments, 1K is spontaneous. In other embodiments, 1K is an EM10. In some embodiments, 1M is spontaneous. In other embodiments, 1M is an EM12.

In one embodiment, the MMP comprises 1A. In another embodiment, the MMP comprises 1B. In another embodiment, the MMP comprises 1C. In yet another embodiment, the MMP comprises 1D. In one embodiment, the MMP comprises 1E. In another embodiment, the MMP comprises 1F. In another embodiment, the MMP comprises 1G. In yet another embodiment, the MMP comprises 1H. In one embodiment, the MMP comprises 1I. In another embodiment, the MMP comprises 1J. In another embodiment, the MMP comprises 1K. In yet another embodiment, the MMP comprises 1L. In yet another embodiment, the MMP comprises 1M. In another embodiment, the MMP comprises 1N. In yet another embodiment, the MMP comprises 1O. Any combination of two, three, four, five, six, seven, eight, nine, ten, eleven, twelve, thirteen, fourteen or fifteen MMPEs 1A, 1B, 1C, 1D, 1E, 1F, 1G, 1H, 1I, 1J, 1K, 1L, 1M, 1N, and 1O is also contemplated.

In some embodiments, the MMP is a MMP depicted in FIG. 1.

In one aspect, provided herein is a NNOMO having a MMP, wherein said organism comprises at least one exogenous nucleic acid encoding a MMPE expressed in a sufficient amount to enhance the availability of reducing equivalents in the presence of methanol, wherein said MMP comprises: (i) 1A and 1B, (ii) 1J; or (iii) 1J and 1K. In one embodiment, the MMP comprises 1A and 1B. In another embodiment, the MMP comprises 1J. In one embodiment, the MMP comprises 1J and 1K. In certain embodiments, the MMP comprises 1A, 1B, 1C, 1D, and 1E. In some embodiments. the MMP comprises 1A, 1B, 1C, 1D and 1F. In some embodiments, the MMP comprises 1J, 1C, 1D and 1E. In one embodiment, the MMP comprises 1J, 1C, 1D and 1F. In another embodiment, the MMP comprises 1J and 1L. In yet another embodiment, the MMP comprises 1J, 1M, 1N and 1O. In certain embodiments, the MMP comprises 1J, 1N and 1O. In some embodiments, the MMP comprises 1J, 1K, 1C, 1D and 1E. In one embodiment, the MMP comprises 1J, 1K, 1C, 1D and 1F. In some embodiments, 1K is spontaneous. In other embodiments, 1K is an EM10. In some embodiments, 1M is spontaneous. In other embodiments, 1M is an EM12.

In certain embodiments, the MMP comprises 1I. In certain embodiments, the MMP comprises 1A, 1B, 1C, 1D, 1E and 1I. In some embodiments. the MMP comprises 1A, 1B, 1C, 1D, 1F and 1I. In some embodiments, the MMP comprises 1J, 1C, 1D, 1E and 1I. In one embodiment, the MMP comprises 1J, 1C, 1D, 1F and 1I. In another embodiment, the MMP comprises 1J, 1L and 1I. In yet another embodiment, the MMP comprises 1J, 1M, 1N, 1O and 1I. In certain embodiments, the MMP comprises 1J, 1N, 1O and 1I. In some embodiments, the MMP comprises 1J, 1K, 1C, 1D, 1E and 1I. In one embodiment, the MMP comprises 1J, 1K, 1C, 1D, 1F and 1I. In some embodiments, 1K is spontaneous. In other embodiments, 1K is an EM10. In some embodiments, 1M is spontaneous. In other embodiments, 1M is an EM12.

In certain embodiments, the MMP comprises 1G. In certain embodiments, the MMP comprises 1A, 1B, 1C, 1D, 1E and 1G. In some embodiments. the MMP comprises 1A, 1B, 1C, 1D, 1F and 1G. In some embodiments, the MMP comprises 1J, 1C, 1D, 1E and 1G. In one embodiment, the MMP comprises 1J, 1C, 1D, 1F and 1G. In another embodiment, the MMP comprises 1J, 1L and 1G. In yet another embodiment, the MMP comprises 1J, 1M, 1N, 1O and 1G. In certain embodiments, the MMP comprises 1J, 1N, 1O and 1G. In some embodiments, the MMP comprises 1J, 1K, 1C, 1D, 1E and 1G. In one embodiment, the MMP comprises 1J, 1K, 1C, 1D, 1F and 1G. In some embodiments, 1K is spontaneous. In other embodiments, 1K is an EM10. In some embodiments, 1M is spontaneous. In other embodiments, 1M is an EM12.

In certain embodiments, the MMP comprises 1G and 1H. In certain embodiments, the MMP comprises 1A, 1B, 1C, 1D, 1E, 1G and 1H. In some embodiments. the MMP comprises 1A, 1B, 1C, 1D, 1F, 1G and 1H. In some embodiments, the MMP comprises 1J, 1C, 1D, 1E, 1G and 1H. In one embodiment, the MMP comprises 1J, 1C, 1D, 1F, 1G and 1H. In another embodiment, the MMP comprises 1J, 1L, 1G and 1H. In yet another embodiment, the MMP comprises 1J, 1M, 1N, 1O, 1G and 1H. In certain embodiments, the MMP comprises 1J, 1N, 1O, 1G and 1H. In some embodiments, the MMP comprises 1J, 1K, 1C, 1D, 1E, 1G and 1H. In one embodiment, the MMP comprises 1J, 1K, 1C, 1D, 1F, 1G and 1H. In some embodiments, 1K is spontaneous. In other embodiments, 1K is an EM10. In some embodiments, 1M is spontaneous. In other embodiments, 1M is an EM12.

In certain embodiments, the formation of 5-hydroxymethylglutathione from formaldehyde is spontaneous (see, e.g., FIG. 1, step M). In some embodiments, the formation of 5-hydroxymethylglutathione from formaldehyde is catalyzed by an EM12 (see, e.g., FIG. 1, step M). In certain embodiments, the formation of methylene-THF from formaldehyde is spontaneous (see, e.g., FIG. 1, step K). In certain embodiments, the formation of methylene-THF from formaldehyde is catalyzed by an EM10 (see, e.g., FIG. 1, step K).

In certain embodiments, the organism comprises two, three, four, five, six or seven exogenous nucleic acids, each encoding a MMPE. In certain embodiments, the organism comprises two exogenous nucleic acids, each encoding a MMPE. In certain embodiments, the organism comprises three exogenous nucleic acids, each encoding a MMPE. In certain embodiments, the organism comprises four exogenous nucleic acids, each encoding a MMPE. In certain embodiments, the organism comprises five exogenous nucleic acids, each encoding a MMPE. In certain embodiments, the organism comprises six exogenous nucleic acids, each encoding a MMPE. In certain embodiments, the organism comprises seven exogenous nucleic acids, each encoding a MMPE.

Any non-naturally occurring eukaryotic organism comprising a MMP and engineered to comprise a MMPE, such as those provided herein, can be engineered to further comprise one or more AdiPEs, 6-ACAPEs, HMDAPEs or CapPEs. Such organisms can further be engineered to comprise a FAP, a FRP, or both a FAP and a FRP as provided herein.

In one embodiment, the NNOMO further comprises an AdiP, wherein said organism comprises at least one exogenous nucleic acid encoding an AdiPE expressed in a sufficient amount to produce adipate. In certain embodiments, the AdiPE is selected from the group consisting of EA1, EA2, EA3, EA4, EA11A, EA11B, EA11C and EA11D.

In another embodiment, the NNOMO further comprises a 6-ACAP, wherein said organism comprises at least one exogenous nucleic acid encoding a 6-ACAPE expressed in a sufficient amount to produce 6-ACA. In certain embodiments, the 6-ACAPE is selected from the group consisting of EA1, EA2, EA3, EA4, EA5, EA6A and EA6B.

In one embodiment, the NNOMO further comprises a HMDAP, wherein said organism comprises at least one exogenous nucleic acid encoding a HMDAPE expressed in a sufficient amount to produce HMDA. In certain embodiments, the HMDAPE is selected from the group consisting of EA1, EA2, EA3, EA4, EA5, EA6A, EA6B, EA7A, EA7B, EA9, EA10A, and EA10B.

In other embodiments, the NNOMO has a CapP, wherein said organism comprises at least one exogenous nucleic acid encoding a CapPE expressed in a sufficient amount to produce caprolactam. In certain embodiments, the CapPE is selected from the group consisting of EA1, EA2, EA3, EA4, EA5, EA6A, EA6B, EA7A, and EA7B. In other embodiments, the CapPE is selected from the group consisting of EA1, EA2, EA3, EA4, EA5, EA6A, EA6B, and EA8.

In some embodiments, the NNOMOs having an adipate, 6-ACA, HMDA or caprolactam pathway include a set of AdiPEs, 6-ACAPEs, HMDAPEs or CapPEs.

Enzymes, genes and methods for engineering pathways from succinyl-CoA or acetyl-CoA to various products, such as adipate, 6-ACA, HMDA or caprolactam, into a microorganism, are now known in the art, as are enzymes for the conversion of glucose to phosphoenolpyruvate (PEP), phosphoenolpyruvate to oxaloacetate, oxaloacetate to succinyl CoA, phosphoenolpyruvate to pyruvate, and pyruvate to acetyl-CoA (see, e.g., U.S. Publ. No. 2011/0201089 and WO 2012/135789, which is herein incorporated by reference in its entirety). A set of AdiPEs, 6-ACAPEs, HMDAPEs or CapPEs represents a group of enzymes that can convert succinyl-CoA or acetyl-CoA to adipate, 6-ACA, HMDA or caprolactam, respectively, as shown in FIG. 2. The additional reducing equivalents obtained from the MMPs, as disclosed herein, improve the yields of all these products when utilizing carbohydrate-based feedstock.

Exemplary enzymes for the conversion succinyl-CoA or acetyl CoA to adipate include EA1 (FIG. 2, step A), EA2 (FIG. 2, step B), EA3 (FIG. 2, step C), EA4 (FIG. 2, step D), EA11A, EA11B, EA11C and EA11D (FIG. 2, step L).

In one aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) an AdiP, wherein said organism comprises at least one exogenous nucleic acid encoding an AdiPE expressed in a sufficient amount to produce adipate. In one embodiment, the at least one exogenous nucleic acid encoding the MMPE enhances the availability of reducing equivalents in the presence of methanol in a sufficient amount to increase the amount of adipate produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the AdiP comprises 2A, 2B, 2C, 2D or 2L, or any combination thereof, wherein 2A is an EA1; 2B is an EA2; 2C is an EA3; 2D is an EA4; and 2L is an EA11A, an EA11B, an EA11C or an EA11D. In some embodiments, 1K is spontaneous. In other embodiments, 1K is an EM10. In some embodiments, 1M is spontaneous. In other embodiments, 1M is an EM12. In some embodiments, 2L is an EA11A. In other embodiments, 2L is an EA11B. In some embodiments, 2L is an EA11C. In another embodiment, 2L is an EA11D.

In one embodiment, the AdiP comprises 2A. In another embodiment, the AdiP comprises 2B. In an embodiment, the AdiP comprises 2C. In another embodiment, the AdiP comprises 2D. In another embodiment, the AdiP comprises 2L. Any combination of two, three, four or five AdiPEs 2A, 2B, 2C, 2D and 2L is also contemplated. In some embodiments, 2L is an EA11A. In other embodiments, 2L is an EA11B. In some embodiments, 2L is an EA11C. In another embodiment, 2L is an EA11D.

In some embodiments, the MMP is a MMP depicted in FIG. 1, and the AdiP is an AdiP depicted in FIG. 2.

An exemplary set of AdiPEs to convert succinyl-CoA or acetyl-CoA to adipate, according to FIG. 2, includes 2A, 2B, 2C, 2D and 2L. In some embodiments, 2L is an EA11A. In other embodiments, 2L is an EA11B. In some embodiments, 2L is an EA11C. In another embodiment, 2L is an EA11D.

In one embodiment, (1) the MMP comprises 1A and 1B; and (2) the AdiP comprises 2A, 2B, 2C, 2D and 2L. In another embodiment, (1) the MMP comprises 1J; and (2) the AdiP comprises 2A, 2B, 2C, 2D and 2L. In one embodiment, (1) the MMP comprises 1J and 1K; and (2) the AdiP comprises 2A, 2B, 2C, 2D and 2L. In certain embodiments, (1) the MMP comprises 1A, 1B, 1C, 1D, and 1E; and (2) the AdiP comprises 2A, 2B, 2C, 2D and 2L. In some embodiments, (1) the MMP comprises 1A, 1B, 1C, 1D and 1F; and (2) the AdiP comprises 2A, 2B, 2C, 2D and 2L. In some embodiments, (1) the MMP comprises 1J, 1C, 1D and 1E; and (2) the AdiP comprises 2A, 2B, 2C, 2D and 2L. In one embodiment, (1) the MMP comprises 1J, 1C, 1D and 1F; and (2) the AdiP comprises 2A, 2B, 2C, 2D and 2L. In another embodiment, (1) the MMP comprises 1J and 1L; and (2) the AdiP comprises 2A, 2B, 2C, 2D and 2L. In yet another embodiment, (1) the MMP comprises 1J, 1M, 1N and 1O; and (2) the AdiP comprises 2A, 2B, 2C, 2D and 2L. In certain embodiments, (1) the MMP comprises 1J, 1N and 1O; and (2) the AdiP comprises 2A, 2B, 2C, 2D and 2L. In some embodiments, (1) the MMP comprises 1J, 1K, 1C, 1D and 1E; and (2) the AdiP comprises 2A, 2B, 2C, 2D and 2L. In one embodiment, (1) the MMP comprises 1J, 1K, 1C, 1D and 1F; and (2) the AdiP comprises 2A, 2B, 2C, 2D and 2L. In certain embodiments, (1) the MMP comprises 1I; and (2) the AdiP comprises 2A, 2B, 2C, 2D and 2L. In certain embodiments, (1) the MMP comprises 1A, 1B, 1C, 1D, 1E and 1I; and (2) the AdiP comprises 2A, 2B, 2C, 2D and 2L. In some embodiments, (1) the MMP comprises 1A, 1B, 1C, 1D, 1F and 1I; and (2) the AdiP comprises 2A, 2B, 2C, 2D and 2L. In some embodiments, (1) the MMP comprises 1J, 1C, 1D, 1E and 1I; and (2) the AdiP comprises 2A, 2B, 2C, 2D and 2L. In one embodiment, (1) the MMP comprises 1J, 1C, 1D, 1F and 1I; and (2) the AdiP comprises 2A, 2B, 2C, 2D and 2L. In another embodiment, (1) the MMP comprises 1J, 1L and 1I; and (2) the AdiP comprises 2A, 2B, 2C, 2D and 2L. In yet another embodiment, (1) the MMP comprises 1J, 1M, 1N, 1O and 1I; and (2) the AdiP comprises 2A, 2B, 2C, 2D and 2L. In certain embodiments, (1) the MMP comprises 1J, 1N, 1O and 1I; and (2) the AdiP comprises 2A, 2B, 2C, 2D and 2L. In some embodiments, (1) the MMP comprises 1J, 1K, 1C, 1D, 1E and 1I; and (2) the AdiP comprises 2A, 2B, 2C, 2D and 2L. In one embodiment, (1) the MMP comprises 1J, 1K, 1C, 1D, 1F and 1I; and (2) the AdiP comprises 2A, 2B, 2C, 2D and 2L. In certain embodiments, (1) the MMP comprises 1G; and (2) the AdiP comprises 2A, 2B, 2C, 2D and 2L. In certain embodiments, (1) the MMP comprises 1A, 1B, 1C, 1D, 1E and 1G; and (2) the AdiP comprises 2A, 2B, 2C, 2D and 2L. In some embodiments, (1) the MMP comprises 1A, 1B, 1C, 1D, 1F and 1G; and (2) the AdiP comprises 2A, 2B, 2C, 2D and 2L. In some embodiments, (1) the MMP comprises 1J, 1C, 1D, 1E and 1G; and (2) the AdiP comprises 2A, 2B, 2C, 2D and 2L. In one embodiment, (1) the MMP comprises 1J, 1C, 1D, 1F and 1G; and (2) the AdiP comprises 2A, 2B, 2C, 2D and 2L. In another embodiment, (1) the MMP comprises 1J, 1L and 1G; and (2) the AdiP comprises 2A, 2B, 2C, 2D and 2L. In yet another embodiment, (1) the MMP comprises 1J, 1M, 1N, 1O and 1G; and (2) the AdiP comprises 2A, 2B, 2C, 2D and 2L. In certain embodiments, (1) the MMP comprises 1J, 1N, 1O and 1G; and (2) the AdiP comprises 2A, 2B, 2C, 2D and 2L. In some embodiments, (1) the MMP comprises 1J, 1K, 1C, 1D, 1E and 1G; and (2) the AdiP comprises 2A, 2B, 2C, 2D and 2L. In one embodiment, (1) the MMP comprises 1J, 1K, 1C, 1D, 1F and 1G; and (2) the AdiP comprises 2A, 2B, 2C, 2D and 2L. In certain embodiments, (1) the MMP comprises 1G and 1H; and (2) the AdiP comprises 2A, 2B, 2C, 2D and 2L. In certain embodiments, (1) the MMP comprises 1A, 1B, 1C, 1D, 1E, 1G and 1H; and (2) the AdiP comprises 2A, 2B, 2C, 2D and 2L. In some embodiments, (1) the MMP comprises 1A, 1B, 1C, 1D, 1F, 1G and 1H; and (2) the AdiP comprises 2A, 2B, 2C, 2D and 2L. In some embodiments, (1) the MMP comprises 1J, 1C, 1D, 1E, 1G and 1H; and (2) the AdiP comprises 2A, 2B, 2C, 2D and 2L. In one embodiment, (1) the MMP comprises 1J, 1C, 1D, 1F, 1G and 1H; and (2) the AdiP comprises 2A, 2B, 2C, 2D and 2L. In another embodiment, (1) the MMP comprises 1J, 1L, 1G and 1H; and (2) the AdiP comprises 2A, 2B, 2C, 2D and 2L. In yet another embodiment, (1) the MMP comprises 1J, 1M, 1N, 1O, 1G and 1H; and (2) the AdiP comprises 2A, 2B, 2C, 2D and 2L. In certain embodiments, (1) the MMP comprises 1J, 1N, 1O, 1G and 1H; and (2) the AdiP comprises 2A, 2B, 2C, 2D and 2L. In some embodiments, (1) the MMP comprises 1J, 1K, 1C, 1D, 1E, 1G and 1H; and (2) the AdiP comprises 2A, 2B, 2C, 2D and 2L. In one embodiment, (1) the MMP comprises 1J, 1K, 1C, 1D, 1F, 1G and 1H; and (2) the AdiP comprises 2A, 2B, 2C, 2D and 2L. In some embodiments, 1K is spontaneous. In other embodiments, 1K is an EM10. In some embodiments, 1M is spontaneous. In other embodiments, 1M is an EM12. In some embodiments, 2L is an EA11A. In other embodiments, 2L is an EA11B. In some embodiments, 2L is an EA11C. In another embodiment, 2L is an EA11D.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) an AdiP. In some embodiments, 1K is spontaneous. In other embodiments, 1K is an EM10. In some embodiments, 1M is spontaneous. In other embodiments, 1M is an EM12.

Any MMP provided herein can be combined with any AdiP provided herein.

In certain embodiments, the AdiP further comprises enzymes depicted in FIG. 5. In one embodiment, the AdiP further comprises 5T, 5U, 5V, 5W, and/or 5X, wherein 5T is a PEP carboxylase (EFR16A) or PEP carboxykinase (EFR16B); 5U is a pyruvate carboxylase (EFR17); 5V is a malate dehydrogenase (EFR18); 5W is a malic enzyme (EFR19); and 5X is a fumarase (EFR20A), fumarate reductase (EFR20B), succinyl-CoA synthetase (EFR20C), succinyl-CoA ligase (EFR20D), or succinyl-CoA transferase (EFR20E). In one embodiment, the AdiP comprises 5T. In another embodiment, the AdiP comprises 5U. In another embodiment, the AdiP comprises 5V. In other embodiment, the AdiP comprises 5W. In another embodiment, the AdiP comprises 5X. In another embodiment, the AdiP comprises 5Y. In some embodiments, the AdiP comprises 5T, 5V and 5X. In another embodiment, the AdiP comprises 5U, 5V and 5X. In another embodiment, the AdiP comprises 5W and 5X. In one embodiment, 5T is EFR16A. In other embodiments, 5T is EFR16B. In some embodiments, 5X is EFR20A. In other embodiments, 5X is EFR20B. In other embodiments, 5X is EFR20C. In one embodiment, 5X is EFR20D. In another embodiment, 5X is EFR20E.

Exemplary enzymes for the conversion succinyl-CoA or acetyl CoA to 6-ACA include EA1 (FIG. 2, step A), EA2 (FIG. 2, step B), EA3 (FIG. 2, step C), EA4 (FIG. 2, step D), EA5 (FIG. 2, step E), and EA6A or EA6B (FIG. 2, step F).

In another aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) an 6-ACAP, wherein said organism comprises at least one exogenous nucleic acid encoding an 6-ACAPE expressed in a sufficient amount to produce 6-ACA. In one embodiment, the at least one exogenous nucleic acid encoding the MMPE enhances the availability of reducing equivalents in the presence of methanol in a sufficient amount to increase the amount of 6-ACA produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1T is an EM9; 1K is spontaneous or EM10; 1L is an EM11; 1M is spontaneous or an EM12; 1N is EM13 and 1O is EM14; and (2) the 6-ACAP comprises 2A, 2B, 2C, 2D, 2E or 2F, or any combination thereof, wherein 2A is an EA1; 2B is an EA2; 2C is an EA3; 2D is an EA4; 2E is an EA5, and 2F is an EA6A or an EA6B. In some embodiments, 1K is spontaneous. In other embodiments, 1K is an EM10. In some embodiments, 1M is spontaneous. In other embodiments, 1M is an EM12. In some embodiments, 2F is an EA6A. In other embodiments, 2F is an EA6B.

In one embodiment, the 6-ACAP comprises 2A. In another embodiment, the 6-ACAP comprises 2B. In an embodiment, the 6-ACAP comprises 2C. In another embodiment, the 6-ACAP comprises 2D. In one embodiment, the 6-ACAP comprises 2E. In yet another embodiment, the 6-ACAP comprises 2F. Any combination of two, three, four, five or six 6-ACAPEs 2A, 2B, 2C, 2D, 2E and 2F is also contemplated.

In some embodiments, the MMP is a MMP depicted in FIG. 1, and the 6-ACAP is an 6-ACAPEs depicted in FIG. 2.

An exemplary set of 6-ACAPEs to convert succinyl-CoA or acetyl-CoA to G-ACA, according to FIG. 2, includes 2A, 2B, 2C, 2D, 2E and 2F.

In one embodiment, (1) the MMP comprises 1A and 1B; and (2) the 6-ACAP comprises 2A, 2B, 2C, 2D, 2E and 2F. In another embodiment, (1) the MMP comprises 1J; and (2) the 6-ACAP comprises 2A, 2B, 2C, 2D, 2E and 2F. In one embodiment, (1) the MMP comprises 1J and 1K; and (2) the 6-ACAP comprises 2A, 2B, 2C, 2D, 2E and 2F. In certain embodiments, (1) the MMP comprises 1A, 1B, 1C, 1D, and 1E; and (2) the 6-ACAP comprises 2A, 2B, 2C, 2D, 2E and 2F. In some embodiments, (1) the MMP comprises 1A, 1B, 1C, 1D and 1F; and (2) the 6-ACAP comprises 2A, 2B, 2C, 2D, 2E and 2F. In some embodiments, (1) the MMP comprises 1J, 1C, 1D and 1E; and (2) the 6-ACAP comprises 2A, 2B, 2C, 2D, 2E and 2F. In one embodiment, (1) the MMP comprises 1J, 1C, 1D and 1F; and (2) the 6-ACAP comprises 2A, 2B, 2C, 2D, 2E and 2F. In another embodiment, (1) the MMP comprises 1J and 1L; and (2) the 6-ACAP comprises 2A, 2B, 2C, 2D, 2E and 2F. In yet another embodiment, (1) the MMP comprises 1J, 1M, 1N and 1O; and (2) the 6-ACAP comprises 2A, 2B, 2C, 2D, 2E and 2F. In certain embodiments, (1) the MMP comprises 1J, 1N and 1O; and (2) the 6-ACAP comprises 2A, 2B, 2C, 2D, 2E and 2F. In some embodiments, (1) the MMP comprises 1J, 1K, 1C, 1D and 1E; and (2) the 6-ACAP comprises 2A, 2B, 2C, 2D, 2E and 2F. In one embodiment, (1) the MMP comprises 1J, 1K, 1C, 1D and 1F; and (2) the 6-ACAP comprises 2A, 2B, 2C, 2D, 2E and 2F. In certain embodiments, (1) the MMP comprises 1I; and (2) the 6-ACAP comprises 2A, 2B, 2C, 2D, 2E and 2F. In certain embodiments, (1) the MMP comprises 1A, 1B, 1C, 1D, 1E and 1I; and (2) the 6-ACAP comprises 2A, 2B, 2C, 2D, 2E and 2F. In some embodiments, (1) the MMP comprises 1A, 1B, 1C, 1D, 1F and 1I; and (2) the 6-ACAP comprises 2A, 2B, 2C, 2D, 2E and 2F. In some embodiments, (1) the MMP comprises 1J, 1C, 1D, 1E and 1I; and (2) the 6-ACAP comprises 2A, 2B, 2C, 2D, 2E and 2F. In one embodiment, (1) the MMP comprises 1J, 1C, 1D, 1F and 1I; and (2) the 6-ACAP comprises 2A, 2B, 2C, 2D, 2E and 2F. In another embodiment, (1) the MMP comprises 1J, 1L and 1I; and (2) the 6-ACAP comprises 2A, 2B, 2C, 2D, 2E and 2F. In yet another embodiment, (1) the MMP comprises 1J, 1M, 1N, 1O and 1I; and (2) the 6-ACAP comprises 2A, 2B, 2C, 2D, 2E and 2F. In certain embodiments, (1) the MMP comprises 1J, 1N, 1O and 1I; and (2) the 6-ACAP comprises 2A, 2B, 2C, 2D, 2E and 2F. In some embodiments, (1) the MMP comprises 1J, 1K, 1C, 1D, 1E and 1I; and (2) the 6-ACAP comprises 2A, 2B, 2C, 2D, 2E and 2F. In one embodiment, (1) the MMP comprises 1J, 1K, 1C, 1D, 1F and 1I; and (2) the 6-ACAP comprises 2A, 2B, 2C, 2D, 2E and 2F. In certain embodiments, (1) the MMP comprises 1G; and (2) the 6-ACAP comprises 2A, 2B, 2C, 2D, 2E and 2F. In certain embodiments, (1) the MMP comprises 1A, 1B, 1C, 1D, 1E and 1G; and (2) the 6-ACAP comprises 2A, 2B, 2C, 2D, 2E and 2F. In some embodiments, (1) the MMP comprises 1A, 1B, 1C, 1D, 1F and 1G; and (2) the 6-ACAP comprises 2A, 2B, 2C, 2D, 2E and 2F. In some embodiments, (1) the MMP comprises 1J, 1C, 1D, 1E and 1G; and (2) the 6-ACAP comprises 2A, 2B, 2C, 2D, 2E and 2F. In one embodiment, (1) the MMP comprises 1J, 1C, 1D, 1F and 1G; and (2) the 6-ACAP comprises 2A, 2B, 2C, 2D, 2E and 2F. In another embodiment, (1) the MMP comprises 1J, 1L and 1G; and (2) the 6-ACAP comprises 2A, 2B, 2C, 2D, 2E and 2F. In yet another embodiment, (1) the MMP comprises 1J, 1M, 1N, 1O and 1G; and (2) the 6-ACAP comprises 2A, 2B, 2C, 2D, 2E and 2F. In certain embodiments, (1) the MMP comprises 1J, 1N, 1O and 1G; and (2) the 6-ACAP comprises 2A, 2B, 2C, 2D, 2E and 2F. In some embodiments, (1) the MMP comprises 1J, 1K, 1C, 1D, 1E and 1G; and (2) the 6-ACAP comprises 2A, 2B, 2C, 2D, 2E and 2F. In one embodiment, (1) the MMP comprises 1J, 1K, 1C, 1D, 1F and 1G; and (2) the 6-ACAP comprises 2A, 2B, 2C, 2D, 2E and 2F. In certain embodiments, (1) the MMP comprises 1G and 1H; and (2) the 6-ACAP comprises 2A, 2B, 2C, 2D, 2E and 2F. In certain embodiments, (1) the MMP comprises 1A, 1B, 1C, 1D, 1E, 1G and 1H; and (2) the 6-ACAP comprises 2A, 2B, 2C, 2D, 2E and 2F. In some embodiments, (1) the MMP comprises 1A, 1B, 1C, 1D, 1F, 1G and 1H; and (2) the 6-ACAP comprises 2A, 2B, 2C, 2D, 2E and 2F. In some embodiments, (1) the MMP comprises 1J, 1C, 1D, 1E, 1G and 1H; and (2) the 6-ACAP comprises 2A, 2B, 2C, 2D, 2E and 2F. In one embodiment, (1) the MMP comprises 1J, 1C, 1D, 1F and 1H; and (2) the 6-ACAP comprises 2A, 2B, 2C, 2D, 2E and 2F. In another embodiment, (1) the MMP comprises 1J, 1L, 1G and 1H; and (2) the 6-ACAP comprises 2A, 2B, 2C, 2D, 2E and 2F. In yet another embodiment, (1) the MMP comprises 1J, 1M, 1N, 1O, 1G and 1H; and (2) the 6-ACAP comprises 2A, 2B, 2C, 2D, 2E and 2F. In certain embodiments, (1) the MMP comprises 1J, 1N, 1O, 1G and 1H; and (2) the 6-ACAP comprises 2A, 2B, 2C, 2D, 2E and 2F. In some embodiments, (1) the MMP comprises 1J, 1K, 1C, 1D, 1E, 1G and 1H; and (2) the 6-ACAP comprises 2A, 2B, 2C, 2D, 2E and 2F. In one embodiment, (1) the MMP comprises 1J, 1K, 1C, 1D, 1F, 1G and 1H; and (2) the 6-ACAP comprises 2A, 2B, 2C, 2D, 2E and 2F. In some embodiments, 1K is spontaneous. In other embodiments, 1K is an EM10. In some embodiments, 1M is spontaneous. In other embodiments, 1M is an EM12. In some embodiments, 2F is an EA6A. In other embodiments, 2F is an EA6B.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a 6-ACAP. In some embodiments, 1K is spontaneous. In other embodiments, 1K is an EM10. In some embodiments, 1M is spontaneous. In other embodiments, 1M is an EM12.

Any MMP provided herein can be combined with any 6-ACAP provided herein.

In certain embodiments, the 6-ACAP further comprises enzymes depicted in FIG. 5. In one embodiment, the 6-ACAP further comprises 5T, 5U, 5V, 5W, and/or 5X, wherein 5T is a PEP carboxylase (EFR16A) or PEP carboxykinase (EFR16B); 5U is a pyruvate carboxylase (EFR17); 5V is a malate dehydrogenase (EFR18); 5W is a malic enzyme (EFR19); and 5X is a fumarase (EFR20A), fumarate reductase (EFR20B), succinyl-CoA synthetase (EFR20C), succinyl-CoA ligase (EFR20D), or succinyl-CoA transferase (EFR20E). In one embodiment, the 6-ACAP comprises 5T. In another embodiment, the 6-ACAP comprises 5U. In another embodiment, the 6-ACAP comprises 5V. In other embodiment, the 6-ACAP comprises 5W. In another embodiment, the 6-ACAP comprises 5X. In another embodiment, the 6-ACAP comprises 5Y. In some embodiments, the 6-ACAP comprises 5T, 5V and 5X. In another embodiment, the 6-ACAP comprises 5U, 5V and 5X. In another embodiment, the 6-ACAP comprises 5W and 5X. In one embodiment, 5T is EFR16A. In other embodiments, 5T is EFR16B. In some embodiments, 5X is EFR20A. In other embodiments, 5X is EFR20B. In other embodiments, 5X is EFR20C. In one embodiment, 5X is EFR20D. In another embodiment, 5X is EFR20E.

Exemplary enzymes for the conversion succinyl-CoA or acetyl CoA to HMDA include EA1 (FIG. 2, step A), EA2 (FIG. 2, step B), EA3 (FIG. 2, step C), EA4 (FIG. 2, step D), EA5 (FIG. 2, step E), and EA6A or EA6B (FIG. 2, step F), EA7A or EA7B (FIG. 2, step G), EA9 (FIG. 2, step J), and EA10A or EA10B (FIG. 2, step K).

In another aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) an HMDAP, wherein said organism comprises at least one exogenous nucleic acid encoding an HMDAPE expressed in a sufficient amount to produce HMDA. In one embodiment, the at least one exogenous nucleic acid encoding the MMPE enhances the availability of reducing equivalents in the presence of methanol in a sufficient amount to increase the amount of HMDA produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the HMDAP comprises 2A, 2B, 2C, 2D, 2E, 2F, 2G, 2J or 2K, or any combination thereof, wherein 2A is an EA1; 2B is an EA2; 2C is an EA3; 2D is an EA4; 2E is an EA5, and 2F is an EA6A or EA6B; 2G is an EA7A or an EA7B; 2J is an EA9; 2K is an EA10A or an EA10B. In some embodiments, 1K is spontaneous. In other embodiments, 1K is an EM10. In some embodiments, 1M is spontaneous. In other embodiments, 1M is an EM12. In some embodiments, 2F is an EA6A. In other embodiments, 2F is an EA6B. In some embodiments, 2G is an EA7A. In other embodiments, 2G is an EA7B. In some embodiments, 2K is an EA10A. In other embodiments, 2K is an EA10B.

In one embodiment, the HMDAP comprises 2A. In another embodiment, the HMDAP comprises 2B. In an embodiment, the HMDAP comprises 2C. In another embodiment, the HMDAP comprises 2D. In one embodiment, the HMDAP comprises 2E. In yet another embodiment, the HMDAP comprises 2F. In another embodiment, the HMDAP comprises 2G. In one embodiment, the HMDAP comprises 2J. In yet another embodiment, the HMDAP comprises 2K. Any combination of two, three, four, five, six, seven, eight or nine HMDAPEs 2A, 2B, 2C, 2D, 2E, 2F, 2G, 2J and 2K is also contemplated.

In some embodiments, the MMP is a MMP depicted in FIG. 1, and the HMDAP is an HMDAP depicted in FIG. 2.

An exemplary set of HMDAPEs to convert succinyl-CoA or acetyl-CoA to HMDA, according to FIG. 2, includes 2A, 2B, 2C, 2D, 2E, 2F, 2G, 2J and 2K.

In one embodiment, (1) the MMP comprises 1A and 1B; and (2) the HMDAP comprises 2A, 2B, 2C, 2D, 2E, 2F, 2G, 2J and 2K. In another embodiment, (1) the MMP comprises 1J; and (2) the HMDAP comprises 2A, 2B, 2C, 2D, 2E, 2F, 2G, 2J and 2K. In one embodiment, (1) the MMP comprises 1J and 1K; and (2) the HMDAP comprises 2A, 2B, 2C, 2D, 2E, 2F, 2G, 2J and 2K. In certain embodiments, (1) the MMP comprises 1A, 1B, 1C, 1D, and 1E; and (2) the HMDAP comprises 2A, 2B, 2C, 2D, 2E, 2F, 2G, 2J and 2K. In some embodiments, (1) the MMP comprises 1A, 1B, 1C, 1D and 1F; and (2) the HMDAP comprises 2A, 2B, 2C, 2D, 2E, 2F, 2G, 2J and 2K. In some embodiments, (1) the MMP comprises 1J, 1C, 1D and 1E; and (2) the HMDAP comprises 2A, 2B, 2C, 2D, 2E, 2F, 2G, 2J and 2K. In one embodiment, (1) the MMP comprises 1J, 1C, 1D and 1F; and (2) the HMDAP comprises 2A, 2B, 2C, 2D, 2E, 2F, 2G, 2J and 2K. In another embodiment, (1) the MMP comprises 1J and 1L; and (2) the HMDAP comprises 2A, 2B, 2C, 2D, 2E, 2F, 2G, 2J and 2K. In yet another embodiment, (1) the MMP comprises 1J, 1M, 1N and 1O; and (2) the HMDAP comprises 2A, 2B, 2C, 2D, 2E, 2F, 2G, 2J and 2K. In certain embodiments, (1) the MMP comprises 1J, 1N and 1O; and (2) the HMDAP comprises 2A, 2B, 2C, 2D, 2E, 2F, 2G, 2J and 2K. In some embodiments, (1) the MMP comprises 1J, 1K, 1C, 1D and 1E; and (2) the HMDAP comprises 2A, 2B, 2C, 2D, 2E, 2F, 2G, 2J and 2K. In one embodiment, (1) the MMP comprises 1J, 1K, 1C, 1D and 1F; and (2) the HMDAP comprises 2A, 2B, 2C, 2D, 2E, 2F, 2G, 2J and 2K. In certain embodiments, (1) the MMP comprises 1I; and (2) the HMDAP comprises 2A, 2B, 2C, 2D, 2E, 2F, 2G, 2J and 2K. In certain embodiments, (1) the MMP comprises 1A, 1B, 1C, 1D, 1E and 1I; and (2) the HMDAP comprises 2A, 2B, 2C, 2D, 2E, 2F, 2G, 2J and 2K. In some embodiments, (1) the MMP comprises 1A, 1B, 1C, 1D, 1F and 1I; and (2) the HMDAP comprises 2A, 2B, 2C, 2D, 2E, 2F, 2G, 2J and 2K. In some embodiments, (1) the MMP comprises 1J, 1C, 1D, 1E and 1I; and (2) the HMDAP comprises 2A, 2B, 2C, 2D, 2E, 2F, 2G, 2J and 2K. In one embodiment, (1) the MMP comprises 1J, 1C, 1D, 1F and 1I; and (2) the HMDAP comprises 2A, 2B, 2C, 2D, 2E, 2F, 2G, 2J and 2K. In another embodiment, (1) the MMP comprises 1J, 1L and 1I; and (2) the HMDAP comprises 2A, 2B, 2C, 2D, 2E, 2F, 2G, 2J and 2K. In yet another embodiment, (1) the MMP comprises 1J, 1M, 1N, 1O and 1I; and (2) the HMDAP comprises 2A, 2B, 2C, 2D, 2E, 2F, 2G, 2J and 2K. In certain embodiments, (1) the MMP comprises 1J, 1N, 1O and 1I; and (2) the HMDAP comprises 2A, 2B, 2C, 2D, 2E, 2F, 2G, 2J and 2K. In some embodiments, (1) the MMP comprises 1J, 1K, 1C, 1D, 1E and 1I; and (2) the HMDAP comprises 2A, 2B, 2C, 2D, 2E, 2F, 2G, 2J and 2K. In one embodiment, (1) the MMP comprises 1J, 1K, 1C, 1D, 1F and 1I; and (2) the HMDAP comprises 2A, 2B, 2C, 2D, 2E, 2F, 2G, 2J and 2K. In certain embodiments, (1) the MMP comprises 1G; and (2) the HMDAP comprises 2A, 2B, 2C, 2D, 2E, 2F, 2G, 2J and 2K. In certain embodiments, (1) the MMP comprises 1A, 1B, 1C, 1D, 1E and 1G; and (2) the HMDAP comprises 2A, 2B, 2C, 2D, 2E, 2F, 2G, 2J and 2K. In some embodiments, (1) the MMP comprises 1A, 1B, 1C, 1D, 1F and 1G; and (2) the HMDAP comprises 2A, 2B, 2C, 2D, 2E, 2F, 2G, 2J and 2K. In some embodiments, (1) the MMP comprises 1J, 1C, 1D, 1E and 1G; and (2) the HMDAP comprises 2A, 2B, 2C, 2D, 2E, 2F, 2G, 2J and 2K. In one embodiment, (1) the MMP comprises 1J, 1C, 1D, 1F and 1G; and (2) the HMDAP comprises 2A, 2B, 2C, 2D, 2E, 2F, 2G, 2J and 2K. In another embodiment, (1) the MMP comprises 1J, 1L and 1G; and (2) the HMDAP comprises 2A, 2B, 2C, 2D, 2E, 2F, 2G, 2J and 2K. In yet another embodiment, (1) the MMP comprises 1J, 1M, 1N, 1O and 1G; and (2) the HMDAP comprises 2A, 2B, 2C, 2D, 2E, 2F, 2G, 2J and 2K. In certain embodiments, (1) the MMP comprises 1J, 1N, 1O and 1G; and (2) the HMDAP comprises 2A, 2B, 2C, 2D, 2E, 2F, 2G, 2J and 2K. In some embodiments, (1) the MMP comprises 1J, 1K, 1C, 1D, 1E and 1G; and (2) the HMDAP comprises 2A, 2B, 2C, 2D, 2E, 2F, 2G, 2J and 2K. In one embodiment, (1) the MMP comprises 1J, 1K, 1C, 1D, 1F and 1G; and (2) the HMDAP comprises 2A, 2B, 2C, 2D, 2E, 2F, 2G, 2J and 2K. In certain embodiments, (1) the MMP comprises 1G and 1H; and (2) the HMDAP comprises 2A, 2B, 2C, 2D, 2E, 2F, 2G, 2J and 2K. In certain embodiments, (1) the MMP comprises 1A, 1B, 1C, 1D, 1E, 1G and 1H; and (2) the HMDAP comprises 2A, 2B, 2C, 2D, 2E, 2F, 2G, 2J and 2K. In some embodiments, (1) the MMP comprises 1A, 1B, 1C, 1D, 1F, 1G and 1H; and (2) the HMDAP comprises 2A, 2B, 2C, 2D, 2E, 2F, 2G, 2J and 2K. In some embodiments, (1) the MMP comprises 1J, 1C, 1D, 1E, 1G and 1H; and (2) the HMDAP comprises 2A, 2B, 2C, 2D, 2E, 2F, 2G, 2J and 2K. In one embodiment, (1) the MMP comprises 1J, 1C, 1D, 1F, 1G and 1H; and (2) the HMDAP comprises 2A, 2B, 2C, 2D, 2E, 2F, 2G, 2J and 2K. In another embodiment, (1) the MMP comprises 1J, 1L, 1G and 1H; and (2) the HMDAP comprises 2A, 2B, 2C, 2D, 2E, 2F, 2G, 2J and 2K. In yet another embodiment, (1) the MMP comprises 1J, 1M, 1N, 1O, 1G and 1H; and (2) the HMDAP comprises 2A, 2B, 2C, 2D, 2E, 2F, 2G, 2J and 2K. In certain embodiments, (1) the MMP comprises 1J, 1N, 1O, 1G and 1H; and (2) the HMDAP comprises 2A, 2B, 2C, 2D, 2E, 2F, 2G, 2J and 2K. In some embodiments, (1) the MMP comprises 1J, 1K, 1C, 1D, 1E, 1G and 1H; and (2) the HMDAP comprises 2A, 2B, 2C, 2D, 2E, 2F, 2G, 2J and 2K. In one embodiment, (1) the MMP comprises 1J, 1K, 1C, 1D, 1F, 1G and 1H; and (2) the HMDAP comprises 2A, 2B, 2C, 2D, 2E, 2F, 2G, 2J and 2K. In some embodiments, 1K is spontaneous. In other embodiments, 1K is an EM10. In some embodiments, 1M is spontaneous. In other embodiments, 1M is an EM12. In some embodiments, 2F is an EA6A. In other embodiments, 2F is an EA6B. In some embodiments, 2G is an EA7A. In other embodiments, 2G is an EA7B. In some embodiments, 2K is an EA10A. In other embodiments, 2K is an EA10B.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a HMDAP. In some embodiments, 1K is spontaneous. In other embodiments, 1K is an EM10. In some embodiments, 1M is spontaneous. In other embodiments, 1M is an EM12.

Any MMP provided herein can be combined with any HMDAP provided herein.

In certain embodiments, the HMDAP further comprises enzymes depicted in FIG. 5. In one embodiment, the HMDAP further comprises 5T, 5U, 5V, 5W, and/or 5X, wherein 5T is a PEP carboxylase (EFR16A) or PEP carboxykinase (EFR16B); 5U is a pyruvate carboxylase (EFR17); 5V is a malate dehydrogenase (EFR18); 5W is a malic enzyme (EFR19); and 5X is a fumarase (EFR20A), fumarate reductase (EFR20B), succinyl-CoA synthetase (EFR20C), succinyl-CoA ligase (EFR20D), or succinyl-CoA transferase (EFR20E). In one embodiment, the HMDAP comprises 5T. In another embodiment, the HMDAP comprises 5U. In another embodiment, the HMDAP comprises 5V. In other embodiment, the HMDAP comprises 5W. In another embodiment, the HMDAP comprises 5X. In another embodiment, the HMDAP comprises 5Y. In some embodiments, the HMDAP comprises 5T, 5V and 5X. In another embodiment, the HMDAP comprises 5U, 5V and 5X. In another embodiment, the HMDAP comprises 5W and 5X. In one embodiment, 5T is EFR16A. In other embodiments, 5T is EFR16B. In some embodiments, 5X is EFR20A. In other embodiments, 5X is EFR20B. In other embodiments, 5X is EFR20C. In one embodiment, 5X is EFR20D. In another embodiment, 5X is EFR20E.

Exemplary enzymes for the conversion succinyl-CoA or acetyl CoA to caprolactam include EA1 (FIG. 2, step A), EA2 (FIG. 2, step B), EA3 (FIG. 2, step C), EA4 (FIG. 2, step D), EA5 (FIG. 2, step E), and EA6A or EA6B (FIG. 2, step F), EA7A or EA7B (FIG. 2, step G), and the pathway can optionally include spontaneous cyclization (FIG. 2, step I). Other exemplary enzymes for the conversion succinyl-CoA or acetyl CoA to caprolactam include EA1 (FIG. 2, step A), EA2 (FIG. 2, step B), EA3 (FIG. 2, step C), EA4 (FIG. 2, step D), EA5 (FIG. 2, step E), and EA6A or EA6B (FIG. 2, step F), EA7A or EA7B (FIG. 2, step G). EA8 (FIG. 2, step H).

In another aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) an CapP, wherein said organism comprises at least one exogenous nucleic acid encoding an CapPE expressed in a sufficient amount to produce caprolactam. In one embodiment, the at least one exogenous nucleic acid encoding the MMPE enhances the availability of reducing equivalents in the presence of methanol in a sufficient amount to increase the amount of caprolactam produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the CapP comprises 2A, 2B, 2C, 2D, 2E, 2F, 2G or 2H, or any combination thereof, wherein 2A is an EA1; 2B is an EA2; 2C is an EA3; 2D is an EA4; 2E is an EA5, and 2F is a 6-aminocaproate transaminase or a 6-aminocaproate dehydrogenase; 2G is an EA7A or an EA7B; and 2H is an EA8. In some embodiments, 1K is spontaneous. In other embodiments, 1K is an EM10. In some embodiments, 1M is spontaneous. In other embodiments, 1M is an EM12. In some embodiments, 2F is a 6-aminocaproate transaminase. In other embodiments, 2F is a 6-aminocaproate dehydrogenase. In some embodiments, 2G is an EA7A. In one embodiment, 2G is an EA7A. In another embodiment, 2G is an EA7B.

In one embodiment, the CapP comprises 2A. In another embodiment, the CapP comprises 2B. In an embodiment, the CapP comprises 2C. In another embodiment, the CapP comprises 2D. In one embodiment, the CapP comprises 2E. In another embodiment, the CapP comprises 2F. In another embodiment, the CapP comprises 2G. In one embodiment, the CapP comprises 2H. In one embodiment, the CapP comprises 2H. Any combination of two, three, four, five, six, seven or eight CapPEs 2A, 2B, 2C, 2D, 2E, 2F, 2G and 2H is also contemplated.

In some embodiments, the MMP is a MMP depicted in FIG. 1, and the CapP is an CapP depicted in FIG. 2.

Exemplary sets of CapPEs to convert succinyl-CoA or acetyl-CoA to caprolactam, according to FIG. 2, include (i) 2A, 2B, 2C, 2D, 2E, 2F and 2G; and (ii) 2A, 2B, 2C, 2D, 2E, 2F and 2H.

In one embodiment, (1) the MMP comprises 1A and 1B; and (2) the CapP comprises 2A, 2B, 2C, 2D, 2E, 2F and 2G. In another embodiment, (1) the MMP comprises 1J; and (2) the CapP comprises 2A, 2B, 2C, 2D, 2E, 2F and 2G. In one embodiment, (1) the MMP comprises 1J and 1K; and (2) the CapP comprises 2A, 2B, 2C, 2D, 2E, 2F and 2G. In certain embodiments, (1) the MMP comprises 1A, 1B, 1C, 1D, and 1E; and (2) the CapP comprises 2A, 2B, 2C, 2D, 2E, 2F and 2G. In some embodiments, (1) the MMP comprises 1A, 1B, 1C, 1D and 1F; and (2) the CapP comprises 2A, 2B, 2C, 2D, 2E, 2F and 2G. In some embodiments, (1) the MMP comprises 1J, 1C, 1D and 1E; and (2) the CapP comprises 2A, 2B, 2C, 2D, 2E, 2F and 2G. In one embodiment, (1) the MMP comprises 1J, 1C, 1D and 1F; and (2) the CapP comprises 2A, 2B, 2C, 2D, 2E, 2F and 2G. In another embodiment, (1) the MMP comprises 1J and 1L; and (2) the CapP comprises 2A, 2B, 2C, 2D, 2E, 2F and 2G. In yet another embodiment, (1) the MMP comprises 1J, 1M, 1N and 1O; and (2) the CapP comprises 2A, 2B, 2C, 2D, 2E, 2F and 2G. In certain embodiments, (1) the MMP comprises 1J, 1N and 1O; and (2) the CapP comprises 2A, 2B, 2C, 2D, 2E, 2F and 2G. In some embodiments, (1) the MMP comprises 1J, 1K, 1C, 1D and 1E; and (2) the CapP comprises 2A, 2B, 2C, 2D, 2E, 2F and 2G. In one embodiment, (1) the MMP comprises 1J, 1K, 1C, 1D and 1F; and (2) the CapP comprises 2A, 2B, 2C, 2D, 2E, 2F and 2G. In certain embodiments, (1) the MMP comprises 1I; and (2) the CapP comprises 2A, 2B, 2C, 2D, 2E, 2F and 2G. In certain embodiments, (1) the MMP comprises 1A, 1B, 1C, 1D, 1E and 1I; and (2) the CapP comprises 2A, 2B, 2C, 2D, 2E, 2F and 2G. In some embodiments, (1) the MMP comprises 1A, 1B, 1C, 1D, 1F and 1I; and (2) the CapP comprises 2A, 2B, 2C, 2D, 2E, 2F and 2G. In some embodiments, (1) the MMP comprises 1J, 1C, 1D, 1E and 1I; and (2) the CapP comprises 2A, 2B, 2C, 2D, 2E, 2F and 2G. In one embodiment, (1) the MMP comprises 1J, 1C, 1D, 1F and 1I; and (2) the CapP comprises 2A, 2B, 2C, 2D, 2E, 2F and 2G. In another embodiment, (1) the MMP comprises 1J, 1L and 1I; and (2) the CapP comprises 2A, 2B, 2C, 2D, 2E, 2F and 2G. In yet another embodiment, (1) the MMP comprises 1J, 1M, 1N, 1O and 1I; and (2) the CapP comprises 2A, 2B, 2C, 2D, 2E, 2F and 2G. In certain embodiments, (1) the MMP comprises 1J, 1N, 1O and 1I; and (2) the CapP comprises 2A, 2B, 2C, 2D, 2E, 2F and 2G. In some embodiments, (1) the MMP comprises 1J, 1K, 1C, 1D, 1E and 1I; and (2) the CapP comprises 2A, 2B, 2C, 2D, 2E, 2F and 2G. In one embodiment, (1) the MMP comprises 1J, 1K, 1C, 1D, 1F and 1I; and (2) the CapP comprises 2A, 2B, 2C, 2D, 2E, 2F and 2G. In certain embodiments, (1) the MMP comprises 1G; and (2) the CapP comprises 2A, 2B, 2C, 2D, 2E, 2F and 2G. In certain embodiments, (1) the MMP comprises 1A, 1B, 1C, 1D, 1E and 1G; and (2) the CapP comprises 2A, 2B, 2C, 2D, 2E, 2F and 2G. In some embodiments, (1) the MMP comprises 1A, 1B, 1C, 1D, 1F and 1G; and (2) the CapP comprises 2A, 2B, 2C, 2D, 2E, 2F and 2G. In some embodiments, (1) the MMP comprises 1J, 1C, 1D, 1E and 1G; and (2) the CapP comprises 2A, 2B, 2C, 2D, 2E, 2F and 2G. In one embodiment, (1) the MMP comprises 1J, 1C, 1D, 1F and 1G; and (2) the CapP comprises 2A, 2B, 2C, 2D, 2E, 2F and 2G. In another embodiment, (1) the MMP comprises 1J, 1L and 1G; and (2) the CapP comprises 2A, 2B, 2C, 2D, 2E, 2F and 2G. In yet another embodiment, (1) the MMP comprises 1J, 1M, 1N, 1O and 1G; and (2) the CapP comprises 2A, 2B, 2C, 2D, 2E, 2F and 2G. In certain embodiments, (1) the MMP comprises 1J, 1N, 1O and 1G; and (2) the CapP comprises 2A, 2B, 2C, 2D, 2E, 2F and 2G. In some embodiments, (1) the MMP comprises 1J, 1K, 1C, 1D, 1E and 1G; and (2) the CapP comprises 2A, 2B, 2C, 2D, 2E, 2F and 2G. In one embodiment, (1) the MMP comprises 1J, 1K, 1C, 1D, 1F and 1G; and (2) the CapP comprises 2A, 2B, 2C, 2D, 2E, 2F and 2G. In certain embodiments, (1) the MMP comprises 1G and 1H; and (2) the CapP comprises 2A, 2B, 2C, 2D, 2E, 2F and 2G. In certain embodiments, (1) the MMP comprises 1A, 1B, 1C, 1D, 1E, 1G and 1H; and (2) the CapP comprises 2A, 2B, 2C, 2D, 2E, 2F and 2G. In some embodiments, (1) the MMP comprises 1A, 1B, 1C, 1D, 1F, 1G and 1H; and (2) the CapP comprises 2A, 2B, 2C, 2D, 2E, 2F and 2G. In some embodiments, (1) the MMP comprises 1J, 1C, 1D, 1E, 1G and 1H; and (2) the CapP comprises 2A, 2B, 2C, 2D, 2E, 2F and 2G. In one embodiment, (1) the MMP comprises 1J, 1C, 1D, 1F, 1G and 1H; and (2) the CapP comprises 2A, 2B, 2C, 2D, 2E, 2F and 2G. In another embodiment, (1) the MMP comprises 1J, 1L, 1G and 1H; and (2) the CapP comprises 2A, 2B, 2C, 2D, 2E, 2F and 2G. In yet another embodiment, (1) the MMP comprises 1J, 1M, 1N, 1O, 1G and 1H; and (2) the CapP comprises 2A, 2B, 2C, 2D, 2E, 2F and 2G. In certain embodiments, (1) the MMP comprises 1J, 1N, 1O, 1G and 1H; and (2) the CapP comprises 2A, 2B, 2C, 2D, 2E, 2F and 2G. In some embodiments, (1) the MMP comprises 1J, 1K, 1C, 1D, 1E, 1G and 1H; and (2) the CapP comprises 2A, 2B, 2C, 2D, 2E, 2F and 2G. In one embodiment, (1) the MMP comprises 1J, 1K, 1C, 1D, 1F, 1G and 1H; and (2) the CapP comprises 2A, 2B, 2C, 2D, 2E, 2F and 2G. In some embodiments, 1K is spontaneous. In other embodiments, 1K is an EM10. In some embodiments, 1M is spontaneous. In other embodiments, 1M is an EM12. In some embodiments, 2F is a 6-aminocaproate transaminase. In other embodiments, 2F is a 6-aminocaproate dehydrogenase. In some embodiments, 2G is an EA7A. In one embodiment, 2G is an EA7A. In another embodiment, 2G is an EA7B. In some embodiments, the pathway includes spontaneous cyclization to convert 6-aminocaproyl-CoA to caprolactam (FIG. 2, step I).

In one embodiment, (1) the MMP comprises 1A and 1B; and (2) the CapP comprises 2A, 2B, 2C, 2D, 2E, 2F and 2H. In another embodiment, (1) the MMP comprises 1J; and (2) the CapP comprises 2A, 2B, 2C, 2D, 2E, 2F and 2H. In one embodiment, (1) the MMP comprises 1J and 1K; and (2) the CapP comprises 2A, 2B, 2C, 2D, 2E, 2F and 2H. In certain embodiments, (1) the MMP comprises 1A, 1B, 1C, 1D, and 1E; and (2) the CapP comprises 2A, 2B, 2C, 2D, 2E, 2F and 2H. In some embodiments, (1) the MMP comprises 1A, 1B, 1C, 1D and 1F; and (2) the CapP comprises 2A, 2B, 2C, 2D, 2E, 2F and 2H. In some embodiments, (1) the MMP comprises 1J, 1C, 1D and 1E; and (2) the CapP comprises 2A, 2B, 2C, 2D, 2E, 2F and 2H. In one embodiment, (1) the MMP comprises 1J, 1C, 1D and 1F; and (2) the CapP comprises 2A, 2B, 2C, 2D, 2E, 2F and 2H. In another embodiment, (1) the MMP comprises 1J and 1L; and (2) the CapP comprises 2A, 2B, 2C, 2D, 2E, 2F and 2H. In yet another embodiment, (1) the MMP comprises 1J, 1M, 1N and 1O; and (2) the CapP comprises 2A, 2B, 2C, 2D, 2E, 2F and 2H. In certain embodiments, (1) the MMP comprises 1J, 1N and 1O; and (2) the CapP comprises 2A, 2B, 2C, 2D, 2E, 2F and 2H. In some embodiments, (1) the MMP comprises 1J, 1K, 1C, 1D and 1E; and (2) the CapP comprises 2A, 2B, 2C, 2D, 2E, 2F and 2H. In one embodiment, (1) the MMP comprises 1J, 1K, 1C, 1D and 1F; and (2) the CapP comprises 2A, 2B, 2C, 2D, 2E, 2F and 2H. In certain embodiments, (1) the MMP comprises 1I; and (2) the CapP comprises 2A, 2B, 2C, 2D, 2E, 2F and 2H. In certain embodiments, (1) the MMP comprises 1A, 1B, 1C, 1D, 1E and 1I; and (2) the CapP comprises 2A, 2B, 2C, 2D, 2E, 2F and 2H. In some embodiments, (1) the MMP comprises 1A, 1B, 1C, 1D, 1F and 1I; and (2) the CapP comprises 2A, 2B, 2C, 2D, 2E, 2F and 2H. In some embodiments, (1) the MMP comprises 1J, 1C, 1D, 1E and 1I; and (2) the CapP comprises 2A, 2B, 2C, 2D, 2E, 2F and 2H. In one embodiment, (1) the MMP comprises 1J, 1C, 1D, 1F and 1I; and (2) the CapP comprises 2A, 2B, 2C, 2D, 2E, 2F and 2H. In another embodiment, (1) the MMP comprises 1J, 1L and 1I; and (2) the CapP comprises 2A, 2B, 2C, 2D, 2E, 2F and 2H. In yet another embodiment, (1) the MMP comprises 1J, 1M, 1N, 1O and 1I; and (2) the CapP comprises 2A, 2B, 2C, 2D, 2E, 2F and 2H. In certain embodiments, (1) the MMP comprises 1J, 1N, 1O and 1I; and (2) the CapP comprises 2A, 2B, 2C, 2D, 2E, 2F and 2H. In some embodiments, (1) the MMP comprises 1J, 1K, 1C, 1D, 1E and 1I; and (2) the CapP comprises 2A, 2B, 2C, 2D, 2E, 2F and 2H. In one embodiment, (1) the MMP comprises 1J, 1K, 1C, 1D, 1F and 1I; and (2) the CapP comprises 2A, 2B, 2C, 2D, 2E, 2F and 2H. In certain embodiments, (1) the MMP comprises 1G; and (2) the CapP comprises 2A, 2B, 2C, 2D, 2E, 2F and 2H. In certain embodiments, (1) the MMP comprises 1A, 1B, 1C, 1D, 1E and 1G; and (2) the CapP comprises 2A, 2B, 2C, 2D, 2E, 2F and 2H. In some embodiments, (1) the MMP comprises 1A, 1B, 1C, 1D, 1F and 1G; and (2) the CapP comprises 2A, 2B, 2C, 2D, 2E, 2F and 2H. In some embodiments, (1) the MMP comprises 1J, 1C, 1D, 1E and 1G; and (2) the CapP comprises 2A, 2B, 2C, 2D, 2E, 2F and 2H. In one embodiment, (1) the MMP comprises 1J, 1C, 1D, 1F and 1G; and (2) the CapP comprises 2A, 2B, 2C, 2D, 2E, 2F and 2H. In another embodiment, (1) the MMP comprises 1J, 1L and 1G; and (2) the CapP comprises 2A, 2B, 2C, 2D, 2E, 2F and 2H. In yet another embodiment, (1) the MMP comprises 1J, 1M, 1N, 1O and 1G; and (2) the CapP comprises 2A, 2B, 2C, 2D, 2E, 2F and 2H. In certain embodiments, (1) the MMP comprises 1J, 1N, 1O and 1G; and (2) the CapP comprises 2A, 2B, 2C, 2D, 2E, 2F and 2H. In some embodiments, (1) the MMP comprises 1J, 1K, 1C, 1D, 1E and 1G; and (2) the CapP comprises 2A, 2B, 2C, 2D, 2E, 2F and 2H. In one embodiment, (1) the MMP comprises 1J, 1K, 1C, 1D, 1F and 1G; and (2) the CapP comprises 2A, 2B, 2C, 2D, 2E, 2F and 2H. In certain embodiments, (1) the MMP comprises 1G and 1H; and (2) the CapP comprises 2A, 2B, 2C, 2D, 2E, 2F and 2H. In certain embodiments, (1) the MMP comprises 1A, 1B, 1C, 1D, 1E, 1G and 1H; and (2) the CapP comprises 2A, 2B, 2C, 2D, 2E, 2F and 2H. In some embodiments, (1) the MMP comprises 1A, 1B, 1C, 1D, 1F, 1G and 1H; and (2) the CapP comprises 2A, 2B, 2C, 2D, 2E, 2F and 2H. In some embodiments, (1) the MMP comprises 1J, 1C, 1D, 1E, 1G and 1H; and (2) the CapP comprises 2A, 2B, 2C, 2D, 2E, 2F and 2H. In one embodiment, (1) the MMP comprises 1J, 1C, 1D, 1F, 1G and 1H; and (2) the CapP comprises 2A, 2B, 2C, 2D, 2E, 2F and 2H. In another embodiment, (1) the MMP comprises 1J, 1L, 1G and 1H; and (2) the CapP comprises 2A, 2B, 2C, 2D, 2E, 2F and 2H. In yet another embodiment, (1) the MMP comprises 1J, 1M, 1N, 1O, 1G and 1H; and (2) the CapP comprises 2A, 2B, 2C, 2D, 2E, 2F and 2H. In certain embodiments, (1) the MMP comprises 1J, 1N, 1O, 1G and 1H; and (2) the CapP comprises 2A, 2B, 2C, 2D, 2E, 2F and 2H. In some embodiments, (1) the MMP comprises 1J, 1K, 1C, 1D, 1E, 1G and 1H; and (2) the CapP comprises 2A, 2B, 2C, 2D, 2E, 2F and 2H. In one embodiment, (1) the MMP comprises 1J, 1K, 1C, 1D, 1F, 1G and 1H; and (2) the CapP comprises 2A, 2B, 2C, 2D, 2E, 2F and 2H. In some embodiments, 1K is spontaneous. In other embodiments, 1K is an EM10. In some embodiments, 1M is spontaneous. In other embodiments, 1M is an EM12. In some embodiments, 2F is a 6-aminocaproate transaminase. In other embodiments, 2F is a 6-aminocaproate dehydrogenase.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a CapP. In some embodiments, 1K is spontaneous. In other embodiments, 1K is an EM10. In some embodiments, 1M is spontaneous. In other embodiments, 1M is an EM12.

Any MMP provided herein can be combined with any CapP provided herein.

In certain embodiments, the CapP further comprises enzymes depicted in FIG. 5. In one embodiment, the CapP further comprises 5T, 5U, 5V, 5W, and/or 5X, wherein 5T is a PEP carboxylase (EFR16A) or PEP carboxykinase (EFR16B); 5U is a pyruvate carboxylase (EFR17); 5V is a malate dehydrogenase (EFR18); 5W is a malic enzyme (EFR19); and 5X is a fumarase (EFR20A), fumarate reductase (EFR20B), succinyl-CoA synthetase (EFR20C), succinyl-CoA ligase (EFR20D), or succinyl-CoA transferase (EFR20E). In one embodiment, the CapP comprises 5T. In another embodiment, the CapP comprises 5U. In another embodiment, the CapP comprises 5V. In other embodiment, the CapP comprises 5W. In another embodiment, the CapP comprises 5X. In another embodiment, the CapP comprises 5Y. In some embodiments, the CapP comprises 5T, 5V and 5X. In another embodiment, the CapP comprises 5U, 5V and 5X. In another embodiment, the CapP comprises 5W and 5X. In one embodiment, 5T is EFR16A. In other embodiments, 5T is EFR16B. In some embodiments, 5X is EFR20A. In other embodiments, 5X is EFR20B. In other embodiments, 5X is EFR20C. In one embodiment, 5X is EFR20D. In another embodiment, 5X is EFR20E.

Figure 3:
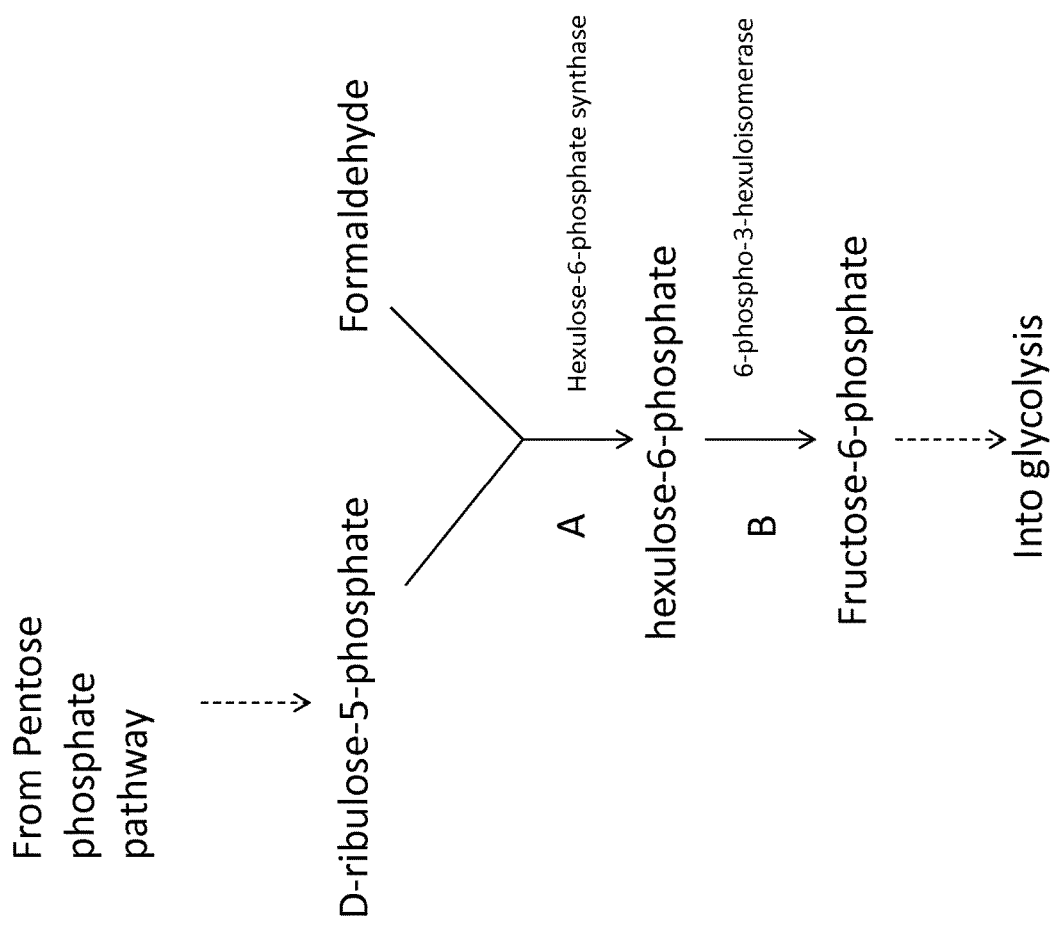
FIG. 3 shows an exemplary FAP. The enzymatic transformations are carried out by the following enzymes: 3A) a H6P synthase (EF1), and 3B) a 6-phospho-3-hexuloisomerase (EF2).

Also provided herein are exemplary pathways, which utilize formaldehyde produced from the oxidation of methanol (e.g., as provided in FIG. 1, step J) in the formation of intermediates of certain central metabolic pathways that can be used for the formation of biomass. One exemplary FAP that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6p is converted into F6P by EF2 (FIG. 3, step B). Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from DHA synthase is then further phosphorylated to form DHAP by an EF4 (FIG. 4, step B). DHAP can be assimilated into glycolysis and several other pathways. Rather than converting formaldehyde to formate and on to $CO_2$ off-gassed, the pathways provided in FIGS. 3 and 4 show that carbon is assimilated, going into the final product.

In certain embodiments, the FAP comprises an EF1 and an EF2. In other embodiments, the FAP comprises an EF3. In other embodiments, the FAP comprises an EF3 and an EF4. In some embodiments, the FAP comprises an EF1, an EF2 and an EF3. In other embodiments, the FAP comprises an EF1, an EF2, an EF3 and an EF4. Such FAPs (and FAPEs) provided herein can be used in combination with any AdiP, 6-ACAP, HMDAP, CapP, MMP, or FRP provided herein.

Thus, in one embodiment, an organism having a MMP, either alone or in combination with an adipate, 6-ACA, HMDA or caprolactam pathway, as provided herein, further comprises a FAP that utilizes formaldehyde, e.g., obtained from the oxidation of methanol, in the formation of intermediates of certain central metabolic pathways that can be used, for example, in the formation of biomass. In some of embodiments, the FAP comprises 3A or 3B, wherein 3A is an EF1 and 3B is an EF2 In other embodiments, the FAP comprises 4A or 4B, wherein 4A is an EF3 and 4B is a EF4.

In certain embodiments, provided herein is a NNOMO having a MMP, wherein said organism comprises at least one exogenous nucleic acid encoding an EM9 (1J) expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis and/or a metabolic pathway that can be used, for example, in the formation of biomass. In certain embodiments, the FAPE is selected from the group consisting of an EF1 (3A), EF2 (3B), EF3 (4A) and EF4 (4B). In certain embodiments, the NNOMO further comprises an AdiP, 6-ACAP, HMDAP or CapP. In some embodiments, the NNOMO further comprises a FRP.

In some embodiments, the exogenous nucleic acid encoding an EM9 is expressed in a sufficient amount to produce an amount of formaldehyde greater than or equal to 1 µM, 10 µM, 20 µM, or 50 µM, or a range thereof, in culture medium or intracellularly. In other embodiments, the exogenous nucleic acid encoding an EM9 is capable of producing an amount of formaldehyde greater than or equal to 1 µM, 10 µM, 20 µM, or 50 µM, or a range thereof, in culture medium or intracellularly. In some embodiments, the range is from 1 µM to 50 µM or greater. In other embodiments, the range is from 10 µM to 50 µM or greater. In other embodiments, the range is from 20 µM to 50 µM or greater. In other embodiments, the amount of formaldehyde production is 50 µM or greater, for example, 55 mM, 60 µM, 65 mM, 70 µM, 75 µM, 80 µM, 85 µM, 90 µM, 95 µM or 100 µM. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In certain embodiments, the exogenous nucleic acid encoding an EM9 is expressed in a sufficient amount to produce at least 1×, 2×, 3×, 4×, 5×, 6×, 7×, 8×, 9×, 10×, 15×, 20×, 30×, 40×, 50×, 100× or more formaldehyde in culture medium or intracellularly. In other embodiments, the exogenous nucleic acid encoding an EM9 is capable of producing an amount of formaldehyde at least 1×, 2×, 3×, 4×, 5×, 6×, 7×, 8×, 9×, 10×, 15×, 20×, 30×, 40×, 50×, 100×, or a range thereof, in culture medium or intracellularly. In some embodiments, the range is from 1× to 100×. In other embodiments, the range is from 2× to 100×. In other embodiments, the range is from 5× to 100×. In other embodiments, the range is from 10× to 100×. In other embodiments, the range is from 50× to 100×. In some embodiments, the amount of formaldehyde production is at least 20×. In other embodiments, the amount of formaldehyde production is at least 50×. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In one aspect, provided herein is a NNOMO, comprising (1) a MMP, wherein said organism comprises at least one exogenous nucleic acid encoding a MMPE in a sufficient amount to enhance the availability of reducing equivalents in the presence of methanol and/or expressed in a sufficient amount to convert methanol to formaldehyde; and (2) a FAP, wherein said organism comprises at least one exogenous nucleic acid encoding a FAPE expressed in a sufficient amount to produce an intermediate of glycolysis and/or a metabolic pathway that can be used, for example, in the formation of biomass. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In specific embodiments, the MMP comprises an EM9 (1J). In certain embodiments, the FAPE is 3A, and the intermediate is a H6P, a F6P, or a combination thereof. In other embodiments, the FAPE is 3B, and the intermediate is a H6P, a F6P, or a combination thereof. In yet other embodiments, the FAPE is 3A and 3B, and the intermediate is a H6P, a F6P, or a combination thereof. In some embodiments, the FAPE is 4A, and the intermediate is a DHA, a DHAP, or a combination thereof. In other embodiments, the FAPE is 4B, and the intermediate is a DHA, a DHAP, or a combination thereof. In yet other embodiments, the FAPE is 4A and 4B, and the intermediate is a DHA, a DHAP, or a combination thereof. In one embodiment, the at least one exogenous nucleic acid encoding the MMPE, in the presence of methanol, sufficiently enhances the availability of reducing equivalents and sufficiently increases formaldehyde assimilation to increase the production of adipate, G-ACA, HMDA, caprolactam or other products described herein by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the FAP comprises 3A, 3B or a combination thereof, wherein 3A is an EF1, and 3B is an EF2. In some embodiments, 1K is spontaneous. In other embodiments, 1K is an EM10. In some embodiments, 1M is spontaneous. In other embodiments, 1M is an EM12. In some embodiments, the intermediate is a H6P. In other embodiments, the intermediate is a F6P. In yet other embodiments, the intermediate is a H6P and a F6P.

In one embodiment, the FAP comprises 3A. In another embodiment, the FAP comprises 3B. In one embodiment, the FAP comprises 3A and 3B.

In some embodiments, the MMP is a MMP depicted in FIG. 1, and a FAP depicted in FIG. 3. An exemplary set of FAPEs to convert D-ribulose-5-phosphate and formaldehyde to F6P (via H6P) according to FIG. 3 include 3A and 3B.

In a specific embodiment, (1) the MMP comprises 1J; and (2) the FAP comprises 3A and 3B. In other embodiments, (1) the MMP comprises 1J and 1K; and (2) the FAP comprises 3A and 3B. In some embodiments, (1) the MMP comprises 1J, 1C, 1D and 1E; and (2) the FAP comprises 3A and 3B. In one embodiment, (1) the MMP comprises 1J, 1C, 1D and 1F; and (2) the FAP comprises 3A and 3B. In another embodiment, (1) the MMP comprises 1J and 1L; and (2) the FAP comprises 3A and 3B. In yet another embodiment, (1) the MMP comprises 1J, 1M, 1N and 1O; and (2) the FAP comprises 3A and 3B. In certain embodiments, (1) the MMP comprises 1J, 1N and 1O; and (2) the FAP comprises 3A and 3B. In some embodiments, (1) the MMP comprises 1J, 1K, 1C, 1D and 1E; and (2) the FAP comprises 3A and 3B. In one embodiment, (1) the MMP comprises 1J, 1K, 1C, 1D and 1F; and (2) the FAP comprises 3A and 3B. In some embodiments, (1) the MMP comprises 1J, 1C, 1D, 1E and 1I; and (2) the FAP comprises 3A and 3B. In one embodiment, (1) the MMP comprises 1J, 1C, 1D, 1F and 1I; and (2) the FAP comprises 3A and 3B. In another embodiment, (1) the MMP comprises 1J, 1L and 1I; and (2) the FAP comprises 3A and 3B. In yet another embodiment, (1) the MMP comprises 1J, 1M, 1N, 1O and 1I; and (2) the FAP comprises 3A and 3B. In certain embodiments, (1) the MMP comprises 1J, 1N, 1O and 1I; and (2) the FAP comprises 3A and 3B. In some embodiments, (1) the MMP comprises 1J, 1K, 1C, 1D, 1E and 1I; and (2) the FAP comprises 3A and 3B. In one embodiment, (1) the MMP comprises 1J, 1K, 1C, 1D, 1F and 1I; and (2) the FAP comprises 3A and 3B. In some embodiments, (1) the MMP comprises 1J, 1C, 1D, 1E and 1G; and (2) the FAP comprises 3A and 3B. In one embodiment, (1) the MMP comprises 1J, 1C, 1D, 1F and 1G; and (2) the FAP comprises 3A and 3B. In another embodiment, (1) the MMP comprises 1J, 1L and 1G; and (2) the FAP comprises 3A and 3B. In yet another embodiment, (1) the MMP comprises 1J, 1M, 1N, 1O and 1G; and (2) the FAP comprises 3A and 3B. In certain embodiments, (1) the MMP comprises 1J, 1N, 1O and 1G; and (2) the FAP comprises 3A and 3B. In some embodiments, (1) the MMP comprises 1J, 1K, 1C, 1D, 1E and 1G; and (2) the FAP comprises 3A and 3B. In one embodiment, (1) the MMP comprises 1J, 1K, 1C, 1D, 1F and 1G; and (2) the FAP comprises 3A and 3B. In some embodiments, (1) the MMP comprises 1J, 1C, 1D, 1E, 1G and 1H; and (2) the FAP comprises 3A and 3B. In one embodiment, (1) the MMP comprises 1J, 1C, 1D, 1F, 1G and 1H; and (2) the FAP comprises 3A and 3B. In another embodiment, (1) the MMP comprises 1J, 1L, 1G and 1H; and (2) the FAP comprises 3A and 3B. In yet another embodiment, (1) the MMP comprises 1J, 1M, 1N, 1O, 1G and 1H; and (2) the FAP comprises 3A and 3B. In certain embodiments, (1) the MMP comprises 1J, 1N, 1O, 1G and 1H; and (2) the FAP comprises 3A and 3B. In some embodiments, (1) the MMP comprises 1J, 1K, 1C, 1D, 1E, 1G and 1H; and (2) the FAP comprises 3A and 3B. In one embodiment, (1) the MMP comprises 1J, 1K, 1C, 1D, 1F, 1G and 1H; and (2) the FAP comprises 3A and 3B. In some embodiments, 1K is spontaneous. In other embodiments, 1K is an EM10. In some embodiments, 1M is spontaneous. In some embodiments, the intermediate is a H6P. In other embodiments, the intermediate is a F6P. In yet other embodiments, the intermediate is a H6P and a F6P.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the FAP comprises 4A, 4B or a combination thereof, wherein 4A is an EF3 and 4B is an EF4. In some embodiments, 1K is spontaneous. In other embodiments, 1K is an EM10. In some embodiments, 1M is spontaneous. In other embodiments, 1M is an EM12. In some embodiments, the intermediate is a DHA. In other embodiments, the intermediate is a DHAP. In yet other embodiments, the intermediate is a DHA and a DHAP.

In one embodiment, the FAP comprises 4A. In another embodiment, the FAP comprises 4B. In one embodiment, the FAP comprises 4A and 4B.

In some embodiments, the MMP is a MMP depicted in FIG. 1, and a FAP depicted in FIG. 4. An exemplary set of FAPEs to convert xyulose-5-phosphate and formaldehyde to DHAP (via DHA) according to FIG. 4 include 4A and 4B.

In a specific embodiment, (1) the MMP comprises 1J; and (2) the FAP comprises 4A and 4B. In other embodiments, (1) the MMP comprises 1J and 1K; and (2) the FAP comprises 4A and 4B. In some embodiments, (1) the MMP comprises 1J, 1C, 1D and 1E; and (2) the FAP comprises 4A and 4B. In one embodiment, (1) the MMP comprises 1J, 1C, 1D and 1F; and (2) the FAP comprises 4A and 4B. In another embodiment, (1) the MMP comprises 1J and 1L; and (2) the FAP comprises 4A and 4B. In yet another embodiment, (1) the MMP comprises 1J, 1M, 1N and 1O; and (2) the FAP comprises 4A and 4B. In certain embodiments, (1) the MMP comprises 1J, 1N and 1O; and (2) the FAP comprises 4A and 4B. In some embodiments, (1) the MMP comprises 1J, 1K, 1C, 1D and 1E; and (2) the FAP comprises 4A and 4B. In one embodiment, (1) the MMP comprises 1J, 1K, 1C, 1D and 1F; and (2) the FAP comprises 4A and 4B. In some embodiments, (1) the MMP comprises 1J, 1C, 1D, 1E and 1I; and (2) the FAP comprises 4A and 4B. In one embodiment, (1) the MMP comprises 1J, 1C, 1D, 1F and 1I; and (2) the FAP comprises 4A and 4B. In another embodiment, (1) the MMP comprises 1J, 1L and 1I; and (2) the FAP comprises 4A and 4B. In yet another embodiment, (1) the MMP comprises 1J, 1M, 1N, 1O and 1I; and (2) the FAP comprises 4A and 4B. In certain embodiments, (1) the MMP comprises 1J, 1N, 1O and 1I; and (2) the FAP comprises 4A and 4B. In some embodiments, (1) the MMP comprises 1J, 1K, 1C, 1D, 1E and 1I; and (2) the FAP comprises 4A and 4B. In one embodiment, (1) the MMP comprises 1J, 1K, 1C, 1D, 1F and 1I; and (2) the FAP comprises 4A and 4B. In some embodiments, (1) the MMP comprises 1J, 1C, 1D, 1E and 1G; and (2) the FAP comprises 4A and 4B. In one embodiment, (1) the MMP comprises 1J, 1C, 1D, 1F and 1G; and (2) the FAP comprises 4A and 4B. In another embodiment, (1) the MMP comprises 1J, 1L and 1G; and (2) the FAP comprises 4A and 4B. In yet another embodiment, (1) the MMP comprises 1J, 1M, 1N, 1O and 1G; and (2) the FAP comprises 4A and 4B. In certain embodiments, (1) the MMP comprises 1J, 1N, 1O and 1G; and (2) the FAP comprises 4A and 4B. In some embodiments, (1) the MMP comprises 1J, 1K, 1C, 1D, 1E and 1G; and (2) the FAP comprises 4A and 4B. In one embodiment, (1) the MMP comprises 1J, 1K, 1C, 1D, 1F and 1G; and (2) the FAP comprises 4A and 4B. In some embodiments, (1) the MMP comprises 1J, 1C, 1D, 1E, 1G and 1H; and (2) the FAP comprises 4A and 4B. In one embodiment, (1) the MMP comprises 1J, 1C, 1D, 1F, 1G and 1H; and (2) the FAP comprises 4A and 4B. In another embodiment, (1) the MMP comprises 1J, 1L, 1G and 1H; and (2) the FAP comprises 4A and 4B. In yet another embodiment, (1) the MMP comprises 1J, 1M, 1N, 1O, 1G and 1H; and (2) the FAP comprises 4A and 4B. In certain embodiments, (1) the MMP comprises 1J, 1N, 1O, 1G and 1H; and (2) the FAP comprises 4A and 4B. In some embodiments, (1) the MMP comprises 1J, 1K, 1C, 1D, 1E, 1G and 1H; and (2) the FAP comprises 4A and 4B. In one embodiment, (1) the MMP comprises 1J, 1K, 1C, 1D, 1F, 1G and 1H; and (2) the FAP comprises 4A and 4B. In some embodiments, 1K is spontaneous. In other embodiments, 1K is an EM10. In some embodiments, 1M is spontaneous. In some embodiments, the intermediate is a DHA. In other embodiments, the intermediate is a DHAP. In yet other embodiments, the intermediate is a DHA and a DHAP.

Any MMP provided herein can be combined with any FAP provided herein. In addition, any MMP provided herein can be combined with any adipate, 6-ACA, HMDA or caprolactam pathway, and any FAP provided herein. In other embodiments, these pathways can be further combined with any FRP provided herein.

Also provided herein are methods of producing formaldehyde comprising culturing a NNOMO having a MMP provided herein. In some embodiments, the MMP comprises 1J. In certain embodiments, the organism is cultured in a substantially anaerobic culture medium. In specific embodiments, the formaldehyde is an intermediate that is consumed (assimilated) in the production of adipate, 6-ACA, HMDA, caprolactam and other products described herein.

Also provided herein are methods of producing an intermediate of glycolysis and/or a metabolic pathway that can be used, for example, in the formation of biomass, comprising culturing a NNOMO having a MMP and a FAP, as provided herein, under conditions and for a sufficient period of time to produce the intermediate. In some embodiments, the intermediate is a H6P. In other embodiments, the intermediate is a F6P. In yet other embodiments, the intermediate is a H6P and a F6P. In some embodiments, the intermediate is a DHA. In other embodiments, the intermediate is a DHAP. In yet other embodiments, the intermediate is a DHA and a DHAP. In some embodiments, the MMP comprises 1J. In certain embodiments, the organism is cultured in a substantially anaerobic culture medium. Such biomass can also be used in methods of producing any of the products, such as the biobased products, provided elsewhere herein.

In certain embodiments, the organism comprises two, three, four, five, six, seven, eight or nine exogenous nucleic acids, each encoding an adipate, 6-ACA, HMDA or caprolactam pathway enzyme. In some embodiments, the organism comprises two exogenous nucleic acids, each encoding an adipate, 6-ACA, HMDA or caprolactam pathway enzyme. In some embodiments, the organism comprises three exogenous nucleic acids, each encoding an adipate, 6-ACA, HMDA or caprolactam pathway enzyme. In other embodiments, the organism comprises four exogenous nucleic acids, each encoding an adipate, 6-ACA, HMDA or caprolactam pathway enzyme. In some embodiments, the organism comprises eight exogenous nucleic acids, each encoding an adipate, 6-ACA, HMDA or caprolactam pathway enzyme. In other embodiments, the organism comprises five exogenous nucleic acids, each encoding an adipate, 6-ACA, HMDA or caprolactam pathway enzyme. In some embodiments, the organism comprises six exogenous nucleic acids, each encoding an adipate, 6-ACA, HMDA or caprolactam pathway enzyme. In other embodiments, the organism comprises seven exogenous nucleic acids, each encoding an adipate, 6-ACA, HMDA or caprolactam pathway enzyme. In some embodiments, the organism comprises eight exogenous nucleic acids, each encoding an adipate, 6-ACA, HMDA or caprolactam pathway enzyme. In other embodiments, the organism comprises nine exogenous nucleic acids, each encoding an adipate, 6-ACA, HMDA or caprolactam pathway enzyme. In certain embodiments, the organism comprises two, three, four, five, six or seven exogenous nucleic acids, each encoding an Adipate, 6-ACA, HMDA or caprolactam pathway enzyme; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the organism comprises two or more exogenous nucleic acids, each encoding a FAPE. In some embodiments, the organism comprises two exogenous nucleic acids, each encoding a FAPE. In certain embodiments, the organism comprises two exogenous nucleic acids, each encoding a FAPE; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the at least one exogenous nucleic acid encoding a MMPE is a heterologous nucleic acid. In other embodiments, the at least one exogenous nucleic acid encoding an adipate, 6-ACA, HMDA or caprolactam pathway enzyme is a heterologous nucleic acid. In other embodiments, the at least one exogenous nucleic acid encoding a FAPE is a heterologous nucleic acid. In certain embodiments, the at least one exogenous nucleic acid encoding a MMPE is a heterologous nucleic acid, and the at least one exogenous nucleic acid encoding an adipate, 6-ACA, HMDA or caprolactam pathway enzyme is a heterologous nucleic acid. In other embodiments, the at least one exogenous nucleic acid encoding a MMPE is a heterologous nucleic acid, and the at least one exogenous nucleic acid encoding a FAPE is a heterologous nucleic acid.

In certain embodiments, the organism is in a substantially anaerobic culture medium.

In some embodiments, provided herein is a NNOMO comprising a MMP. In certain embodiments, provided herein is a NNOMO comprising a FAP. In other embodiments, provided herein is a FRP. In some embodiments, provided herein is a NNOMO comprising an AdiP. In other embodiments, provided herein is a NNOMO comprising a 6-ACAP. In other embodiments, provided herein is a HMDAP. In yet other embodiments, provided herein is a CapP. A NNOMO comprising any combination of one, two, three, four or five of the various FAPs, FRPs, MMPs, AdiPs, 6-ACAPs, HMDAPs or CapPs provided herein are also contemplated. In one embodiment, a NNOMO comprises a MMP and an AdiP provided herein. In another embodiment, a NNOMO comprises a MMP, a FAP and an AdiP provided herein. In other embodiments, a NNOMO comprises a MMP, a FAP, a FRP and an AdiP provided herein. In one embodiment, a NNOMO comprises a MMP and a 6-ACAP provided herein. In another embodiment, a NNOMO comprises a MMP, a FAP and a 6-ACAP provided herein. In other embodiments, a NNOMO comprises a MMP, a FAP, a FRP and a 6-ACAP provided herein. In one embodiment, a NNOMO comprises a MMP and a HMDAP provided herein. In another embodiment, a NNOMO comprises a MMP, a FAP and a HMDAP provided herein. In other embodiments, a NNOMO comprises a MMP, a FAP, a FRP and a HMDAP provided herein. In one embodiment, a NNOMO comprises a MMP and a CapP provided herein. In another embodiment, a NNOMO comprises a MMP, a FAP and a CapP pathway provided herein. In other embodiments, a NNOMO comprises a MMP, a FAP, a FRP and a CapP provided herein. Exemplary MMPs, FAPs, AdiPs, 6-ACAPs, HMDAPs and CapPs are provided in FIGS. 1-5 and elsewhere herein.

In certain embodiments, the NNOMOs provided herein comprises at least one exogenous nucleic acid encoding a MMP, a FAP, a FRP, an AdiP, a 6-ACAP, a HMDAP, and/or a CapP enzyme or protein. In some embodiments, the NNOMO comprises an exogenous nucleic acid encoding a MMP enzyme or protein. In some embodiments, the NNOMO comprises an exogenous nucleic acid encoding a FAP enzyme or protein. In some embodiments, the NNOMO comprises an exogenous nucleic acid encoding a FRP enzyme or protein. In some embodiments, the NNOMO comprises an exogenous nucleic acid encoding an AdiP enzyme or protein. In some embodiments, the NNOMO comprises an exogenous nucleic acid encoding a 6-ACAP enzyme or protein. In some embodiments, the NNOMO comprises an exogenous nucleic acid encoding a HMDAP enzyme or protein. In some embodiments, the NNOMO comprises an exogenous nucleic acid encoding a CapP enzyme or protein. In certain embodiments, the exogenous nucleic acid is a heterologous nucleic acid.

In certain embodiments, provided herein is a NNOMO having a FAP and a FRP. In certain embodiments, the organism comprises (i) at least one exogenous nucleic acid encoding a FAPE, wherein said FAP comprises 3A (see also 5B), 3B (see also 5C), or 4A (see also 5D) or any combination thereof, wherein 3A is a 3-hexulose-6-phosphate synthase (EF1), wherein 3B is a 6-phospho-3-hexuloisomerase (EF2), wherein 4A is a DHA synthase (EF3). In certain embodiments, the FAPE is expressed in a sufficient amount to produce pyruvate. In certain embodiments, the NNOMO further comprises a MMP provided herein. In other embodiments, the NNOMO further comprises an AdiP, 6-ACAP, HMDAP or CapP provided herein. In some embodiments, the NNOMO further comprises a MMP and an AdiP, 6-ACAP, HMDAP or CapP provided herein.

In certain embodiments, the organism comprises at least one exogenous nucleic acid encoding a FRP enzyme (FRPE), wherein said FRP comprises 5E, 5F, 5G, 5H, 5I, 5J, 5K, 5L, 5M, 5N, 5O, or 5P or any combination thereof, wherein 5E is a formate reductase (EFR1), 5F is a formate ligase (EFR2A), a formate transferase (EFR2B), or a formate synthetase (EFR2C), wherein 5G is a formyl-CoA reductase (EFR3), wherein 5H is a formyltetrahydrofolate synthetase (EFR4), wherein 5I is a methenyltetrahydrofolate cyclohydrolase (EFR5), wherein 5J is a methylenetetrahydrofolate dehydrogenase (EFR6), wherein 5K is a formaldehyde-forming enzyme (EFR7) or spontaneous, wherein 5L is a glycine cleavage system (EFR8), wherein 5M is a serine hydroxymethyltransferase (EFR9), wherein 5N is a serine deaminase (EFR10), wherein 5O is a methylenetetrahydrofolate reductase (EFR11), wherein 5P is an acetyl-CoA synthase (EFR12). In certain embodiments, the FRPE is expressed in a sufficient amount to produce formaldehyde. In certain embodiments, the FRPE is expressed in a sufficient amount to produce pyruvate. In certain embodiments, the FRPE is expressed in a sufficient amount to produce acetyl-CoA. In some embodiments, 5K is spontaneous. In some embodiments, 5F is an EFR2A. In other embodiments, 5F is an EFR2B. In other embodiments, 5F is an EFR2C. In certain embodiments, the NNOMO further comprises a MMP provided herein. In other embodiments, the NNOMO further comprises an AdiP, 6-ACAP, HMDAP or CapP provided herein. In some embodiments, the NNOMO further comprises a MMP and an AdiP, 6-ACAP, HMDAP or CapP provided herein.

In one embodiment, the FAP comprises 3A. In one embodiment, the FAP comprises 3B. In one embodiment, the FAP comprises 4A. In one embodiment, the FRP comprises 5E. In one embodiment, the FRP comprises 5F. In some embodiments, 5F is an EFR2A. In other embodiments, 5F is an EFR2B. In other embodiments, 5F is an EFR2C. In one embodiment, the FRP comprises 5G. In one embodiment, the FRP comprises 5H. In one embodiment, the FRP comprises 4I. In one embodiment, the FRP comprises 5J. In one embodiment, the FRP comprises 5K. In some embodiments, 5K is spontaneous. In one embodiment, the FRP comprises 5L. In one embodiment, the FRP comprises 5M. In one embodiment, the FRP comprises 5N. In one embodiment, the FRP comprises 5O. In one embodiment, the FRP comprises 5P. Any combination of two, three, four, five, six, seven, eight, nine, ten, eleven, twelve, thirteen, fourteen, fifteen pathway enzymes of 3A, 3B, 4A, 5E, 5F, 5G, 5H, 5I, 5J, 5K, 5L, 5M, 5N, 5O, or 5P is also contemplated.

In one aspect, provided herein is a NNOMO having a FAP and a FRP, wherein said organism comprises (i) at least one exogenous nucleic acid encoding a FAPE, wherein said FAP comprises: (5) 3A and 3B; or (2) 4A; and (ii) at least one exogenous nucleic acid encoding a FRPE, wherein said FRP comprises a pathway selected from: (3) 5E; (4) 5F, and 5G; (5) 5H, 5I, 5J, and 5K; (6) 5H, 5I, 5J, 5L, 5M, and 5N; (7) 5E, 5H, 5I, 5J, 5L, 5M, and 5N; (8) 5F, 5G, 5H, 5I, 5J, 5L, 5M, and 5N; (9) 5K, 5H, 5I, 5J, 5L, 5M, and 5N; and (10) 5H, 5I, 5J, 5O, and 5P. In certain embodiments, the FAPE is expressed in a sufficient amount to produce pyruvate. In some embodiments, the FRPE is expressed in a sufficient amount to produce formaldehyde. In other embodiments, the FRPE is expressed in a sufficient amount to produce pyruvate. In certain embodiments, the FRPE is expressed in a sufficient amount to produce acetyl-CoA. In some embodiments, 5K is spontaneous. In some embodiments, 5F is an EFR2A. In other embodiments, 5F is an EFR2B. In other embodiments, 5F is an EFR2C. In certain embodiments, the NNOMO further comprises a MMP provided herein. In other embodiments, the NNOMO further comprises an AdiP, 6-ACAP, HMDAP or CapP provided herein. In some embodiments, the NNOMO further comprises a MMP and a 3 AdiP, 6-ACAP, HMDAP or CapP provided herein.

In certain embodiments, the FAP comprises 3A and 3B. In certain embodiments, the FAP comprises 3A and 3B, and the FRP comprises 5E. In certain embodiments, the FAP comprises 3A and 3B, and the FRP comprises 5F and 5G. In certain embodiments, the FAP comprises 3A and 3B, and the FRP comprises 5H, 5I, 5J, and 5K. In certain embodiments, the FAP comprises 3A and 3B, and the FRP comprises 5H, 5I, 5J, 5L, 5M, and 5N. In certain embodiments, the FAP comprises 3A and 3B, and the FRP comprises 5E, 5H, 5I, 5J, 5L, 5M, and 5N. In certain embodiments, the FAP comprises 3A and 3B, and the FRP comprises 5F, 5G, 5H, 5I, 5J, 5L, 5M, and 5N. In certain embodiments, the FAP comprises 3A and 3B, and the FRP comprises 5K, 5H, 5I, 5J, 5L, 5M, and 5N. In certain embodiments, the FAP comprises 3A and 3B, and the FRP comprises 5H, 5I, 5J, 5O, and 5P. In some embodiments, 5K is spontaneous. In some embodiments, 5F is an EFR2A. In other embodiments, 5F is an EFR2B. In other embodiments, 5F is an EFR2C.

In certain embodiments, the FAP comprises 4A. In certain embodiments, the FAP comprises 4A, and the FRP comprises 5E. In certain embodiments, the FAP comprises 4A, and the FRP comprises 5F, and 5G. In certain embodiments, the FAP comprises 4A, and the FRP comprises 5H, 5I, 5J, and 5K. In certain embodiments, the FAP comprises 4A, and the FRP comprises 5H, 5I, 5J, 5L, 5M, and 5N. In certain embodiments, the FAP comprises 4A, and the FRP comprises 5E, 5H, 5I, 5J, 5L, 5M, and 5N. In certain embodiments, the FAP comprises 4A, and the FRP comprises 5F, 5G, 5H, 5I, 5J, 5L, 5M, and 5N. In certain embodiments, the FAP comprises 4A, and the FRP comprises 5K, 5H, 5I, 5J, 5L, 5M, and 5N. In certain embodiments, the FAP comprises 4A, and the FRP comprises 5H, 5I, 5J, 5O, and 5P. In some embodiments, 5K is spontaneous. In some embodiments, 5F is an EFR2A. In other embodiments, 5F is an EFR2B. In other embodiments, 5F is an EFR2C.

In certain embodiments, the FRP further comprises 5Q, 5R, or 5S or any combination thereof, wherein 5Q is a pyruvate formate lyase (EFR13); 5R is a pyruvate dehydrogenase (EFR14A), a pyruvate ferredoxin oxidoreductase (EFR14B), or a pyruvate:NADP+ oxidoreductase (EFR14C); and 5S is a formate dehydrogenase (EFR15). Thus, in certain embodiments the FRP comprises 5Q. In certain embodiments the FRP comprises 5R. In certain embodiments the FRP comprises 5S. In certain embodiments, the FRP comprises 5R and 5S. In some embodiments, 5R is an EFR14A. In other embodiments, 5R is an EFR14B. In other embodiments, 5R is an EFR14C.

In certain embodiments, FRP comprises 5Q, or 5R and 5S, and the FAP comprises 3A and 3B. In certain embodiments, FRP comprises 5Q, or 5R and 5S, and the FAP comprises 4A. In certain embodiments the FAP comprises 3A and 3B, and the FRP comprises 5Q, and 5E. In certain embodiments, the FAP comprises 3A and 3B, and the FRP comprises 5Q, 5F, and 5G. In certain embodiments, the FAP comprises 3A and 3B, and the FRP comprises 5Q, 5H, 5I, 5J, and 5K. In certain embodiments, the FAP comprises 3A and 3B, and the FRP comprises 5Q, 5H, 5I, 5J, 5L, 5M, and 5N. In certain embodiments, the FAP comprises 3A and 3B, and the FRP comprises 5Q, 5E, 5H, 5I, 5J, 5L, 5M, and 5N. In certain embodiments, the FAP comprises 3A and 3B, and the FRP comprises 5Q, 5F, 5G, 5H, 5I, 5J, 5L, 5M, and 5N. In certain embodiments, the FAP comprises 3A and 3B, and the FRP comprises 5Q, 5K, 5H, 5I, 5J, 5L, 5M, and 5N. In certain embodiments, the FAP comprises 3A and 3B, and the FRP comprises 5Q, 5H, 5I, 5J, 5O, and 5P. In certain embodiments the FAP comprises 4A, and the FRP comprises 5Q, and 5E. In certain embodiments, the FAP comprises 4A, and the FRP comprises 5Q, 5F, and 5G. In certain embodiments, the FAP comprises 4A, and the FRP comprises 5Q, 5H, 5I, 5J, and 5K. In certain embodiments, the FAP comprises 4A, and the FRP comprises 5Q, 5H, 5I, 5J, 5L, 5M, and 5N. In certain embodiments, the FAP comprises 4A, and the FRP comprises 5Q, 5E, 5H, 5I, 5J, 5L, 5M, and 5N. In certain embodiments, the FAP comprises 4A, and the FRP comprises 5Q, 5F, 5G, 5H, 5I, 5J, 5L, 5M, and 5N. In certain embodiments, the FAP comprises 4A, and the FRP comprises 5Q, 5K, 5H, 5I, 5J, 5L, 5M, and 5N. In certain embodiments, the FAP comprises 4A, and the FRP comprises 5Q, 5H, 5I, 5J, 5O, and 5P. In certain embodiments the FAP comprises 3A and 3B, and the FRP comprises 5R, 5S, and 5E. In certain embodiments, the FAP comprises 3A and 3B, and the FRP comprises 5R, 5S, 5F, and 5G. In certain embodiments, the FAP comprises 3A and 3B, and the FRP comprises 5R, 5S, 5H, 5I, 5J, and 5K. In certain embodiments, the FAP comprises 3A and 3B, and the FRP comprises 5R, 5S, 5H, 5I, 5J, 5L, 5M, and 5N. In certain embodiments, the FAP comprises 3A and 3B, and the FRP comprises 5R, 5S, 5E, 5H, 5I, 5J, 5L, 5M, and 5N. In certain embodiments, the FAP comprises 3A and 3B, and the FRP comprises 5R, 5S, 5F, 5G, 5H, 5I, 5J, 5L, 5M, and 5N. In certain embodiments, the FAP comprises 3A and 3B, and the FRP comprises 5R, 5S, 5K, 5H, 5I, 5J, 5L, 5M, and 5N. In certain embodiments, the FAP comprises 3A and 3B, and the FRP comprises 5R, 5S, 5H, 5I, 5J, 5O, and 5P. In certain embodiments the FAP comprises 4A, and the FRP comprises 5R, 5S, and 5E. In certain embodiments, the FAP comprises 4A, and the FRP comprises 5R, 5S, 5F, and 5G. In certain embodiments, the FAP comprises 4A, and the FRP comprises 5R, 5S, 5H, 5I, 5J, and 5K. In certain embodiments, the FAP comprises 4A, and the FRP comprises 5R, 5S, 5H, 5I, 5J, 5L, 5M, and 5N. In certain embodiments, the FAP comprises 4A, and the FRP comprises 5R, 5S, 5E, 5H, 5I, 5J, 5L, 5M, and 5N. In certain embodiments, the FAP comprises 4A, and the FRP comprises 5R, 5S, 5F, 5G, 5H, 5I, 5J, 5L, 5M, and 5N. In certain embodiments, the FAP comprises 4A, and the FRP comprises 5R, 5S, 5K, 5H, 5I, 5J, 5L, 5M, and 5N. In certain embodiments, the FAP comprises 4A, and the FRP comprises 5R, 5S, 5H, 5I, 5J, 5O, and 5P. In some embodiments, 5K is spontaneous. In some embodiments, 5F is an EFR2A. In other embodiments, 5F is an EFR2B. In other embodiments, 5F is an EFR2C. In some embodiments, 5R is an EFR14A. In other embodiments, 5R is an EFR14B. In other embodiments, 5R is an EFR14C.

In certain embodiments, the FAP is a pathway depicted in FIG. 3. In certain embodiments, the FAP is a pathway depicted in FIG. 4. In certain embodiments, the FAP is a pathway depicted in FIG. 5. In certain embodiments, the FRP is a pathway depicted in FIG. 5. In certain embodiments, the FAP and the FRP is a pathway depicted in FIG. 5.

In certain embodiments, provided herein is a NNOMO having a FAP, a FRP and a MMP. In some embodiments, the organism comprises (i) at least one exogenous nucleic acid encoding a FAPE, wherein said FAP comprises: (1) 3A and 3B; or (2) 4A; (ii) at least one exogenous nucleic acid encoding a FRPE, wherein said FRP comprises a pathway selected from: (3) 5E; (4) 5F, and 5G; (5) 5H, 5I, 5J, and 5K; (6) 5H, 5I, 5J, 5L, 5M, and 5N; (7) 5E, 5H, 5I, 5J, 5L, 5M, and 5N; (8) 5F, 5G, 5H, 5I, 5J, 5L, 5M, and 5N; (9) 5K, 5H, 5I, 5J, 5L, 5M, and 5N; and (10) 5H, 5I, 5J, 5O, and 5P, and (iii) at least one exogenous nucleic acid encoding a MMPE, wherein said MMP comprises a pathway selected from: (1) 1J; (2) 1A and 1B; (3) 1A, 1B and 1C; (4) 1J, 1K and 1C; (5) 1J, 1M, and 1N; (6) 1J and 1L; (7) 1A, 1B, 1C, 1D, and 1E; (8) 1A, 1B, 1C, 1D, and 1F; (9) 1J, 1K, 1C, 1D, and 1E; (10) 1J, 1K, 1C, 1D, and 1F; (11) 1J, 1M, 1N, and 1O; (12) 1A, 1B, 1C, 1D, 1E, and 1G; (13) 1A, 1B, 1C, 1D, 1F, and 1G; (14) 1J, 1K, 1C, 1D, 1E, and 1G; (15) 1J, 1K, 1C, 1D, 1F, and 1G; (16) 1J, 1M, 1N, 1O, and 1G; (17) 1A, 1B, 1C, 1D, 1E, and 1I; (18) 1A, 1B, 1C, 1D, 1F, and 1I; (19) 1J, 1K, 1C, 1D, 1E, and 1I; (20) 1J, 1K, 1C, 1D, 1F, and 1I; and (21) 1J, 1M, 1N, 1O, and 1I. In certain embodiments, the FAPE is expressed in a sufficient amount to produce pyruvate. In some embodiments, the FRPE is expressed in a sufficient amount to produce formaldehyde. In other embodiments, the FRPE is expressed in a sufficient amount to produce pyruvate. In certain embodiments, the FRPE is expressed in a sufficient amount to produce acetyl-CoA. In some embodiments, the MMP enzyme expressed in a sufficient amount to produce formaldehyde and/or produce or enhance the availability of reducing equivalents in the presence of methanol. In some embodiments, 5K is spontaneous. In some embodiments, 5F is an EFR2A. In other embodiments, 5F is an EFR2B. In other embodiments, 5F is an EFR2C. In some embodiments, 1K is spontaneous. In other embodiments, 1K is an EM10. In some embodiments, 1M is spontaneous. In other embodiments, 1M is an EM12. In certain embodiments, NNOMO further comprises an AdiP, 6-ACAP, HMDAP or CapP provided herein.

In certain embodiments, the MMP comprises 1A. In certain embodiments, the MMP comprises 1B. In certain embodiments, the MMP comprises 1C. In certain embodiments, the MMP comprises 1D. In certain embodiments, the MMP comprises 1E. In certain embodiments, the MMP comprises 1F. In certain embodiments, the MMP comprises 1G. In certain embodiments, the MMP comprises 1H. In certain embodiments, the MMP comprises 1I. In certain embodiments, the MMP comprises 1J. In certain embodiments, the MMP comprises 1K. In certain embodiments, the MMP comprises 1L. In certain embodiments, the MMP comprises 1M. In certain embodiments, the MMP comprises 1N. In certain embodiments, the MMP comprises 1O. In some embodiments, 1K is spontaneous. In other embodiments, 1K is an EM10. In some embodiments, 1M is spontaneous. In other embodiments, 1M is an EM12. In certain embodiments, the MMP comprises 1J. In certain embodiments, the MMP comprises 1A and 1B. In certain embodiments, the MMP comprises 1A, 1B and 1C. In certain embodiments, the MMP comprises 1J, 1K and 1C. In certain embodiments, the MMP comprises 1J, 1M, and 1N. In certain embodiments, the MMP comprises 1J and 1L. In certain embodiments, the MMP comprises 1A, 1B, 1C, 1D, and 1E. In certain embodiments, the MMP comprises 1A, 1B, 1C, 1D, and 1F. In certain embodiments, the MMP comprises 1J, 1K, 1C, 1D, and 1E. In certain embodiments, the MMP comprises 1J, 1K, 1C, 1D, and 1F. In certain embodiments, the MMP comprises 1J, 1M, 1N, and 1O. In certain embodiments, the MMP comprises 1A, 1B, 1C, 1D, 1E, and 1G. In certain embodiments, the MMP comprises 1A, 1B, 1C, 1D, 1F, and 1G. In certain embodiments, the MMP comprises 1J, 1K, 1C, 1D, 1E, and 1G. In certain embodiments, the MMP comprises 1J, 1K, 1C, 1D, 1F, and 1G. In certain embodiments, the MMP comprises 1J, 1M, 1N, 1O, and 1G. In certain embodiments, the MMP comprises 1A, 1B, 1C, 1D, 1E, and 1I. In certain embodiments, the MMP comprises 1A, 1B, 1C, 1D, 1F, and 1I. In certain embodiments, the MMP comprises 1J, 1K, 1C, 1D, 1E, and 1I. In certain embodiments, the MMP comprises 1J, 1K, 1C, 1D, 1F, and 1I. In certain embodiments, the MMP comprises 1J, 1M, 1N, 1O, and 1I. In some embodiments, 1K is spontaneous. In other embodiments, 1K is an EM10. In some embodiments, 1M is spontaneous. In other embodiments, 1M is an EM12.

In certain embodiments, provided herein is a NNOMO having a FAP, a FRP and a MMP. In some embodiments, the organism comprises (i) at least one exogenous nucleic acid encoding a FAPE, wherein said FAP comprises: (1) 3A and 3B; or (2) 4A, (ii) at least one exogenous nucleic acid encoding a FRPE, wherein said FRP comprises a pathway selected from: (3) 5E; (4) 5F, and 5G; (5) 5H, 5I, 5J, and 5K; (6) 5H, 5I, 5J, 5L, 5M, and 5N; (7) 5E, 5H, 5I, 5J, 5L, 5M, and 5N; (8) 5F, 5G, 5H, 5I, 5J, 5L, 5M, and 5N; (9) 5K, 5H, 5I, 5J, 5L, 5M, and 5N; and (10) 5H, 5I, 5J, 5O, and 5P, and (iii) at least one exogenous nucleic acid encoding a MMPE (e.g., a methanol oxidation pathway enzyme) expressed in a sufficient amount to produce formaldehyde in the presence of methanol, wherein said MMP comprises 1J (see also 5A). In certain embodiments, the FAPE is expressed in a sufficient amount to produce pyruvate. In some embodiments, the FRPE is expressed in a sufficient amount to produce formaldehyde. In other embodiments, the FRPE is expressed in a sufficient amount to produce pyruvate. In certain embodiments, the FRPE is expressed in a sufficient amount to produce acetyl-CoA. In some embodiments, 5K is spontaneous. In some embodiments, 5F is an EFR2A. In other embodiments, 5F is an EFR2B. In other embodiments, 5F is an EFR2C. In certain embodiments, NNOMO further comprises an AdiP, 6-ACAP, HMDAP or CapP provided herein.

In certain embodiments, provided herein is a NNOMO having a FAP and a MMP. In some embodiments, the organism comprises (i) at least one exogenous nucleic acid encoding a FAPE, wherein said FAP comprises: (1) 3A and 3B; or (2) 4A; and (ii) at least one exogenous nucleic acid encoding a MMPE (e.g., a methanol oxidation pathway enzyme) expressed in a sufficient amount to produce formaldehyde in the presence of methanol, wherein said MMP comprises 1J. In certain embodiments, the FAPE is expressed in a sufficient amount to produce pyruvate. In certain embodiments, NNOMO further comprises an AdiP, 6-ACAP, HMDAP or CapP provided herein.

In certain embodiments, provided herein is a NNOMO having a FAP, a FRP, and a MMP. In certain embodiments, the organism further comprises 1H or 1P, wherein 1H is a hydrogenase (EM16) and 1P a carbon monoxide dehydrogenase that converts CO to $CO_2$. In some embodiments, the organism comprises (i) at least one exogenous nucleic acid encoding a FAPE, wherein said FAP comprises: (1) 3A and 3B; or (2) 4A, (ii) at least one exogenous nucleic acid encoding a FRPE, wherein said FRP comprises a pathway selected from: (3) 5E; (4) 5F, and 5G; (5) 5H, 5I, 5J, and 5K; (6) 5H, 5I, 5J, 5L, 5M, and 5N; (7) 5E, 5H, 5I, 5J, 5L, 5M, and 5N; (8) 5F, 5G, 5H, 5I, 5J, 5L, 5M, and 5N; (9) 5K, 5H, 5I, 5J, 5L, 5M, and 5N; and (10) 5H, 5I, 5J, 5O, and 5P; and (iii) at least one exogenous nucleic acid encoding a MMP enzyme, wherein said MMP comprises a pathway selected from: (1) 1J; (2) 1A and 1B; (3) 1A, 1B and 1C; (4) 1J, 1K and 1C; (5) 1J, 1M, and 1N; (6) 1J and 1L; (7) 1A, 1B, 1C, 1D, and 1E; (8) 1A, 1B, 1C, 1D, and 1F; (9) 1J, 1K, 1C, 1D, and 1E; (10) 1J, 1K, 1C, 1D, and 1F; (11) 1J, 1M, 1N, and 1O; (12) 1A, 1B, 1C, 1D, 1E, and 1G; (13) 1A, 1B, 1C, 1D, 1F, and 1G; (14) 1J, 1K, 1C, 1D, 1E, and 1G; (15) 1J, 1K, 1C, 1D, 1F, and 1G; (16) 1J, 1M, 1N, 1O, and 1G; (17) 1A, 1B, 1C, 1D, 1E, and 1I; (18) 1A, 1B, 1C, 1D, 1F, and 1I; (19) 1J, 1K, 1C, 1D, 1E, and 1I; (20) 1J, 1K, 1C, 1D, 1F, and 1I; and (21) 1J, 1M, 1N, 1O, and 1I. In certain embodiments, the FAPE is expressed in a sufficient amount to produce pyruvate. In some embodiments, the FRPE is expressed in a sufficient amount to produce formaldehyde. In other embodiments, the FRPE is expressed in a sufficient amount to produce pyruvate. In certain embodiments, the FRPE is expressed in a sufficient amount to produce acetyl-CoA. In some embodiments, the MMP enzyme expressed in a sufficient amount to produce formaldehyde and/or produce or enhance the availability of reducing equivalents in the presence of methanol. In some embodiments, 5K is spontaneous. In some embodiments, 5F is an EFR2A. In other embodiments, 5F is an EFR2B. In other embodiments, 5F is an EFR2C. In some embodiments, 1K is spontaneous. In other embodiments, 1K is an EM10. In some embodiments, 1M is spontaneous. In other embodiments, 1M is an EM12. In certain embodiments, NNOMO further comprises an AdiP, 6-ACAP, HMDAP or CapP provided herein.

In certain embodiments, provided herein is a NNOMO having a FAP, a FRP, and a MMP. In certain embodiments, the organism further comprises 1H or 1P, wherein 1H is a hydrogenase (EM16) and 1P a carbon monoxide dehydrogenase that converts CO to $CO_2$. In some embodiments, the organism comprises (i) at least one exogenous nucleic acid encoding a FAPE, wherein said FAP comprises: (1) 3A and 3B; or (2) 4A, wherein 3A is a 3-hexulose-6-phosphate synthase, wherein 3B is a 6-phospho-3-hexuloisomerase, wherein 4A is a DHA synthase, (ii) at least one exogenous nucleic acid encoding a FRPE, wherein said FRP comprises a pathway selected from: (3) 5E; (4) 5F, and 5G; (5) 5H, 5I, 5J, and 5K; (6) 5H, 5I, 5J, 5L, 5M, and 5N; (7) 5E, 5H, 5I, 5J, 5L, 5M, and 5N; (8) 5F, 5G, 5H, 5I, 5J, 5L, 5M, and 5N; (9) 5K, 5H, 5I, 5J, 5L, 5M, and 5N; and (10) 5H, 5I, 5J, 5O, and 5P, and (iii) at least one exogenous nucleic acid encoding a MMPE (e.g., a methanol oxidation pathway enzyme) expressed in a sufficient amount to produce formaldehyde in the presence of methanol, wherein said MMP comprises 1J. In certain embodiments, the FAPE is expressed in a sufficient amount to produce pyruvate. In some embodiments, the FRPE is expressed in a sufficient amount to produce formaldehyde. In other embodiments, the FRPE is expressed in a sufficient amount to produce pyruvate. In certain embodiments, the FRPE is expressed in a sufficient amount to produce acetyl-CoA. In some embodiments, 5K is spontaneous. In some embodiments, 5F is an EFR2A. In other embodiments, 5F is an EFR2B. In other embodiments, 5F is an EFR2C. In certain embodiments, NNOMO further comprises an AdiP, 6-ACAP, HMDAP or CapP provided herein.

In certain embodiments, provided herein is a NNOMO having a FAP, a FRP, a MMP (e.g., a methanol oxidation pathway, comprising 1J), a hydrogenase, a carbon monoxide dehydrogenase or any combination described above, wherein the organism further comprises an AdiP. In other embodiments, provided herein is a NNOMO having a FAP, a FRP, a MMP (e.g., a methanol oxidation pathway, comprising 1J), a hydrogenase, a carbon monoxide dehydrogenase or any combination described above, wherein the organism further comprises a 6-ACAP. In other embodiments, provided herein is a NNOMO having a FAP, a FRP, a MMP (e.g., a methanol oxidation pathway, comprising 1J), a hydrogenase, a carbon monoxide dehydrogenase or any combination described above, wherein the organism further comprises a HMDAP. In other embodiments, provided herein is a NNOMO having a FAP, a FRP, a MMP (e.g., a methanol oxidation pathway, comprising 1J), a hydrogenase, a carbon monoxide dehydrogenase or any combination described above, wherein the organism further comprises a CapP.

In some embodiments, formaldehyde produced from EM9 (FIG. 1, step J) in certain of the NNOMO provided herein is used for generating energy, redox and/or formation of biomass. Two such pathways are shown in FIG. 3. Additionally, several organisms use an alternative pathway called the "serine cycle" for formaldehyde assimilation. These organisms include the methylotroph, *Methylobacterium extorquens* AM1, and another, *Methylobacterium organophilum*. The net balance of this cycle is the fixation of two mols of formaldehyde and 1 mol of $CO_2$ into 1 mol of 3-phosphoglycerate, which is used for biosynthesis, at the expense of 2 mols ATP and the oxidation of 2 mols of NAD(P)H.

In the first reaction of the serine pathway, formaldehyde reacts with glycine to form serine. The reaction is catalyzed by serine hydroxymethyltransferase (SHMT), an enzyme that uses tetrahydrofolate (THF) as a cofactor. This leads to the formation of 5,10-methylenetetrahydrofolate. During the reaction, formaldehyde is transferred from 5,10-methylenetetrahydrofolate to the glycine, forming L-serine. In the next step, serine is transaminated with glyoxylate as the amino group acceptor by the enzyme serine-glyoxylate aminotransferase, to produce hydroxypyruvate and glycine. Hydroxypyruvate is reduced to glycerate by hydroxypyruvate reductase. Glycerate 2-kinase catalyzes the addition of a phosphate group from ATP to produce 2-phosphoglycerate.

Some of the 2-phosphoglycerate is converted by phosphoglycerate mutase to 3-phosphoglycerate, which is an intermediate of the central metabolic pathways and used for biosynthesis. The rest of the 2-phosphoglycerate is converted by an *enolase* to phosphoenolpyruvate (PEP). PEP carboxylase then catalyzes the fixation of carbon dioxide coupled to the conversion of PEP to oxaloacetate, which is reduced to malate by malate dehydrogenase, an NAD-linked enzyme. In some embodiments, the exogenous malate dehydrogenase genes are *Rhizopus delemar* malate dehydrogenase genes encoding the amino acid sequence disclosed in WO2013112939 as SEQ ID NO:167 or its variants. Malate is activated to malyl coenzyme A by malate thiokinase and is cleaved by malyl coenzyme A lyase into acetyl CoA and glyoxylate. These two enzymes (malate thiokinase and malyl coenzyme A lyase), as well as hydroxypyruvate reductase and glycerate-2-kinase, are uniquely present in methylotrophs that contain the serine pathway.

In organisms that possess isocitrate lyase, a key enzyme of the glyoxylate cycle, acetyl CoA is converted to glyoxylate by the glyoxylate cycle. However, if the enzyme is missing, it is converted by another unknown pathway (deVries et al, *FEMS Microbiol Rev,* 6 (1): 57-101 (1990)). The resulting glyoxylate can serve as substrate for serine-glyoxylate aminotransferase, regenerating glycine and closing the circle.

It is understood that any of the pathways disclosed herein, as described in the Examples and exemplified in the figures, including the pathways of FIGS. 1, 2, 3, 4 and 5, can be utilized to generate a NNOMO that produces any pathway intermediate or product, as desired. Non-limiting examples of such intermediate or products are adipate, 6-ACA, HMDA or caprolactam. As disclosed herein, such a microbial organism that produces an intermediate can be used in combination with another microbial organism expressing downstream pathway enzymes to produce a desired product. However, it is understood that a non-naturally occurring eukaryotic organism that produces an adipate, 6-ACA, HMDA or CapP intermediate can be utilized to produce the intermediate as a desired product.

In certain embodiments, a NNOMO comprising a MMP and an adipate, 6-ACA, HMDA or caprolactam pathway provided herein, either alone or in combination with a FAP and/or a FRP provided herein, further comprises one or more gene disruptions. In certain embodiments, the one or more gene disruptions confer increased production of adipate, G-ACA, HMDA or caprolactam in the organism. In other embodiments, a NNOMO comprising a MMP, FAP and/or FRP provided herein, further comprises one or more gene disruptions. In some embodiments, the gene disruption is in an endogenous gene encoding a protein and/or enzyme involved in native production of ethanol, glycerol, acetate, lactate, formate, $CO_2$, amino acids, or any combination thereof, by said microbial organism. In one embodiment, the gene disruption is in an endogenous gene encoding a protein and/or enzyme involved in native production of ethanol. In another embodiment, the gene disruption is in an endogenous gene encoding a protein and/or enzyme involved in native production of glycerol. In other embodiments, the gene disruption is in an endogenous gene encoding a protein and/or enzyme involved in native production of acetate. In another embodiment, the gene disruption is in an endogenous gene encoding a protein and/or enzyme involved in native production of lactate. In one embodiment, the gene disruption is in an endogenous gene encoding a protein and/or enzyme involved in native production of formate. In another embodiment, the gene disruption is in an endogenous gene encoding a protein and/or enzyme involved in native production of $CO_2$. In other embodiments, the gene disruption is in an endogenous gene encoding a protein and/or enzyme involved in native production of amino acids by said microbial organism. In some embodiments, the protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. In certain embodiments, the one or more gene disruptions confer increased production of formaldehyde in the organism. In another embodiment, the gene disruption is in an endogenous gene encoding a protein and/or enzyme involved in a native formaldehyde utilization pathway. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In other embodiments, a NNOMO comprising a MMP and an adipate, 6-ACA, HMDA or caprolactam pathway provided herein, either alone or in combination with a FAP and/or a FRP provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In some embodiments, a NNOMO comprising a MMP and a FAP provided herein, either alone or in combination with a FRP provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In one embodiment the endogenous protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof.

Each of the non-naturally occurring alterations provided herein result in increased production and an enhanced level of adipate, 6-ACA, HMDA or caprolactam, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

In certain embodiments, provided herein are NNOMO having genetic alterations such as gene disruptions that increase production of, for example, adipate, 6-ACA, HMDA or caprolactam, for example, growth-coupled production of adipate, 6-ACA, HMDA or caprolactam. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Appropriate conditions include, for example, those disclosed herein, including conditions such as particular carbon sources or reactant availabilities and/or adaptive evolution.

Given the teachings and guidance provided herein, those skilled in the art will understand that to introduce a metabolic alteration, such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction provided herein. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification provided herein. Similarly, some or all of enzymes involved in a reaction or metabolic modification provided herein can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding an Enzyme of a targeted metabolic reaction can be practiced in the methods provided herein and incorporated into the NNOMOs provided herein in order to achieve the increased production of adipate, 6-ACA, HMDA or caprolactam or growth-coupled product production.

Given the teachings and guidance provided herein, those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3): 351-357 (2012); O'Sullivan, *Anal. Bioanal. Chem.* 372(1): 44-48 (2002); and Lee et al., *Curr. Opin. Biotechnol.* 14(5): 505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in an Eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., Genetics 120(4):875-885 (1988); Hayes, Annu Rev. Genet. 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell*, 136(4):763-776 (2009); or in bacteria, for example, introduction of a transfer-messenger RNA (tmRNA) tag, which can lead to RNA degradation and ribosomal stalling (Sunoharan Et al., *RNA* 10(3):378-386 (2004); and Sunoharan Et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2):125-131 (2005); modifying regions outside the coding sequence, such as introducing secondary structure into an untranslated region (UTR) to block translation or reduce efficiency of translation (Ringnér et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5): 883-932 (2010); introducing antisense RNA oligomers or antisense transcripts (Nashizawan Et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., *Comparative and Functional Genomics*, Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in an Eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The adipate, 6-ACA, HMDA or caprolactam-production strategies identified by the methods disclosed herein such as the OptKnock framework are generally ranked on the basis of their (i) theoretical yields, and (ii) growth-coupled adipate, 6-ACA, HMDA or caprolactam formation characteristics.

The adipate-, 6-ACA-, HMDA- or caprolactam-production strategies provided herein can be disrupted to increase production of adipate, 6-ACA, HMDA or caprolactam. Accordingly, also provided herein is a NNOMO having metabolic modifications coupling adipate, 6-ACA, HMDA or caprolactam production to growth of the organism, where the metabolic modifications includes disruption of one or more genes selected from the genes encoding proteins and/or enzymes provided herein.

Each of the strains can be supplemented with additional deletions if it is determined that the strain designs do not sufficiently increase the production of adipate, G-ACA, HMDA or caprolactam and/or couple the formation of the product with biomass formation. Alternatively, some other enzymes not known to possess significant activity under the growth conditions can become active due to adaptive evolution or random mutagenesis. Such activities can also be knocked out. However, gene deletions provided herein allow the construction of strains exhibiting high-yield production of 3 adipate, 6-ACA, HMDA or caprolactam, including growth-coupled production of adipate, 6-ACA, HMDA or caprolactam.

In another aspect, provided herein is a method for producing adipate, 6-ACA, HMDA or caprolactam, comprising culturing any one of the NNOMOs comprising a MMP and an adipate, 6-ACA, HMDA or caprolactam pathway provided herein under conditions and for a sufficient period of time to produce adipate, 6-ACA, HMDA or caprolactam. In certain embodiments, the organism is cultured in a substantially anaerobic culture medium.

In one embodiment, provided herein are methods for producing adipate, comprising culturing an organism provided herein (e.g., a NNOMOs comprising a MMP and an AdiP, either alone or in combination with a FAP and/or a FRP provided herein) under conditions and for a sufficient period of time to produce adipate. In some embodiments, the method comprises culturing, for a sufficient period of time to produce adipate, a NNOMO, comprising (1) a MMP, wherein said organism comprises at least one exogenous nucleic acid encoding a MMPE in a sufficient amount to enhance the availability of reducing equivalents in the presence of methanol; and (2) an AdiP, comprising at least one exogenous nucleic acid encoding an AdiPE expressed in a sufficient amount to produce adipate. In certain embodiments, the NNOMO further comprises a FAP, comprising at least one exogenous nucleic acid encoding a FAPE as provided herein; and/or a FRP, comprising at least one exogenous nucleic acid encoding a RFPE as provided herein.

In another embodiment, provided herein are methods for producing 6-ACA, comprising culturing an organism provided herein (e.g., a NNOMOs comprising a MMP and an 6-ACAP, either alone or in combination with a FAP and/or a FRP provided herein) under conditions and for a sufficient period of time to produce 6-ACA. In some embodiments, the method comprises culturing, for a sufficient period of time to produce 6-ACA, a NNOMO, comprising (1) a MMP, wherein said organism comprises at least one exogenous nucleic acid encoding a MMPE in a sufficient amount to enhance the availability of reducing equivalents in the presence of methanol; and (2) an 6-ACAP, comprising at least one exogenous nucleic acid encoding an 6-ACAPE expressed in a sufficient amount to produce 6-ACA. In certain embodiments, the NNOMO further comprises a FAP, comprising at least one exogenous nucleic acid encoding a FAPE as provided herein; and/or a FRP, comprising at least one exogenous nucleic acid encoding a RFPE as provided herein.

In other embodiments, provided herein are methods for producing HMDA, comprising culturing an organism provided herein (e.g., a NNOMOs comprising a MMP and an HMDAP, either alone or in combination with a FAP and/or a FRP provided herein) under conditions and for a sufficient period of time to produce HMDA. In some embodiments, the method comprises culturing, for a sufficient period of time to produce HMDA, a NNOMO, comprising (1) a MMP, wherein said organism comprises at least one exogenous nucleic acid encoding a MMPE in a sufficient amount to enhance the availability of reducing equivalents in the presence of methanol; and (2) an HMDAP, comprising at least one exogenous nucleic acid encoding an HMDAPE expressed in a sufficient amount to produce HMDA. In certain embodiments, the NNOMO further comprises a FAP, comprising at least one exogenous nucleic acid encoding a FAPE as provided herein; and/or a FRP, comprising at least one exogenous nucleic acid encoding a RFPE as provided herein.

In yet other embodiments, provided herein are methods for producing caprolactam, comprising culturing an organism provided herein (e.g., a NNOMOs comprising a MMP and an CapP, either alone or in combination with a FAP and/or a FRP provided herein) under conditions and for a sufficient period of time to produce caprolactam. In some embodiments, the method comprises culturing, for a sufficient period of time to produce caprolactam, a NNOMO, comprising (1) a MMP, wherein said organism comprises at least one exogenous nucleic acid encoding a MMPE in a sufficient amount to enhance the availability of reducing equivalents in the presence of methanol; and (2) an CapP, comprising at least one exogenous nucleic acid encoding an CapPE expressed in a sufficient amount to produce caprolactam. In certain embodiments, the NNOMO further comprises a FAP, comprising at least one exogenous nucleic acid encoding a FAPE as provided herein; and/or a FRP, comprising at least one exogenous nucleic acid encoding a RFPE as provided herein.

In certain embodiments of the methods provided herein, the organism further comprises at least one nucleic acid encoding an adipate, 6-ACA, HMDA or caprolactam pathway enzyme expressed in a sufficient amount to produce adipate, 6-ACA, HMDA or caprolactam. In some embodiments, the nucleic acid is an exogenous nucleic acid. In other embodiments, the nucleic acid is an endogenous nucleic acid. In some embodiments, the organism further comprises one or more gene disruptions provided herein that confer increased production of adipate, 6-ACA, HMDA or caprolactam in the organism. In certain embodiments, the one or more gene disruptions occurs in an endogenous gene encoding a protein or enzyme involved in native production of ethanol, glycerol, acetate, lactate, formate, $CO_2$ and/or amino acids by said microbial organism. In other embodiments, the organism further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In certain embodiments, the organism is a Crabtree positive, eukaryotic organism, and the organism is cultured in a culture medium comprising glucose. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more. In certain embodiments, the NNOMO further comprises a FAP, comprising at least one exogenous nucleic acid encoding a FAPE as provided herein; and/or a FRP, comprising at least one exogenous nucleic acid encoding a RFPE as provided herein.

In an additional embodiment, provided is a NNOMO having an adipate, 6-ACA, HMDA or CapP, FAP and/or MMP, wherein the NNOMO comprises at least one exogenous nucleic acid encoding an enzyme or protein that converts a substrate to a product. By way of example, in FIG. 1, the substrate of 1J is methanol, and the product is formaldehyde; the substrate of 1L is formaldehyde, and the product is formate; and so forth. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, provided herein are NNOMOs containing at least one exogenous nucleic acid encoding an enzyme or protein, where the enzyme or protein converts the substrates and products of a MMP, such as that shown in FIG. 1; an adipate, 6-ACA, HMDA or caprolactam, such as that shown in FIG. 2; a FAP, such as that shown in FIGS. 3-5, and/or a FRP, such as that shown in FIG. 5.

While generally described herein as a microbial organism that contains an AdiP, 6-ACAP, HMDAP or CapP, FAP, FRP and/or a MMP, it is understood that provided herein are also NNOMO comprising at least one exogenous nucleic acid encoding an AdiP, 6-ACAP, HMDAP or CapP, FAP, FRP, and/or a MMPE expressed in a sufficient amount to produce an intermediate of an AdiP, 6-ACAP, HMDAP or CapP, FAP, FRP, and/or a MMP intermediate. For example, as disclosed herein, an AdiP, 6-ACAP, HMDAP or CapP is exemplified in FIG. 2. Therefore, in addition to a microbial organism containing an AdiP, 6-ACAP, HMDAP or CapP that produces adipate, 6-ACA, HMDA or caprolactam, also provided herein is a NNOMO comprising at least one exogenous nucleic acid encoding an adipate, 6-ACA, HMDA or caprolactam pathway enzyme, where the microbial organism produces an AdiP, 6-ACAP, HMDAP or CapP intermediate.

In some embodiments, the carbon feedstock and other cellular uptake sources such as phosphate, ammonia, sulfate, chloride and other halogens can be chosen to alter the isotopic distribution of the atoms present in adipate, 6-ACA, HMDA and/or caprolactam or any adipate, 6-ACA, HMDA and/or caprolactam pathway intermediate. The various carbon feedstock and other uptake sources enumerated above will be referred to herein, collectively, as "uptake sources." Uptake sources can provide isotopic enrichment for any atom present in the product adipate, 6-ACA, HMDA or a caprolactam and/or adipate, 6-ACA, HMDA or caprolactam pathway intermediate, or for side products generated in reactions diverging away from an adipate, 6-ACA, HMDA and/or caprolactam pathway. Isotopic enrichment can be achieved for any target atom including, for example, carbon, hydrogen, oxygen, nitrogen, sulfur, phosphorus, chloride or other halogens. The same holds true for the MMPs FAPs, and FRPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950)$^{14}C/^{12}C$ ratio of 1.176±0.010×$10^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonnan Et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable BDO and renewable terephthalic acid resulted in bio-based content exceeding 90% (Colonnan Et al., supra, 2011).

Accordingly, in some embodiments, the present invention provides adipate, G-ACA, HMDA or caprolactam, or an adipate, 6-ACA, HMDA or caprolactam pathway intermediate that has a carbon-12, carbon-13, and carbon-14 ratio that reflects an atmospheric carbon, also referred to as environmental carbon, uptake source. For example, in some aspects, the adipate, 6-ACA, HMDA or caprolactam, or an adipate, 6-ACA, HMDA or caprolactam intermediate thereof can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides adipate, 6-ACA, HMDA or caprolactam, or an adipate, 6-ACA, HMDA or caprolactam intermediate thereof, that has a carbon-12, carbon-13, and carbon-14 ratio that reflects petroleum-based carbon uptake source. In this aspect, an adipate, 6-ACA, HMDA or caprolactam, or an adipate, G-ACA, HMDA or caprolactam intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides an adipate, 6-ACA, HMDA or caprolactam, or an adipate, 6-ACA, HMDA or caprolactam intermediate thereof, that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates, in part, to biologically produced adipate, G-ACA, HMDA or caprolactam, or an adipate, 6-ACA, HMDA or caprolactam intermediate thereof, as disclosed herein, and to the products derived therefrom, wherein an adipate, G-ACA, HMDA or caprolactam, or an intermediate thereof, has a carbon-12, carbon-13, and carbon-14 isotope ratio of about the same value as the $CO_2$ that occurs in the environment. For example, in some aspects provided is bioderived adipate, 6-ACA, HMDA or caprolactam, or an intermediate thereof, having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived adipate, 6-ACA, HMDA or caprolactam, or an intermediate thereof, as disclosed herein, wherein the bioderived product is chemically modified to generate a final product. Methods of chemically modifying a bioderived product of adipate, 6-ACA, HMDA or caprolactam, or an intermediate thereof, to generate a desired product are well known to those skilled in the art, as described herein. The invention further provides polymers, plastics, epoxy resins, nylons (e.g., nylon-6 or nylon 6-6), textiles, polyurethanes, plasticizers, unsaturated polyesters, fibers, polyester polyols, polyurethane, lubricant components, polyvinyl chloride (PVC), food additives, food ingredients, flavorants, gelling aids, food and oral medicinal coatings/products, and the like, having a carbon-12 versus carbon-13 versus carbon-14 isotope ratio of about the same value as the $CO_2$ that occurs in the environment, wherein the polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, are generated directly from or in combination with bioderived adipate, 6-ACA, HMDA or caprolactam or a bioderived intermediate thereof, as disclosed herein.

Adipate, 6-ACA, HMDA and caprolactam, as well as intermediates thereof, are chemicals used in commercial and industrial applications. Non-limiting examples of such applications include production of polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like. Moreover, adipate, 6-ACA, HMDA and caprolactam are also used as a raw material in the production of a wide range of products including polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like. Accordingly, in some embodiments, provided is biobased polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising one or more of bioderived adipate, 6-ACA, HMDA or caprolactam, or a bioderived intermediate thereof, produced by a NNOMO provided herein or produced using a method disclosed herein.

In one embodiment, the product is a polymer. In one embodiment, the product is a plastic. In one embodiment, the product is an epoxy resin. In one embodiment, the product is a nylon (e.g., nylon-6 or nylon 6-6). In one embodiment, the product is a textile. In one embodiment, the product is a polyurethane. In one embodiment, the product is a plasticizer. In one embodiment, the product is an unsaturated polyester. In one embodiment, the product is a fiber. In one embodiment, the product is a polyester polyol. In one embodiment, the product is a polyurethane. In one embodiment, the product is a lubricant component. In one embodiment, the product is a PVC. In one embodiment, the product is a food additive. In one embodiment, the product is a food ingredient. In one embodiment, the product is a flavorant. In one embodiment, the product is a gelling aid. In one embodiment, the product is a food coating. In one embodiment, the product is a food product. In one embodiment, the product is an oral medicinal coatings. In one embodiment, the product is an oral product As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound provided herein. A biobased or bioderived product is in contrast to a petroleum derived product, wherein such a product is derived from or synthesized from petroleum or a petrochemical feedstock.

In some embodiments, provided are polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising bioderived adipate, 6-ACA, HMDA or caprolactam, or a bioderived intermediate thereof, wherein the bioderived adipate, 6-ACA, HMDA or caprolactam, or bioderived intermediate thereof, includes all or part of an adipate, 6-ACA, HMDA or caprolactam, or an intermediate thereof, used in the production of polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like. Thus, in some aspects, provided is a biobased polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived adipate, 6-ACA, HMDA or caprolactam, or a bioderived adipate, 6-ACA, HMDA or caprolactam intermediate, as disclosed herein. Additionally, in some aspects, provided is biobased polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, wherein an adipate, 6-ACA, HMDA or caprolactam, or an adipate, 6-ACA, HMDA or caprolactam intermediate, used in its production is a combination of bioderived and petroleum derived adipate, 6-ACA, HMDA or caprolactam, or an adipate, 6-ACA, HMDA or caprolactam intermediate thereof. For example, biobased polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, can be produced using 50% bioderived adipate, 6-ACA, HMDA or caprolactam and 50% petroleum derived adipate, 6-ACA, HMDA or caprolactam or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing polymers, plastics, epoxy resins, nylons (e.g., nylon-6 or nylon 6-6), textiles, polyurethanes, plasticizers, unsaturated polyesters, fibers, polyester polyols, polyurethane, lubricant components, PVC, food additives, food ingredients, flavorants, gelling aids, food and oral medicinal coatings/products, and the like, using the bioderived adipate, 6-ACA, HMDA or caprolactam, or a bioderived adipate, 6-ACA, HMDA or caprolactam intermediate thereof, provided herein are well known in the art.

In some embodiments, provided herein is a culture medium comprising bioderived adipate. In some embodiments, the bioderived adipate is produced by culturing a NNOMO having a MMP and AdiP, as provided herein. In certain embodiments, the bioderived adipate has a carbon-12, carbon-13 and carbon-14 isotope ratio that reflects an atmospheric carbon dioxide uptake source. In one embodiment, the culture medium is separated from a NNOMO having a MMP and AdiP.

In other embodiments, provided herein is a bioderived adipate. In some embodiments, the bioderived adipate is produced by culturing a NNOMO having a MMP and AdiP, as provided herein. In certain embodiments, the bioderived adipate has a carbon-12, carbon-13 and carbon-14 isotope ratio that reflects an atmospheric carbon dioxide uptake source. In some embodiments, the bioderived adipate has an Fm value of at least 80%, at least 85%, at least 90%, at least 95% or at least 98%. In certain embodiments, the bioderived adipate is a component of culture medium.

In certain embodiments, provided herein is a composition comprising a bioderived adipate provided herein, for example, a bioderived adipate produced by culturing a NNOMO having a MMP and AdiP, as provided herein. In some embodiments, the composition further comprises a compound other than said bioderived adipate. In certain embodiments, the compound other than said bioderived adipate is a trace amount of a cellular portion of a NNOMO having a MMP and an AdiP, as provided herein.

In some embodiments, provided herein is a biobased product comprising a bioderived adipate provided herein. In certain embodiments, the biobased product is a polymer, plastic, epoxy resin, nylon (e.g., nylon-6 or nylon 6-6), textile, polyurethane, plasticizer, unsaturated polyester, fiber, polyester polyol, polyurethane, lubricant component, PVC, food additive, food ingredient, flavorant, gelling aid, food coating/product, or oral medicinal coatings/product. In certain embodiments, the biobased product comprises at least 5% bioderived adipate. In certain embodiments, the biobased product comprises at least 10% bioderived adipate. In some embodiments, the biobased product comprises at least 20% bioderived adipate. In other embodiments, the biobased product comprises at least 30% bioderived adipate. In some embodiments, the biobased product comprises at least 40% bioderived adipate. In other embodiments, the biobased product comprises at least 50% bioderived adipate. In one embodiment, the biobased product comprises a portion of said bioderived adipate as a repeating unit. In another embodiment, provided herein is a molded product obtained by molding the biobased product provided herein. In other embodiments, provided herein is a process for producing a biobased product provided herein, comprising chemically reacting said bioderived adipate with itself or another compound in a reaction that produces said biobased product.

In certain embodiments, provided herein is a polymer comprising or obtained by converting the bioderived adipate. In other embodiments, provided herein is a method for producing a polymer, comprising chemically of enzymatically converting the bioderived adipate to the polymer. In yet other embodiments, provided herein is a composition comprising the bioderived adipate, or a cell lysate or culture supernatant thereof.

In some embodiments, provided herein is a culture medium comprising bioderived 6-ACA. In some embodiments, the bioderived 6-ACA is produced by culturing a NNOMO having a MMP and 6-ACAP, as provided herein. In certain embodiments, the bioderived 6-ACA has a carbon-12, carbon-13 and carbon-14 isotope ratio that reflects an atmospheric carbon dioxide uptake source. In one embodiment, the culture medium is separated from a NNOMO having a MMP and 6-ACAP.

In other embodiments, provided herein is a bioderived 6-ACA. In some embodiments, the bioderived 6-ACA is produced by culturing a NNOMO having a MMP and 6-ACAP, as provided herein. In certain embodiments, the bioderived 6-ACA has a carbon-12, carbon-13 and carbon-14 isotope ratio that reflects an atmospheric carbon dioxide uptake source. In some embodiments, the bioderived 6-ACA has an Fm value of at least 80%, at least 85%, at least 90%, at least 95% or at least 98%. In certain embodiments, the bioderived 6-ACA is a component of culture medium.

In certain embodiments, provided herein is a composition comprising a bioderived 6-ACA provided herein, for example, a bioderived 6-ACA produced by culturing a NNOMO having a MMP and 6-ACAP, as provided herein. In some embodiments, the composition further comprises a compound other than said bioderived 6-ACA. In certain embodiments, the compound other than said bioderived 6-ACA is a trace amount of a cellular portion of a NNOMO having a MMP and a 6-ACAP, as provided herein.

In some embodiments, provided herein is a biobased product comprising a bioderived 6-ACA provided herein. In certain embodiments, the biobased product is a polymer, plastic, epoxy resin, nylon (e.g., nylon-6 or nylon 6-6), textile, polyurethane, plasticizer, unsaturated polyester, fiber, polyester polyol, polyurethane, lubricant component, PVC, food additive, food ingredient, flavorant, gelling aid, food coating/product, or oral medicinal coatings/product. In certain embodiments, the biobased product comprises at least 5% bioderived 6-ACA. In certain embodiments, the biobased product comprises at least 10% bioderived 6-ACA. In some embodiments, the biobased product comprises at least 20% bioderived 6-ACA. In other embodiments, the biobased product comprises at least 30% bioderived 6-ACA. In some embodiments, the biobased product comprises at least 40% bioderived 6-ACA. In other embodiments, the biobased product comprises at least 50% bioderived 6-ACA. In one embodiment, the biobased product comprises a portion of said bioderived 6-ACA as a repeating unit. In another embodiment, provided herein is a molded product obtained by molding the biobased product provided herein. In other embodiments, provided herein is a process for producing a biobased product provided herein, comprising chemically reacting said bioderived 6-ACA with itself or another compound in a reaction that produces said biobased product. In certain embodiments, provided herein is a polymer comprising or obtained by converting the bioderived 6-ACA. In other embodiments, provided herein is a method for producing a polymer, comprising chemically of enzymatically converting the bioderived 6-ACA to the polymer. In yet other embodiments, provided herein is a composition comprising the bioderived 6-ACA, or a cell lysate or culture supernatant thereof.

In some embodiments, provided herein is a culture medium comprising bioderived HMDA. In some embodiments, the bioderived HMDA is produced by culturing a NNOMO having a MMP and HMDAP, as provided herein. In certain embodiments, the bioderived HMDA has a carbon-12, carbon-13 and carbon-14 isotope ratio that reflects an atmospheric carbon dioxide uptake source. In one embodiment, the culture medium is separated from a NNOMO having a MMP and HMDAP.

In other embodiments, provided herein is a bioderived HMDA. In some embodiments, the bioderived HMDA is produced by culturing a NNOMO having a MMP and HMDAP, as provided herein. In certain embodiments, the bioderived HMDA has a carbon-12, carbon-13 and carbon-14 isotope ratio that reflects an atmospheric carbon dioxide uptake source. In some embodiments, the bioderived HMDA has an Fm value of at least 80%, at least 85%, at least 90%, at least 95% or at least 98%. In certain embodiments, the bioderived HMDA is a component of culture medium.

In certain embodiments, provided herein is a composition comprising a bioderived HMDA provided herein, for example, a bioderived HMDA produced by culturing a NNOMO having a MMP and HMDAP, as provided herein. In some embodiments, the composition further comprises a compound other than said bioderived HMDA. In certain embodiments, the compound other than said bioderived HMDA is a trace amount of a cellular portion of a NNOMO having a MMP and a HMDAP, as provided herein.

In some embodiments, provided herein is a biobased product comprising a bioderived HMDA provided herein. In certain embodiments, the biobased product is a polymer, plastic, epoxy resin, nylon (e.g., nylon-6 or nylon 6-6), textile, polyurethane, plasticizer, unsaturated polyester, fiber, polyester polyol, polyurethane, lubricant component, PVC, food additive, food ingredient, flavorant, gelling aid, food coating/product, or oral medicinal coatings/product. In certain embodiments, the biobased product comprises at least 5% bioderived HMDA. In certain embodiments, the biobased product comprises at least 10% bioderived HMDA. In some embodiments, the biobased product comprises at least 20% bioderived HMDA. In other embodiments, the biobased product comprises at least 30% bioderived HMDA. In some embodiments, the biobased product comprises at least 40% bioderived HMDA. In other embodiments, the biobased product comprises at least 50% bioderived HMDA. In one embodiment, the biobased product comprises a portion of said bioderived HMDA as a repeating unit. In another embodiment, provided herein is a molded product obtained by molding the biobased product provided herein. In other embodiments, provided herein is a process for producing a biobased product provided herein, comprising chemically reacting said bioderived HMDA with itself or another compound in a reaction that produces said biobased product. In certain embodiments, provided herein is a polymer comprising or obtained by converting the bioderived HMDA. In other embodiments, provided herein is a method for producing a polymer, comprising chemically of enzymatically converting the bioderived HMDA to the polymer. In yet other embodiments, provided herein is a composition comprising the bioderived HMDA, or a cell lysate or culture supernatant thereof.

In some embodiments, provided herein is a culture medium comprising bioderived caprolactam. In some embodiments, the bioderived caprolactam is produced by culturing a NNOMO having a MMP and CapP, as provided herein. In certain embodiments, the bioderived caprolactam has a carbon-12, carbon-13 and carbon-14 isotope ratio that reflects an atmospheric carbon dioxide uptake source. In one embodiment, the culture medium is separated from a NNOMO having a MMP and CapP.

In other embodiments, provided herein is a bioderived caprolactam. In some embodiments, the bioderived caprolactam is produced by culturing a NNOMO having a MMP and CapP, as provided herein. In certain embodiments, the bioderived caprolactam has a carbon-12, carbon-13 and carbon-14 isotope ratio that reflects an atmospheric carbon dioxide uptake source. In some embodiments, the bioderived caprolactam has an Fm value of at least 80%, at least 85%, at least 90%, at least 95% or at least 98%. In certain embodiments, the bioderived caprolactam is a component of culture medium.

In certain embodiments, provided herein is a composition comprising a bioderived caprolactam provided herein, for example, a bioderived caprolactam produced by culturing a NNOMO having a MMP and CapP, as provided herein. In some embodiments, the composition further comprises a compound other than said bioderived caprolactam. In certain embodiments, the compound other than said bioderived caprolactam is a trace amount of a cellular portion of a NNOMO having a MMP and a CapP, as provided herein.

In some embodiments, provided herein is a biobased product comprising a bioderived caprolactam provided herein. In certain embodiments, the biobased product is a polymer, plastic, epoxy resin, nylons (e.g., nylon-6 or nylon 6-6), textile, polyurethane, plasticizer, unsaturated polyester, fiber, polyester polyol, polyurethane, lubricant component, PVC, food additive, food ingredient, flavorant, gelling aid, food coating/product, or oral medicinal coatings/product. In certain embodiments, the biobased product comprises at least 5% bioderived caprolactam. In certain embodiments, the biobased product comprises at least 10% bioderived caprolactam. In some embodiments, the biobased product comprises at least 20% bioderived caprolactam. In other embodiments, the biobased product comprises at least 30% bioderived caprolactam. In some embodiments, the biobased product comprises at least 40% bioderived caprolactam. In other embodiments, the biobased product comprises at least 50% bioderived caprolactam. In one embodiment, the biobased product comprises a portion of said bioderived caprolactam as a repeating unit. In another embodiment, provided herein is a molded product obtained by molding the biobased product provided herein. In other embodiments, provided herein is a process for producing a biobased product provided herein, comprising chemically reacting said bioderived caprolactam with itself or another compound in a reaction that produces said biobased product. In certain embodiments, provided herein is a polymer comprising or obtained by converting the bioderived caprolactam. In other embodiments, provided herein is a method for producing a polymer, comprising chemically of enzymatically converting the bioderived caprolactam to the polymer. In yet other embodiments, provided herein is a composition comprising the bioderived caprolactam, or a cell lysate or culture supernatant thereof.

Also provided herein is a method of producing formaldehyde, comprising culturing a NNOMO provided herein (e.g., comprising an exogenous nucleic acid encoding an EM9 (1J)) under conditions and for a sufficient period of time to produce formaldehyde. In certain embodiments, the formaldehyde is consumed to provide a reducing equivalent. In other embodiments, the formaldehyde is consumed to incorporate into adipate, 6-ACA, HMDA and/or caprolactam. In yet other embodiments, the formaldehyde is consumed to incorporate into another target product.

Also provided herein is a method of producing an intermediate of glycolysis and/or an intermediate of a metabolic pathway that can be used in the formation of biomass, comprising culturing a NNOMO provided herein (e.g., comprising an exogenous nucleic acid encoding an EM9 (1J)) under conditions and for a sufficient period of time to produce the intermediate. In one embodiment, the method is a method of producing an intermediate of glycolysis. In other embodiments, the method is a method of producing an intermediate of a metabolic pathway that can be used in the formation of biomass. In certain embodiments, the intermediate is consumed to provide a reducing equivalent. In other embodiment, the intermediate is consumed to incorporate into adipate, 6-ACA, HMDA and/or caprolactam. In yet other embodiments, the formaldehyde is consumed to incorporate into another target product.

A reducing equivalent can be readily obtained from the glycolysis intermediate by any of several central metabolic reactions including glyceraldehyde-3-phosphate dehydrogenase, pyruvate dehydrogenase, pyruvate formate lyase and NAD(P)-dependant formate dehydrogenase, isocitrate dehydrogenase, alpha-ketoglutarate dehydrogenase, succinate dehydrogenase, and malate dehydrogenase. Additionally, reducing equivalents can be generated from glucose 6-phosphate-1-dehydrogenase and 6-phosphogluconate dehydrogenase of the pentose phosphate pathway. Overall, at most twelve reducing equivalents can be obtained from a C6 glycolysis intermediate (e.g., glucose-6-phosphate, F6P, fructose-1,6-diphosphate) and at most six reducing equivalents can be generated from a C3 glycolysis intermediate (e.g., DHAP, glyceraldehyde-3-phosphate).

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constituents also references the gene or genes encoding the enzymes that catalyze, or proteins involved in, the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction.

Microbial organisms generally lack the capacity to synthesize adipate, 6-ACA, HMDA and/or caprolactam, and therefore any of the compounds disclosed herein to be within the adipate, 6-ACA, HMDA or caprolactam family of compounds, or otherwise known by those in the art to be within the adipate, 6-ACA, HMDA or caprolactam family of compounds. Moreover, organisms having all of the requisite metabolic enzymatic capabilities are not known to produce adipate, 6-ACA, HMDA or caprolactam from the enzymes described and biochemical pathways exemplified herein. In contrast, the NNOMOs provided herein can generate adipate, 6-ACA, HMDA or caprolactam as a product, as well as intermediates thereof. The biosynthesis of adipate, 6-ACA, HMDA or caprolactam, as well as intermediates thereof, is particularly useful in chemical synthesis of adipate, 6-ACA, HMDA or caprolactam family of compounds, it also allows for the further biosynthesis of adipate, 6-ACA, HMDA or caprolactam family compounds and avoids altogether chemical synthesis procedures.

The NNOMOs provided herein that can produce adipate, 6-ACA, HMDA or caprolactam are produced by ensuring that a host microbial organism includes functional capabilities for the complete biochemical synthesis of at least one adipate, 6-ACA, HMDA or caprolactam biosynthetic pathway provided herein. Ensuring at least one requisite adipate, 6-ACA, HMDA or caprolactam biosynthetic pathway confers adipate, 6-ACA, HMDA or caprolactam biosynthesis capability onto the host microbial organism.

The organisms and methods are described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The NNOMOs described herein can be produced by introducing expressible nucleic acids encoding one or more of the enzymes or proteins participating in one or more methanol metabolic, formaldehyde assimilation, formate reutilization (assimilation), and/or adipate, 6-ACA, HMDA or caprolactam biosynthetic pathways. Depending on the host microbial organism chosen for biosynthesis, nucleic acids for some or all of a particular methanol metabolic, formaldehyde assimilation, formate assimilation, and/or adipate, G-ACA, HMDA or caprolactam biosynthetic pathway can be expressed. For example, if a chosen host is deficient in one or more enzymes or proteins for a desired metabolic, assimilation, or biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve adipate, 6-ACA, HMDA or caprolactam biosynthesis and/or methanol metabolism. Thus, a NNOMO described herein can be produced by introducing exogenous enzyme or protein activities to obtain a desired metabolic pathway and/or a desired biosynthetic pathway can be obtained by introducing one or more exogenous enzyme or protein activities that, together with one or more endogenous enzymes or proteins, produces a desired product such as adipate, 6-ACA, HMDA or caprolactam.

Host microbial organisms can be selected from, and the NNOMOs generated in, for example, bacteria, yeast, fungus or any of a variety of other microorganisms applicable or suitable to fermentation processes. Exemplary bacteria include any species selected from the order Enterobacteriales, family Enterobacteriaceae, including the generan *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

In some embodiments, the host microbial organism can be a recombinant microbial organism having increased succinate (succinic acid) production as compared to the wild-type microbial organism. Increased succinate production can be generated by introduction of one or more gene disruptions of a host microbial organism gene and/or an exogenous nucleic acid. Methods of increasing succinate production in a microbial organism are well known in the art. For example, the host microbial organism can be a recombinant bacteria, such as a rumen bacteria, that includes a gene disruption in one or more genes selected from a lactate dehydrogenase gene (ldhA), a pyruvate formate-lyase gene (pfl), a phosphotransacetylase gene (pta), and an acetate kinase gene (ackA) as described in U.S. Publication 2007-0054387, published Mar. 8, 2007, now U.S. Pat. No. 7,470,530, and U.S. Publication 2009-0203095, published Aug. 13, 2009. For example, in one aspect, the host microbial organism can include a gene disruption in a gene encoding ldhA, pta, and ackA, without disrupting a gene encoding pfl. Accordingly, in some aspects, the bacteria that can be used as a host microbial organism include, but are not limited to, a *Mannheimia* species (e.g., *Mannheimia* sp. LPK, *Mannheimia* sp. LPK4,

*Mannheimia* sp. LPK7, *Mannheimia* sp. LPK (KCTC 10558BP), *Mannheimia succiniciproducens* MBEL55E (KCTC 0769BP), *Mannheimia succiniciproducens* PALK (KCTC10973BP), *Mannheimia succiniciproducens* ALK, or *Mannheimia succiniciproducens* ALKt), an *Actinobacillus* species (e.g., *Actinobacillus succinogenes*), a *Bacteroides* species, a *Succinimonas* species, a *Succinivibrio* species, or an *Anaerobiospirillum* species (e.g., *Anaerobiospirillum succiniciproducens*).

Additional methods for producing a host microbial organism having increased succinate production are also well known in the art. For example, the host microbial organism can have genes disruptions in genes encoding ldhA, pfl and a phosphopyruvate carboxylase (ppc), or alternatively/additionally gene disruptions in genes encoding a glucose phosphotransferase (ptsG) and a pyruvate kinase (pykA and pykF), or alternatively/additionally gene disruptions in a gene encoding a succinic semialdehyde dehydrogenase (GabD), or alternatively/additionally introduction or amplification of a nucleic acid encoding a C4-dicarboxylate transport protein (DctA), which is associated with transport of succinate, as described in U.S. Publication 2010-0330634, published Dec. 30, 2010. Accordingly, a host microbial organism can include a Lumen bacteria, a *Corynebacterium* species, a *Brevibacterium* species or an *Escherichia* species (e.g., *Escherichia coli*, in particular strain W3110GFA, as disclosed in U.S. Publication 2009-0075352, published Mar. 19, 2009). As yet another example, a host microbial organism having increased succinate production can be generated by introducing an exogenous nucleic acid encoding an enzyme or protein that increases production of succinate are described in U.S. Publication 2007-0042476, published Feb. 22, 2007, U.S. Publication 2007-0042477, published Feb. 22, 2007, and U.S. Publication 2008-0020436, published Jan. 24, 2008, which disclose introduction of a nucleic acid encoding a malic enzyme B (maeB), a fumarate hydratase C (fumC), a formate dehydrogenase D (fdhD) or a formate dehydrogenase E (fdhE). Additional useful host microbial organisms include, but are not limited to, a microbial organism that can produce succinate using glycerol as a carbon source, as disclosed in WO 2009/048202, or an organism that simultaneously use sucrose and glycerol as carbon sources to produce succinate by weakening a catabolic inhibition mechanism of the glycerol by sucrose as described in EP 2612905.

Additional microbes having high succinate production suitable for use as a host microbial organism for the pathways and methods described herein include those bacterial strains described in International Publications WO 2010/092155 and WO 2009/024294, and U.S. Publication 2010-0159542, published Jun. 24, 2010 and those yeast strains described in International Publication WO 2013/112939, published Aug. 1, 2013. For example, bacterial strains of the genus *Pasteurella*, which are gram negative, facultative anaerobes, motile, pleimorphic and often catalase- and oxidase-positive, specifically *Pasteurella* strain DD land its variants, are suitable host microbial organisms. *Pasteurella* strain DD1 is the bacterial strain deposited under the Budapest Treaty with DSMZ (Deutsche Sammlungvon Mikroorganismen and Zellkulturen, GmbH), Germany, having deposit number DSM18541, and was originally isolated from the rumen of a cow of German origin. Improved variants of DD1, are described in WO 2010/092155, are also suitable host microbial organisms, and include, but are not limited to, LU15348 (DD1 with deletion of pfl gene); LU15050 (DD1 deletion of ldh gene); and LU15224 (DD1 with deletion of both pfl and ldh genes). Additional host bacteria include succinate-producers isolated from bovine rumen belonging to the genus *Mannheimia*, specifically the species *Mannheimia succiniciproducens*, and strain *Mannheimia succiniciproducens* MBEL55E and its variants.

Exemplary host yeast strains, as described in WO 2013/112939, can be genetically modified yeast cells that include modifications to enhance succinate production and/or export, and, in some aspects, selected for succinate tolerance. Accordingly, in some embodiments, the high succinate producing host cell can be a yeast cell comprising a genetic modification to enhance succinate production and/or export, and in some aspects be tolerant of increased intracellular and/or extracellular succinate concentrations. In some embodiments, the genetically modified yeast cell belongs to a genus selected from the group consisting of *Issatchenkia, Candida, Pichia, Zygosaccharomyces, Kluyveromyces, Saccharomyces, Debaryomyces*, and *Saccharomycopsis*. Thus, in some embodiments, the genetically modified yeast cell is a species selected from the group consisting of *Issatchenkia orientalis, Candida lambica, Candida sorboxylosa, Candida zemplinina, Candida geochares, Pichia membranifaciens, Zygosaccharomyces kombuchaensis, Candida sorbosivorans, Kluyveromyces marxianus, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii, Candidan Etchellsii, Kluyveromyces lactis, Pichia jadinii, Pichia anomala, Saccharomycopsis crataegensis*, and *Pichia jadinii*. In some embodiments, the genetically modified yeast cell is from the *Pichia fermentans/Issatchenkia orientalis* clade.

Depending on the adipate, 6-ACA, HMDA or caprolactam biosynthetic, methanol metabolic and/or FAP constituents of a selected host microbial organism, the NNOMOs provided herein will include at least one exogenously expressed adipate, 6-ACA, HMDA or caprolactam, formaldehyde assimilation, formate reutilization, and/or MMP-encoding nucleic acid and up to all encoding nucleic acids for one or more adipate, 6-ACA, HMDA or caprolactam biosynthetic pathways, FAPs, FRPs and/or MMPs. For example, adipate, G-ACA, HMDA or caprolactam biosynthesis can be established in a host deficient in a pathway enzyme or protein through exogenous expression of the corresponding encoding nucleic acid. In a host deficient in all enzymes or proteins of an adipate, 6-ACA, HMDA or caprolactam pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of adipate, 6-ACA, HMDA or caprolactam can be included. The same holds true for the MMPs and FAPs provided herein.

Given the teachings and guidance provided herein, those skilled in the art will understand that the number of encoding nucleic acids to introduce in an expressible form will, at least, parallel the AdiP, 6-ACAP, HMDAP or CapP, FAP, FRP and MMP deficiencies of the selected host microbial organism. Therefore, a NNOMO provided herein can have one, two, three, four, five, six, seven, eight, nine, or up to all nucleic acids encoding the enzymes or proteins constituting a MMP, FAP, FRP and/or adipate, 6-ACA, HMDA or caprolactam biosynthetic pathway disclosed herein. In some embodiments, the NNOMOs also can include other genetic modifications that facilitate or optimize adipate, 6-ACA, HMDA or caprolactam biosynthesis, formaldehyde assimilation, formate reutilization and/or methanol metabolism or that confer other useful functions onto the host microbial organism. One such other functionality can include, for example, augmentation of the synthesis of one or more of the adipate, 6-ACA, HMDA or caprolactam pathway precursors.

Generally, a host microbial organism is selected such that it produces the precursor of an adipate, 6-ACA, HMDA or caprolactam pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of an adipate, 6-ACA, HMDA or caprolactam pathway, either alone or in combination with a MMP, FAP and/or FRP.

In some embodiments, a NNOMO provided herein is generated from a host that contains the enzymatic capability to synthesize adipate, 6-ACA, HMDA or caprolactam, assimilate formaldehyde, reutilize formate and/or metabolize methanol. In this specific embodiment it can be useful to increase the synthesis or accumulation of an Adipate, 6-ACA, HMDA or caprolactam pathway product, FAP product, FRP product and/or MMP product (e.g., reducing equivalents and/or formaldehyde) to, for example, drive adipate, 6-ACA, HMDA or caprolactam pathway reactions toward adipate, 6-ACA, HMDA or caprolactam production. Increased synthesis or accumulation can be accomplished by, for example, overexpression of nucleic acids encoding one or more of the above-described AdiP, 6-ACAP, HMDAP or CapP, FAP, FRP and/or MMP enzymes or proteins. Over expression the enzyme(s) and/or protein(s) of the AdiP, 6-ACAP, HMDAP, CapP, FAP, FRP and/or MMP can occur, for example, through exogenous expression of the endogenous gene(s), or through exogenous expression of the heterologous gene(s). Therefore, naturally occurring organisms can be readily generated to be NNOMOs, for example, producing adipate, 6-ACA, HMDA or caprolactam through overexpression of one, two, three, four, five, six, seven, eight, up to all nucleic acids encoding adipate, 6-ACA, HMDA or caprolactam biosynthetic pathway, and/or MMP enzymes or proteins. Naturally occurring organisms can also be readily generated to be NNOMOs, for example, assimilating formaldehyde, through overexpression of one, two, three, four, five, six, seven, eight, up to all nucleic acids encoding FAP, FRP and/or MMP enzymes or proteins. In addition, a non-naturally occurring organism can be generated by mutagenesis of an endogenous gene that results in an increase in activity of an enzyme in the adipate, 6-ACA, HMDA or caprolactam, formaldehyde assimilation, formate reutilization, and/or MMP biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a NNOMO.

It is understood that, in methods provided herein, any of the one or more exogenous nucleic acids can be introduced into a microbial organism to produce a NNOMO provided herein. The nucleic acids can be introduced so as to confer, for example, an Adipate, 6-ACA, HMDA or caprolactam biosynthetic, formaldehyde assimilation, formate reutilization and/or MMP onto the microbial organism. Alternatively, encoding nucleic acids can be introduced to produce an intermediate microbial organism having the biosynthetic capability to catalyze some of the required reactions to confer adipate, 6-ACA, HMDA or caprolactam biosynthetic, formaldehyde assimilation, formate reutilization and/or methanol metabolic capability. For example, a NNOMO having an Adipate, 6-ACA, HMDA or caprolactam biosynthetic pathway, FAP, FRP and/or MMP can comprise at least two exogenous nucleic acids encoding desired enzymes or proteins. Thus, it is understood that any combination of two or more enzymes or proteins of a biosynthetic pathway, FAP, FRP and/or methanol metabolic pathway can be included in a NNOMO provided herein. Similarly, it is understood that any combination of three or more enzymes or proteins of a biosynthetic pathway, FAP, FRP, and/or metabolic pathway can be included in a NNOMO provided herein, as desired, so long as the combination of enzymes and/or proteins of the desired biosynthetic pathway, FAP, FRP and/or metabolic pathway results in production of the corresponding desired product. Similarly, any combination of four or more enzymes or proteins of a biosynthetic pathway, FAP, FRP and/or MMP as disclosed herein can be included in a NNOMO provided herein, as desired, so long as the combination of enzymes or proteins of the desired biosynthetic, assimilation, reutilization and/or metabolic pathway results in production of the corresponding desired product. In specific embodiments, the biosynthetic pathway is an Adipate, 6-aminocaproate, HMDA or caprolactam biosynthetic pathway.

In addition to the metabolism of methanol, assimilation of formaldehyde, reutilization of formate and biosynthesis of adipate, 6-ACA, HMDA or caprolactam, as described herein, the NNOMOs and methods provided also can be utilized in various combinations with each other and with other microbial organisms and methods well known in the art to achieve product biosynthesis by other routes. For example, one alternative to produce adipate, 6-ACA, HMDA or caprolactam, other than use of the adipate, 6-ACA, HMDA or caprolactam producers is through addition of another microbial organism capable of converting an adipate, 6-ACA, HMDA or caprolactam pathway intermediate to adipate, G-ACA, HMDA or caprolactam. One such procedure includes, for example, the fermentation of a microbial organism that produces an adipate, 6-ACA, HMDA or caprolactam pathway intermediate. The adipate, 6-ACA, HMDA or caprolactam pathway intermediate can then be used as a substrate for a second microbial organism that converts the adipate, 6-ACA, HMDA or caprolactam pathway intermediate to adipate, 6-ACA, HMDA or caprolactam. The adipate, 6-ACA, HMDA or caprolactam pathway intermediate can be added directly to another culture of the second organism or the original culture of the adipate, 6-ACA, HMDA or caprolactam pathway intermediate producers can be depleted of these microbial organisms by, for example, cell separation, and then subsequent addition of the second organism to the fermentation broth can be utilized to produce the final product without intermediate purification steps. The same holds true for the MMPs, FAPs and FRPs provided herein.

In other embodiments, the NNOMOs and methods provided herein can be assembled in a wide variety of subpathways to achieve biosynthesis of, for example, adipate, 6-ACA, HMDA or caprolactam. In these embodiments, biosynthetic pathways for a desired product can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of adipate, 6-ACA, HMDA or caprolactam can be accomplished by constructing a microbial organism that contains biosynthetic pathways for conversion of one pathway intermediate to another pathway intermediate or the product. Alternatively, adipate, 6-ACA, HMDA or caprolactam also can be biosynthetically produced from microbial organisms through co-culture or co-fermentation using two organisms in the same vessel, where the first microbial organism produces an adipate, 6-ACA, HMDA or caprolactam intermediate and the second microbial organism converts the intermediate to adipate, 6-ACA, HMDA or caprolactam. The same holds true for the MMPs, FAPs and FRPs provided herein.

Given the teachings and guidance provided herein, those skilled in the art will understand that a wide variety of combinations and permutations exist for the NNOMOs and methods together with other microbial organisms, with the co-culture of other NNOMOs having subpathways and with combinations of other chemical and/or biochemical procedures well known in the art to produce adipate, 6-ACA, HMDA or caprolactam and/or metabolize methanol.

Sources of encoding nucleic acids for an adipate, 6-ACA, HMDA or caprolactam, formaldehyde assimilation, formate reutilization or methanol metabolic pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonian Eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum*, marine gamma proteobacterium, butyrate producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum M, Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, the sources of encoding nucleic acids for an AdiPE, 6-ACAPE, HMDAPE, or CapPE include *Achromobacter denitrificans, Acidaminococcus fermentans, Acinetobacter baylyi, Acinetobacter calcoaceticus, Acinetobacter* sp. ADP1, *Acinetobacter* sp. Strain M-1, *Agrobacterium tumefaciens, Alkaliphilus metalliredigenes* QYF, *Archaeoglobus fulgidus* DSM 4304, *Bacillus cereus, Bacillus subtilis, Bos Taurus, Clostridium acetobutylicum, Clostridium beijerinckii, Clostridium difficile* 630, *Clostridium kluyveri, Clostridium saccharoperbutylacetonicum, Corynebacterium glutamicum* ATCC 13032, *Escherichia coli, Escherichia coli* K12, *Euglena gracilis, Geobacillus stearothermophilus, Haloarcula marismortui* ATCC 43049, *Halobacterium salinarum, Helicobacter pylori, Homo sapiens, Leuconostoc mesenteroides, Metallosphaera sedula, Mus musculus, Penicillium chrysogenum, Porphyromonas gingivalis, Pseudomonas aeruginosa, Pseudomonas chlororaphis, Pseudomonas fluorescens, Pseudomonas knackmussii* (B13), *Pseudomonas putida, Pseudomonas* sp, *Pyrobaculum aerophilum* str. IM2, *Ralstonian Eutropha, Rattus norvegicus, Rhodobacter sphaeroides, Saccharomyces cerevisiae, Saccharomyces kluyveri, Salmonella typhimurium, Streptomyces clavuligenus, Streptomyces coelicolor, Streptomyces* sp. 2065, *Sulfolobus acidocaldarius, Sulfolobus solfataricus, Sulfolobus solfataricus, Sulfolobus tokodaii, Sus scrofa, Thermoanaerobacter* sp. X514, *Thermoanaerobacter tengcongensis* MB4, *Thermotoga maritime, Thermotoga maritime, Treponema denticola*, and *Zoogloea ramigera*, as well as other exemplary species disclosed herein or available as source organisms for corresponding genes.

In certain embodiments, sources of encoding nucleic acids for a MMPE include, *Acinetobacter baumannii* Naval- 82, *Actinobacillus succinogenes* 130Z, *Allochromatium vinosum* DSM 180, *Azotobacter vinelandii* DJ, *Bacillus alcalophilus* ATCC 27647, *Bacillus azotoformans* LMG 9581, *Bacillus coagulans* 36D1, *Bacillus methanolicus* MGA3, *Bacillus methanolicus* PB1, *Bacillus methanolicus* PB-1, *Bacillus smithii*, *Bacillus subtilis*, *Burkholderia cenocepacia*, *Burkholderia cepacia*, *Burkholderia multivorans*, *Burkholderia pyrrocinia*, *Burkholderia stabilis*, *Burkholderia thailandensis* E264, *Burkholderiales* bacterium Joshi_001, *Campylobacter jejuni*, *Candida boidinii*, *Candida methylica*, *Carboxydothermus hydrogenoformans*, *Carboxydothermus hydrogenoformans* Z-2901, *Caulobacter* sp. AP07, *Clostridium acetobutylicum* ATCC 824, *Clostridium acidurici*, *Clostridium carboxidivorans* P7, *Clostridium cellulovorans* 743B, *Clostridium kluyveri*, *Clostridium kluyveri* DSM 555, *Clostridium ljungdahlii*, *Clostridium ljungdahlii* DSM 13528, *Clostridium pasteurianum*, *Clostridium pasteurianum* DSM 525, *Clostridium perfringens*, *Clostridium perfringens* ATCC 13124, *Clostridium perfringens* str. 13, *Clostridium phytofermentans* ISDg, *Corynebacterium glutamicum* ATCC 14067, *Corynebacterium glutamicum* R, *Corynebacterium* sp. U-96, *Corynebacterium variabile*, *Cupriavidus necator* N-1, *Desulfitobacterium hafniense*, *Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. 'Miyazaki F', *Escherichia coli*, *Escherichia coli* K-12, *Escherichia coli* K-12 MG1655, *Flavobacterium frigoris*, *Geobacillus* sp. Y4.1MC1, *Geobacillus themodenitrificans* NG80-2, *Geobacter bemidjiensis* Bem, *Geobacter sulfurreducens*, *Geobacter sulfurreducens* PCA, *Helicobacter pylori*, *Homo sapiens*, human gut metagenome, *Hydrogenobacter thermophilus*, *Hyphomicrobium denitrificans* ATCC 51888, *Hyphomicrobium zavarzinii*, *Klebsiella pneumoniae* subsp. *pneumoniae* MGH 78578, *Lysinibacillus fusiformis*, *Lysinibacillus sphaericus*, *Mesorhizobium loti* MAFF303099, *Methanosarcina acetivorans*, *Methanosarcina acetivorans* C2A, *Methanosarcina barkeri*, *Methanosarcina mazei* Tuc01, *Methylobacter marinus*, *Methylobacterium extorquens*, *Methylobacterium extorquens* AM1, *Methylococcus capsulatis*, *Moorella thermoacetica*, *Mycobacterium smegmatis*, *Nitrosopumilus salaria* BD31, *Nitrososphaera gargensis* Ga9.2, *Nostoc* sp. PCC 7120, *Paenibacillus peoriae* KCTC 3763, *Paracoccus denitrificans*, *Photobacterium profundum* 3TCK, *Pichia pastoris*, *Picrophilus torridus* DSM9790, *Pseudomonas aeruginosa* PA01, *Pseudomonas putida*, *Pseudomonas syringae* pv. *syringae* B728a, *Ralstonian Eutropha*, *Ralstonian Eutropha* H16, *Rhodobacter capsulatus*, *Rhodobacter sphaeroides*, *Rhodobacter sphaeroides* ATCC 17025, *Rhodopseudomonas palustris*, *Rhodopseudomonas palustris* CGA009, *Rhodopseudomonas palustris* DX-1, *Rhodospirillum rubrum*, *Saccharomyces cerevisiae*, *Saccharomyces cerevisiae* S288c, *Salmonellan Enterica* subsp. *enterica* serovar Typhimurium str. LT2, *Sebaldella termitidis* ATCC 33386, *Shewanella oneidensis* MR-1, *Sinorhizobium meliloti* 1021, *Sulfolobus acidocalarius*, *Sulfolobus solfataricus* P-2, *Synechocystis* str. PCC 6803, *Syntrophobacter fumaroxidans*, *Thauera aromatics*, *Thermoanaerobacter* sp. X514, *Thermococcus litoralis*, *Thermoplasma acidophilum*, *Thiocapsa roseopersicina*, *Vibrio harveyi* ATCC BAA-1116, *Xanthobacter autotrophicus* Py2, and *Zea mays*, as well as other exemplary species disclosed herein or available as source organisms for corresponding genes.

In certain embodiments, sources of encoding nucleic acids for a FAPE include *Aminomonas aminovorus*, *Bacillus methanolicus* MGA3, *Bacillus methanolicus* PB1, *Bacillus subtilis*, *Candida boidinii*, *Citrobacter freundii*, *Escherichia coli*, *Geobacillus* sp. GHH01, *Geobacillus* sp. M10EXG, *Geobacillus* sp. Y4.1MC1, *Klebsiella pneumonia*, *Methylobacillus flagellates*, *Methylobacillus flagellatus* KT, *Methylococcus capsulatas*, *Methylomicrobium album* BG8, *Methylomonas aminofaciens*, *Methylovorus glucosetrophus* SIP3-4, *Methylovorus* sp. MP688, *Mycobacter* sp. strain JC1 DSM 3803, *Mycobacterium gastri*, *Ogataea angusta*, *Ogataea parapolymorpha* DL-1 (*Hansenula polymorphs* DL-1), *Pyrococcus abyssi*, *Pyrococcus furiosus*, *Pyrococcus horikoshii* OT3, *Saccharomyces cerevisiae* S288c, and *Thermococcus kodakaraensis*, as well as other exemplary species disclosed herein or available as source organisms for corresponding genes.

In certain embodiments, sources of encoding nucleic acids for a FRPE include *Acinetobacter baylyi*, *Acinetobacter calcoaceticus*, *Acinetobacter* sp. Strain M-1, *Archaeglubus fulgidus*, *Archaeoglobus fulgidus* DSM 4304, *Arthrobacter globiformis*, *Bacillus methanolicus* MGA3, *Bacillus methanolicus* PB1, *Bacillus selenitireducens* MLS10, *Bacillus subtilis*, *Burkholderia stabilis*, *Campylobacter jejuni*, *Candida albicans*, *Candida boidinii*, *Candida methylica*, *Carboxydothermus hydrogenoformans*, *Chlamydomonas reinhardtii*, *Citrobacter koseri* ATCC BAA-895, *Clostridium acetobutylicum*, *Clostridium acetobutylicum* ATCC 824, *Clostridium acidurici*, *Clostridium beijerinckii*, *Clostridium carboxidivorans* P7, *Clostridium cellulovorans* 743B, *Clostridium kluyveri*, *Clostridium kluyveri* DSM 555, *Clostridium ljungdahlii* DSM, *Clostridium ljungdahlii* DSM 13528, *Clostridium pasteurianum*, *Clostridium perfringens*, *Clostridium phytofermentans* ISDg, *Clostridium saccharoperbutylacetonicum*, *Corynebacterium glutamicum*, *Corynebacterium* sp., *Cryptosporidium parvum* Iowa II, *Cyanobium* PCC7001, *Desulfatibacillum alkenivorans* AK-01, *Desulfitobacterium hafniense*, *Desulfovibrio africanus*, *Desulfovibrio fructosovorans* JJ, *Dictyostelium discoideum* AX4, *Escherichia coli*, *Euglena gracilis*, *Fusobacterium nucleatum*, *Geobacter sulfurreducens* PCA, *Haloarcula marismortui* ATCC 43049, *Helicobacter pylori*, *Homo sapiens*, *Klebsiella pneumoniae*, *Lactobacillus acidophilus*, *Lactobacillus brevis* ATCC 367, *Lactococcus lactis*, *Leuconostoc mesenteroides*, *Metallosphaera sedula*, *Metarhizium acridum* CQMa 102, *Methanosarcina acetivorans*, *Methanothermobacter thermautotrophicus*, *Methylobacterium extorquens*, *Moorella thermoacetica*, *Mus musculus*, *Mycobacterium avium* subsp. *paratuberculosis* K-10, *Mycobacterium bovis* BCG, *Mycobacterium marinum* M, *Mycobacterium smegmatis* MC2 155, *Nocardia farcinica* IFM 10152, *Nocardia iowensis* (sp. NRRL 5646), *Oxalobacter formigenes*, *Penicillium chrysogenum*, *Perkinsus marinus* ATCC 50983, *Porphyromonas gingivalis*, *Porphyromonas gingivalis* W83, *Pseudomonas putida*, *Pseudomonas* sp, *Pyrobaculum aerophilum* str. IM2, *Ralstonian Eutropha*, *Ralstonian Eutropha* H16, *Rattus norvegicus*, *Rhizopus oryzae*, *Rhodococcus opacus* B4, *Saccharomyces cerevisiae*, *Saccharomyces cerevisiae* S288c, *Salmonellan Enterica*, *Salmonellan Enterica* subsp. *enterica* serovar Typhimurium str. LT2, *Salmonellan Enterica Typhimurium*, *Salmonella typhimurium*, *Schizosaccharomyces pombe*, *Streptococcus mutans*, *Streptomyces griseus* subsp. *griseus* NBRC 13350, *Sulfolobus acidocaldarius*, *Sulfolobus solfataricus*, *Sulfolobus tokodaii*, *Syntrophobacter fumaroxidans*, *Thermoanaerobacter tengcongensis* MB4, *Trichomonas vaginalis* G3, *Trypanosoma brucei*, and *Tsukamurella paurometabola* DSM 20162, as well as other exemplary species disclosed herein or available as source organisms for corresponding genes.

However, with the complete genome sequence available for now more than 550 species (with more than half of these available on public databases such as the NCBI), including 395 microorganism genomes and a variety of yeast, fungi, plant, and mammalian genomes, the identification of genes encoding the requisite adipate, 6-ACA, HMDA or caprolactam biosynthetic pathway, methanol metabolic, formaldehyde assimilation and/or formate reutilization activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of adipate, G-ACA, HMDA or caprolactam, metabolism of methanol, assimilation of formaldehyde and/or reutilization or formate described herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative adipate, 6-ACA, HMDA or caprolactam biosynthetic, formaldehyde assimilation, formate reutilization, and/or methanol metabolic pathway exists in an unrelated species, adipate, 6-ACA, HMDA or caprolactam biosynthesis, formaldehyde assimilation, formate reutilization, and/or methanol metabolism can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods provided herein can be applied to all microbial organisms using the cognate metabolic alterations to those exemplified herein to construct a microbial organism in a species of interest that will synthesize adipate, 6-ACA, HMDA or caprolactam, assimilate formaldehyde, reutilize formate, and/or metabolize methanol.

A nucleic acid molecule encoding an AdiP, 6-ACAP, HMDAP or CapP enzyme or protein can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity to a nucleic acid described herein.

Stringent hybridization refers to conditions under which hybridized polynucleotides are stable. As known to those of skill in the art, the stability of hybridized polynucleotides is reflected in the melting temperature (Tm) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5×Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding an AdiP, 6-ACAP, HMDAP or CapP enzyme or protein can have at least a certain sequence identity to a nucleotide sequence disclosed herein. According, in some aspects of the invention, a nucleic acid molecule encoding an AdiP, 6-ACAP, HMDAP or CapP enzyme or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Methods for constructing and testing the expression levels of a non-naturally occurring adipate-, 6-ACA-, HMDA- or caprolactam-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for metabolism of methanol, assimilation of formaldehyde, reutilization of formate, and/or production of adipate, 6-ACA, HMDA or caprolactam can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more adipate, 6-ACA, HMDA or caprolactam biosynthetic, formaldehyde assimilation, formate reutilization, and/or methanol metabolic pathway-encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Suitable purification and/or assays to test, e.g., for the production of adipate, G-ACA, HMDA or caprolactam can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. Exemplary assays for the activity of methanol dehydrogenase (FIG. 1, step J) are provided in the Example I.

The adipate, 6-ACA, HMDA or caprolactam can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the NNOMOs described herein can be cultured to produce and/or secrete the biosynthetic products, or intermediates thereof. For example, the adipate, 6-ACA, HMDA or caprolactam producers can be cultured for the biosynthetic production of adipate, 6-ACA, HMDA or caprolactam. Accordingly, in some embodiments, provided is culture medium having an adipate, 6-ACA, HMDA or caprolactam, formaldehyde assimilation, formate reutilization and/or methanol metabolic pathway intermediate described herein. In some aspects, the culture medium can also be separated from the NNOMOs provided herein that produced the adipate, 6-ACA, HMDA or caprolactam, formaldehyde assimilation, formate reutilization and/or methanol metabolic pathway intermediate. Methods for separating a microbial organism from culture medium are well known in the art. Exemplary methods include filtration, flocculation, precipitation, centrifugation, sedimentation, and the like.

In certain embodiments, for example, for the production of the production of adipate, 6-ACA, HMDA or caprolactam, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in U.S. Publ. No. 2009/0047719. Fermentations can be performed in a batch, fed-batch or continuous manner, as disclosed herein. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high, 6-ACA, HMDA or caprolactam yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the NNOMO. Such sources include, for example, sugars such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose. In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol. In certain embodiments, methanol is used alone as the sole source of carbon or in combination with other carbon sources described herein or known in the art. In a specific embodiment, the methanol is the only (sole) carbon source. In one embodiment, the carbon source is chemoelectro-generated carbon (see, e.g., Liao et al. (2012) Science 335:1596). In one embodiment, the chemoelectro-generated carbon is methanol. In one embodiment, the chemoelectro-generated carbon is formate. In one embodiment, the chemo-electro-generated carbon is formate and methanol. In one embodiment, the carbon source is a carbohydrate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. In some embodiments, the carbon source is a sugar-containing biomass, methanol and a carbohydrate. Other sources of carbohydrate include, for example, renewable feedstocks and biomass. Exemplary types of biomasses that can be used as feedstocks in the methods provided herein include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of adipate, 6-ACA, HMDA or caprolactam, and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol. In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in the FAPs provided herein. In one embodiment, the carbon source is methanol or formate. In other embodiments, formate is used as a carbon source in the FAPs provided herein. In specific embodiments, methanol is used as a carbon source in the MMPs provided herein, either alone or in combination with the product pathways provided herein. In one embodiment, the carbon source is methanol. In another embodiment, the carbon source is formate.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

Given the teachings and guidance provided herein, those skilled in the art will understand that a NNOMO can be produced that secretes the biosynthesized compounds when grown on a carbon source such as a carbohydrate. Such compounds include, for example, adipate, 6-ACA, HMDA or caprolactam and any of the intermediate metabolites in the adipate, 6-ACA, HMDA or caprolactam pathway. All that is required is to engineer in one or more of the required enzyme or protein activities to achieve biosynthesis of the desired compound or intermediate including, for example, inclusion of some or all of the adipate, G-ACA, HMDA or caprolactam biosynthetic pathways. Accordingly, provided herein is a NNOMO that produces and/or secretes adipate, 6-ACA, HMDA or caprolactam when grown on a carbohydrate or other carbon source and produces and/or secretes any of the intermediate metabolites shown in the adipate, 6-ACA, HMDA or caprolactam pathway when grown on a carbohydrate or other carbon source. The adipate-, 6-ACA-, HMDA- or caprolactam-producing microbial organisms provided herein can initiate synthesis from an intermediate. The same holds true for intermediates in the formaldehyde assimilation, formate reutilization, and methanol metabolic pathways.

The NNOMOs provided herein are constructed using methods well known in the art as exemplified herein to exogenously express at least one nucleic acid encoding an adipate, 6-ACA, HMDA or caprolactam biosynthetic pathway and/or MMP enzyme or protein in sufficient amounts to produce adipate, 6-ACA, HMDA or caprolactam. It is understood that the microbial organisms are cultured under conditions sufficient to produce adipate, 6-ACA, HMDA or caprolactam. Following the teachings and guidance provided herein, the NNOMOs can achieve biosynthesis of adipate, 6-ACA, HMDA or caprolactam, resulting in intracellular concentrations between about 0.1-500 mM or more. Generally, the intracellular concentration of adipate, 6-ACA, HMDA or caprolactam is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the NNOMOs provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. Publ. No. 2009/0047719. Any of these conditions can be employed with the NNOMOs as well as other anaerobic conditions well known in the art. Under such anaerobic or substantially anaerobic conditions, the adipate, 6-ACA, HMDA or caprolactam producers can synthesize adipate, G-ACA, HMDA or caprolactam at intracellular concentrations of 5-100 mM or more as well as all other concentrations exemplified herein. It is understood that, even though the above description refers to intracellular concentrations, adipate, 6-ACA, HMDA or caprolactam can produce adipate, 6-ACA, HMDA or caprolactam intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, N2/CO2 mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of adipate, 6-ACA, HMDA or caprolactam can include the addition of an osmoprotectant to the culturing conditions. In certain embodiments, the NNOMOs provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropirnate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products provided herein can be obtained under anaerobic or substantially anaerobic culture conditions.

As described herein, one exemplary growth condition for achieving biosynthesis of adipate, 6-ACA, HMDA or caprolactam, as well as other pathway intermediates, includes anaerobic culture or fermentation conditions. In certain embodiments, the NNOMOs provided can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of adipate, 6-ACA, HMDA or caprolactam. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of adipate, 6-ACA, HMDA or caprolactam. Generally, and as with non-continuous culture procedures, the continuous and/or near-continuous production of adipate, 6-ACA, HMDA or caprolactam will include culturing a non-naturally occurring adipate, 6-ACA, HMDA or caprolactam producing organism provided herein in sufficient nutrients and medium to sustain and/or nearly sustain growth in an exponential phase. Continuous culture under such conditions can be included, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms provided can be cultured for hours, if suitable for a particular application. It is to be understood that the continuous and/or near-continuous culture conditions also can include all time intervals in between these exemplary periods. It is further understood that the time of culturing the microbial organism provided herein is for a sufficient period of time to produce a sufficient amount of product for a desired purpose.

Fermentation procedures are well known in the art. Briefly, fermentation for the biosynthetic production of adipate, 6-ACA, HMDA or caprolactam can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the adipate, 6-ACA, HMDA or caprolactam producers for continuous production of substantial quantities of adipate, 6-ACA, HMDA or caprolactam, the adipate, 6-ACA, HMDA or caprolactam producers also can be, for example, simultaneously subjected to chemical synthesis procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. Publ. Nos. 2002/0012939, 2003/0224363, 2004/0029149, 2004/0072723, 2003/0059792, 2002/0168654 and 2004/0009466, and U.S. Pat. No. 7,127,379). Modeling analysis allows reliable predictions of the effects on cell growth of shifting the metabolism towards more efficient production of adipate, 6-ACA, HMDA or caprolactam.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Therefore, this computational methodology can be used to either identify alternative pathways that lead to biosynthesis of a desired product or used in connection with the NNOMOs for further optimization of biosynthesis of a desired product. The metabolic modeling and simulation methods referred to herein as OptKnock are described in, for example, U.S. Publ. No. 2002/0168654, International Patent Application No. PCT/US02/00660, and U.S. Publ. No. 2009/0047719.

Another computational method for identifying and designing metabolic alterations favoring biosynthetic production of a product is a metabolic modeling and simulation system termed SimPheny®. This computational method and system is described in, for example, U.S. Publ. No. 2003/0233218, and International Patent Application No. PCT/US03/18838. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. An in silico stoichiometric model of *E. coli* metabolism can be employed to identify essential genes for metabolic pathways as exemplified previously and described in, for example, U.S. Publ. Nos. 2002/0012939, 2003/0224363, 2004/0029149, 2004/0072723, 2003/0059792, 2002/0168654 and 2004/0009466, and in U.S. Pat. No. 7,127,379.

Given the teachings and guidance provided herein, those skilled in the art will be able to apply various computational frameworks for metabolic modeling and simulation to design and implement biosynthesis of a desired compound in host microbial organisms.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations.

The methods exemplified herein allow the construction of cells and organisms that biosynthetically produce a desired product, including the obligatory coupling of production of a target biochemical product to growth of the cell or organism engineered to harbor the identified genetic alterations. The set of metabolic modifications can include, for example, addition of one or more biosynthetic pathway enzymes and/or functional disruption of one or more metabolic reactions including, for example, disruption by gene deletion.

As disclosed herein, a nucleic acid encoding a desired activity of an AdiP, 6-ACAP, HMDAP or CapP, FAP, FRP and/or MMP can be introduced into a host organism. In some cases, it can be desirable to modify an activity of an AdiP, 6-ACAP, HMDAP, CapP, FAP, FRP, or MMP enzyme or protein to increase production of adipate, 6-ACA, HMDA or caprolactam; formaldehyde, and/or reducing equivalents. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >10$^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of an AdiP, 6-ACAP, HMDAP or CapP and/or a MMP enzyme or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA) (Fujii et al., *Nucleic Acids Res.* 32:e145 (2004); and Fujii et al., *Nat. Protocols* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP) (Zhao et al., *Nat. Biotechnol.* 16:258-261 (1998)) and Random Priming Recombination (RPR) (Shao et al., *Nucleic Acids Res.* 26:681-683 (1998)).

Additional methods include Heteroduplex Recombination (Volkov et al, *Nucleic Acids Res.* 27:e18 (1999); and Volkov et al., *Methods Enzymol.* 328:456-463 (2000)); Random Chimeragenesis on Transient Templates (RACHITT) (Coco et al., *Nat. Biotechnol.* 19:354-359 (2001)); Recombined Extension on Truncated templates (RETT) (Lee et al., *J. Molec. Catalysis* 26:119-129 (2003)); Degenerate Oligonucleotide Gene Shuffling (DOGS) (Bergquist and Gibbs, *Methods Mol. Biol.* 352:191-204 (2007) and Bergquist et al., *Biomol. Eng.* 22:63-72 (2005); Gibbs et al., *Gene* 271:13-20 (2001)); Incremental Truncation for the Creation of Hybrid Enzymes (ITCHY) (Ostermeier et al., *Proc. Natl. Acad. Sci. U.S.A.* 96:3562-3567 (1999) and Ostermeier et al., *Nat. Biotechnol.* 17:1205-1209 (1999)); Thio-Incremental Truncation for the Creation of Hybrid Enzymes (THIO-ITCHY) (Lutz et al., *Nucleic Acids Res.* 29:E16 (2001)); SCRATCHY (Lutz et al., *Proc. Natl. Acad. Sci. U.S.A.* 98:11248-11253 (2001)); Random Drift Mutagenesis (Bergquist et al., *Biomol. Eng.* 22:63-72 (2005)); Sequence Saturation Mutagenesis (SeSaM) (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling (Ness et al., *Nat. Biotechnol.* 20:1251-1255 (2002)); Nucleotide Exchange and Excision Technology NexT (Muller et al., *Nucleic Acids Res.* 33:e117 (2005)).

Further methods include Sequence Homology-Independent Protein Recombination (SHIPREC) (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); and Combinatorial Multiple Cassette Mutagenesis (CMCM) (Reetz et al., *Angew. Chem. Int. Ed Engl.* 40:3589-3591 (2001)); Look-Through Mutagenesis (LTM) (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation); in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM) (Reetz et al., *Nat. Protocols* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Adipate, 6-ACA, HMDA or caprolactam can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of adipate, 6-ACA, HMDA or caprolactam can be produced.

Therefore, additionally provided is a method for producing adipate, 6-ACA, HMDA or caprolactam that includes culturing a non-naturally occurring microbial organism having one or more gene disruptions, as disclosed herein. The disruptions can occur in one or more genes encoding an enzyme that increases production of adipate, 6-ACA, HMDA or caprolactam, including optionally coupling adipate, 6-ACA, HMDA or caprolactam production to growth of the microorganism when the gene disruption reduces or eliminates an activity of the enzyme. For example, the disruptions can confer stable growth-coupled production of adipate, 6-ACA, HMDA or caprolactam onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of adipate, 6-ACA, HMDA or caprolactam, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of adipate, 6-ACA, HMDA or caprolactam production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarran Et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

There are a number of developed technologies for carrying out adaptive evolution. Exemplary methods are disclosed herein. In some embodiments, optimization of a NNOMOs provided herein includes utilizing adaptive evolution techniques to increase adipate, 6-ACA, HMDA or caprolactam production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad. Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

An alternative method to adaptively evolve a production strain is Evolugator™, which is a continuous culture device developed by Evolugate, LLC (Gainesville, Fla.) and exhibits significant time and effort savings over traditional evolution techniques (de Crecy et al., *Appl. Microbiol. Biotechnol.* 77:489-496 (2007)).

In one aspect, provided herein is a non-naturally occurring microbial organism (NNOMO) comprising: (A) a methanol metabolic pathway (MMP), wherein said organism comprises at least one exogenous nucleic acid encoding a MMP enzyme (MMPE) expressed in a sufficient amount to enhance the availability of reducing equivalents in the presence of methanol, wherein said MMP comprises: (i) a methanol dehydrogenase (EM9); (ii) an EM9 and a formaldehyde activating enzyme (EM10); or (iii) a methanol methyltransferase (EM1) and a methylenetetrahydrofolate reductase (EM2); and (B) an AdiP, wherein said organism comprises at least one exogenous nucleic acid encoding an AdiPE expressed in a sufficient amount to produce adipate, wherein said AdiP comprises (i) a 3-oxoadipyl-CoA thiolase (EA1); (ii) an EA2; (iii) an EA3; (iv) an EA4; and (v) an EA11A, an EA11B, an EA11C or an EA11D. In one embodiment, the AdiP comprises an EA11A. In another embodiment, the AdiP comprises an EA11B. In another embodiment, the AdiP comprises an EA11C. In another embodiment, the AdiP comprises an EA11D. In one embodiment, the organism comprises two, three, four or five exogenous nucleic acids, each encoding an AdiPE. In another embodiment, the at least one exogenous nucleic acid encoding an AdiPE is a heterologous nucleic acid.

In another aspect, provided herein is a NNOMO comprising: (A) a MMP, wherein said organism comprises at least one exogenous nucleic acid encoding a MMPE expressed in a sufficient amount to enhance the availability of reducing equivalents in the presence of methanol, wherein said MMP comprises: (i) an EM9; (ii) an EM9 and an EM10; or (iii) an EM1 and an EM2; and (B) a 6-ACAP, wherein said organism comprises at least one exogenous nucleic acid encoding a 6-ACAPE expressed in a sufficient amount to produce G-ACA, wherein said 6-ACAP comprises (i) an EA1; (ii) an EA2; (iii) an EA3; (iv) an EA4; (v) EA5; and (vi) an EA6A or an EA6B. In one embodiment, the 6-ACAP comprises an EA6A. In another embodiment, the 6-ACAP comprises an EA6B. In another embodiment, the organism comprises two, three, four, five or six exogenous nucleic acids, each encoding a 6-ACAPE. In one embodiment, the at least one exogenous nucleic acid encoding a 6-ACAPE is a heterologous nucleic acid. In another aspect, provided herein is a NNOMO comprising: (A) a MMP, wherein said organism comprises at least one exogenous nucleic acid encoding a MMPE expressed in a sufficient amount to enhance the availability of reducing equivalents in the presence of methanol, wherein said MMP comprises: (i) an EM9; (ii) an EM9 and an EM10; or (iii) an EM1 and an EM2; and (B) a HMDAP, wherein said organism comprises at least one exogenous nucleic acid encoding a HMDAPE expressed in a sufficient amount to produce HMDA, wherein said HMDAP comprises (i) an EA1; (ii) a EA2; (iii) an EA3; (iv) an EA4; (v) an EA5; (vi) a EA6A or an EA6B; (vii) an EA7A or EA7B; (viii) an EA9; and (ix) an EA10A or an EA10B. In one embodiment, the HMDAP comprises an EA6A. In another embodiment, the HMDAP comprises an EA6B. In another embodiment, the HMDAP comprises an EA7A. In another embodiment, the HMDAP comprises an EA7B. In another embodiment, the HMDAP comprises an EA10A. In another embodiment, the HMDAP comprises an EA10B. In another embodiment, the organism comprises two, three, four, five, six, seven, eight or nine exogenous nucleic acids, each encoding a HMDAPE. In another embodiment, at least one exogenous nucleic acid encoding a HMDAPE is a heterologous nucleic acid.

In another aspect, provided herein is a NNOMO comprising: (A) a MMP, wherein said organism comprises at least one exogenous nucleic acid encoding a MMPE expressed in a sufficient amount to enhance the availability of reducing equivalents in the presence of methanol, wherein said MMP comprises: (i) an EM9; (ii) an EM9 and an EM10; or (iii) an EM1 and an EM2; and (B) a CapP, wherein said organism comprises at least one exogenous nucleic acid encoding a CapPE expressed in a sufficient amount to produce caprolactam, wherein said CapP comprises (1) (i) an EA1; (ii) an EA2; (iii) an EA3; (iv) an EA4; (v) an EA5; (vi) an EA6A or an EA6B; and (vii) EA7A or EA7B; or (2) (i) an EA1; (ii) an EA2; (iii) an EA3; (iv) an EA4; (v) an EA5; (vi) an EA6A or an EA6B; and (vii) an EA8. In one embodiment, the CapP comprises (i) an EA1; (ii) an EA2; (iii) an EA3; (iv) an EA4; (v) an EA5; (vi) an EA6A or an EA6B; and (vii) EA7A or an EA7B. In another embodiment, the CapP comprises an EA6A. In another embodiment, the CapP comprises an EA6B. In another embodiment, the CapP comprises an EA7A. In another embodiment, the CapP comprises an EA7B. In another embodiment, CapP further comprises a spontaneous cyclization, which converts a 6-aminocaproyl-CoA to caprolactam. In another embodiment, the CapP comprises (i) an EA1; (ii) an EA2; (iii) an EA3; (iv) an EA4; (v) an EA5; (vi) an EA6A or an EA6B; and (vii) an EA8. In another embodiment, CapP comprises an EA6A. In another embodiment, the CapP comprises an EA6B. In another embodiment, the organism comprises two, three, four, five, six or seven exogenous nucleic acids, each encoding a CapPE. In another embodiment, at least one exogenous nucleic acid encoding a CapPE is a heterologous nucleic acid.

In certain embodiments of the NNOMOs provided herein, the MMP comprises an EM1 and an EM2. In some embodiments, the MMP comprises an EM9. In some embodiments, he MMP comprises an EM9 and an EM10. In some embodiments, the MMP comprises an EM1, an EM2, an EM3, an EM4, and an EM5. In some embodiments, the MMP comprises an EM1, an EM2, an EM3, an EM4 and an EM6. In some embodiments, the MMP comprises an EM9, an EM3, an EM4 and an EM5. In some embodiments, the MMP comprises an EM9, an EM3, an EM4 and an EM6. In some embodiments, the MMP comprises an EM9 and an EM11. In some embodiments, the MMP comprises an EM9, an EM12, an EM13 and an EM14. In some embodiments, the MMP comprises an EM9, an EM13 and an EM14. In some embodiments, the MMP comprises an EM9, an EM10, an EM3, an EM4 and an EM5. In some embodiments, the MMP comprises an EM9, an EM10, an EM3, an EM4 and an EM6. In some embodiments, the MMP further comprises an EM8. In some embodiments, the MMP further comprises an EM15. In some embodiments, the MMP further comprises an EM16. In certains embodiments, organism comprises two, three, four, five, six or seven exogenous nucleic acids, each encoding a MMPE. In some embodiments, at least one exogenous nucleic acid encoding a MMPE is a heterologous nucleic acid.

In some embodiments of the NNOMO provided herein, the organism further comprises one or more gene disruptions, wherein said one or more gene disruptions occur in one or more endogenous genes encoding protein(s) or enzyme(s) involved in native production of ethanol, glycerol, acetate, lactate, formate, $CO_2$, and/or amino acids, by said microbial organism, and wherein said one or more gene disruptions confers increased production of adipate, 6-ACA, HMDA or caprolactam in said microbial organism.

In some embodiments of the NNOMO provided herein, one or more endogenous enzymes involved in: native production of ethanol, glycerol, acetate, lactate, formate, $CO_2$ and/or amino acids by said microbial organism, has attenuated enzyme activity or expression levels.

In other embodiments of the NNOMO provided herein, the organism further comprises a FAP, wherein said organism comprises at least one exogenous nucleic acid encoding a FAPE expressed in a sufficient amount to produce an intermediate of glycolysis and/or a metabolic pathway that can be used in the formation of biomass, and wherein said FAP comprises an EF1 and an EF2. In one embodiment, the intermediate is a H6P, a F6P, or a combination thereof. In other embodiments of the NNOMO provided herein, the organism further comprises a FAP, wherein said organism comprises at least one exogenous nucleic acid encoding a FAPE expressed in a sufficient amount to produce an intermediate of glycolysis and/or a metabolic pathway that can be used in the formation of biomass, and wherein said FAP comprises an EF3 and an EF4. In some embodiments, the intermediate is a DHA, a DHAP, or a combination thereof. In other embodiments, the organism comprises two exogenous nucleic acids, each encoding a FAPE. In other embodiments, at least one exogenous nucleic acid is a heterologous nucleic acid.

In other embodiments, the organism is in a substantially anaerobic culture medium. In certain embodiments, the microbial organism is a species of bacteria, yeast, or fungus.

In some embodiments, also provided herein is a method for producing adipate, comprising culturing a NNOMO having an AdiP provided herein under conditions and for a sufficient period of time to produce adipate. Also provided herein is a bioderived or biobased product comprising adipate, or an intermediate thereof, produced according to the method.

In some embodiments, also provided herein is a method for producing 6-ACA, comprising culturing a NNOMO having a 6-ACAP provided herein under conditions and for a sufficient period of time to produce adipate. Also provided herein is a bioderived or biobased product comprising 6-ACA, or an intermediate thereof, produced according to the method.

In some embodiments, also provided herein is a method for producing HMDA, comprising culturing a NNOMO having a HMDAP provided herein under conditions and for a sufficient period of time to produce adipate. Also provided herein is a bioderived or biobased product comprising HMDA, or an intermediate thereof, produced according to the method.

In some embodiments, also provided herein is a method for producing caprolactam, comprising culturing a NNOMO having an CapP provided herein under conditions and for a sufficient period of time to produce adipate. Also provided herein is a bioderived or biobased product comprising caprolactam, or an intermediate thereof, produced according to the method.

In certain embodiments, the bioderived or biobased product is selected from the group consisting of a polymer, plastic, epoxy resin, nylon, nylon-6, nylon 6-6, textile, polyurethane, plasticizer, unsaturated polyester, fiber, clothing, polyester polyol, polyurethane, lubricant component, PVC, food additive, food ingredient, flavorant, gelling aid, food, oral or other medicinal coating, and an oral or other medicinal product.

In some embodiments, also provided herein is a bioderived adipate, 6-ACA, HMDA or caprolactam produced according to a method of producing adipate, 6-ACA, HMDA or caprolactam, respectively, provided herein. Also provided herein is a culture medium comprising the bioderived adipate, 6-ACA, HMDA or caprolactam. In certain embodiments, the bioderived adipate, 6-ACA, HMDA or caprolactam has a carbon-12, carbon-13 and carbon-14 isotope ratio that reflects an atmospheric carbon dioxide uptake source. In some embodiments, the culture medium is separated from the NNOMO having the adipate, 6-ACA, HMDA or CapP. In some embodiments, the culture medium comprises a bioderived adipate, 6-ACA, HMDA or caprolactam, wherein said bioderived adipate, 6-ACA, HMDA or caprolactam has a carbon-12, carbon-13 and carbon-14 isotope ratio that reflects an atmospheric carbon dioxide uptake source. In some embodiments, the bioderived adipate, 6-ACA, HMDA or caprolactam has an Fm value of at least 80%, at least 85%, at least 90%, at least 95% or at least 98%. Also provided herein is a composition comprising said bioderived adipate, 6-ACA, HMDA or caprolactam provided herein, and a compound other than said bioderived adipate, 6-ACA, HMDA or caprolactam. In certain embodiments, the compound other than said bioderived adipate, 6-ACA, HMDA or caprolactam is a trace amount of a cellular portion of a NNOMO having an Adipate, 6-ACA, HMDA or CapP. In some embodiments, also provided herein is a biobased product comprising said bioderived adipate, 6-ACA, HMDA or caprolactam, wherein said biobased product is a polymer, plastic, epoxy resin, nylon, nylon-6, nylon 6-6, textile, polyurethane, plasticizer, unsaturated polyester, fiber, clothing, polyester polyol, polyurethane, lubricant component, PVC, food additive, food ingredient, flavorant, gelling aid, food, oral or other medicinal coating, an oral or other medicinal product. In certain embodiments, the biobased product comprises at least 5%, at least 10%, at least 20%, at least 30%, at least 40% or at least 50% bioderived adipate, 6-ACA, HMDA or caprolactam. In some embodiments, the biobased product comprises a portion of said bioderived adipate, 6-ACA, HMDA or caprolactam as a repeating unit. In some embodiments, also provided herein is a molded product obtained by molding a biobased product provided herein. In some embodiments, also provided herein is a process for producing the biobased product provided herein comprising chemically reacting said bioderived adipate, 6-ACA, HMDA or caprolactam with itself or another compound in a reaction that produces said biobased product. In other embodiments, provided herein is a polymer comprising or obtained by converting the bioderived adipate, 6-ACA, HMDA or caprolactam provided herein. In some embodiments also provided is a method for producing a polymer, comprising chemically of enzymatically converting the bioderived adipate, G-ACA, HMDA or caprolactam to the polymer. In other embodiments, provided herein is a composition comprising the bioderived adipate, 6-ACA, HMDA or caprolactam, or a cell lysate or culture supernatant thereof.

Also provided herein is a method of producing formaldehyde, comprising culturing a NNOMO provided herein under conditions and for a sufficient period of time to produce formaldehyde and optionally wherein the formaldehyde is consumed to provide a reducing equivalent or to incorporate into adipate, 6-ACA, HMDA, caprolactam or target product.

Also provided herein is a method of producing an intermediate of glycolysis and/or an intermediate of a metabolic pathway that can be used in the formation of biomass, comprising culturing a NNOMO provided herein under conditions and for a sufficient period of time to produce the intermediate, and optionally wherein the intermediate is consumed to provide a reducing equivalent or to incorporate into adipate, 6-ACA, HMDA, caprolactam or target product.

In certain embodiments, the organism is cultured in a medium comprising biomass, glucose, xylose, arabinose, galactose, mannose, fructose, sucrose, starch, glycerol, methanol, carbon dioxide, formate, methane, or any combination thereof as a carbon source.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

4. EXAMPLES

4.1 Example I

Production of Reducing Equivalents Via a MMP

Exemplary MMPs are provided in FIG. 1.
FIG. 1, Step A—Methanol Methyltransferase (EM1)

A complex of 3-methyltransferase proteins, denoted MtaA, MtaB, and MtaC, perform the desired EM1 activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoaceticum* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri, M. acetivorans*, and *M. thermoaceticum* can be identified by their following GenBank accession numbers.

| Protein | GenBank ID | GI number | Organism |
|---|---|---|---|
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |
| MtaC2 | YP_307081 | 73671066 | *Methanosarcina barkeri* |
| MtaB3 | YP_304612 | 73668597 | *Methanosarcina barkeri* |
| MtaC3 | YP_304611 | 73668596 | *Methanosarcina barkeri* |

-continued

| Protein | GenBank ID | GI number | Organism |
|---|---|---|---|
| MtaB1 | NP_615421 | 20089346 | *Methanosarcina acetivorans* |
| MtaB1 | NP_615422 | 20089347 | *Methanosarcina acetivorans* |
| MtaB2 | NP_619254 | 20093179 | *Methanosarcina acetivorans* |
| MtaC2 | NP_619253 | 20093178 | *Methanosarcina acetivorans* |
| MtaB3 | NP_616549 | 20090474 | *Methanosarcina acetivorans* |
| MtaC3 | NP_616550 | 20090475 | *Methanosarcina acetivorans* |
| MtaB | YP_430066 | 83590057 | *Moorella thermoacetica* |
| MtaC | YP_430065 | 83590056 | *Moorella thermoacetica* |
| MtaA | YP_430064 | 83590056 | *Moorella thermoacetica* |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying EM1s because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from $CH_3$-MtaC are difficult to identify bioinformatically as they share similarity to other corrinoid protein methyltransferases and are not oriented adjacent to the MtaB and MtaC genes on the chromosomes. Nevertheless, a number of MtaAn Encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | *Methanosarcina barkeri* |
| MtaA1 | NP_619241 | 20093166 | *Methanosarcina acetivorans* |
| MtaA2 | NP_616548 | 20090473 | *Methanosarcina acetivorans* |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaAn Encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from $CH_3$-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaAn Encoding genes from *M. thermoacetica* can be identified by the following GenBank accession numbers.

| Protein | GenBank ID | GI number | Organism |
| --- | --- | --- | --- |
| MtaA | YP_430937 | 83590928 | *Moorella thermoacetica* |
| MtaA | YP_431175 | 83591166 | *Moorella thermoacetica* |
| MtaA | YP_430935 | 83590926 | *Moorella thermoacetica* |
| MtaA | YP_430064 | 83590056 | *Moorella thermoacetica* |

FIG. 1, Step B—Methylenetetrahydrofolate Reductase (EM2)

The conversion of methyl-THF to methylenetetrahydrofolate is catalyzed by EM2. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative EM16 and heterodisulfide reductase genes. Some additional gene candidates found bioinformatically are listed below. In *Acetobacterium woodii* metF is coupled to the Rnf complex through RnfC2 (Poehlein et al, PLoS One. 7:e33439). Homologs of RnfC are found in other organisms by blast search. The Rnf complex is known to be a reversible complex (Fuchs (2011) Annu Rev. Microbiol. 65:631-658).

| Protein | GenBank ID | GInumber | Organism |
| --- | --- | --- | --- |
| Moth_1191 | YP_430048.1 | 83590039 | *Moorella thermoacetica* |
| Moth_1192 | YP_430049.1 | 83590040 | *Moorella thermoacetica* |
| metF | NP_418376.1 | 16131779 | *Escherichia coli* |
| CHY_1233 | YP_360071.1 | 78044792 | *Carboxydothermus hydrogenoformans* |
| CLJU_c37610 | YP_003781889.1 | 300856905 | *Clostridium ljungdahlii* DSM 13528 |
| DesfrDRAFT_3717 | ZP_07335241.1 | 303248996 | *Desulfovibrio fructosovorans* JJ |
| CcarbDRAFT_2950 | ZP_05392950.1 | 255526026 | *Clostridium carboxidivorans* P7 |
| Ccel74_010100023124 | ZP_07633513.1 | 307691067 | *Clostridium cellulovorans* 743B |
| Cphy_3110 | YP_001560205.1 | 160881237 | *Clostridium phytofermentans* ISDg |

FIG. 1, Steps C and D—Methylenetetrahydrofolate Dehydrogenase (EM3), Methenyltetrahydrofolate Cyclohydrolase (EM4)

In *M. thermoacetica*, *E. coli*, and *C. hydrogenoformans*, EM4 and EM3 are carried out by the bi-functional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
| --- | --- | --- | --- |
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonian Eutropha* H16 |
| folD | NP_348702.1 | 15895353 | *Clostridium acetobutylicum* ATCC 824 |
| folD | YP_696506.1 | 110800457 | *Clostridium perfringens* |
| MGA3_09460 | EIJ83438.1 | 387591119 | *Bacillus methanolicus* MGA3 |
| PB1_14689 | ZP_10132349.1 | 387929672 | *Bacillus methanolicus* PB1 |

FIG. 1, Step E—Formyltetrahydrofolate Deformylase (EM5)

This enzyme catalyzes the hydrolysis of 10-formyltetrahydrofolate (formyl-THF) to THF and formate. In *E. coli*, this enzyme is encoded by purU and has been overproduced, purified, and characterized (Nagy, et al., *J. Bacteriol.* 3:1292-1298 (1995)). Homologs exist in *Corynebacterium* sp. U-96 (Suzuki, et al., Biosci. Biotechnol. Biochem. 69(5): 952-956 (2005)), *Corynebacterium glutamicum* ATCC 14067, *Salmonellan Enterica*, and several additional organisms.

| Protein | GenBank ID | GI number | Organism |
|---|---|---|---|
| purU | AAC74314.1 | 1787483 | *Escherichia coli* K-12 MG1655 |
| purU | BAD97821.1 | 63002616 | *Corynebacterium* sp. U-96 |
| purU | EHE84645.1 | 354511740 | *Corynebacterium glutamicum* ATCC 14067 |
| purU | NP_460715.1 | 16765100 | *Salmonellan Enterica* subsp. *enterica* serovar *Typhimurium* str. LT2 |

FIG. 1, Step F—Formyltetrahydrofolate Synthetase (EM6)

EM6 ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium* acidurici (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
|---|---|---|---|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| Fhs | YP_001393842.1 | 153953077 | *Clostridium kluyveri* DSM 555 |
| Fhs | YP_003781893.1 | 300856909 | *Clostridium ljungdahlii* DSM 13528 |
| MGA3_08300 | EIJ83208.1 | 387590889 | *Bacillus methanolicus* MGA3 |
| PB1_13509 | ZP_10132113.1 | 387929436 | *Bacillus methanolicus* PB1 |

FIG. 1, Step G—Formate Hydrogen Lyase (EM15)

AN EM15 enzyme can be employed to convert formate to carbon dioxide and hydrogen. An exemplary EM15 enzyme can be found in *Escherichia coli*. The *E. coli* EM15 consists of hydrogenase 3 and formate dehydrogenase-H (Maedan Et al., *Appl Microbiol Biotechnol* 77:879-890 (2007)). It is activated by the gene product of fhlA. (Maedan Et al., *Appl Microbiol Biotechnol* 77:879-890 (2007)). The addition of the trace elements, selenium, nickel and molybdenum, to a fermentation broth has been shown to enhance EM15 activity (Soini et al., *Microb. Cell Fact.* 7:26 (2008)). Various hydrogenase 3, EM8 and transcriptional activator genes are shown below.

| Protein | GenBank ID | GI number | Organism |
|---|---|---|---|
| hycA | NP_417205 | 16130632 | *Escherichia coli* K-12 MG1655 |
| hycB | NP_417204 | 16130631 | *Escherichia coli* K-12 MG1655 |
| hycC | NP_417203 | 16130630 | *Escherichia coli* K-12 MG1655 |
| hycD | NP_417202 | 16130629 | *Escherichia coli* K-12 MG1655 |
| hycE | NP_417201 | 16130628 | *Escherichia coli* K-12 MG1655 |
| hycF | NP_417200 | 16130627 | *Escherichia coli* K-12 MG1655 |
| hycG | NP_417199 | 16130626 | *Escherichia coli* K-12 MG1655 |
| hycH | NP_417198 | 16130625 | *Escherichia coli* K-12 MG1655 |
| hycI | NP_417197 | 16130624 | *Escherichia coli* K-12 MG1655 |
| fdhF | NP_418503 | 16131905 | *Escherichia coli* K-12 MG1655 |
| fhlA | NP_417211 | 16130638 | *Escherichia coli* K-12 MG1655 |

AN EM15 enzyme also exists in the hyperthermophilic archaeon, *Thermococcus litoralis* (Takacs et al., *BMC. Microbiol* 8:88 (20081).

| Protein | GenBank ID | GI number | Organism |
|---|---|---|---|
| mhyC | ABW05543 | 157954626 | *Thermococcus litoralis* |
| mhyD | ABW05544 | 157954627 | *Thermococcus litoralis* |
| mhyE | ABW05545 | 157954628 | *Thermococcus litoralis* |
| myhF | ABW05546 | 157954629 | *Thermococcus litoralis* |
| myhG | ABW05547 | 157954630 | *Thermococcus litoralis* |
| myhH | ABW05548 | 157954631 | *Thermococcus litoralis* |
| fdhA | AAB94932 | 2746736 | *Thermococcus litoralis* |
| fdhB | AAB94931 | 157954625 | *Thermococcus litoralis* |

Additional EM15 systems have been found in *Salmonella typhimurium*, *Klebsiella pneumoniae*, *Rhodospirillum rubrum*, *Methanobacterium formicicum* (Vardar-Scharan Et al., Microbial Biotechnology 1:107-125 (2008)).

FIG. 1, Step H—Hydrogenase (EM16)

Hydrogenase enzymes can convert hydrogen gas to protons and transfer electrons to acceptors such as ferredoxins, NAD+, or NADP+. *Ralstonian Eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble EM16 encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble EM16 enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Syn-* echocystis enzyme is capable of generating NADPH from hydrogen. Overexpression of both the Hox operon from Synechocystis str. PCC 6803 and the accessory genes encoded by the Hyp operon from Nostoc sp. PCC 7120 led to increased EM16 activity compared to expression of the Hox genes alone (Germer, J. Biol. Chem. 284(52), 36462-36472 (2009)).

| Protein | GenBank ID | GI Number | Organism |
| --- | --- | --- | --- |
| HoxF | NP_942727.1 | 38637753 | Ralstonian Eutropha H16 |
| HoxU | NP_942728.1 | 38637754 | Ralstonian Eutropha H16 |
| HoxY | NP_942729.1 | 38637755 | Ralstonian Eutropha H16 |
| HoxH | NP_942730.1 | 38637756 | Ralstonian Eutropha H16 |
| HoxW | NP_942731.1 | 38637757 | Ralstonian Eutropha H16 |
| HoxI | NP_942732.1 | 38637758 | Ralstonian Eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

The genomes of E. coli and other enteric bacteria encode up to four EM16 enzymes (Sawers, G., Antonie Van Leeuwenhoek 66:57-88 (1994); Sawers et al., J Bacteriol. 164:1324-1331 (1985); Sawers and Boxer, Eur. J Biochem. 156:265-275 (1986); Sawers et al., J Bacteriol. 168:398-404 (1986)). Given the multiplicity of enzyme activities E. coli or another host organism can provide sufficient EM16 activity to split incoming molecular hydrogen and reduce the corresponding acceptor. Endogenous hydrogen-lyase enzymes of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. EM16 activity in E. coli is also dependent upon the expression of the hyp genes whose corresponding proteins are involved in the assembly of the EM16 complexes (Jacobi et al., Arch. Microbiol 158:444-451 (1992); Rangarajan et al., J Bacteriol. 190:1447-1458 (2008)). The M. thermoacetica and Clostridium ljungdahli EM16s are suitable for a host that lacks sufficient endogenous EM16 activity. M. thermoacetica and C. ljungdahli can grow with $CO_2$ as the exclusive carbon source indicating that reducing equivalents are extracted from $H_2$ to enable acetyl-CoA synthesis via the Wood-Ljungdahl pathway (Drake, H. L., J Bacteriol. 150:702-709 (1982); Drake and Daniel, Res Microbiol 155:869-883 (2004); Kellum and Drake, J Bacteriol. 160:466-469 (1984)). M. thermoacetica has homologs to several hyp, hyc, and hyf genes from E. coli. These protein sequences encoded for by these genes are identified by the following GenBank accession numbers. In addition, several gene clusters encoding EM16 functionality are present in M. thermoacetica and C. ljungdahli (see for example US 2012/0003652).

| Protein | GenBank ID | GI Number | Organism |
| --- | --- | --- | --- |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

Proteins in M. thermoacetica whose genes are homologous to the E. coli EM16 genes are shown below.

| Protein | GenBank ID | GI Number | Organism |
| --- | --- | --- | --- |
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |

| Protein | GenBank ID | GI Number | Organism |
|---|---|---|---|
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |

-continued

| Protein | GenBank ID | GI Number | Organism |
|---|---|---|---|
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Genes encoding EM16 enzymes from *C. ljungdahli* are shown below.

| Protein | GenBank ID | GI Number | Organism |
|---|---|---|---|
| CLJU_c20290 | ADK15091.1 | 300435324 | Clostridium ljungdahli |
| CLJU_c07030 | ADK13773.1 | 300434006 | Clostridium ljungdahli |
| CLJU_c07040 | ADK13774.1 | 300434007 | Clostridium ljungdahli |
| CLJU_c07050 | ADK13775.1 | 300434008 | Clostridium ljungdahli |
| CLJU_c07060 | ADK13776.1 | 300434009 | Clostridium ljungdahli |
| CLJU_c07070 | ADK13777.1 | 300434010 | Clostridium ljungdahli |
| CLJU_c07080 | ADK13778.1 | 300434011 | Clostridium ljungdahli |
| CLJU_c14730 | ADK14541.1 | 300434774 | Clostridium ljungdahli |
| CLJU_c14720 | ADK14540.1 | 300434773 | Clostridium ljungdahli |
| CLJU_c14710 | ADK14539.1 | 300434772 | Clostridium ljungdahli |
| CLJU_c14700 | ADK14538.1 | 300434771 | Clostridium ljungdahli |
| CLJU_c28670 | ADK15915.1 | 300436148 | Clostridium ljungdahli |
| CLJU_c28660 | ADK15914.1 | 300436147 | Clostridium ljungdahli |
| CLJU_c28650 | ADK15913.1 | 300436146 | Clostridium ljungdahli |
| CLJU_c28640 | ADK15912.1 | 300436145 | Clostridium ljungdahli |

In some cases, EM16 encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-I was also shown to exhibit intense CO oxidation and $CO_2$ reduction activities when linked to an electrode (Parkin et al., *J Am. Chem. Soc.* 129:10328-10329 (2007)).

| Protein | GenBank ID | GI Number | Organism |
|---|---|---|---|
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus_hydrogenoformans |

Some EM16 and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdxl encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans* P7, *Clostridium ljungdahli* and *Rhodospirillum rubrum* are predicted to encode several ferredoxins, listed below.

| Protein | GenBank ID | GI Number | Organism |
| --- | --- | --- | --- |
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |
| fdxN | AAA26460.1 | 152605 | Rhodospirillum rubrum |
| Alvin_2884 | ADC63789.1 | 288897953 | Allochromatium vinosum DSM 180 |
| Fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| Fdx | CAA12251.1 | 3724172 | Thauera aromatics |
| CHY_2405 | YP_361202.1 | 78044690 | Carboxydothermus hydrogenoformans |
| Fer | YP_359966.1 | 78045103 | Carboxydothermus hydrogenoformans |
| Fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_c17980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The Helicobacter pylori FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in Campylobacter jejuni (St Maurice et al., J. Bacteriol. 189: 4764-4773 (2007)). A ferredoxin:NADP+ oxidoreductase enzyme is encoded in the E. coli genome by fpr (Bianchi et al. 1993). Ferredoxin:NAD+ oxidoreductase utilizes reduced ferredoxin to generate NADH from NAD+. In several organisms, including E. coli, this enzyme is a component of multifunctional dioxygenase enzyme complexes. The ferredoxin:NAD+ oxidoreductase of E. coli, encoded by hcaD, is a component of the 3-phenylproppionate dioxygenase system involved in involved in aromatic acid utilization (Diaz et al. 1998). NADH:ferredoxin reductase activity was detected in cell extracts of Hydrogenobacter thermophilus, although a gene with this activity has not yet been indicated (Yoon et al. 2006). Additional ferredoxin:NAD(P)+ oxidoreductases have been annotated in Clostridium carboxydivorans P7. The NADH-dependent reduced ferredoxin: NADP oxidoreductase of C. kluyveri, encoded by nfnAB, catalyzes the concomitant reduction of ferredoxin and NAD+ with two equivalents of NADPH (Wang et al, J Bacteriol 192: 5115-5123 (2010)). Finally, the energy-conserving membrane-associated Rnf-type proteins (Seedorf et al, PNAS 105:2128-2133 (2008); and Herrmann, J. Bacteriol 190:784-791 (2008)) provide a means to generate NADH or NADPH from reduced ferredoxin.

| Protein | GenBank ID | GI Number | Organism |
| --- | --- | --- | --- |
| fqrB | NP_207955.1 | 15645778 | Helicobacter pylori |
| fqrB | YP_001482096.1 | 157414840 | Campylobacter jejuni |
| RPA3954 | CAE29395.1 | 39650872 | Rhodopseudomonas palustris |
| Fpr | BAH29712.1 | 225320633 | Hydrogenobacter thermophilus |
| yumC | NP_391091.2 | 255767736 | Bacillus subtilis |

-continued

| Protein | GenBank ID | GI Number | Organism |
|---|---|---|---|
| Fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CLJU_c11410 (RnfB) | ADK14209.1 | 300434442 | Clostridium ljungdahlii |
| CLJU_c11400 (RnfA) | ADK14208.1 | 300434441 | Clostridium ljungdahlii |
| CLJU_c11390 (RnfE) | ADK14207.1 | 300434440 | Clostridium ljungdahlii |
| CLJU_c11380 (RnfG) | ADK14206.1 | 300434439 | Clostridium ljungdahlii |
| CLJU_c11370 (RnfD) | ADK14205.1 | 300434438 | Clostridium ljungdahlii |
| CLJU_c11360 (RnfC) | ADK14204.1 | 300434437 | Clostridium ljungdahlii |
| MOTH_1518 (NfnA) | YP_430370.1 | 83590361 | Moorella thermoacetica |
| MOTH_1517 (NfnB) | YP_430369.1 | 83590360 | Moorella thermoacetica |
| CHY_1992 (NfnA) | YP_360811.1 | 78045020 | Carboxydothermus hydrogenoformans |
| CHY_1993 (NfnB) | YP_360812.1 | 78044266 | Carboxydothermus hydrogenoformans |
| CLJU_c37220 (NfnAB) | YP_003781850.1 | 300856866 | Clostridium ljungdahlii |

FIG. 1, Step I—Formate Dehydrogenase (EM8)

Formate dehydrogenase (FDH; EM8) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and EM16s (EC 1.1.99.33). FDH enzymes have been characterized from Moorella thermoacetica (Andreesen and Ljungdahl, J Bacteriol 116:867-873 (1973); Li et al., J Bacteriol 92:405-412 (1966); Yamamoto et al., J Biol Chem. 258:1826-1832 (1983). The loci, Moth_2312 is responsible for encoding the alpha subunit of EM8 while the beta subunit is encoded by Moth_2314 (Pierce et al., Environ Microbiol (2008)). Another set of genes encoding EM8 activity with a propensity for $CO_2$ reduction is encoded by Sfum_2703 through Sfum_2706 in Syntrophobacter fumaroxidans (de Bok et al., Eur J Biochem. 270:2476-2485 (2003)); Redan Et al., PNAS 105:10654-10658 (2008)). A similar set of genes presumed to carry out the same function are encoded by CHY_0731, CHY_0732, and CHY_0733 in C. hydrogenoformans (Wu et al., PLoS Genet 1:e65 (2005)). EM8s are also found many additional organisms including C. carboxidivorans P7, Bacillus methanolicus, Burkholderia stabilis, Moorella thermoacetica ATCC 39073, Candida boidinii, Candida methylica, and Saccharomyces cerevisiae S288c. The soluble EM8 from Ralstonian Eutropha reduces $NAD^+$ (fdsG, -B, -A, -C, -D) (Oh and Bowien, 1998).

Several EM8 enzymes have been identified that have higher specificity for NADP as the cofactor as compared to NAD. This enzyme has been deemed as the NADP-dependent formate dehydrogenase and has been reported from 5 species of the Burkholderia cepacia complex. It was tested and verified in multiple strains of Burkholderia multivorans, Burkholderia stabilis, Burkholderia pyrrocinia, and Burkholderia cenocepacia (Hatrongjit et al., Enzyme and Microbial Tech., 46: 557-561 (2010)). The enzyme from Burkholderia stabilis has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

| Protein | GenBank ID | GI Number | Organism |
|---|---|---|---|
| Moth_2312 | YP_431142 | 148283121 | Moorella thermoacetica |
| Moth_2314 | YP_431144 | 83591135 | Moorella thermoacetica |
| Sfum_2703 | YP_846816.1 | 116750129 | Syntrophobacter fumaroxidans |
| Sfum_2704 | YP_846817.1 | 116750130 | Syntrophobacter fumaroxidans |
| Sfum_2705 | YP_846818.1 | 116750131 | Syntrophobacter fumaroxidans |
| Sfum_2706 | YP_846819.1 | 116750132 | Syntrophobacter fumaroxidans |
| CHY_0731 | YP_359585.1 | 78044572 | Carboxydothermus hydrogenoformans |

| Protein | GenBank ID | GI Number | Organism |
|---|---|---|---|
| CHY_0732 | YP_359586.1 | 78044500 | Carboxydothermus hydrogenoformans |
| CHY_0733 | YP_359587.1 | 78044647 | Carboxydothermus hydrogenoformans |
| CcarbDRAFT_0901 | ZP_05390901.1 | 255523938 | Clostridium carboxidivorans P7 |
| CcarbDRAFT_4380 | ZP_05394380.1 | 255527512 | Clostridium carboxidivorans P7 |
| fdhA, MGA3_06625 | EIJ82879.1 | 387590560 | Bacillus methanolicus MGA3 |
| fdhA, PB1_11719 | ZP_10131761.1 | 387929084 | Bacillus methanolicus PB1 |
| fdhD, MGA3_06630 | EIJ82880.1 | 387590561 | Bacillus methanolicus MGA3 |
| fdhD, PB1_11724 | ZP_10131762.1 | 387929085 | Bacillus methanolicus PB1 |
| fdh | ACF35003.1 | 194220249 | Burkholderia stabilis |
| fdh | ACF35004.1 | 194220251 | Burkholderia pyrrocinia |
| fdh | ACF35002.1 | 194220247 | Burkholderia cenocepacia |
| fdh | ACF35001.1 | 194220245 | Burkholderia multivorans |
| fdh | ACF35000.1 | 194220243 | Burkholderia cepacia |
| FDH1 | AAC49766.1 | 2276465 | Candida boidinii |
| fdh | CAA57036.1 | 1181204 | Candida methylica |
| FDH2 | P0CF35.1 | 294956522 | Saccharomyces cerevisiae S288c |
| FDH1 | NP_015033.1 | 6324964 | Saccharomyces cerevisiae S288c |
| fdsG | YP_725156.1 | 113866667 | Ralstonian Eutropha |
| fdsB | YP_725157.1 | 113866668 | Ralstonian Eutropha |
| fdsA | YP_725158.1 | 113866669 | Ralstonian Eutropha |
| fdsC | YP_725159.1 | 113866670 | Ralstonian Eutropha |
| fdsD | YP_725160.1 | 113866671 | Ralstonian Eutropha |

FIG. 1, Step J—Methanol Dehydrogenase (EM9)

NAD+ dependent EM9 enzymes (EC 1.1.1.244) catalyze the conversion of methanol and NAD+ to formaldehyde and NADH. An enzyme with this activity was first characterized in Bacillus methanolicus (Heggeset, et al., Applied and Environmental Microbiology, 78(15):5170-5181 (2012)). This enzyme is zinc and magnesium dependent, and activity of the enzyme is enhanced by the activating enzyme encoded by act (Kloosterman et al, J Biol Chem 277:34785-92 (2002)). The act is a Nudix hydrolase. Several of these candidates have been identified and shown to have activity on methanol. Additional NAD(P)+ dependent enzymes can be identified by sequence homology. EM9 enzymes utilizing different electron acceptors are also known in the art. Examples include cytochrome dependent enzymes such as mxaIF of the methylotroph Methylobacterium extorquens (Nunn et al, Nucl Acid Res 16:7722 (1988)). EM9 enzymes of methanotrophs such as Methylococcus capsulatis function in a complex with methane monooxygenase (MMO) (Myronovan Et al., Biochem 45:11905-14 (2006)). Methanol can also be oxidized to formaldehyde by alcohol oxidase enzymes such as methanol oxidase (EC 1.1.3.13) of Candida boidinii (Sakai et al., Gene 114: 67-73 (1992)).

| Protein | GenBank ID | GI Number | Organism |
|---|---|---|---|
| mdh, MGA3_17392 | EIJ77596.1 | 387585261 | Bacillus methanolicus MGA3 |
| mdh2, MGA3_07340 | EIJ83020.1 | 387590701 | Bacillus methanolicus MGA3 |
| mdh3, MGA3_10725 | EIJ80770.1 | 387588449 | Bacillus methanolicus MGA3 |
| act, MGA3_09170 | EIJ83380.1 | 387591061 | Bacillus methanolicus MGA3 |
| mdh, PB1_17533 | ZP_10132907.1 | 387930234 | Bacillus methanolicus PB1 |
| mdh1, PB1_14569 | ZP_10132325.1 | 387929648 | Bacillus methanolicus PB1 |
| mdh2, PB1_12584 | ZP_10131932.1 | 387929255 | Bacillus methanolicus PB1 |
| act, PB1_14394 | ZP_10132290.1 | 387929613 | Bacillus methanolicus PB1 |
| BFZC1_05383 | ZP_07048751.1 | 299535429 | Lysinibacillus fusiformis |
| BFZC1_20163 | ZP_07051637.1 | 299538354 | Lysinibacillus fusiformis |
| Bsph_4187 | YP_001699778.1 | 169829620 | Lysinibacillus sphaericus |
| Bsph_1706 | YP_001697432.1 | 169827274 | Lysinibacillus sphaericus |
| mdh2 | YP_004681552.1 | 339322658 | Cupriavidus necator N-1 |
| nudF1 | YP_004684845.1 | 339325152 | Cupriavidus necator N-1 |
| BthaA_010200007655 | ZP_05587334.1 | 257139072 | Burkholderia thailandensis E264 |
| BTH_I1076 (MutT/NUDIX NTP pyrophosphatase) | YP_441629.1 | 83721454 | Burkholderia thailandensis E264 |
| BalcAV_11743 | ZP_10819291.1 | 402299711 | Bacillus alcalophilus ATCC 27647 |
| BalcAV_05251 | ZP_10818002.1 | 402298299 | Bacillus alcalophilus ATCC 27647 |
| alcohol dehydrogenase | YP_725376.1 | 113866887 | Ralstonian Eutropha H16 |
| alcohol dehydrogenase | YP_001447544 | 156976638 | Vibrio harveyi ATCC BAA-1116 |

-continued

| Protein | GenBank ID | GI Number | Organism |
|---|---|---|---|
| P3TCK_27679 | ZP_01220157.1 | 90412151 | *Photobacterium profundum* 3TCK |
| alcohol dehydrogenase | YP_694908 | 110799824 | *Clostridium perfringens* ATCC 13124 |
| adhB | NP_717107 | 24373064 | *Shewanella oneidensis* MR-1 |
| alcohol dehydrogenase | YP_237055 | 66047214 | *Pseudomonas syringae* pv. *syringae* B728a |
| alcohol dehydrogenase | YP_359772 | 78043360 | *Carboxydothermus hydrogenoformans* Z-2901 |
| alcohol dehydrogenase | YP_003990729 | 312112413 | *Geobacillus* sp. Y4.1MC1 |
| PpeoK3_010100018471 | ZP_10241531.1 | 390456003 | *Paenibacillus peoriae* KCTC 3763 |
| OBE_12016 | EKC54576 | 406526935 | human gut metagenome |
| alcohol dehydrogenase | YP_003310546 | 269122369 | *Sebaldella termitidis* ATCC 33386 |
| alcohol dehydrogenase | YP_001343716 | 152978087 | *Actinobacillus succinogenes* 130Z |
| dhaT | AAC45651 | 2393887 | *Clostridium pasteurianum* DSM 525 |
| alcohol dehydrogenase | NP_561852 | 18309918 | *Clostridium perfringens* str. 13 |
| BAZO_10081 | ZP_11313277.1 | 410459529 | *Bacillus azotoformans* LMG 9581 |
| alcohol dehydrogenase | YP_007491369 | 452211255 | *Methanosarcina mazei* Tuc01 |
| alcohol dehydrogenase | YP_004860127 | 347752562 | *Bacillus coagulans* 36D1 |
| alcohol dehydrogenase | YP_002138168 | 197117741 | *Geobacter bemidjiensis* Bem |
| DesmeDRAFT_1354 | ZP_08977641.1 | 354558386 | *Desulfitobacterium metallireducens* DSM 15288 |
| alcohol dehydrogenase | YP_001337153 | 152972007 | *Klebsiella pneumoniae* subsp. *pneumoniae* MGH 78578 |
| alcohol dehydrogenase | YP_001113612 | 134300116 | *Desulfotomaculum reducens* MI-1 |
| alcohol dehydrogenase | YP_001663549 | 167040564 | *Thermoanaerobacter* sp. X514 |
| ACINNAV82_2382 | ZP_16224338.1 | 421788018 | *Acinetobacter baumannii* Naval-82 |
| DVU2405 | YP_011618 | 46580810 | *Desulfovibrio vulgaris* str. Hildenborough |
| alcohol dehydrogenase | YP_005052855 | 374301216 | *Desulfovibrio africanus* str. Walvis Bay |
| alcohol dehydrogenase | YP_002434746 | 218885425 | *Desulfovibrio vulgaris* str. 'Miyazaki F' |
| alcohol dehydrogenase | AGF87161 | 451936849 | uncultured organism |
| DesfrDRAFT_3929 | ZP_07335453.1 | 303249216 | *Desulfovibrio fructosovorans* JJ |
| alcohol dehydrogenase | NP_617528 | 20091453 | *Methanosarcina acetivorans* C2A |
| alcohol dehydrogenase | NP_343875.1 | 15899270 | *Sulfolobus solfataricus* P-2 |
| adh4 | YP_006863258 | 408405275 | *Nitrososphaera gargensis* Ga9.2 |
| BD31_I0957 | ZP_10117398.1 | 386875211 | *Nitrosopumilus salaria* BD31 |
| alcohol dehydrogenase | YP_004108045.1 | 316933063 | *Rhodopseudomonas palustris* DX-1 |
| Ta0841 | NP_394301.1 | 16081897 | *Thermoplasma acidophilum* |
| PTO1151 | YP_023929.1 | 48478223 | *Picrophilus torridus* DSM9790 |
| alcohol dehydrogenase | ZP_10129817.1 | 387927138 | *Bacillus methanolicus* PB-1 |
| cgR_2695 | YP_001139613.1 | 145296792 | *Corynebacterium glutamicum* R |
| alcohol dehydrogenase | YP_004758576.1 | 340793113 | *Corynebacterium variabile* |
| HMPREF1015_01790 | ZP_09352758.1 | 365156443 | *Bacillus smithii* |
| ADH1 | NP_014555.1 | 6324486 | *Saccharomyces cerevisiae* |
| NADH-dependent butanol dehydrogenase A | YP_001126968.1 | 138896515 | *Geobacillus themodenitrificans* NG80-2 |
| alcohol dehydrogenase | WP_007139094.1 | 494231392 | *Flavobacterium frigoris* |
| methanol dehydrogenase | WP_003897664.1 | 489994607 | *Mycobacterium smegmatis* |
| ADH1B | NP_000659.2 | 34577061 | *Homo sapiens* |

| Protein | GenBank ID | GI Number | Organism |
| --- | --- | --- | --- |
| PMI01_01199 | ZP_10750164.1 | 399072070 | *Caulobacter* sp. AP07 |
| BurJ1DRAFT_3901 | ZP_09753449.1 | 375107188 | *Burkholderiales bacterium* Joshi_001 |
| YiaY | YP_026233.1 | 49176377 | *Escherichia coli* |
| MCA0299 | YP_112833.1 | 53802410 | *Methylococcus capsulatis* |
| MCA0782 | YP_113284.1 | 53804880 | *Methylococcus capsulatis* |
| mxaI | YP_002965443.1 | 240140963 | *Methylobacterium extorquens* |
| mxaF | YP_002965446.1 | 240140966 | *Methylobacterium extorquens* |
| AOD1 | AAA34321.1 | 170820 | *Candida boidinii* |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking frmA, frmB, frmR was created using Lamba Red recombinase technology (Datsenko and Wanner, *Proc. Natl. Acad. Sci. USA*, 6 97(12): 6640-5 (2000). Plasmids expressing methanol dehydrogenases were transformed into the strain, then grown to saturation in LB medium+antibiotic at 37° C. with shaking Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, Mich.) according to manufacturer's instructions. The frmA, frmB, frmR deletions resulted in the native formaldehyde utilization pathway to be deleted, which enables the formation of formaldehyde that can be used to detect methanol dehydrogenase activity in the NNOMO.

The activity of several enzymes was measured using the assay described above. The results of four independent experiments are provided in Table 1 below.

TABLE 1

Results of in vivo assays showing formaldehyde (HCHO) production by various NNOMO comprising a plasmid expressing a methanol dehydrogenase.

| Accession number | HCHO ($\mu$M) |
| --- | --- |
| Experiment 1 | |
| EIJ77596.1 | >50 |
| EIJ83020.1 | >20 |
| EIJ80770.1 | >50 |
| ZP_10132907.1 | >20 |
| ZP_10132325.1 | >20 |
| ZP_10131932.1 | >50 |
| ZP_07048751.1 | >50 |
| YP_001699778.1 | >50 |
| YP_004681552.1 | >10 |
| ZP_10819291.1 | <1 |
| Empty vector | 2.33 |
| Experiment 2 | |
| EIJ77596.1 | >50 |
| NP_00659.2 | >50 |
| YP_004758576.1 | >20 |
| ZP_09352758.1 | >50 |

TABLE 1-continued

Results of in vivo assays showing formaldehyde (HCHO) production by various NNOMO comprising a plasmid expressing a methanol dehydrogenase.

| Accession number | HCHO ($\mu$M) |
| --- | --- |
| ZP_10129817.1 | >20 |
| YP_001139613.1 | >20 |
| NP_014555.1 | >10 |
| WP_007139094.1 | >10 |
| NP_343875.1 | >1 |
| YP_006863258 | >1 |
| NP_394301.1 | >1 |
| ZP_10750164.1 | >1 |
| YP_023929.1 | >1 |
| ZP_08977641.1 | <1 |
| ZP_10117398.1 | <1 |
| YP_004108045.1 | <1 |
| ZP_09753449.1 | <1 |
| Empty vector | 0.17 |
| Experiment 3 | |
| EIJ77596.1 | >50 |
| NP_561852 | >50 |
| YP_002138168 | >50 |
| YP_026233.1 | >50 |
| YP_001447544 | >50 |
| Metalibrary | >50 |
| YP_359772 | >50 |
| ZP_01220157.1 | >50 |
| ZP_07335453.1 | >20 |
| YP_001337153 | >20 |
| YP_694908 | >20 |
| NP_717107 | >20 |
| AAC45651 | >10 |
| ZP_11313277.1 | >10 |
| ZP_16224338.1 | >10 |
| YP_001113612 | >10 |
| YP_004860127 | >10 |
| YP_003310546 | >10 |
| YP_001343716 | >10 |
| NP_717107 | >10 |
| CAA80989.1 | >50 |
| YP_002434746 | >10 |
| Empty vector | 0.11 |
| Experiment 4 | |
| EIJ77596.1 | >50 |
| ZP_10241531.1 | >90 |
| YP_005052855 | >85 |
| ZP_10132907.1 | >50 |
| NP_617528 | >50 |
| NP_617528 | >50 |
| ZP_08977641.1 | >20 |
| YP_237055 | >20 |
| Empty vector | 49.36 |

FIG. 1, Step K—Spontaneous or Formaldehyde Activating Enzyme (EM10)

The conversion of formaldehyde and THF to methylenetetrahydrofolate can occur spontaneously. It is also possible that the rate of this reaction can be enhanced by an EM10. A formaldehyde activating enzyme (Fae) has been identified in *Methylobacterium extorquens* AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms including *Xanthobacter autotrophicus* Py2 and *Hyphomicrobium denitrificans* ATCC 51888.

| Protein | GenBank ID | GI Number | Organism |
| --- | --- | --- | --- |
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

FIG. 1, Step L—Formaldehyde Dehydrogenase (EM11)

Oxidation of formaldehyde to formate is catalyzed by EM11. An NAD+ dependent EM11 enzyme is encoded by fdhA of *Pseudomonas putida* (Ito et al, J Bacteriol 176: 2483-2491 (1994)). Additional EM11 enzymes include the NAD+ and glutathione independent EM11 from *Hyphomicrobium zavarzinii* (Jerome et al, Appl Microbiol Biotechnol 77:779-88 (2007)), the glutathione dependent EM11 of *Pichia pastoris* (Sungan et al., Gene 330:39-47 (2004)) and the NAD(P)+ dependent EM11 of *Methylobacter marinus* (Speer et al, FEMS Microbiol Lett, 121(3):349-55 (1994)).

| Protein | GenBank ID | GI Number | Organism |
| --- | --- | --- | --- |
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| fdh | P47734.2 | 221222447 | *Methylobacter marinus* |

In addition to the EM11 enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, J Bacteriol 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12). FIG. 1, Step M—Spontaneous or S-(Hydroxymethyl)Glutathione Synthase (EM12)

While conversion of formaldehyde to S-hydroxymethylglutathione can occur spontaneously in the presence of glutathione, it has been shown by Goenrich et at (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for glutathione-dependent formaldehyde dehydrogenase, which catalyzes the subsequent oxidation of S-hydroxymethylglutathione. Putative proteins with sequence identity to Gfa from *P. denitrificans* are present also in *Rhodobacter sphaeroides, Sinorhizobium meliloti*, and *Mesorhizobium loti*.

| Protein | GenBank ID | GI Number | Organism |
| --- | --- | --- | --- |
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizobium loti* MAFF303099 |

FIG. 1, Step N—Glutathione-Dependent Formaldehyde Dehydrogenase (EM13)

Glutathione-dependent formaldehyde dehydrogenase (GS-FDH) belongs to the family of class III alcohol dehydrogenases. Glutathione and formaldehyde combine nonenzymatically to form hydroxymethylglutathione, the true substrate of the GS-FDH catalyzed reaction. The product, S-formylglutathione, is further metabolized to formic acid.

| Protein | GenBank ID | GI Number | Organism |
| --- | --- | --- | --- |
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 1, Step O—S-Formylglutathione Hydrolase (EM14)

EM14 is a glutathione thiol esterase found in bacteria, plants and animals. It catalyzes conversion of S-formylglutathione to formate and glutathione. The fghA gene of *P. denitrificans* is located in the same operon with gfa and flhA, two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
| --- | --- | --- | --- |
| frmB | NP_414889.1 | 16128340 | *Escherichia coli* K-12 MG1655 |
| yeiG | AAC75215.1 | 1788477 | *Escherichia coli* K-12 MG1655 |
| fghA | AAC44554.1 | 1002868 | *Paracoccus denitrificans* |

4.2 Example II

Enhanced Yield of Adipate, 6-ACA, HMDA and/or Caprolactam from Carbohydrates Using Methanol Exemplary MMPs for enhancing the availability of reducing equivalents are provided in FIG. 1.

Adipate, 6-ACA, HMDA and/or caprolactam production can be achieved in a recombinant organism by the pathway shown in FIG. 2. For example, adipate, 6-ACA, HMDA and/or caprolactam can be produced from succinyl-CoA or acetyl-CoA via an Adipyl-CoA intermediate as shown in FIG. 2. Exemplary enzymes for the conversion of succinyl-CoA or acetyl-CoA to adipate, 6-ACA, HMDA and/or caprolactam by this route include EA1; EA2; EA3; EA4; EA5; EA6A or EA6B; EA7A or EA7B; EA8; EA9; EA10A or EA10B; and EA11A, EA11B, EA11C or EA11D.

Described below are various exemplary pathways leading to the production of caprolactam, HMDA (HMDA), or 6-ACA from common central metabolites. One described pathway entails the activation of 6-ACA to 6-aminocaproyl-CoA by a transferase or synthase enzyme (FIG. 2, step G) followed by the spontaneous cyclization of 6-aminocaproyl-CoA to form caprolactam (FIG. 2, step I). Another described pathway entails the activation of 6-ACA to 6-aminocaproyl-CoA (FIG. 2, step G), followed by a reduction (FIG. 2, step J) and amination (FIG. 2, step K) to form HMDA. 6-aminocaproic acid can alternatively be activated to 6-aminocaproyl-phosphate instead of 6-aminocaproyl-CoA. 6-Aminocaproyl-phosphate can spontaneously cyclize to form caprolactam. Alternatively, 6-aminocaproyl-phosphate can be reduced to 6-ACA semialdehyde, which can be then converted to HMDA. In either this case, the amination reaction can occur relatively quickly to minimize the spontaneous formation of the cyclic imine of 6-ACA semialdehyde. Linking or scaffolding the participating enzymes represents a potentially powerful option for ensuring that the G-ACA semialdehyde intermediate is efficiently channeled from the reductase enzyme to the amination enzyme.

Another option for minimizing or even eliminating the formation of the cyclic imine or caprolactam during the conversion of 6-aminocaproic acid to HMDA entails adding a functional group (for example, acetyl, succinyl) to the amine group of 6-aminocaproic acid to protect it from cyclization. This is analogous to ornithine formation from L-glutamate in *Escherichia coli*. Specifically, glutamate is first converted to N-acetyl-L-glutamate by N-acetylglutamate synthase. N-Acetyl-L-glutamate is then activated to N-acetylglutamyl-phosphate, which is reduced and transaminated to form N-acetyl-L-ornithine. The acetyl group is then removed from N-acetyl-L-ornithine by N-acetyl-L-ornithine deacetylase forming L-ornithine. Such a route is necessary because formation of glutamate-5-phosphate from glutamate followed by reduction to glutamate-5-semialdehyde leads to the formation of (S)-1-pyrroline-5-carboxylate, a cyclic imine formed spontaneously from glutamate-5-semialdehyde. In the case of forming HMDA from 6-aminocaproic acid, the steps can involve acetylating 6-aminocaproic acid to acetyl-6-aminocaproic acid, activating the carboxylic acid group with a CoA or phosphate group, reducing, aminating, and deacetylating.

Transformations depicted in FIG. 2 fall into at least 10 general categories of transformations shown in the Table below. The first three digits of each label correspond to the first three Enzyme Commission number digits which denote the general type of transformation independent of substrate specificity. Below is described a number of biochemically characterized candidate genes in each category. Specifically listed are exemplary genes that can be applied to catalyze the appropriate transformations in FIG. 2 when cloned and expressed.

| Step | Label | Function |
| --- | --- | --- |
| FIG. 2, step B | 1.1.1.a | Oxidoreductase (ketone to hydroxyl or aldehyde to alcohol) |
| FIG. 2, steps E and J | 1.2.1.b | Oxidoreductase (acyl-CoA to aldehyde) |
| FIG. 2, step D | 1.3.1.a | Oxidoreductase operating on CH—CH donors |
| FIG. 2, steps F and K | 1.4.1.a | Oxidoreductase operating on amino acids |
| FIG. 2, step A | 2.3.1.b | Acyltransferase |
| FIG. 2, steps F and K | 2.6.1.a | Aminotransferase |
| FIG. 2, steps G and L | 2.8.3.a | Coenzyme-A transferase |
| FIG. 2, steps G and L | 6.2.1.a | Acid-thiol ligase |
| FIG. 2, Step H | 6.3.1.a/6.3.2.a | Amide synthases/peptide synthases |
| FIG. 2, step I | No enzyme required | Spontaneous cyclization |

FIG. 2, Step A—3-Oxoadipyl-CoA Thiolase (EA1)
2.3.1.b Acyl Transferase.

The first step in the pathway combines acetyl-CoA and succinyl-CoA to form 3-oxoadipyl-CoA. FIG. 2, step A can involve an EA1, or equivalently, succinyl CoA:acetyl CoA acyl transferase (β-ketothiolase). The gene products encoded by pcaF in *Pseudomonas* strain B13 (Kaschabek et al., *J. Bacteriol.* 184:207-215 (2002)), phaD in *Pseudomonas putida* U (Oliveran Et al., *Proc. Natl. Acad. Sci. USA* 95:6419-6424 (1998)), paaE in *Pseudomonas fluorescens* ST (Di Gennaro et al., *Arch. Microbiol.* 188:117-125 (2007)), and paaJ from *E. coli* (Nogales et al., *Microbiol.* 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the synthesis of 3-oxoadipyl-CoA. For example, the ketothiolase phaA from *R. eutropha* combines two molecules of acetyl-CoA to form acetoacetyl-CoA (Sato et al., *J Biosci Bioeng* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. The protein sequences for the above-mentioned gene products are well known in the art and can be accessed in the public databases such as GenBank using the following accession numbers.

| Gene name | GI Number | GenBank ID | Organism |
| --- | --- | --- | --- |
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| paaE | 106636097 | ABF82237.1 | *Pseudomonas fluorescens* |

These exemplary sequences can be used to identify homologue proteins in GenBank or other databases through sequence similarity searches (for example, BLASTp). The resulting homologue proteins and their corresponding gene sequences provide additional exogenous DNA sequences for transformation into *E. coli* or other suitable host microorganisms to generate production hosts.

For example, orthologs of paaJ from *Escherichia coli* K12 can be found using the following GenBank accession numbers:

| GI Number | GenBank ID | Organism |
| --- | --- | --- |
| 152970031 | YP_001335140.1 | *Klebsiella pneumoniae* |
| 157371321 | YP_001479310.1 | *Serratia proteamaculans* |
| 3253200 | AAC24332.1 | *Pseudomonas putida* |

Example orthologs of pcaF from *Pseudomonas knackmussii* can be found using the following GenBank accession numbers:

| GI Number | GenBank ID | Organism |
| --- | --- | --- |
| 4530443 | AAD22035.1 | *Streptomyces* sp. 2065 |
| 24982839 | AAN67000.1 | *Pseudomonas putida* |
| 115589162 | ABJ15177.1 | *Pseudomonas aeruginosa* |

Additional native candidate genes for the ketothiolase step include atoB, which can catalyze the reversible condensation of 2 acetyl-CoA molecules (Sato et al., *J. Biosci. Bioengineer.* 103:38-44 (2007)), and its homolog yqeF. Non-native gene candidates include phaA (Sato et al., supra, 2007) and bktB (Slater et al., *J. Bacteriol.* 180:1979-1987 (1998)) from *R. eutropha*, and the two ketothiolases, thiA and thiB, from *Clostridium acetobutylicum* (Winzer et al., *J. Mol. Microbiol. Biotechnol.* 2:531-541 (2000)). The protein sequences for each of these exemplary gene products can be found using the following GenBank accession numbers:

| Gene Name | GenBank ID | Organism |
| --- | --- | --- |
| atoB | NP_416728.1 | *Escherichia coli* |
| yqeF | NP_417321.2 | *Escherichia coli* |
| phaA | YP_725941 | *Ralstonian Eutropha* |
| bktB | AAC38322.1 | *Ralstonian Eutropha* |
| thiA | NP_349476.1 | *Clostridium acetobutylicum* |
| thiB | NP_149242.1 | *Clostridium acetobutylicum* |

2-Amino-4-oxopentanoate (AKP) thiolase or AKP thiolase (AKPT) enzymes present additional candidates for performing step A in FIG. 2. AKPT is a pyridoxal phosphate-dependent enzyme participating in ornithine degradation in *Clostridium sticklandii* (Jeng et al., *Biochemistry* 13:2898-2903 (1974); Kenklies et al., *Microbiology* 145:819-826 (1999)). A gene cluster encoding the alpha and beta subunits of AKPT (or-2 (ortA) and or-3 (ortB)) was recently identified and the biochemical properties of the enzyme were characterized (Fonknechten et al., *J. Bacteriol.* In Press (2009)). The enzyme is capable of operating in both directions and naturally reacts with the D-isomer of alanine AKPT from *Clostridium sticklandii* has been characterized but its protein sequence has not yet been published. Enzymes with high sequence homology are found in *Clostridium difficile*, *Alkaliphilus* metalliredigenes QYF, *Thermoanaerobacter* sp. X514, and *Thermoanaerobacter tengcongensis* MB4 (Fonknechten et al., supra).

| Gene name | GI Number | GenBank ID | Organism |
| --- | --- | --- | --- |
| ortA (α) | 126698017 | YP_001086914.1 | *Clostridium difficile* 630 |
| ortB (β) | 126698018 | YP_001086915.1 | *Clostridium difficile* 630 |
| Amet_2368 (α) | 150390132 | YP_001320181.1 | *Alkaliphilus metalliredigenes* QYF |
| Amet_2369 (β) | 150390133 | YP_001320182.1 | *Alkaliphilus metalliredigenes* QYF |
| Teth514_1478 (α) | 167040116 | YP_001663101.1 | *Thermoanaerobacter* sp. X514 |
| Teth514_1479 (β) | 167040117 | YP_001663102.1 | *Thermoanaerobacter* sp. X514 |
| TTE1235 (α) | 20807687 | NP_622858.1 | *Thermoanaerobacter tengcongensis* MB4 |
| thrC (β) | 20807688 | NP_622859.1 | *Thermoanaerobacter tengcongensis* MB4 |

FIG. 2, Step B—3-Oxoadipyl-CoA Reductase (EA2)
1.1.1.a Oxidoreductases.

Certain transformations depicted in FIG. 2 involve oxidoreductases that convert a ketone functionality to a hydroxyl group. For example, FIG. 2, step B involves the reduction of a 3-oxoacyl-CoA to a 3-hydroxyacyl-CoA.

Exemplary enzymes that can convert 3-oxoacyl-CoA molecules, such as 3-oxoadipyl-CoA, into 3-hydroxyacyl-CoA molecules, such as 3-hydroxyadipyl-CoA, include enzymes whose natural physiological roles are in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71:403-411 (1981)). Furthermore, the gene products encoded by phaC in *Pseudomonas putida* U (Oliveran Et al., *Proc. Natl. Acad. Sci. USA* 95:6419-6424 (1998)) and paaC in *Pseudomonas fluorescens* ST (Di Gennaro et al., *Arch. Microbiol.* 188:117-125 (2007)) catalyze the reverse reaction of step B in FIG. 2, that is, the oxidation of 3-hydroxyadipyl-CoA to form 3-oxoadipyl-CoA, during the catabolism of phenylacetate or styrene. Note that the reactions catalyzed by such enzymes are reversible. A similar transformation is also carried out by the gene product of hbd in *Clostridium acetobutylicum* (Atsumi et al., *Metab. Eng.* (epub Sep. 14, 2007); Boynton et al., *J. Bacteriol.* 178:3015-3024 (1996)). This enzyme converts acetoacetyl-CoA to 3-hydroxybutyryl-CoA. In addition, given the proximity in *E. coli* of paaH to other genes in the phenylacetate degradation operon (Nogales et al., *Microbiology* 153:357-365 (2007)) and the fact that paaH mutants cannot grow on phenylacetate (Ismail et al., *Eur. J Biochem.* 270:3047-3054 (2003)), it is expected that the *E. coli* paaH gene encodes a 3-hydroxyacyl-CoA dehydrogenase.

| Gene name | GI Number | GenBank ID | Organism |
| --- | --- | --- | --- |
| fadB | 119811 | P21177.2 | *Escherichia coli* |
| fadJ | 3334437 | P77399.1 | *Escherichia coli* |
| paaH | 16129356 | NP_415913.1 | *Escherichia coli* |
| phaC | 26990000 | NP_745425.1 | *Pseudomonas putida* |
| paaC | 106636095 | ABF82235.1 | *Pseudomonas fluorescens* |

Additional exemplary oxidoreductases capable of converting 3-oxoacyl-CoA molecules to their corresponding 3-hydroxyacyl-CoA molecules include 3-hydroxybutyryl-CoA dehydrogenases. The enzyme from *Clostridium acetobutylicum*, encoded by hbd, has been cloned and functionally expressed in *E. coli* (Youngleson et al., *J. Bacteriol.* 171:6800-6807 (1989)). Additional gene candidates include Hbd1 (C-terminal domain) and Hbd2 (N-terminal domain)

in *Clostridium kluyveri* (Hillmer et al., *FEBS Lett.* 21:351-354 (1972)) and HSD17B10 in *Bos taurus* (Wakil et al., *J. Biol. Chem.* 207:631-638 (1954)). Yet other gene candidates demonstrated to reduce acetoacetyl-CoA to 3-hydroxybutyryl-CoA are phbB from *Zoogloea ramigera* (Ploux et al., *Eur. J. Biochem.* 174:177-182 (1988)) and phaB from *Rhodobacter sphaeroides* (Alber et al., *Mol. Microbiol* 61:297-309 (2006)). The former gene candidate is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as a substrate besides acetoacetyl-CoA (Ploux et al., supra).

| Gene name | GI Number | GenBank ID | Organism |
| --- | --- | --- | --- |
| hbd | 18266893 | P52041.2 | *Clostridium acetobutylicum* |
| Hbd2 | 146348271 | EDK34807.1 | *Clostridium kluyveri* |
| Hbd1 | 146345976 | EDK32512.1 | *Clostridium kluyveri* |
| HSD17B10 | 3183024 | O02691.3 | *Bos taurus* |
| phbB | 130017 | P23238.1 | *Zoogloea ramigera* |
| phaB | 146278501 | YP_001168660.1 | *Rhodobacter sphaeroides* |

A number of similar enzymes have been found in other species of *Clostridia* and in *Metallosphaera sedula* (Berg et al., *Science* 318:1782-1786 (2007)).

| Gene name | GI Number | GenBank ID | Organism |
| --- | --- | --- | --- |
| hbd | 15895965 | NP_349314.1 | *Clostridium acetobutylicum* |
| hbd | 20162442 | AAM14586.1 | *Clostridium beijerinckii* |
| Msed_1423 | 146304189 | YP_001191505 | *Metallosphaera sedula* |
| Msed_0399 | 146303184 | YP_001190500 | *Metallosphaera sedula* |
| Msed_0389 | 146303174 | YP_001190490 | *Metallosphaera sedula* |
| Msed_1993 | 146304741 | YP_001192057 | *Metallosphaera sedula* |

FIG. 2, Step C—3-Hydroxyadipyl-CoA Dehydratase (EA3)

FIG. 2, step C can involve an EA3. The gene product of crt from *C. acetobutylicum* catalyzes the dehydration of 3-hydroxybutyryl-CoA to crotonyl-CoA (see FIG. 2) (Atsumi et al., *Metab. Eng.* (epub Sep. 14, 2007); Boynton et al., *J. Bacteriol.* 178:3015-3024 (1996)). Homologs of this gene are strong candidates for carrying out the third step (step C) in the synthesis pathways exemplified in FIG. 2. In addition, genes known to catalyze the hydroxylation of double bonds in enoyl-CoA compounds represent additional candidates given the reversibility of such enzymatic transformations. For example, the enoyl-CoA hydratases, phaA and phaB, of *P. putida* are believed to carry out the hydroxylation of double bonds during phenylacetate catabolism (Oliveran Et al., *Proc. Natl. Acad. Sci. USA* 95:6419-6424 (1998)) and thus represent additional candidates for incorporation into *E. coli*. The deletion of these genes precludes phenylacetate degradation in *P. putida*. The paaA and paaB from *P. fluorescens* catalyze analogous transformations (Oliveran Et al., *Proc. Natl. Acad. Sci. USA* 95:6419-6424 (1998)). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Biotechnol. Bioeng.* 86:681-686 (2004); Park and Lee, *Appl. Biochem. Biotechnol.* 113-116: 335-346 (2004)), and paaG (Ismail et al., supra, 2003; Park and Lee, supra, 2003; Park and Lee, supra, 2004). The protein sequences for each of these exemplary gene products can be found using the following GenBank accession numbers:

| Gene Name | GenBank ID | Organism |
| --- | --- | --- |
| maoC | NP_415905.1 | *Escherichia coli* |
| paaF | NP_415911.1 | *Escherichia coli* |
| paaG | NP_415912.1 | *Escherichia coli* |
| crt | NP_349318.1 | *Clostridium acetobutylicum* |
| paaA | NP_745427.1 | *Pseudomonas putida* |
| paaB | NP_745426.1 | *Pseudomonas putida* |
| phaA | ABF82233.1 | *Pseudomonas fluorescens* |
| phaB | ABF82234.1 | *Pseudomonas fluorescens* |

Alternatively, β-oxidation genes are candidates for the first three steps in adipate synthesis. Candidate genes for the proposed adipate synthesis pathway also include the native fatty acid oxidation genes of *E. coli* and their homologs in other organisms. The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al., *Biochem.* 30:6788-6795 (1991); Yang et al., *J. Biol. Chem.* 265:10424-10429 (1990); Yang et al., *J. Biol. Chem.* 266:16255 (1991); Nakahigashi and Inokuchi, *Nucl. Acids Res.* 18: 4937 (1990)). These activities are mechanistically similar to the first three transformations shown in FIG. 2. The fadI and fadJ genes encode similar functions and are naturally expressed only anaerobically (Campbell et al., *Mol. Microbiol.* 47:793-805 (2003)). These gene products naturally operate to degrade short, medium, and long chain fatty-acyl-CoA compounds to acetyl-CoA, rather than to convert succinyl-CoA and acetyl-CoA into 5-carboxy-2-pentenoyl-CoA as proposed in FIG. 2. However, it is well known that the ketoacyl-CoA thiolase, 3-hydroxyacyl-CoA dehydrogenase, and enoyl-CoA hydratase enzymes catalyze reversible transformations. Furthermore, directed evolution and related approaches can be applied to tailor the substrate specificities of the native β-oxidation machinery of *E. coli*. Thus these enzymes or homologues thereof can be applied for adipate production. If the native genes operate to degrade adipate or its precursors in vivo, the appropriate genetic modifications are made to attenuate or eliminate these functions. However, it may not be necessary since a method for producing poly[(R)-3-hydroxybutyrate] in *E. coli* that involves activating fadB, by knocking out a negative regulator, fadR, and co-expressing a non-native ketothiolase, phaA from *Ralstonian Eutropha*, has been described (Sato et al., *J. Biosci. Bioeng.* 103:38-44 (2007)). This work clearly demonstrated that a β-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors. The protein sequences for each of these exemplary gene products can be found using the following GenBank accession numbers:

| Gene Name | GenBank ID | Organism |
| --- | --- | --- |
| fadA | YP_026272.1 | *Escherichia coli* |
| fadB | NP_418288.1 | *Escherichia coli* |
| fadI | NP_416844.1 | *Escherichia coli* |
| fadJ | NP_416843.1 | *Escherichia coli* |
| fadR | NP_415705.1 | *Escherichia coli* |

FIG. 2, Step D—5-Carboxy-2-Pentenoyl-CoA Reductase (EA4)

1.3.1.a Oxidoreductase Operating on CH—CH Donors.

FIG. 2, step D involves the conversion of 5-carboxy-2-pentenoyl-CoA to adipyl-CoA by EA4. Enoyl-CoA reductase enzymes are suitable enzymes for this transformation.

Whereas the ketothiolase, dehydrogenase, and enoyl-CoA hydratase steps are generally reversible, the enoyl-CoA reductase step is almost always oxidative and irreversible under physiological conditions (Hoffmeister et al., *J. Biol. Chem.* 280:4329-4338 (2005)). FadE catalyzes this likely irreversible transformation in *E. coli* (Campbell and Cronan, *J. Bacteriol.* 184:3759-3764 (2002)). The pathway can involve an enzyme that reduces a 2-enoyl-CoA intermediate, not one such as FadE that will only oxidize an acyl-CoA to a 2-enoyl-CoA compound. Furthermore, although it has been suggested that *E. coli* naturally possesses enzymes for enoyl-CoA reduction (Mizugaki et al., *J. Biochem.* 92:1649-1654 (1982); Nishimaki et al., *J. Biochem.* 95:1315-1321 (1984)), no *E. coli* gene possessing this function has been biochemically characterized.

One exemplary enoyl-CoA reductase is the gene product of bcd from *C. acetobutylicum* (Boynton et al., *J Bacteriol.* 178:3015-3024 (1996); Atsumi et al., *Metab. Eng.* 2008 10(6):305-311 (2008)(Epub Sep. 14, 2007), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli* resulting in an active enzyme (Hoffmeister et al., supra). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci et al., *FEBS Letters* 581:1561-1566 (2007)).

| Gene name | GI Number | GenBank ID | Organism |
| --- | --- | --- | --- |
| bcd | 15895968 | NP_349317.1 | *Clostridium acetobutylicum* |
| etfA | 15895966 | NP_349315.1 | *Clostridium acetobutylicum* |
| etfB | 15895967 | NP_349316.1 | *Clostridium acetobutylicum* |
| TER | 62287512 | Q5EU90.1 | *Euglena gracilis* |
| TDE0597 | 42526113 | NP_971211.1 | *Treponema denticola* |

FIG. 2, Step E—Adipyl-CoA Reductase (Aldehyde Forming) (EA5)

1.2.1.b Oxidoreductase (Acyl-CoA to Aldehyde).

The transformation of adipyl-CoA to adipate semialdehyde (FIG. 2, step E) can involve an acyl-CoA dehydrogenases capable of reducing an acyl-CoA to its corresponding aldehyde. Exemplary genes that encode such enzymes include the *Acinetobacter calcoaceticus* acyl encoding a fatty acyl-CoA reductase (Reiser et al., *J. Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinate semialdehyde dehydrogenase encoded by the sucD gene in *Clostridium kluyveri* (Sohling et al., *J. Bacteria* 178:871-880 (1996)). SucD of *P. gingivalis* is another succinate semialdehyde dehydrogenase (Takahashi et al., *J. Bacteriol.* 182:4704-4710 (2000)). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahayan Et al., *J. Gen. Appl. Microbiol.* 18:43-55 (1972); Koo et al., *Biotechnol Lett.* 27:505-510 (2005)).

| Gene name | GI Number | GenBank ID | Organism |
| --- | --- | --- | --- |
| acr1 | 50086359 | YP_047869.1 | *Acinetobacter calcoaceticus* |
| acr1 | 1684886 | AAC45217 | *Acinetobacter baylyi* |
| acr1 | 18857901 | BAB85476.1 | *Acinetobacter* sp. Strain M-1 |
| sucD | 172046062 | P38947.1 | *Clostridium kluyveri* |
| sucD | 34540484 | NP_904963.1 | *Porphyromonas gingivalis* |
| bphG | 425213 | BAA03892.1 | *Pseudomonas* sp |
| adhE | 55818563 | AAV66076.1 | *Leuconostoc mesenteroides* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); Thauer R. K., *Science* 318:1732-1733 (2007)). The enzyme utilizes NADPH as a cofactor and has been characterized in *Metallosphaera* and *Sulfolobus* spp (Alber et al., *J. Bacterial.* 188:8551-8559 (2006); Hugler et al., *J. Bacteriol.* 184:2404-2410 (2002)). The enzyme is encoded by Msed_0709 in *Metallosphaera sedula* (Alber et al., supra; Berg et al., supra). A gene encoding a malonyl-CoA reductase from *Sulfolobus tokodaii* was cloned and heterologously expressed in *E. coli* (Alber et al., supra). This enzyme has also been shown to catalyze the conversion of methylmalonyl-CoA to its corresponding aldehyde (WO 2007/141208). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl Environ Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra).

| Gene name | GI Number | GenBank ID | Organism |
| --- | --- | --- | --- |
| Msed_0709 | 146303492 | YP_001190808.1 | *Metallosphaera sedula* |
| mcr | 15922498 | NP_378167.1 | *Sulfolobus tokodaii* |

| Gene name | GI Number | GenBank ID | Organism |
|---|---|---|---|
| asd-2 | 15898958 | NP_343563.1 | Sulfolobus solfataricus |
| Saci_2370 | 70608071 | YP_256941.1 | Sulfolobus acidocaldarius |
| Ald | 49473535 | AAT66436 | Clostridium beijerinckii |
| eutE | 687645 | AAA80209 | Salmonella typhimurium |
| eutE | 2498347 | P77445 | Escherichia coli |

FIG. 2, Step F—6-ACA Transaminase (EA6A) or 6-ACA Dehydrogenase (EA6B)

1.4.1.a Oxidoreductase Operating on Amino Acids.

FIG. 2, step F depicts a reductive amination involving the conversion of adipate semialdehyde to 6-ACA.

Most oxidoreductases operating on amino acids catalyze the oxidative deamination of alpha-amino acids with NAD+ or NADP+ as acceptor, though the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., *Nucleic. Acids Res.* 11:5257-5266 (1983); Korber et al., *J. Mol. Biol.* 234:1270-1273 (1993)), gdh from *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene.* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Stoyan et al., *J. Biotechnol* 54:77-80 (1997); Ansorge et al., *Biotechnol Bioeng.* 68:557-562 (2000)). The nadX gene from *Thermotoga maritime* encoding for the aspartate dehydrogenase is involved in the biosynthesis of NAD (Yang et al., *J. Biol. Chem.* 278:8804-8808 (2003)).

| Gene name | GI Number | GenBank ID | Organism |
|---|---|---|---|
| gdhA | 118547 | P00370 | Escherichia coli |
| gdh | 6226595 | P96110.4 | Thermotoga maritima |
| gdhA1 | 15789827 | NP_279651.1 | Halobacterium salinarum |
| ldh | 61222614 | POA393 | Bacillus cereus |
| nadX | 15644391 | NP_229443.1 | Thermotoga maritima |

The lysine 6-dehydrogenase (deaminating), encoded by the lysDH genes, catalyze the oxidative deamination of the 8-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989); Misono et al., supra), and *Achromobacter denitrificans* (Ruldeekulthamrong et al., *BMB. Rep.* 41:790-795 (2008)). Such enzymes are particularly good candidates for converting adipate semialdehyde to 6-ACA given the structural similarity between adipate semialdehyde and 2-aminoadipate-6-semialdehyde.

| Gene name | GI Number | GenBank ID | Organism |
|---|---|---|---|
| lysDH | 13429872 | BAB39707 | Geobacillus stearothermophilus |
| lysDH | 15888285 | NP_353966 | Agrobacterium tumefaciens |
| lysDH | 74026644 | AAZ94428 | Achromobacter denitrificans |

2.6.1.a Aminotransferase.

Step F of FIG. 2 can also, in certain embodiments, involve the transamination of a 6-aldehyde to an amine. This transformation can be catalyzed by gamma-aminobutyrate transaminase (GABA transaminase). One *E. coli* GABA transaminase is encoded by gabT and transfers an amino group from glutamate to the terminal aldehyde of succinyl semialdehyde (Bartsch et al., *J. Bacteria* 172:7035-7042 (1990)). The gene product of puuE catalyzes another 4-aminobutyrate transaminase in *E. coli* (Kuriharan Et al., *J. Biol. Chem.* 280:4602-4608 (2005)). GABA transaminases in *Mus musculus, Pseudomonas fluorescens*, and *Sus scrofa* have been shown to react with 6-aminocaproic acid (Cooper, *Methods Enzymol.* 113:80-82 (1985); Scott et al., *J. Biol. Chem.* 234:932-936 (1959)).

| Gene name | GI Number | GenBank ID | Organism |
|---|---|---|---|
| gabT | 16130576 | NP_417148.1 | Escherichia coli |
| puuE | 16129263 | NP_415818.1 | Escherichia coli |
| abat | 37202121 | NP_766549.2 | Mus musculus |
| gabT | 70733692 | YP_257332.1 | Pseudomonas fluorescens |
| abat | 47523600 | NP_999428.1 | Sus scrofa |

Additional enzyme candidates include putrescine aminotransferases or other diamine aminotransferases. Such enzymes are particularly well suited for carrying out the conversion of 6-ACA semialdehyde to HMDA. The *E. coli* putrescine aminotransferase is encoded by the ygjG gene and the purified enzyme also was able to transaminate cadaverine and spermidine (Samsonovan Et al., *BMC Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonovan Et al., supra; Kim, K. H., *J Biol Chem* 239:783-786 (1964)). A putrescine aminotransferase with higher activity with pyruvate as the amino acceptor than alpha-ketoglutarate is the spuC gene of *Pseudomonas aeruginosa* (Lu et al., *J Bacteriol* 184:3765-3773 (2002)).

| Gene name | GI Number | GenBank ID | Organism |
|---|---|---|---|
| ygjG | 145698310 | NP_417544 | Escherichia coli |
| spuC | 9946143 | AAG03688 | Pseudomonas aeruginosa |

Yet additional candidate enzymes include beta-alanine/alpha-ketoglutarate aminotransferases which produce malonate semialdehyde from beta-alanine (WO08027742). The gene product of SkPYD4 in *Saccharomyces kluyveri* was also shown to preferentially use beta-alanine as the amino group donor (Andersen et al., *FEBS. J.* 274:1804-1817 (2007)). SkUGA1 encodes a homologue of *Saccharomyces cerevisiae* GABA aminotransferase, UGA1 (Ramos et al., *Eur. J. Biochem.,* 149:401-404 (1985)), whereas SkPYD4 encodes an enzyme involved in both β-alanine and GABA transamination (Andersen et al., supra). 3-Amino-2-methylpropionate transaminase catalyzes the transformation from methylmalonate semialdehyde to 3-amino-2-methylpropionate. This enzyme has been characterized in *Rattus* norvegicus and Sus scrofa and is encoded by Abat (Tamaki et al, Methods Enzymol, 324:376-389 (2000)).

| Gene name | GI Number | GenBank ID | Organism |
|---|---|---|---|
| SkyPYD4 | 98626772 | ABF58893.1 | Saccharomyces kluyveri |
| SkUGA1 | 98626792 | ABF58894.1 | Saccharomyces kluyveri |
| UGA1 | 6321456 | NP_011533.1 | Saccharomyces cerevisiae |
| Abat | 122065191 | P50554.3 | Rattus norvegicus |
| Abat | 120968 | P80147.2 | Sus scrofa |

FIG. 2, Step G—6-Aminocaproyl-CoA/Acyl-CoA Transferase (EA7A) or 6-Aminocaproyl-CoA Synthase (EA7B)

2.8.3.a Coenzyme-A Transferase.

CoA transferases catalyze reversible reactions that involve the transfer of a CoA moiety from one molecule to another. For example, step G of FIG. 2 can be catalyzed by a 6-aminocaproyl-CoA/Acyl CoA transferase. One candidate enzyme for these steps is the two-unit enzyme encoded by pcaI and pcaJ in Pseudomonas, which has been shown to have 3-oxoadipyl-CoA/succinate transferase activity ((Kaschabek and Reineke, J. Bacteriol. 177:320-325 (1995); and Kaschabek. and Reineke, J. Bacteriol. 175:6075-6081 (1993)). Similar enzymes based on homology exist in Acinetobacter sp. ADP1 (Kowalchuk et al., Gene 146:23-30 (1994)) and Streptomyces coelicolor. Additional exemplary succinyl-CoA:3:oxoacid-CoA transferases are present in Helicobacter pylori (Corthesy-Theulaz et al., J. Biol. Chem. 272:25659-25667 (1997)) and Bacillus subtilis (Stols et al., Protein. Expr. Purif. 53:396-403 (2007)).

| Gene name | GI Number | GenBank ID | Organism |
|---|---|---|---|
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |

A 3-oxoacyl-CoA transferase that can utilize acetate as the CoA acceptor is acetoacetyl-CoA transferase, encoded by the E. coli atoA (alpha subunit) and atoD (beta subunit) genes (Vanderwinkel et al., Biochem. Biophys. Res Commun. 33:902-908 (1968); Korolev et al., Acta Crystallogr. D Biol Crystallogr. 58:2116-2121 (2002)). This enzyme has also been shown to transfer the CoA moiety to acetate from a variety of branched and linear acyl-CoA substrates, including isobutyrate (Matthies et al., Appl Environ Microbiol 58:1435-1439 (1992)), valerate (Vanderwinkel et al., supra) and butanoate (Vanderwinkel et al., supra). Similar enzymes exist in Corynebacterium glutamicum ATCC 13032 (Duncan et al., Appl Environ Microbiol 68:5186-5190 (2002)), Clostridium acetobutylicum (Cary et al., Appl Environ Microbiol 56:1576-1583 (1990)), and Clostridium saccharoperbutylacetonicum (Kosakan Et al., Biosci. Biotechnol Biochem. 71:58-68 (2007)).

| Gene name | GI Number | GenBank ID | Organism |
|---|---|---|---|
| atoA | 2492994 | P76459.1 | Escherichia coli K12 |
| atoD | 2492990 | P76458.1 | Escherichia coli K12 |

| Gene name | GI Number | GenBank ID | Organism |
|---|---|---|---|
| actA | 62391407 | YP_226809.1 | Corynebacterium glutamicum ATCC 13032 |
| cg0592 | 62389399 | YP_224801.1 | Corynebacterium glutamicum ATCC 13032 |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

The above enzymes may also exhibit the desired activities on 6-ACA and 6-aminocaproyl-CoA (FIG. 2, step G). Nevertheless, additional exemplary transferase candidates are catalyzed by the gene products of cat1, cat2, and cat3 of Clostridium kluyveri which have been shown to exhibit succinyl-CoA, 4-hydroxybutyryl-CoA, and butyryl-CoA transferase activity, respectively (Seedorf et al., supra; Sohling et al., Eur. J Biochem. 212:121-127 (1993);Sohling et al., J Bacteriol. 178:871-880 (1996)).

| Gene name | GI Number | GenBank ID | Organism |
|---|---|---|---|
| cat1 | 729048 | P38946.1 | Clostridium kluyveri |
| cat2 | 172046066 | P38942.2 | Clostridium kluyveri |
| cat3 | 146349050 | EDK35586.1 | Clostridium kluyveri |

The glutaconate-CoA-transferase (EC 2.8.3.12) enzyme from anaerobic bacterium Acidaminococcus fermentans reacts with diacid glutaconyl-CoA and 3-butenoyl-CoA (Mack et al., FEBS Lett. 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., Eur. J. Biochem. 118:315-321 (1981)). The enzyme has been cloned and expressed in E. coli (Mack et al., Eur. J. Biochem. 226:41-51 (1994)).

| Gene name | GI Number | GenBank ID | Organism |
|---|---|---|---|
| gctA | 559392 | CAA57199.1 | Acidaminococcus fermentans |
| gctB | 559393 | CAA57200.1 | Acidaminococcus fermentans |

6.2.1.a Acid-Thiol Ligase.

Step G of FIG. 2 can also involve an acid-thiol ligase or synthetase functionality (the terms ligase, synthetase, and synthase are used herein interchangeably and refer to the same enzyme class). Exemplary genes encoding enzymes to carry out these transformations include the sucCD genes of E. coli which naturally form a succinyl-CoA synthetase complex. This enzyme complex naturally catalyzes the formation of succinyl-CoA from succinate with the concaminant consumption of one ATP, a reaction which is reversible in vivo (Buck et al., Biochem. 24:6245-6252 (1985)). Given the structural similarity between succinate and adipate, that is, both are straight chain dicarboxylic acids, it is reasonable to expect some activity of the sucCD enzyme on adipyl-CoA.

| Gene name | GI Number | GenBank ID | Organism |
| --- | --- | --- | --- |
| sucC | 16128703 | NP_415256.1 | Escherichia coli |
| sucD | 1786949 | AAC73823.1 | Escherichia coli |

Additional exemplary CoA-ligases include the rat dicarboxylate-CoA ligase for which the sequence is yet uncharacterized (Vamecq et al., Biochemical Journal 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178(14):4122-4130 (1996)). Additional candidate enzymes are acetoacetyl-CoA synthetases from Mus musculus (Hasegawan Et al., Biochim Biophys Acta 1779:414-419 (2008)) and Homo sapiens (Ohgami et al., Biochem Pharmacol 65:989-994 (2003)) which naturally catalyze the ATP-dependant conversion of acetoacetate into acetoacetyl-CoA.

| Gene name | GI Number | GenBank ID | Organism |
| --- | --- | --- | --- |
| phl | 77019264 | CAJ15517.1 | Penicillium chrysogenum |
| phlB | 152002983 | ABS19624.1 | Penicillium chrysogenum |
| paaF | 22711873 | AAC24333.2 | Pseudomonas putida |
| bioW | 50812281 | NP_390902.2 | Bacillus subtilis |
| AACS | 21313520 | NP_084486.1 | Mus musculus |
| AACS | 31982927 | NP_076417.2 | Homo sapiens |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD1 from Archaeoglobus fulgidus, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., J Bacteriol 184:636-644 (2002)). The enzyme from Haloarcula marismortui (annotated as a succinyl-CoA synthetase) accepts propionate, butyrate, and branched-chain acids (isovalerate and isobutyrate) as substrates, and was shown to operate in the forward and reverse directions (Brasen et al., Arch Microbiol 182:277-287 (2004)). The ACD encoded by PAE3250 from hyperthermophilic crenarchaeon Pyrobaculum aerophilum showed the broadest substrate range of all characterized ACDs, reacting with acetyl-CoA, isobutyryl-CoA (preferred substrate) and phenylacetyl-CoA (Brasen et al., supra). The enzymes from A. fulgidus, H. marismortui and P. aerophilum have all been cloned, functionally expressed, and characterized in E. coli (Musfeldt et al., supra; Brasen et al., supra).

| Gene name | GI Number | GenBank ID | Organism |
| --- | --- | --- | --- |
| AF1211 | 11498810 | NP_070039.1 | Archaeoglobus fulgidus DSM 4304 |
| Scs | 55377722 | YP_135572.1 | Haloarcula marismortui ATCC 43049 |
| PAE3250 | 18313937 | NP_560604.1 | Pyrobaculum aerophilum str. IM2 |

Yet another option is to employ a set of enzymes with net ligase or synthetase activity. For example, phosphotransadipylase and adipate kinase enzymes are catalyzed by the gene products of buk1, buk2, and ptb from C. acetobutylicum (Walter et al., Gene 134:107-111 (1993); Huang et al., J. Mol. Microbiol. Biotechnol. 2:33-38 (2000)). The ptb gene encodes an enzyme that can convert butyryl-CoA into butyryl-phosphate, which is then converted to butyrate via either of the buk gene products with the concomitant generation of ATP.

| Gene name | GI Number | GenBank ID | Organism |
| --- | --- | --- | --- |
| ptb | 15896327 | NP_349676 | Clostridium acetobutylicum |
| buk1 | 15896326 | NP_349675 | Clostridium acetobutylicum |
| buk2 | 20137415 | Q97II1 | Clostridium acetobutylicum |

FIG. 2, Step H—Amidohydrolase (EA8)

6.3.1.a/6.3.2.a Amide Synthases/Peptide Synthases.

The direct conversion of 6-ACA to caprolactam (FIG. 2, step H) can involve the formation of an intramolecular peptide bond. Ribosomes, which assemble amino acids into proteins during translation, are nature's most abundant peptide bond-forming catalysts. Nonribosomal peptide synthetases are peptide bond forming catalysts that do not involve messenger mRNA (Schwarzer et al., Nat Prod. Rep. 20:275-287 (2003)). Additional enzymes capable of forming peptide bonds include acyl-CoA synthetase from Pseudomonas chlororaphis (Abe et al., J Biol Chem 283:11312-11321 (2008)), gamma-Glutamylputrescine synthetase from E. coli (Kuriharan Et al., J Biol Chem 283:19981-19990 (2008)), and beta-lactam synthetase from Streptomyces clavuligerus (Bachmann et al., Proc Natl Acad Sci USA 95:9082-9086 (1998); Bachmann et al., Biochemistry 39:11187-11193 (2000); Miller et al., Nat Struct. Biol 8:684-689 (2001); Miller et al., Proc Natl Acad Sci USA 99:14752-14757 (2002); Tahlan et al., Antimicrob. Agents. Chemother. 48:930-939 (2004)).

| Gene name | GI Number | GenBank ID | Organism |
| --- | --- | --- | --- |
| acsA | 60650089 | BAD90933 | Pseudomonas chlororaphis |
| puuA | 87081870 | AAC74379 | Escherichia coli |
| bls | 41016784 | Q9R8E3 | Streptomyces clavuligerus |

FIG. 2, Step I—Spontaneous Cyclization

The conversion of 6-aminocaproyl-CoA to caprolactam can occur by spontaneous cyclization. Because 6-aminocaproyl-CoA can cyclize spontaneously to caprolactam, it eliminates the need for a dedicated enzyme for this step. A similar spontaneous cyclization is observed with 4-aminobutyryl-CoA which forms pyrrolidinone (Ohsugi et al., J Biol Chem 256:7642-7651 (1981)).

FIG. 2, Step J—6-Aminocaproyl-CoA Reductase (Aldehyde Forming) (EA9)

1.2.1.b Oxidoreductase (Acyl-CoA to Aldehyde).

The transformation of 6-aminocaproyl-CoA to 6-ACA semialdehyde (FIG. 2, step J) can involve an acyl-CoA dehydrogenases capable of reducing an acyl-CoA to its corresponding aldehyde. Exemplary genes that encode such enzymes include the Acinetobacter calcoaceticus acyl encoding a fatty acyl-CoA reductase (Reiser et al., J. Bacteriology 179:2969-2975 (1997)), the Acinetobacter sp. M-1 fatty acyl-CoA reductase (Ishige et al., Appl. Environ. Microbiol. 68:1192-1195 (2002)), and a CoA- and NADP-dependent succinate semialdehyde dehydrogenase encoded by the sucD gene in *Clostridium kluyveri* (Sohling et al., *J. Bacteriol.* 178:871-880 (1996)). SucD of *P. gingivalis* is another succinate semialdehyde dehydrogenase (Takahashi et al., *J. Bacteriol.* 182:4704-4710 (2000)). The enzyme acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahayan Et al., *J. Gen. Appl. Microbiol.* 18:43-55 (1972); Koo et al., *Biotechnol Lett.* 27:505-510 (2005)).

| Gene name | GI Number | GenBank ID | Organism |
| --- | --- | --- | --- |
| acr1 | 50086359 | YP_047869.1 | *Acinetobacter calcoaceticus* |
| acr1 | 1684886 | AAC45217 | *Acinetobacter baylyi* |
| acr1 | 18857901 | BAB85476.1 | *Acinetobacter* sp. Strain M-1 |
| sucD | 172046062 | P38947.1 | *Clostridium kluyveri* |
| sucD | 34540484 | NP_904963.1 | *Porphyromonas gingivalis* |
| bphG | 425213 | BAA03892.1 | *Pseudomonas* sp |
| adhE | 55818563 | AAV66076.1 | *Leuconostoc mesenteroides* |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., supra; Thauer R. K., *Science* 318:1732-1733 (2007)). The enzyme utilizes NADPH as a cofactor and has been characterized in *Metallosphaera* and *Sulfolobus* spp (Alber et al., *J. Bacteriol.* 188:8551-8559 (2006); Hugler et al., *J. Bacteriol.* 184:2404-2410 (2002)). The enzyme is encoded by Msed_0709 in *Metallosphaera sedula* (Alber et al., supra; Berg et al., supra). A gene encoding a malonyl-CoA reductase from *Sulfolobus tokodaii* was cloned and heterologously expressed in *E. coli* (Alber et al., supra). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl Environ Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra).

| Gene name | GI Number | GenBank ID | Organism |
| --- | --- | --- | --- |
| Msed_0709 | 146303492 | YP_001190808.1 | *Metallosphaera sedula* |
| mcr | 15922498 | NP_378167.1 | *Sulfolobus tokodaii* |
| asd-2 | 15898958 | NP_343563.1 | *Sulfolobus solfataricus* |
| Saci_2370 | 70608071 | YP_256941.1 | *Sulfolobus acidocaldarius* |
| Ald | 49473535 | AAT66436 | *Clostridium beijerinckii* |
| eutE | 687645 | AAA80209 | *Salmonella typhimurium* |
| eutE | 2498347 | P77445 | *Escherichia coli* |

FIG. 2, Step K—HMDA Transaminase (EA10A) or HMDA Dehydrogenase (EA10B)

1.4.1.a Oxidoreductase Operating on Amino Acids.

Step K of FIG. 2 depicts a reductive animation and entails the conversion of 6-ACA semialdehyde to HMDA.

Most oxidoreductases operating on amino acids catalyze the oxidative deamination of alpha-amino acids with NAD+ or NADP+ as acceptor, though the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., *Nucleic. Acids Res.* 11:5257-5266 (1983); Korber et al., *J. Mol. Biol.* 234:1270-1273 (1993)), gdh from *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene.* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Stoyan et al., *J. Biotechnol* 54:77-80 (1997); Ansorge et al., *Biotechnol Bioeng.* 68:557-562 (2000)). The nadX gene from *Thermotoga maritime* encoding for the aspartate dehydrogenase is involved in the biosynthesis of NAD (Yang et al., *J. Biol. Chem.* 278:8804-8808 (2003)).

| Gene name | GI Number | GenBank ID | Organism |
| --- | --- | --- | --- |
| gdhA | 118547 | P00370 | *Escherichia coli* |
| gdh | 6226595 | P96110.4 | *Thermotoga maritima* |
| gdhA1 | 15789827 | NP_279651.1 | *Halobacterium salinarum* |
| ldh | 61222614 | P0A393 | *Bacillus cereus* |
| nadX | 15644391 | NP_229443.1 | *Thermotoga maritima* |

The lysine 6-dehydrogenase (deaminating), encoded by the lysDH genes, catalyze the oxidative deamination of the 8-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989); Misono et al., supra), and *Achromobacter denitrificans* (Ruldeekulthamrong et al., *BMB. Rep.* 41:790-795 (2008)). Such enzymes are particularly good candidates for converting adipate semialdehyde to 6-ACA given the structural similarity between adipate semialdehyde and 2-aminoadipate-6-semialdehyde.

| Gene name | GI Number | GenBank ID | Organism |
|---|---|---|---|
| lysDH | 13429872 | BAB39707 | Geobacillus stearothermophilus |
| lysDH | 15888285 | NP_353966 | Agrobacterium tumefaciens |
| lysDH | 74026644 | AAZ94428 | Achromobacter denitrificans |

2.6.1.a Aminotransferase.

Step K of FIG. 2, in certain embodiments, can involve the transamination of a 6-aldehyde to an amine. This transformation can be catalyzed by gamma-aminobutyrate transaminase (GABA transaminase). One *E. coli* GABA transaminase is encoded by gabT and transfers an amino group from glutamate to the terminal aldehyde of succinyl semialdehyde (Bartsch et al., *J. Bacteria* 172:7035-7042 (1990)). The gene product of puuE catalyzes another 4-aminobutyrate transaminase in *E. coli* (Kuriharan Et al., *J. Biol. Chem.* 280:4602-4608 (2005)). GABA transaminases in *Mus musculus*, *Pseudomonas fluorescens*, and *Sus scrofa* have been shown to react with 6-aminocaproic acid (Cooper, *Methods Enzymol.* 113:80-82 (1985); Scott et al., *J. Biol. Chem.* 234:932-936 (1959)).

| Gene name | GI Number | GenBank ID | Organism |
|---|---|---|---|
| gabT | 16130576 | NP_417148.1 | Escherichia coli |
| puuE | 16129263 | NP_415818.1 | Escherichia coli |
| abat | 37202121 | NP_766549.2 | Mus musculus |
| gabT | 70733692 | YP_257332.1 | Pseudomonas fluorescens |
| abat | 47523600 | NP_999428.1 | Sus scrofa |

Additional enzyme candidates include putrescine aminotransferases or other diamine aminotransferases. Such enzymes are particularly well suited for carrying out the conversion of 6-ACA semialdehyde to HMDA. The *E. coli* putrescine aminotransferase is encoded by the ygjG gene and the purified enzyme also was able to transaminate cadaverine and spermidine (Samsonovan Et al., *BMC Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonovan Et al., supra; Kim, K. H., *J Biol Chem* 239:783-786 (1964)). A putrescine aminotransferase with higher activity with pyruvate as the amino acceptor than alpha-ketoglutarate is the spuC gene of *Pseudomonas aeruginosa* (Lu et al., *J Bacteriol* 184:3765-3773 (2002)).

| Gene name | GI Number | GenBank ID | Organism |
|---|---|---|---|
| ygjG | 145698310 | NP_417544 | Escherichia coli |
| spuC | 9946143 | AAG03688 | Pseudomonas aeruginosa |

Yet additional candidate enzymes include beta-alanine/alpha-ketoglutarate aminotransferases which produce malonate semialdehyde from beta-alanine (WO08027742). The gene product of SkPYD4 in *Saccharomyces kluyveri* was also shown to preferentially use beta-alanine as the amino group donor (Andersen et al., *FEBS. J.* 274:1804-1817 (2007)). SkUGA1 encodes a homologue of *Saccharomyces cerevisiae* GABA aminotransferase, UGA1 (Ramos et al., *Eur. J. Biochem.*, 149:401-404 (1985)), whereas SkPYD4 encodes an enzyme involved in both β-alanine and GABA transamination (Andersen et al., supra). 3-Amino-2-methylpropionate transaminase catalyzes the transformation from methylmalonate semialdehyde to 3-amino-2-methylpropionate. This enzyme has been characterized in *Rattus norvegicus* and *Sus scrofa* and is encoded by Abat (Tamaki et al, *Methods Enzymol*, 324:376-389 (2000)).

| Gene name | GI Number | GenBank ID | Organism |
|---|---|---|---|
| SkyPYD4 | 98626772 | ABF58893.1 | Saccharomyces kluyveri |
| SkUGA1 | 98626792 | ABF58894.1 | Saccharomyces kluyveri |
| UGA1 | 6321456 | NP_011533.1 | Saccharomyces cerevisiae |
| Abat | 122065191 | P50554.3 | Rattus norvegicus |
| Abat | 120968 | P80147.2 | Sus scrofa |

FIG. 2, Step L—Adipyl-CoA Hydrolase (EA11A), Adipyl-CoA Ligase (EA11B), Adipyl-CoA Transferase (EA11C) or Phosphotransadipylase/Adipate Kinase (EA11D)

FIG. 2, step L can involve adipyl-CoA synthetase (also referred to as adipate-CoA ligase), EA11D, adipyl-CoA:acetyl-CoA transferase, or EA11A. From an energetic standpoint, it is desirable for the final step in the adipate synthesis pathway to be catalyzed by an enzyme or enzyme pair that can conserve the ATP equivalent stored in the thioester bond of adipyl-CoA. The product of the sucC and sucD genes of *E. coli*, or homologs thereof, can potentially catalyze the final transformation shown in FIG. 2 should they exhibit activity on adipyl-CoA. The sucCD genes naturally form a succinyl-CoA synthetase complex that catalyzes the formation of succinyl-CoA from succinate with the concaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA. An enzyme exhibiting EA11B activity can equivalently carry out the ATP-generating production of adipate from adipyl-CoA, here using AMP and PPi as cofactors, when operating in the opposite physiological. Exemplary CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395, 147-155 (2005); Wang et al., *Biochem. Biophy. Res. Commun.* 360:453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178:4122-4130 (1996)). The protein sequences for each of these exemplary gene products can be found using the following GI numbers and/or GenBank identifiers:

| Gene name | GI Number | GenBank ID | Organism |
|---|---|---|---|
| sucC | 16128703 | NP_415256.1 | Escherichia coli |
| sucD | 1786949 | AAC73823.1 | Escherichia coli |

Another option, using EA11D, is catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)), or homologs thereof. The ptb gene encodes an enzyme that can convert butyryl-CoA into butyryl-phosphate, which is then converted to butyrate via either of the buk gene products with the concomitant generation of ATP. The analogous set of transformations, that is, conversion of adipyl-CoA to adipyl-phosphate followed by conversion of adipyl-phosphate to adipate, can be carried out by the buk1, buk2, and ptb gene products. The protein sequences for each of these exemplary gene products can be found using the following GI numbers and/or GenBank identifiers:

| Gene name | GI Number | GenBank ID | Organism |
|---|---|---|---|
| ptb | 15896327 | NP_349676 | Clostridium acetobutylicum |
| buk1 | 15896326 | NP_349675 | Clostridium acetobutylicum |
| buk2 | 20137415 | Q97II1 | Clostridium acetobutylicum |

Alternatively, an acetyltransferase capable of transferring the CoA group from adipyl-CoA to acetate can be applied. Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Sohling and Gottschalk, *J. Bacteriol.* 178:871-880 (1996); Seedorf et al., *Proc. Natl. Acad. Sci. USA* 105:2128-2133 (2008)). The protein sequences for each of these exemplary gene products can be found using the following GI numbers and/or GenBank identifiers:

| Gene name | GI Number | GenBank ID | Organism |
|---|---|---|---|
| cat1 | 729048 | P38946.1 | Clostridium kluyveri |
| cat2 | 172046066 | P38942.2 | Clostridium kluyveri |
| cat3 | 146349050 | EDK35586.1 | Clostridium kluyveri |

Finally, though not as desirable from an energetic standpoint, the conversion of adipyl-CoA to adipate can also be carried out by an acyl-CoA hydrolase or equivalently a thioesterase. The top *E. coli* gene candidate is tesB (Naggert et al., *J. Biol. Chem.* 266:11044-11050 (1991)), which shows high similarity to the human acot8, which is a dicarboxylic acid acetyltransferase with activity on adipyl-CoA (Westin et al., *J. Biol. Chem.* 280:38125-38132 (2005)). This activity has also been characterized in the rat liver (Deana, *Biochem. Int.* 26:767-773 (1992)). The protein sequences for each of these exemplary gene products can be found using the following GI numbers and/or GenBank identifiers:

| Gene name | GI Number | GenBank ID | Organism |
|---|---|---|---|
| tesB | 16128437 | NP_414986 | Escherichia coli |
| acot8 | 3191970 | CAA15502 | Homo sapiens |
| acot8 | 51036669 | NP_570112 | Rattus norvegicus |

Other native candidate genes include tesA (Bonner and Bloch, *J. Biol. Chem.* 247:3123-3133 (1972)), ybgC (Kuznetsovan Et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). The protein sequences for each of these exemplary gene products can be found using the following GI numbers and/or GenBank identifiers:

| Gene name | GI Number | GenBank ID | Organism |
|---|---|---|---|
| tesA | 16128478 | NP_415027 | Escherichia coli |
| ybgC | 16128711 | NP_415264 | Escherichia coli |
| paaI | 16129357 | NP_415914 | Escherichia coli |
| ybdB | 16128580 | NP_415129 | Escherichia coli |

2.8.3.a Coenzyme-A Transferase.

CoA transferases catalyze reversible reactions that involve the transfer of a CoA moiety from one molecule to another. For example, step L of FIG. 2 can be catalyzed by an EA11C. One candidate enzyme for this step is the two-unit enzyme encoded by pcaI and pcaJ in *Pseudomonas*, which has been shown to have 3-oxoadipyl-CoA/succinate transferase activity (Kaschabek and Reineke, *J. Bacteria* 177:320-325 (1995); and Kaschabek. and Reineke, *J. Bacteria* 175:6075-6081 (1993)). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)).

| Gene name | GI Number | GenBank ID | Organism |
|---|---|---|---|
| pcaI | 24985644 | AAN69545.1 | Pseudomonas putida |
| pcaJ | 26990657 | NP_746082.1 | Pseudomonas putida |
| pcaI | 50084858 | YP_046368.1 | Acinetobacter sp. ADP1 |
| pcaJ | 141776 | AAC37147.1 | Acinetobacter sp. ADP1 |
| pcaI | 21224997 | NP_630776.1 | Streptomyces coelicolor |
| pcaJ | 21224996 | NP_630775.1 | Streptomyces coelicolor |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |

A 3-oxoacyl-CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., *Biochem. Biophys. Res. Commun.* 33:902-908 (1968)) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosakan Et al., *Biosci. Biotechnol Biochem.* 71:58-68 (2007)).

| Gene name | GI Number | GenBank ID | Organism |
|---|---|---|---|
| atoA | 2492994 | P76459.1 | Escherichia coli K12 |
| atoD | 2492990 | P76458.1 | Escherichia coli K12 |
| actA | 62391407 | YP_226809.1 | Corynebacterium glutamicum ATCC 13032 |
| cg0592 | 62389399 | YP_224801.1 | Corynebacterium glutamicum ATCC 13032 |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

The above enzymes may also exhibit the desired activities on adipyl-CoA and adipate (FIG. 2, step L). Nevertheless, additional exemplary transferase candidates are catalyzed by the gene products of cat1, cat2, and cat3 of *Clostridium*

*kluyveri* which have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); Sohling et al., *Eur. J Biochem.* 212:121-127 (1993); Sohling et al., *J Bacteriol.* 178:871-880 (1996)).

| Gene name | GI Number | GenBank ID | Organism |
|---|---|---|---|
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)).

| Gene name | GI Number | GenBank ID | Organism |
|---|---|---|---|
| gctA | 559392 | CAA57199.1 | *Acidaminococcus fermentans* |
| gctB | 559393 | CAA57200.1 | *Acidaminococcus fermentans* |

FIG. 5, Step T—PEP Carboxylase (EFR16A) or PEP Carboxykinase (EFR16B)

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCK1, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high NaHCO$_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

| Protein | GenBank ID | GI Number | Organism |
|---|---|---|---|
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

FIG. 5, Step U—Pyruvate Carboxylase (EFR17)

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | GI Number | Organism |
|---|---|---|---|
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

FIG. 5, Step V—Malate Dehydrogenase (EFR18)

Malate dehydrogenase converts oxaloacetate to malate. Exemplary enzymes are found in several organisms including *E. coli*, *S. cerevisiae*, *Bacillus subtilis*, and *Rhizopus oryzae*. MDH1, MDH2, and MDH3 from *S. cerevisiae* are known to localize to the mitochondrion, cytosol, and peroxisome, respectively.

| Protein | GenBank ID | GI number | Organism |
|---|---|---|---|
| mdh | AAC76268.1 | 1789632 | *Escherichia coli* |
| MDH1 | NP_012838.1 | 6322765 | *Saccharomyces cerevisiae* |
| MDH2 | NP_014515.2 | 116006499 | *Saccharomyces cerevisiae* |
| MDH3 | NP_010205.1 | 6320125 | *Saccharomyces cerevisiae* |
| mdh | NP_390790.1 | 16079964 | *Bacillus subtilis* |
| MDH | ADG65261.1 | 296011196 | *Rhizopus oryzae* |

FIG. 5, Step W—Malic Enzyme (EFR19)

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in E. coli while restoring the lethal Δpfl-ΔldhA phenotype under anaerobic conditions by operating in the carbon-fixing direction (Stols and Donnelly, Appl. Environ. Microbiol. 63(7) 2695-2701 (1997)). A similar observation was made upon overexpressing the malic enzyme from Ascaris suum in E. coli (Stols et al., Appl. Biochem. Biotechnol. 63-65(1), 153-158 (1997)). The second E. coli malic enzyme, encoded by maeB, is NADP-dependent and also decarboxylates oxaloacetate and other alpha-keto acids (Iwakuran Et al., J. Biochem. 85(5):1355-65 (1979)).

| Protein | GenBank ID | GI Number | Organism |
|---------|-----------|-----------|----------|
| maeA | NP_415996 | 90111281 | Escherichia coli |
| maeB | NP_416958 | 16130388 | Escherichia coli |
| NAD-ME | P27443 | 126732 | Ascaris suum |

FIG. 5, Step X—Fumarase (EFR20A), Fumarate Reductase (EFR20B), Succinyl-CoA Synthetase (EFR20C), Succinyl-CoA Ligase (EFR20D), Succinyl-CoA Transferase (EFR20E)

Fumarate hydratase (EC 4.2.1.2) catalyzes the reversible hydration of fumarate to malate. The three fumarases of E. coli, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., J. Bacteriol. 183:461-467 (2001); Woods et al., Biochim. Biophys. Acta 954:14-26 (1988); Guest et al., J. Gen. Microbiol. 131:2971-2984 (1985)). S. cerevisiae contains one copy of a fumarase-encoding gene, FUM1, whose product localizes to both the cytosol and mitochondrion (Sass et al., J. Biol. Chem. 278:45109-45116 (2003)). Additional fumarase enzymes are found in Campylobacter jejuni (Smith et al., Int. J. Biochem. Cell. Biol. 31:961-975 (1999)), Thermus thermophilus (Mizobatan Et al., Arch. Biochem. Biophys. 355:49-55 (1998)) and Rattus norvegicus (Kobayashi et al., J. Biochem. 89:1923-1931 (1981)). Similar enzymes with high sequence homology include fum1 from Arabidopsis thaliana, FUM1 from Rhizopus oryzae, and fumC from Corynebacterium glutamicum. The MmcBC fumarase from Pelotomaculum thermopropionicum is another class of fumarase with two subunits (Shimoyaman Et al., FEMS Microbiol. Lett. 270: 207-213 (2007)).

| Protein | GenBank ID | GI Number | Organism |
|---------|-----------|-----------|----------|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |

| Protein | GenBank ID | GI Number | Organism |
|---------|-----------|-----------|----------|
| MmcB | YP_001211906 | 147677691 | Pelotomaculum thermopropionicum |
| MmcC | YP_001211907 | 147677692 | Pelotomaculum thermopropionicum |
| FUM1 | ADG65260.1 | 296011194 | Rhizopus oryzae |

Fumarate reductase catalyzes the reduction of fumarate to succinate. The fumarate reductase of E. coli, composed of four subunits encoded by frdABCD, is membrane-bound and active under anaerobic conditions. The electron donor for this reaction is menaquinone and the two protons produced in this reaction do not contribute to the proton gradient (Iverson et al., Science 284:1961-1966 (1999)). The yeast genome encodes two soluble fumarate reductase isozymes encoded by FRDS1 (Enomoto et al., DNA Res. 3:263-267 (1996)) and FRDS2 (Muratsubaki et al., Arch. Biochem. Biophys. 352:175-181 (1998)), which localize to the cytosol and promitochondrion, respectively, and are used for anaerobic growth on glucose (Arikawan Et al., FEMS Microbiol. Lett. 165:111-116 (1998)).

| Protein | GenBank ID | GI Number | Organism |
|---------|-----------|-----------|----------|
| FRDS1 | P32614 | 418423 | Saccharomyces cerevisiae |
| FRDS2 | NP_012585 | 6322511 | Saccharomyces cerevisiae |
| frdA | NP_418578.1 | 16131979 | Escherichia coli |
| frdB | NP_418577.1 | 16131978 | Escherichia coli |
| frdC | NP_418576.1 | 16131977 | Escherichia coli |
| frdD | NP_418475.1 | 16131877 | Escherichia coli |

The ATP-dependent acylation of succinate to succinyl-CoA is catalyzed by succinyl-CoA synthetase (EC 6.2.1.5). The product of the LSC1 and LSC2 genes of S. cerevisiae and the sucC and sucD genes of E. coli naturally form a succinyl-CoA synthetase complex that catalyzes the formation of succinyl-CoA from succinate with the concomitant consumption of one ATP, a reaction which is reversible in vivo (Buck et al., Biochemistry 24:6245-6252 (1985)). These proteins are identified below:

| Protein | GenBank ID | GI Number | Organism |
|---------|-----------|-----------|----------|
| LSC1 | NP_014785 | 6324716 | Saccharomyces cerevisiae |
| LSC2 | NP_011760 | 6321683 | Saccharomyces cerevisiae |
| sucC | NP_415256.1 | 16128703 | Escherichia coli |
| sucD | AAC73823.1 | 1786949 | Escherichia coli |

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of Clostridium kluyveri has been shown to exhibit succinyl-CoA: acetyl-CoA transferase activity (Sohling and Gottschalk, J. Bacteriol. 178:871-880 (1996)). In addition, the activity is present in *Trichomonas vaginalis* (van Grinsven et al. 2008) and *Trypanosoma brucei* (Riviere et al. 2004). The succinyl-CoA:acetate CoA-transferase from *Acetobacter aceti*, encoded by aarC, replaces succinyl-CoA synthetase in a variant TCA cycle (Mullins et al. 2008). Similar succinyl-CoA transferase activities are also present in *Trichomonas vaginalis* (van Grinsven et al. 2008), *Trypanosoma brucei* (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

| Protein | GenBank ID | GI Number | Organism |
| --- | --- | --- | --- |
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| pcaI | AAN69545.1 | 24985644 | *Pseudomonas putida* |
| pcaJ | NP_746082.1 | 26990657 | *Pseudomonas putida* |
| aarC | ACD85596.1 | 189233555 | *Acetobacter aceti* |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanakan Et al. 2002). The aforementioned proteins are identified below.

| Protein | GenBank ID | GI Number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

FIG. 5, Step Y—3-Oxoadipyl-CoA Thiolase (EA1)

The conversion of ACCOA and succinyl-CoA to 3-oxoadiply-CoA can be catalyzed by a 3-oxoadipyl-CoA thiolase, as provided above in FIG. 2, step A. The 3-oxoadipyl-CoA can then be used for the subsequent conversion to adipate, 6-ACA, HMDA or caprolactam, or an intermediate thereof, as provided in FIG. 2.

4.3 Example III

Methods of Using Formaldehyde Produced from the Oxidation of Methanol in the Formation of Intermediates of Central Metabolic Pathways for the Formation of Biomass Provided herein are exemplary pathways, which utilize formaldehyde produced from the oxidation of methanol (see, e.g., FIG. 1, step J) in the formation of intermediates of certain central metabolic pathways that can be used for the formation of biomass. Exemplary MMPs for enhancing the availability of reducing equivalents, as well as the producing formaldehyde from methanol (step J), are provided in FIG. 1.

One exemplary pathway that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6p is converted into F6P by EF2 (FIG. 3, step B).

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from DHA synthase is then further phosphorylated to form DHAP by an EF4 (FIG. 4, step B). DHAP can be assimilated into glycolysis and several other pathways.

FIG. 3, Steps A and B—H6P Synthase (EF1) (Step A) and 6-Phospho-3-Hexuloisomerase (EF2) (Step B)

Both of the EF1 and EF2 enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasuedan Et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Oritan Et al., 2007, Appl Microbiol Biotechnol. 76:439-445). In some organisms, these two enzymes naturally exist as a fused version that is bifunctional.

Exemplary candidate genes for hexulose-6-phopshate synthase are:

| Protein | GenBank ID | GI number | Organism |
| --- | --- | --- | --- |
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |
| Hps | YP_544362.1 | 91774606 | *Methylobacillus flagellatus* |
| Hps | YP_545763.1 | 91776007 | *Methylobacillus flagellatus* |
| Hps | AAG29505.1 | 11093955 | *Aminomonas aminovorus* |
| SgbH | YP_004038706.1 | 313200048 | *Methylovorus* sp. MP688 |
| Hps | YP_003050044.1 | 253997981 | *Methylovorus glucosetrophus* SIP3-4 |
| Hps | YP_003990382.1 | 312112066 | *Geobacillus* sp. Y4.1MC1 |
| Hps | gb\|AAR91478.1 | 40795504 | *Geobacillus* sp. M10EXG |
| Hps | YP_007402409.1 | 448238351 | *Geobacillus* sp. GHH01 |

Exemplary gene candidates for EF2 are:

| Protein | GenBank ID | GI number | Organism |
|---|---|---|---|
| Phi | AAR39393.1 | 40074228 | Bacillus methanolicus MGA3 |
| Phi | EIJ81376.1 | 387589056 | Bacillus methanolicus PB1 |
| Phi | BAA83098.1 | 5706383 | Methylomonas aminofaciens |
| RmpB | BAA90545.1 | 6899860 | Mycobacterium gastri |
| Phi | YP_545762.1 | 91776006 | Methylobacillus flagellatus KT |
| Phi | YP_003051269.1 | 253999206 | Methylovorus glucosetrophus SIP3-4 |
| Phi | YP_003990383.1 | 312112067 | Geobacillus sp. Y4.1MC1 |
| Phi | YP_007402408.1 | 448238350 | Geobacillus sp. GHH01 |

Candidates for enzymes where both of these functions have been fused into a single open reading frame include the following:

| Protein | GenBank ID | GI number | Organism |
|---|---|---|---|
| PH1938 | NP_143767.1 | 14591680 | Pyrococcus horikoshii OT3 |
| PF0220 | NP_577949.1 | 18976592 | Pyrococcus furiosus |
| TK0475 | YP_182888.1 | 57640410 | Thermococcus kodakaraensis |
| PAB1222 | NP_127388.1 | 14521911 | Pyrococcus abyssi |
| MCA2738 | YP_115138.1 | 53803128 | Methylococcus capsulatas |
| Metal_3152 | EIC30826.1 | 380884949 | Methylomicrobium album BG8 |

An experimental system was designed to test the ability of a methanol dehydrogenase (MeDH) in conjunction with the enzymes H6P synthase (HPS) and 6-phospho-3-hexuloisomerase (PHI) of the Ribulose Monophosphate (RuMP) pathway to assimilate methanol carbon into the glycolytic pathway and the TCA cycle. Escherichia coli strain ECh-7150 (ΔlacIA, ΔpflB, ΔptsI, ΔPpckA(pckA), ΔPglk(glk), glk::glfB, ΔhycE, ΔfrmR, ΔfrmA, ΔfrmB) was constructed to remove the glutathione-dependent formaldehyde detoxification capability encoded by the FrmA and FrmB enzyme. This strain was then transformed with plasmid pZA23 S variants that either contained or lacked gene 2616 An Encoding a fusion of the HPS and PHI enzymes. These two transformed strains were then each transformed with pZS*13S variants that contained gene 2315 L (encoding an active MeDH), or gene 2315 RIP2 (encoding a catalytically inactive MeDH), or no gene insertion. Genes 2315 and 2616 are internal nomenclatures for NAD-dependent methanol dehydrogenase from Bacillus methanolicus MGA3 and 2616 is a fused phs-hpi constructs as described in Oritan Et al. (2007) Appl Microbiol Biotechnol 76:439-45.

The six resulting strains were aerobically cultured in quadruplicate, in 5 ml minimal medium containing 1% arabinose and 0.6 M 13C-methanol as well as 100 μg/ml carbenicillin and 25 μg/ml kanamycin to maintain selection of the plasmids, and 1 mM IPTG to induce expression of the methanol dehydrogenase and HPS-PHI fusion enzymes. After 18 hours incubation at 37° C., the cell density was measured spectrophotometrically at 600 nM wavelength and a clarified sample of each culture medium was submitted for analysis to detect evidence of incorporation of the labeled methanol carbon into TCA-cycle derived metabolites. The label can be further enriched by deleting the gene araD that competes with ribulose-5-phosphate.

$^{13}$C carbon derived from labeled methanol provided in the experiment was found to be significantly enriched in the TCA-cycle derived amino acid glutamate (and several other TCA compounds and product pathway intermediates), but only in the strain expressing both catalytically active MeDH 2315L and the HPS-PHI fusion 2616A together (data not shown). Moreover, this strain grew significantly better than the strain expressing catalytically active MeDH but lacking expression of the HPS-PHI fusion (data not shown), suggesting that the HPS-PHI enzyme is capable of reducing growth inhibitory levels of formaldehyde that cannot be detoxified by other means in this strain background. These results show that co-expression of an active MeDH and the enzymes of the RuMP pathway can effectively assimilate methanol derived carbon and channel it into TCA-cycle derived products.

FIG. 4, Step A—DHA Synthase (EF3)

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from EF3 is then further phosphorylated to form DHAP by an EF4 (FIG. 4, step B). DHAP can be assimilated into glycolysis and several other pathways.

The EF3 enzyme in Candida boidinii uses thiamine pyrophosphate and $Mg^{2+}$ as cofactors and is localized in the peroxisome. The enzyme from the methanol-growing carboxydobacterium, Mycobacter sp. strain JC1 DSM 3803, was also found to have EF3 and kinase activities (Ro et al., 1997, JBac 179(19):6041-7). EF3 from this organism also has similar cofactor requirements as the enzyme from C. boidinii. The $K_m$s for formaldehyde and xylulose 5-phosphate were reported to be 1.86 mM and 33.3 microM, respectively. Several other mycobacteria, excluding only Mycobacterium tuberculosis, can use methanol as the sole source of carbon and energy and are reported to use EF3 (Part et al., 2003, JBac 185(1):142-7.

| Protein | GenBank ID | GI number | Organism |
|---|---|---|---|
| DAS1 | AAC83349.1 | 3978466 | Candida boidinii |
| HPODL_2613 | EFW95760.1 | 320581540 | Ogataea parapolymorpha DL-1 (Hansenula polymorpha DL-1) |
|  | AAG12171.2 | 18497328 | Mycobacter sp. strain JC1 DSM 3803 |

FIG. 4, Step B—DHA Kinase (EF4)

DHA obtained from EF3 is further phosphorylated to form DHAP by an EF4. DHAP can be assimilated into glycolysis and several other pathways. EF4 has been purified from Ogataea angusta to homogeneity (Bystrkh, 1983, Biokhimiia, 48(10):1611-6). The enzyme, which phosphorylates DHA and, to a lesser degree, glyceraldehyde, is a homodimeric protein of 139 kDa. ATP is the preferred phosphate group donor for the enzyme. When ITP, GTP, CTP and UTP are used, the activity drops to about 30%. In several organisms such as Klebsiella pneumoniae and Citrobacter fruendii (Daniel et al., 1995, JBac 177(15):4392-40), DHA is formed as a result of oxidation of glycerol and is converted into DHAP by the kinase EF4 of K. pneumoniae has been characterized (Jonathan et al, 1984, JBac 160(1): 55-60). It is very specific for DHA, with a $K_m$ of 4 μM, and has two apparent $K_m$ values for ATP, one at 25 to 35 μM, and the other at 200 to 300 μM. DHA can also be phosphorylated by glycerol kinases but the EF4 from K. puemoniae is different from glycerol kinase in several respects. While both enzymes can phosphorylate DHA, EF4 does not phosphorylate glycerol, neither is it inhibited by fructose-1,6-diphosphate. In *Saccharomyces cerevisiae*, EF4s (I and II) are involved in rescuing the cells from toxic effects of DHA (Molin et al., 2003, J Biol Chem. 17; 278(3):1415-23).

In *Escherichia coli*, EF4 is composed of the three subunits DhaK, DhaL, and DhaM and it functions similarly to a phosphotransferase system (PTS) in that it utilizes phosphoenolpyruvate as a phosphoryl donor (Gutknecht et al., 2001, EMBO J. 20(10):2480-6). It differs in not being involved in transport. The phosphorylation reaction requires the presence of the EI and HPr proteins of the PTS system. The DhaM subunit is phosphorylated at multiple sites. DhaK contains the substrate binding site (Garcia-Alles et al., 2004, 43(41):13037-45; Siebold et al., 2003, PNAS. 100(14): 8188-92). The $K_M$ for DHA for the *E. coli* enzyme has been reported to be 6 μM. The K subunit is similar to the N-terminal half of ATP-dependent EF4 of *Citrobacter freundii* and eukaryotes.

Exemplary EF4 gene candidates for this step are:

| Protein | GenBank ID | GI number | Organism |
|---|---|---|---|
| DAK1 | P54838.1 | 1706391 | *Saccharomyces cerevisiae* S288c |
| DAK2 | P43550.1 | 1169289 | *Saccharomyces cerevisiae* S288c |
| D186_20916 | ZP_16280678.1 | 421847542 | *Citrobacter freundii* |
| DAK2 | ZP_18488498.1 | 425085405 | *Klebsiella pneumoniae* |
| DAK | AAC27705.1 | 3171001 | *Ogataea angusta* |
| DhaK | NP_415718.6 | 162135900 | *Escherichia coli* |
| DhaL | NP_415717.1 | 16129162 | *Escherichia coli* |
| DhaM | NP_415716.4 | 226524708 | *Escherichia coli* |

4.4 Example IV

Methods for Handling CO and Anaerobic Cultures

This example describes methods used in handling anaerobic cultures.

A. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry CA). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

B. Anaerobic Microbiology.

Serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 μM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 μM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

4.5 Example V

In Vivo Labeling Assay for Conversion of Methanol to $CO_2$

This example describes a functional methanol pathway in a microbial organism.

Strains with functional reductive TCA branch and pyruvate formate lyase deletion were grown aerobically in LB medium overnight, followed by inoculation of M9 high-seed media containing IPTG and aerobic growth for 4 hrs. These strains had methanol dehydrogenase/ACT pairs in the presence and absence of formaldehyde dehydrogenase or formate dehydrogenase. ACT is an activator protein (a Nudix hydrolase). At this time, strains were pelleted, resuspended in fresh M9 medium high-seed media containing 2% $^{13}CH_3OH$, and sealed in anaerobic vials. Head space was replaced with nitrogen and strains grown for 40 hours at 37° C. Following growth, headspace was analyzed for $^{13}CO_2$. Media was examined for residual methanol as well as BDO and byproducts. All constructs expressing methanol dehydrogenase (MeDH) mutants and MeDH/ACT pairs grew to slightly lower ODs than strains containing empty vector controls. This is likely due to the high expression of these constructs (Data not shown). One construct (2315/2317) displayed significant accumulation of labeled $CO_2$ relative to controls in the presence of FalDH, FDH or no coexpressed protein. This shows a functional MeOH pathway in E. coli and that the endogenous glutathione-dependent formaldehyde detoxification genes (frmAB) are sufficient to carry flux generated by the current MeDH/ACT constructs.

2315 is internal laboratory designation for the MEDH from Bacillus methanolicus MGA3 (GenBank Accession number: EIJ77596.1; GI number: 387585261), and 2317 is internal laboratory designation for the activator protein from the same organism (locus tag: MGA3_09170; GenBank Accession number:EIJ83380; GI number: 387591061).

Sequence analysis of the NADH-dependent methanol dehydrogenase from Bacillus methanolicus places the enzyme in the alcohol dehydrogenase family III. It does not contain any tryptophan residues, resulting in a low extinction coefficient (18,500 $M^{-1}$, $cm^{-1}$) and should be detected on SDS gels by Coomassie staining.

The enzyme has been characterized as a multisubunit complex built from 43 kDa subunits containing one Zn and 1-2 Mg atoms per subunit. Electron microscopy and sedimentation studies determined it to be a decamer, in which two rings with five-fold symmetry are stacked on top of each other (Vonck et al., J. Biol. Chem. 266:3949-3954, 1991). It is described to contain a tightly but not covalently bound cofactor and requires exogenous $NAD^+$ as $e^-$-acceptor to measure activity iin vitro. A strong increase (10-40-fold) of iin vitro activity was observed in the presence of an activator protein (ACT), which is a homodimer (21 kDa subunits) and contains one Zn and one Mg atom per subunit.

The mechanism of the activation was investigated by Kloosterman et al., J. Biol. Chem. 277:34785-34792, 2002, showing that ACT is a Nudix hydrolase and Hektor et al., J. Biol. Chem. 277:46966-46973, 2002, demonstrating that mutation of residue S97 to G or T in MeDH changes activation characteristics along with the affinity for the cofactor. While mutation of residues G15 and D88 had no significant impact, a role of residue G13 for stability as well as of residues G95, D100, and K103 for the activity is suggested. Both papers together propose a hypothesis in which ACT cleaves MeDH-bound $NAD^+$. MeDH retains AMP bound and enters an activated cycle with increased turnover.

The stoichiometric ratio between ACT and MeDH is not well defined in the literature. Kloosterman et al., supra determine the ratio of dimeric Act to decameric MeDH for full iin vitro activation to be 10:1. In contrast, Arfman et al. J. Biol. Chem. 266:3955-3960, 1991 determined a ratio of 3:1 iin vitro for maximum and a 1:6 ratio for significant activation, but observe a high sensitivity to dilution. Based on expression of both proteins in Bacillus, the authors estimate the ratio in vivo to be around 1:17.5.

However, our iin vitro experiments with purified activator protein (2317A) and methanol dehydrogenase (2315A) showed the ratio of ACT to MeDH to be 10:1. This iin vitro test was done with 5 M methanol, 2 mM NAD and 10 μM methanol dehydrogenase 2315A at pH 7.4.

4.6 Example VI

Formate Reutilization (Assimilation) Pathways

This example describes a functional methanol pathway in a microbial organism.

This example describes enzymatic pathways for converting pyruvate to formaldehyde, and optionally in combination with producing acetyl-CoA and/or reproducing pyruvate.

FIG. 5, Step E—Formate Reductase (EFR1)

The conversion of formate to formaldehyde can be carried out by a formate reductase (step E, FIG. 1). A suitable enzyme for these transformations is the aryl-aldehyde dehydrogenase, or equivalently a carboxylic acid reductase, from Nocardia iowensis. Carboxylic acid reductase catalyzes the magnesium, ATP and NADPH-dependent reduction of carboxylic acids to their corresponding aldehydes (Venkitasubramanian et al., J. Biol. Chem. 282:478-485 (2007)). This enzyme, encoded by car, was cloned and functionally expressed in E. coli (Venkitasubramanian et al., J. Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industires, ed. R. N. Patel, Chapter 15, pp. 425-440, CRC Press LLC, Boca Raton, Fla. (2006)). Information related to these proteins and genes is shown below.

| Protein | GenBank ID | GI number | Organism |
|---------|------------|-----------|----------|
| Car | AAR91681.1 | 40796035 | Nocardia iowensis (sp. NRRL 5646) |
| Npt | ABI83656.1 | 114848891 | Nocardia iowensis (sp. NRRL 5646) |

Additional car and npt genes can be identified based on sequence homology.

| Protein | GenBank ID | GI number | Organism |
| --- | --- | --- | --- |
| fadD9 | YP_978699.1 | 121638475 | Mycobacterium bovis BCG |
| BCG_2812c | YP_978898.1 | 121638674 | Mycobacterium bovis BCG |
| nfa20150 | YP_118225.1 | 54023983 | Nocardia farcinica IFM 10152 |
| nfa40540 | YP_120266.1 | 54026024 | Nocardia farcinica IFM 10152 |
| SGR_6790 | YP_001828302.1 | 182440583 | Streptomyces griseus subsp. griseus NBRC 13350 |
| SGR_665 | YP_001822177.1 | 182434458 | Streptomyces griseus subsp. griseus NBRC 13350 |
| MSMEG_2956 | YP_887275.1 | 118473501 | Mycobacterium smegmatis MC2 155 |
| MSMEG_5739 | YP_889972.1 | 118469671 | Mycobacterium smegmatis MC2 155 |
| MSMEG_2648 | YP_886985.1 | 118471293 | Mycobacterium smegmatis MC2 155 |
| MAP1040c | NP_959974.1 | 41407138 | Mycobacterium avium subsp. paratuberculosis K-10 |
| MAP2899c | NP_961833.1 | 41408997 | Mycobacterium avium subsp. paratuberculosis K-10 |
| MMAR_2117 | YP_001850422.1 | 183982131 | Mycobacterium marinum M |
| MMAR_2936 | YP_001851230.1 | 183982939 | Mycobacterium marinum M |
| MMAR_1916 | YP_001850220.1 | 183981929 | Mycobacterium marinum M |
| TpauDRAFT_33060 | ZP_04027864.1 | 227980601 | Tsukamurella paurometabola DSM 20162 |
| TpauDRAFT_20920 | ZP_04026660.1 | 227979396 | Tsukamurella paurometabola DSM 20162 |
| CPCC7001_1320 | ZP_05045132.1 | 254431429 | Cyanobium PCC7001 |
| DDBDRAFT_0187729 | XP_636931.1 | 66806417 | Dictyostelium discoideum AX4 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial. Information related to these proteins and genes is shown below.

| Protein | GenBank ID | GI number | Organism |
| --- | --- | --- | --- |
| griC | YP_001825755.1 | 182438036 | Streptomyces griseus subsp. griseus NBRC 13350 |
| grid | YP_001825756.1 | 182438037 | Streptomyces griseus subsp. griseus NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubian Et al., *J. Biol. Chem.* 278:8250-8256 (2003)). The gene encoding the *P. chrysogenum* PPTase has not been identified to date. Information related to these proteins and genes is shown below.

| Protein | GenBank ID | GI number | Organism |
| --- | --- | --- | --- |
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Tani et at (Agric Biol Chem, 1978, 42: 63-68; Agric Biol Chem, 1974, 38: 2057-2058) showed that purified enzymes from *Escherichia coli* strain B could reduce the sodium salts of different organic acids (e.g. formate, glycolate, acetate, etc.) to their respective aldehydes (e.g. formaldehyde, glycoaldehyde, acetaldehyde, etc.). Of three purified enzymes examined by Tani et at (1978), only the "A" isozyme was shown to reduce formate to formaldehyde. Collectively, this group of enzymes was originally termed glycoaldehyde dehydrogenase; however, their novel reductase activity led the authors to propose the name glycolate reductase as being more appropriate (Moritan Et al, Agric Biol Chem, 1979, 43: 185-186). Moritan Et al (Agric Biol Chem, 1979, 43: 185-186) subsequently showed that glycolate reductase activity is relatively widespread among microorganisms, being found for example in: *Pseudomonas, Agrobacterium, Escherichia, Flavobacterium, Micrococcus, Staphylococcus, Bacillus*, and others. Without wishing to be bound by any particular theory, it is believed that some of these glycolate reductase enzymes are able to reduce formate to formaldehyde.

Any of these CAR or CAR-like enzymes can exhibit formate reductase activity or can be engineered to do so.

FIG. 5, Step F—Formate Ligase (EFR2A), Formate Transferase (EFR2B), Formate Synthetase (EFR2C)

The acylation of formate to formyl-CoA is catalyzed by enzymes with formate transferase, synthetase, or ligase activity (Step F, FIG. 1). Formate transferase enzymes have been identified in several organisms including *Escherichia coli* (Toyota, et al., *J Bacteriol.* 2008 April; 190(7):2556-64), *Oxalobacter formigenes* (Toyota, et al., *J Bacteriol.* 2008 April; 190(7):2556-64; Baetz et al., *J Bacteriol.* 1990 July; 172(7):3537-40; Ricagno, et al., *EMBO J.* 2003 Jul. 1; 22(13):3210-9)), and *Lactobacillus acidophilus* (Azcarate-Peril, et al., *Appl. Environ. Microbiol.* 2006 72(3) 1891-1899). Homologs exist in several other organisms. Enzymes acting on the CoA-donor for formate transferase may also be expressed to ensure efficient regeneration of the CoA-donor. For example, if oxalyl-CoA is the CoA donor substrate for formate transferase, an additional transferase, synthetase, or ligase may be required to enable efficient regeneration of oxalyl-CoA from oxalate. Similarly, if succinyl-CoA or acetyl-CoA is the CoA donor substrate for formate transferase, an additional transferase, synthetase, or ligase may be required to enable efficient regeneration of succinyl-CoA from succinate or acetyl-CoA from acetate, respectively.

| Protein | GenBank ID | GI number | Organism |
|---|---|---|---|
| YfdW | NP_416875.1 | 16130306 | *Escherichia coli* |
| frc | O06644.3 | 21542067 | *Oxalobacter formigenes* |
| frc | ZP_04021099.1 | 227903294 | *Lactobacillus acidophilus* |

Suitable CoA-donor regeneration or formate transferase enzymes are encoded by the gene products of cat1, cat2, and cat3 of *Clostridium kluyveri*. These enzymes have been shown to exhibit succinyl-CoA, 4-hydroxybutyryl-CoA, and butyryl-CoA acetyltransferase activity, respectively (Seedorf et al., *Proc. Natl. Acad. Sci. USA* 105:2128-2133 (2008); Sohling and Gottschalk, *J Bacteriol* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). Yet another transferase capable of the desired conversions is butyryl-CoA: acetoacetate CoA-transferase. Exemplary enzymes can be found in *Fusobacterium nucleatum* (Barker et al., *J. Bacteriol.* 152(1):201-7 (1982)), *Clostridium* SB4 (Barker et al., *J. Biol. Chem.* 253(4):1219-25 (1978)), and *Clostridium acetobutylicum* (Wiesenborn et al., *Appl. Environ. Microbiol.* 55(2):323-9 (1989)). Although specific gene sequences were not provided for butyryl-CoA:acetoacetate CoA-transferase in these references, the genes FNO272 and FNO273 have been annotated as a butyrate-acetoacetate CoA-transferase (Kapatral et al., *J. Bact.* 184(7) 2005-2018 (2002)). Homologs in *Fusobacterium nucleatum* such as FN1857 and FN1856 also likely have the desired acetoacetyl-CoA transferase activity. FN1857 and FN1856 are located adjacent to many other genes involved in lysine fermentation and are thus very likely to encode an acetoacetate:butyrate CoA transferase (Kreimeyer, et al., *J. Biol. Chem.* 282 (10) 7191-7197 (2007)). Additional candidates from *Porphyromonas gingivalis* and *Thermoanaerobacter tengcongensis* can be identified in a similar fashion (Kreimeyer, et al., *J. Biol. Chem.* 282 (10) 7191-7197 (2007)). Information related to these proteins and genes is shown below.

| Protein | GenBank ID | GI number | Organism |
|---|---|---|---|
| Cat1 | P38946.1 | 729048 | *Clostridium kluyveri* |
| Cat2 | P38942.2 | 1705614 | *Clostridium kluyveri* |
| Cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| FN0272 | NP_603179.1 | 19703617 | *Fusobacterium nucleatum* |
| FN0273 | NP_603180.1 | 19703618 | *Fusobacterium nucleatum* |
| FN1857 | NP_602657.1 | 19705162 | *Fusobacterium nucleatum* |
| FN1856 | NP_602656.1 | 19705161 | *Fusobacterium nucleatum* |
| PG1066 | NP_905281.1 | 34540802 | *Porphyromonas gingivalis* W83 |
| PG1075 | NP_905290.1 | 34540811 | *Porphyromonas gingivalis* W83 |
| TTE0720 | NP_622378.1 | 20807207 | *Thermoanaerobacter tengcongensis* MB4 |
| TTE0721 | NP_622379.1 | 20807208 | *Thermoanaerobacter tengcongensis* MB4 |

Additional transferase enzymes of interest include the gene products of atoAD from *E. coli* (Hanai et al., *Appl Environ Microbiol* 73:7814-7818 (2007)), ctfAB from *C. acetobutylicum* (Jojiman Et al., *Appl Microbiol Biotechnol* 77:1219-1224 (2008)), and ctfAB from *Clostridium saccharoperbutylacetonicum* (Kosakan Et al., *Biosci. Biotechnol Biochem.* 71:58-68 (2007)). Information related to these proteins and genes is shown below.

| Protein | GenBank ID | GI number | Organism |
|---|---|---|---|
| AtoA | P76459.1 | 2492994 | *Escherichia coli* |
| AtoD | P76458.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Succinyl-CoA:3-ketoacid-CoA transferase naturally converts succinate to succinyl-CoA while converting a 3-ketoacyl-CoA to a 3-ketoacid. Exemplary succinyl-CoA:3:ketoacid-CoA transferases are present in *Helicobacter pylori* (Corthesy-Theulaz et al., *J. Biol. Chem.* 272:25659-25667 (1997)), *Bacillus subtilis* (Stols et al., *Protein. Expr. Purif.* 53:396-403 (2007)), and *Homo sapiens* (Fukao et al., *Genomics* 68:144-151 (2000); Tanakan Et al., *Mol. Hum. Reprod.* 8:16-23 (2002)). Information related to these proteins and genes is shown below.

| Protein   | GenBank ID | GI number | Organism           |
|-----------|------------|-----------|--------------------|
| HPAG1_0676 | YP_627417 | 108563101 | Helicobacter pylori |
| HPAG1_0677 | YP_627418 | 108563102 | Helicobacter pylori |
| ScoA      | NP_391778  | 16080950  | Bacillus subtilis  |
| ScoB      | NP_391777  | 16080949  | Bacillus subtilis  |
| OXCT1     | NP_000427  | 4557817   | Homo sapiens       |
| OXCT2     | NP_071403  | 11545841  | Homo sapiens       |

Two additional enzymes that catalyze the activation of formate to formyl-CoA reaction are AMP-forming formyl-CoA synthetase and ADP-forming formyl-CoA synthetase. Exemplary enzymes, known to function on acetate, are found in *E. coli* (Brown et al., *J. Gen. Microbiol.* 102:327-336 (1977)), *Ralstonian Eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonellan Enterica* (Gulick et al., *Biochemistry* 42:2866-2873 (2003)) and *Saccharomyces cerevisiae* (Jogl and Tong, *Biochemistry* 43:1425-1431 (2004)). Such enzymes may also acylate formate naturally or can be engineered to do so.

| Protein | GenBank ID | GI Number | Organism |
|---------|------------|-----------|----------|
| acs     | AAC77039.1 | 1790505   | Escherichia coli |
| acoE    | AAA21945.1 | 141890    | Ralstonian Eutropha |
| acs1    | ABC87079.1 | 86169671  | Methanothermobacter thermautotrophicus |
| acs1    | AAL23099.1 | 16422835  | Salmonellan Enterica |
| ACS1    | Q01574.2   | 257050994 | Saccharomyces cerevisiae |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyryate, isovalerate, succinate, fumarate, phenylacetate, indoleacetate (Musfeldt et al., *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra (2004)). The enzymes from *A. fulgidus, H. marismortui* and *P. aerophilum* have all been cloned, functionally expressed, and characterized in *E. coli* (Musfeldt et al., supra; Brasen et al., supra (2004)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). Such enzymes may also acylate formate naturally or can be engineered to do so. Information related to these proteins and genes is shown below.

| Protein | GenBank ID | GI number | Organism |
|---------|------------|-----------|----------|
| AF1211  | NP_070039.1 | 11498810 | Archaeoglobus fulgidus DSM 4304 |
| AF1983  | NP_070807.1 | 11499565 | Archaeoglobus fulgidus DSM 4304 |
| scs     | YP_135572.1 | 55377722 | Haloarcula marismortui ATCC 43049 |
| PAE3250 | NP_560604.1 | 18313937 | Pyrobaculum aerophilum str. IM2 |
| sucC    | NP_415256.1 | 16128703 | Escherichia coli |
| sucD    | AAC73823.1  | 1786949  | Escherichia coli |
| paaF    | AAC24333.2  | 22711873 | Pseudomonas putida |

An alternative method for adding the CoA moiety to formate is to apply a pair of enzymes such as a phosphate-transferring acyltransferase and a kinase. These activities enable the net formation of formyl-CoA with the simultaneous consumption of ATP. An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Homologs exist in several other organisms including Salmonellan *Enterica* and *Chlamydomonas reinhardtii*. Such enzymes may also phosphorylate formate naturally or can be engineered to do so.

| Protein | GenBank ID | GI number | Organism |
|---------|------------|-----------|----------|
| Pta     | NP_416800.1 | 16130232 | Escherichia coli |
| Pta     | NP_461280.1 | 16765665 | Salmonellan Enterica subsp. enterica serovar Typhimurium str. LT2 |
| PAT2    | XP_001694504.1 | 159472743 | Chlamydomonas reinhardtii |
| PAT1    | XP_001691787.1 | 159467202 | Chlamydomonas reinhardtii |

An exemplary acetate kinase is the *E. coli* acetate kinase, encoded by ackA (Skarstedt and Silverstein *J. Biol. Chem.* 251:6775-6783 (1976)). Homologs exist in several other organisms including *Salmonellan Enterica* and *Chlamydomonas reinhardtii*. It is likely that such enzymes naturally possess formate kinase activity or can be engineered to have this activity. Information related to these proteins and genes is shown below:

| Protein | GenBank ID | GI number | Organism |
|---------|------------|-----------|----------|
| AckA    | NP_416799.1 | 16130231 | Escherichia coli |
| AckA    | NP_461279.1 | 16765664 | Salmonellan Enterica subsp. enterica serovar Typhimurium str. LT2 |
| ACK1    | XP_001694505.1 | 159472745 | Chlamydomonas reinhardtii |
| ACK2    | XP_001691682.1 | 159466992 | Chlamydomonas reinhardtii |

The acylation of formate to formyl-CoA can also be carried out by a formate ligase. For example, the product of the LSC1 and LSC2 genes of *S. cerevisiae* and the sucC and sucD genes of *E. coli* naturally form a succinyl-CoA ligase complex that catalyzes the formation of succinyl-CoA from succinate with the concomitant consumption of one ATP, a reaction which is reversible in vivo (Gruys et al., U.S. Pat. No. 5,958,745, filed Sep. 28, 1999). Such enzymes may also acylate formate naturally or can be engineered to do so. Information related to these proteins and genes is shown below.

| Protein | GenBank ID | GI number | Organism |
|---------|------------|-----------|----------|
| SucC | NP_415256.1 | 16128703 | Escherichia coli |
| SucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |

Additional exemplary CoA-ligases include the rat dicarboxylate-CoA ligase for which the sequence is yet uncharacterized (Vamecq et al., Biochemical J. 230:683-693 (1985)), either of the two characterized phenylacetate-CoA ligases from P. chrysogenum (Lamas-Maceiras et al., Biochem. J. 395:147-155 (2005); Wang et al., Biochem Biophy Res Commun 360(2):453-458 (2007)), the phenylacetate-CoA ligase from Pseudomonas putida (Martinez-Blanco et al., J. Biol. Chem. 265:7084-7090 (1990)), and the 6-carboxyhexanoate-CoA ligase from Bacillus subtilis (Bower et al., J. Bacteriol. 178(14):4122-4130 (1996)). Additional candidate enzymes are acetoacetyl-CoA synthetases from Mus musculus (Hasegawan Et al., Biochim. Biophys. Acta 1779:414-419 (2008)) and Homo sapiens (Ohgami et al., Biochem. Pharmacol. 65:989-994 (2003)), which naturally catalyze the ATP-dependant conversion of acetoacetate into acetoacetyl-CoA. 4-Hydroxybutyryl-CoA synthetase activity has been demonstrated in Metallosphaera sedula (Berg et al., Science 318:1782-1786 (2007)). This function has been tentatively assigned to the Msed_1422 gene. Such enzymes may also acylate formate naturally or can be engineered to do so. Information related to these proteins and genes is shown below.

| Protein | GenBank ID | GI number | Organism |
|---------|------------|-----------|----------|
| Phl | CAJ15517.1 | 77019264 | Penicillium chrysogenum |
| PhlB | ABS19624.1 | 152002983 | Penicillium chrysogenum |
| PaaF | AAC24333.2 | 22711873 | Pseudomonas putida |
| BioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

FIG. 5, Step G—Formyl-CoA Reductase (EFR3)

Several acyl-CoA dehydrogenases are capable of reducing an acyl-CoA (e.g., formyl-CoA) to its corresponding aldehyde (e.g., formaldehyde) (Steps F, FIG. 1). Exemplary genes that encode such enzymes include the Acinetobacter calcoaceticus acyl encoding a fatty acyl-CoA reductase (Reiser and Somerville, J. Bacteriol. 179:2969-2975 (1997), the Acinetobacter sp. M-1 fatty acyl-CoA reductase (Ishige et al., Appl. Environ. Microbiol. 68:1192-1195 (2002), and a CoA- and NADP-dependent succinate semialdehyde dehydrogenase encoded by the sucD gene in Clostridium kluyveri (Sohling and Gottschalk, J. Bacteriol. 178:871-880 (1996); Sohling and Gottschalk, J. Bacteriol. 1778:871-880 (1996)). SucD of P. gingivalis is another succinate semialdehyde dehydrogenase (Takahashi et al., J. Bacteriol. 182:4704-4710 (2000). The enzyme acylating acetaldehyde dehydrogenase in Pseudomonas sp, encoded by bphG, is yet another candidate as it has been demonstrated to oxidize and acylate acetaldehyde, propionaldehyde, butyraldehyde, isobutyraldehyde and formaldehyde (Powlowski et al., J. Bacteriol. 175:377-385 (1993)). In addition to reducing acetyl-CoA to ethanol, the enzyme encoded by adhE in Leuconostoc mesenteroides has been shown to oxidize the branched chain compound isobutyraldehyde to isobutyryl-CoA (Kazahayan Et al., J. Gen. Appl. Microbiol. 18:45-55 (1972); Koo et al., Biotechnol. Lett. 27:505-510 (2005)). Butyraldehyde dehydrogenase catalyzes a similar reaction, conversion of butyryl-CoA to butyraldehyde, in solventogenic organisms such as Clostridium saccharoperbutylacetonicum (Kosakan Et al., Biosci. Biotechnol. Biochem. 71:58-68 (2007)). Additional aldehyde dehydrogenase enzyme candidates are found in Desulfatibacillum alkenivorans, Citrobacter koseri, Salmonellan Enterica, Lactobacillus brevis and Bacillus selenitireducens. Such enzymes may be capable of naturally converting formyl-CoA to formaldehyde or can be engineered to do so.

| Protein | GenBank ID | GI number | Organism |
|---------|------------|-----------|----------|
| acr1 | YP_047869.1 | 50086355 | Acinetobacter calcoaceticus |
| acr1 | AAC45217 | 1684886 | Acinetobacter baylyi |
| acr1 | BAB85476.1 | 18857901 | Acinetobacter sp. Strain M-1 |
| sucD | P38947.1 | 172046062 | Clostridium kluyveri |
| sucD | NP_904963.1 | 34540484 | Porphyromonas gingivalis |
| bphG | BAA03892.1 | 425213 | Pseudomonas sp |
| adhE | AAV66076.1 | 55818563 | Leuconostoc mesenteroides |
| Bld | AAP42563.1 | 31075383 | Clostridium saccharoperbutylacetonicum |
| Ald | ACL06658.1 | 218764192 | Desulfatibacillum alkenivorans AK-01 |
| Ald | YP_001452373 | 157145054 | Citrobacter koseri ATCC BAA-895 |
| pduP | NP_460996.1 | 16765381 | Salmonellan Enterica Typhimurium |
| pduP | ABJ64680.1 | 116099531 | Lactobacillus brevis ATCC 367 |
| BselDRAFT_1651 | ZP_02169447 | 163762382 | Bacillus selenitireducens MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., Science 318:1782-1786 (2007); Thauer, Science 318:1732-1733 (2007)). The enzyme utilizes NADPH as a cofactor and has been characterized in Metallosphaera and Sulfolobus spp (Alber et al., J. Bacteriol. 188:8551-8559 (2006); Hugler et al., J. Bacteriol. 184:2404-2410 (2002)). The enzyme is encoded by Msed_0709 in Metallosphaera sedula (Alber et al., supra (2006); Berg et al., Science 318:1782-1786 (2007)). A gene encoding a malonyl-CoA reductase from Sulfolobus tokodaii was cloned and heterologously expressed in E. coli (Alber et al., J. Bacteriol. 188:8551-8559 (2006)). This enzyme has also been shown to catalyze the conversion of methylmalonyl-CoA to its corresponding aldehyde (WO 2007/141208 (2007)). Although the aldehyde dehydrogenase functionality of these enzymes is similar to the bifunctional dehydrogenase from Chloroflexus aurantiacus, there is little sequence Similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl. Environ. Microbiol.* 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., supra). Such enzymes may be capable of naturally converting formyl-CoA to formaldehyde or can be engineered to do so.

| Protein | GenBank ID | GI number | Organism |
|---|---|---|---|
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 9473535 | *Clostridium beijerinckii* |
| eutE | AAA80209 | 687645 | *Salmonella typhimurium* |
| eutE | P77445 | 2498347 | *Escherichia coli* |

FIG. 5, Step H—Formyltetrahydrofolate Synthetase (EFR4)

Formyltetrahydrofolate synthetase ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
|---|---|---|---|
| Moth_0109 | YP_428991.1 | 83588982 | *Moorella thermoacetica* |
| CHY_2385 | YP_361182.1 | 78045024 | *Carboxydothermus hydrogenoformans* |
| FHS | P13419.1 | 120562 | *Clostridium acidurici* |
| CcarbDRAFT_1913 | ZP_05391913.1 | 255524966 | *Clostridium carboxidivorans* P7 |
| CcarbDRAFT_2946 | ZP_05392946.1 | 255526022 | *Clostridium carboxidivorans* P7 |
| Dhaf_0555 | ACL18622.1 | 219536883 | *Desulfitobacterium hafniense* |
| fhs | YP_001393842.1 | 153953077 | *Clostridium kluyveri* DSM 555 |
| fhs | YP_003781893.1 | 300856909 | *Clostridium ljungdahlii* DSM 13528 |
| MGA3_08300 | EIJ83208.1 | 387590889 | *Bacillus methanolicus* MGA3 |
| PB1_13509 | ZP_10132113.1 | 387929436 | *Bacillus methanolicus* PB1 |

FIG. 5, Steps I and J—Formyltetrahydrofolate Synthetase (EFR5) and Methylenetetrahydrofolate dehydrogenase (EFR6)

In *M. thermoacetica*, *E. coli*, and *C. hydrogenoformans*, methenyltetrahydrofolate cyclohydrolase and methylenetetrahydrofolate dehydrogenase are carried out by the bi-functional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
|---|---|---|---|
| Moth_1516 | YP_430368.1 | 83590359 | *Moorella thermoacetica* |
| folD | NP_415062.1 | 16128513 | *Escherichia coli* |
| CHY_1878 | YP_360698.1 | 78044829 | *Carboxydothermus hydrogenoformans* |
| CcarbDRAFT_2948 | ZP_05392948.1 | 255526024 | *Clostridium carboxidivorans* P7 |
| folD | ADK16789.1 | 300437022 | *Clostridium ljungdahlii* DSM 13528 |
| folD-2 | NP_951919.1 | 39995968 | *Geobacter sulfurreducens* PCA |
| folD | YP_725874.1 | 113867385 | *Ralstonian Eutropha* H16 |
| folD | NP_348702.1 | 15895353 | *Clostridium acetobutylicum* ATCC 824 |
| folD | YP_696506.1 | 110800457 | *Clostridium perfringens* |
| MGA3_09460 | EIJ83438.1 | 387591119 | *Bacillus methanolicus* MGA3 |
| PB1_14689 | ZP_10132349.1 | 387929672 | *Bacillus methanolicus* PB1 |

FIG. 5, Step K—Formaldehyde-Forming Enzyme (EFR7) or Spontaneous

Methylene-THF, or active formaldehyde, will spontaneously decompose to formaldehyde and THF (Thorndike and Beck, *Cancer Res.* 1977, 37(4) 1125-32; Ordonez and Caraballo, *Psychopharmacol Commun.* 1975 1(3) 253-60; Kallen and Jencks, 1966, *J Biol Chem* 241(24) 5851-63). To achieve higher rates, a formaldehyde-forming enzyme can be applied. Such an activity can be obtained by engineering an enzyme that reversibly forms methylene-THF from THF and a formaldehyde donor, to release free formaldehyde. Such enzymes include glycine cleavage system enzymes which naturally transfer a formaldehyde group from methylene-THF to glycine (see Step L, FIG. 1 for candidate enzymes). Additional enzymes include serine hydroxymethyltransferase (see Step M, FIG. 1 for candidate enzymes), dimethylglycine dehydrogenase (Porter, et al., *Arch Biochem Biophys.* 1985, 243(2) 396-407; Brizio et al., 2004, (37) 2, 434-442), sarcosine dehydrogenase (Porter, et al., *Arch Biochem Biophys.* 1985, 243(2) 396-407), and dimethylglycine oxidase (Legs, et al., 2003, *The EMBO Journal* 22(16) 4038-4048).

| Protein | GenBank ID | GI number | Organism |
|---|---|---|---|
| dmgo | ZP_09278452.1 | 359775109 | *Arthrobacter globiformis* |
| dmgo | YP_002778684.1 | 226360906 | *Rhodococcus opacus* B4 |
| dmgo | EFY87157.1 | 322695347 | *Metarhizium acridum* CQMa 102 |
| shd | AAD53398.2 | 5902974 | *Homo sapiens* |
| shd | NP_446116.1 | GI:25742657 | *Rattus norvegicus* |
| dmgdh | NP_037523.2 | 24797151 | *Homo sapiens* |
| dmgdh | Q63342.1 | 2498527 | *Rattus norvegicus* |

FIG. 5, Step L—Glycine Cleavage System (EFR8)

The reversible NAD(P)H-dependent conversion of 5,10-methylenetetrahydrofolate and $CO_2$ to glycine is catalyzed by the glycine cleavage complex, also called glycine cleavage system, composed of four protein components; P, H, T and L. The glycine cleavage complex is involved in glycine catabolism in organisms such as *E. coli* and glycine biosynthesis in eukaryotes (Kikuchi et al, *Proc Jpn Acad Ser* 84:246 (2008)). The glycine cleavage system of *E. coli* is encoded by four genes: gcvPHT and lpdA (Okamuran Et al, *Eur J Biochem* 216:539-48 (1993); Heil et al, *Microbiol* 148:2203-14 (2002)). Activity of the glycine cleavage system in the direction of glycine biosynthesis has been demonstrated in vivo in *Saccharomyces cerevisiae* (Maaheimo et al, *Eur J Biochem* 268:2464-79 (2001)). The yeast GCV is encoded by GCV1, GCV2, GCV3 and LPD1.

| Protein | GenBank ID | GI Number | Organism |
|---|---|---|---|
| gcvP | AAC75941.1 | 1789269 | *Escherichia coli* |
| gcvT | AAC75943.1 | 1789272 | *Escherichia coli* |
| gcvH | AAC75942.1 | 1789271 | *Escherichia coli* |
| lpdA | AAC73227.1 | 1786307 | *Escherichia coli* |
| GCV1 | NP_010302.1 | 6320222 | *Saccharomyces cerevisiae* |
| GCV2 | NP_013914.1 | 6323843 | *Saccharomyces cerevisiae* |
| GCV3 | NP_009355.3 | 269970294 | *Saccharomyces cerevisiae* |
| LPD1 | NP_116635.1 | 14318501 | *Saccharomyces cerevisiae* |

FIG. 5, Step M—Serine Hydroxymethyltransferase (EFR9)

Conversion of glycine to serine is catalyzed by serine hydroxymethyltransferase, also called glycine hydroxymethyltranferase. This enzyme reversibly converts glycine and 5,10-methylenetetrahydrofolate to serine and THF. Serine methyltransferase has several side reactions including the reversible cleavage of 3-hydroxyacids to glycine and an aldehyde, and the hydrolysis of 5,10-methenyl-THF to 5-formyl-THF. This enzyme is encoded by glyA of *E. coli* (Plamann et al, *Gene* 22:9-18 (1983)). Serine hydroxymethyltranferase enzymes of *S. cerevisiae* include SHM1 (mitochondrial) and SHM2 (cytosolic) (McNeil et al, *J Biol Chem* 269:9155-65 (1994)). Similar enzymes have been studied in *Corynebacterium glutamicum* and *Methylobacterium extorquens* (Chistoserdovan Et al, *J Bacteriol* 176:6759-62 (1994); Schweitzer et al, *J Biotechnol* 139:214-21 (2009)).

| Protein | GenBank ID | GI Number | Organism |
|---|---|---|---|
| glyA | AAC75604.1 | 1788902 | *Escherichia coli* |
| SHM1 | NP_009822.2 | 37362622 | *Saccharomyces cerevisiae* |
| SHM2 | NP_013159.1 | 6323087 | *Saccharomyces cerevisiae* |
| glyA | AAA64456.1 | 496116 | *Methylobacterium extorquens* |
| glyA | AAK60516.1 | 14334055 | *Corynebacterium glutamicum* |

FIG. 5, Step N—Serine Deaminase (EFR10)

Serine can be deaminated to pyruvate by serine deaminase. Serine deaminase enzymes are present in several organisms including *Clostridium acidurici* (Carter, et al., 1972, *J Bacteriol.*, 109(2) 757-763), *Escherichia coli* (Cicchillo et al., 2004, *J Biol Chem.*, 279(31) 32418-25), and *Corneybacterium* sp. (Netzer et al., *Appl Environ Microbiol.* 2004 December; 70(121:7148-551.

| Protein | GenBank ID | GI Number | Organism |
|---|---|---|---|
| sdaA | YP_490075.1 | 388477887 | *Escherichia coli* |
| sdaB | YP_491005.1 | 388478813 | *Escherichia coli* |
| tdcG | YP_491301.1 | 388479109 | *Escherichia coli* |
| tdcB | YP_491307.1 | 388479115 | *Escherichia coli* |
| sdaA | YP_225930.1 | 62390528 | *Corynebacterium* sp. |

FIG. 5, Step O—Methylenetetrahydrofolate Reductase (EFR11)

In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative hydrogenase and heterodisulfide reductase genes. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu Rev. Microbiol.* 65:631-658).

| Protein | GenBank ID | GI number | Organism |
|---|---|---|---|
| Moth_1191 | YP_430048.1 | 83590039 | *Moorella thermoacetica* |
| Moth_1192 | YP_430049.1 | 83590040 | *Moorella thermoacetica* |

| Protein | GenBank ID | GI number | Organism |
| --- | --- | --- | --- |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljungdahlii DSM 13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Ccel74_010100023124 | ZP_07633513.1 | 307691067 | Clostridium cellulovorans 743B |
| Cphy_3110 | YP_001560205.1 | 160881237 | Clostridium phytofermentans ISDg |

FIG. 5, Step P—Acetyl-CoA Synthase (EFR12)

Acetyl-CoA synthase is the central enzyme of the carbonyl branch of the Wood-Ljungdahl pathway. It catalyzes the synthesis of acetyl-CoA from carbon monoxide, coenzyme A, and the methyl group from a methylated corrinoid-iron-sulfur protein. The corrinoid-iron-sulfur-protein is methylated by methyltetrahydrofolate via a methyltransferase. Expression in a foreign host entails introducing one or more of the following proteins and their corresponding activities: Methyltetrahydrofolate:corrinoid protein methyltransferase (AcsE), Corrinoid iron-sulfur protein (AcsD), Nickel-protein assembly protein (AcsF), Ferredoxin (Orf7), Acetyl-CoA synthase (AcsB and AcsC), Carbon monoxide dehydrogenase (AcsA), and Nickel-protein assembly protein (CooC).

The genes used for carbon-monoxide dehydrogenase/acetyl-CoA synthase activity typically reside in a limited region of the native genome that can be an extended operon (Ragsdale, S. W., *Crit. Rev. Biochem. Mol. Biol.* 39:165-195 (2004); Morton et al., *J. Biol. Chem.* 266:23824-23828 (1991); Roberts et al., *Proc. Natl. Acad. Sci. U.S.A.* 86:32-36 (1989). Each of the genes in this operon from the acetogen, *M. thermoacetica*, has already been cloned and expressed actively in *E. coli* (Morton et al. supra; Roberts et al. supra; Lu et al., *J. Biol. Chem.* 268:5605-5614 (1993). The protein sequences of these genes can be identified by the following GenBank accession numbers.

| Protein | GenBank ID | GI number | Organism |
| --- | --- | --- | --- |
| AcsE | YP_430054 | 83590045 | Moorella thermoacetica |
| AcsD | YP_430055 | 83590046 | Moorella thermoacetica |
| AcsF | YP_430056 | 83590047 | Moorella thermoacetica |
| Orf7 | YP_430057 | 83590048 | Moorella thermoacetica |
| AcsC | YP_430058 | 83590049 | Moorella thermoacetica |
| AcsB | YP_430059 | 83590050 | Moorella thermoacetica |
| AcsA | YP_430060 | 83590051 | Moorella thermoacetica |
| CooC | YP_430061 | 83590052 | Moorella thermoacetica |

The hydrogenic bacterium, *Carboxydothermus hydrogenoformans*, can utilize carbon monoxide as a growth substrate by means of acetyl-CoA synthase (Wu et al., *PLoS Genet.* 1:e65 (2005)). In strain Z-2901, the acetyl-CoA synthase enzyme complex lacks carbon monoxide dehydrogenase due to a frameshift mutation (Wu et al. supra (2005)), whereas in strain DSM 6008, a functional unframeshifted full-length version of this protein has been purified (Svetlitchnyi et al., *Proc. Natl. Acad. Sci. U.S.A.* 101:446-451 (2004)). The protein sequences of the *C. hydrogenoformans* genes from strain Z-2901 can be identified by the following GenBank accession numbers.

| Protein | GenBank ID | GI number | Organism |
| --- | --- | --- | --- |
| AcsE | YP_360065 | 78044202 | Carboxydothermus hydrogenoformans |
| AcsD | YP_360064 | 78042962 | Carboxydothermus hydrogenoformans |
| AcsF | YP_360063 | 78044060 | Carboxydothermus hydrogenoformans |
| Orf7 | YP_360062 | 78044449 | Carboxydothermus hydrogenoformans |
| AcsC | YP_360061 | 78043584 | Carboxydothermus hydrogenoformans |
| AcsB | YP_360060 | 78042742 | Carboxydothermus hydrogenoformans |
| CooC | YP_360059 | 78044249 | Carboxydothermus hydrogenoformans |

Homologous ACS/CODH genes can also be found in the draft genome assembly of *Clostridium carboxidivorans* P7.

| Protein | GenBank ID | GI Number | Organism |
| --- | --- | --- | --- |
| AcsA | ZP_05392944.1 | 255526020 | Clostridium carboxidivorans P7 |
| CooC | ZP_05392945.1 | 255526021 | Clostridium carboxidivorans P7 |
| AcsF | ZP_05392952.1 | 255526028 | Clostridium carboxidivorans P7 |
| AcsD | ZP_05392953.1 | 255526029 | Clostridium carboxidivorans P7 |
| AcsC | ZP_05392954.1 | 255526030 | Clostridium carboxidivorans P7 |
| AcsE | ZP_05392955.1 | 255526031 | Clostridium carboxidivorans P7 |
| AcsB | ZP_05392956.1 | 255526032 | Clostridium carboxidivorans P7 |
| Orf7 | ZP_05392958.1 | 255526034 | Clostridium carboxidivorans P7 |

The methanogenic archaeon, *Methanosarcina acetivorans*, can also grow on carbon monoxide, exhibits acetyl-CoA synthase/carbon monoxide dehydrogenase activity, and produces both acetate and formate (Lessner et al., *Proc. Natl. Acad. Sci. U.S.A.* 103:17921-17926 (2006)). This organism contains two sets of genes that encode ACS/CODH activity (Rother and Metcalf, *Proc. Natl. Acad. Sci. U.S.A.* 101:16929-16934 (2004)). The protein sequences of both sets of *M. acetivorans* genes are identified by the following GenBank accession numbers.

| Protein | GenBank ID | GI number | Organism |
|---|---|---|---|
| AcsC | NP_618736 | 20092661 | Methanosarcina acetivorans |
| AcsD | NP_618735 | 20092660 | Methanosarcina acetivorans |
| AcsF, CooC | NP_618734 | 20092659 | Methanosarcina acetivorans |
| AcsB | NP_618733 | 20092658 | Methanosarcina acetivorans |
| AcsEps | NP_618732 | 20092657 | Methanosarcina acetivorans |
| AcsA | NP_618731 | 20092656 | Methanosarcina acetivorans |
| AcsC | NP_615961 | 20089886 | Methanosarcina acetivorans |
| AcsD | NP_615962 | 20089887 | Methanosarcina acetivorans |
| AcsF, CooC | NP_615963 | 20089888 | Methanosarcina acetivorans |
| AcsB | NP_615964 | 20089889 | Methanosarcina acetivorans |
| AcsEps | NP_615965 | 20089890 | Methanosarcina acetivorans |
| AcsA | NP_615966 | 20089891 | Methanosarcina acetivorans |

The AcsC, AcsD, AcsB, AcsEps, and AcsA proteins are commonly referred to as the gamma, delta, beta, epsilon, and alpha subunits of the methanogenic CODH/ACS. Homologs to the epsilon encoding genes are not present in acetogens such as M thermoacetica or hydrogenogenic bacteria such as C. hydrogenoformans. Hypotheses for the existence of two active CODH/ACS operons in M. acetivorans include catalytic properties (i.e., $K_m$, $V_{max}$, $k_{cat}$) that favor carboxidotrophic or aceticlastic growth or differential gene regulation enabling various stimuli to induce CODH/ACS expression (Rother et al., Arch. Microbiol. 188:463-472 (2007)).

FIG. 5, Step Q—Pyruvate Formate Lyase (EFR13)

Pyruvate formate-lyase (PFL, EC 2.3.1.54), encoded by pflB in E. coli, can convert pyruvate into acetyl-CoA and formate. The activity of PFL can be enhanced by an activating enzyme encoded by pflA (Knappe et al., Proc. Natl. Acad. Sci U.S.A 81:1332-1335 (1984); Wong et al., Biochemistry 32:14102-14110 (1993)). Keto-acid formate-lyase (EC 2.3.1.-), also known as 2-ketobutyrate formate-lyase (KFL) and pyruvate formate-lyase 4, is the gene product of tdcE in E. coli. This enzyme catalyzes the conversion of 2-ketobutyrate to propionyl-CoA and formate during anaerobic threonine degradation, and can also substitute for pyruvate formate-lyase in anaerobic catabolism (Simanshu et al., J Biosci. 32:1195-1206 (2007)). The enzyme is oxygen-sensitive and, like PflB, can require post-translational modification by PFL-AE to activate a glycyl radical in the active site (Hesslinger et al., Mol. Microbiol 27:477-492 (1998)). A pyruvate formate-lyase from Archaeglubus fulgidus encoded by pflD has been cloned, expressed in E. coli and characterized (Lehtio et al., Protein Eng Des Sel 17:545-552 (2004)). The crystal structures of the A. fulgidus and E. coli enzymes have been resolved (Lehtio et al., J Mol. Biol. 357:221-235 (2006); Leppanen et al., Structure. 7:733-744 (1999)). Additional PFL and PFL-AE candidates are found in Lactococcus lactis (Melchiorsen et al., Appl Microbiol Biotechnol 58:338-344 (2002)), and Streptococcus mutans (Takahashi-Abbe et al., Oral. Microbiol Immunol. 18:293-297 (2003)), Chlamydomonas reinhardtii (Hemschemeier et al., Eukaryot. Cell 7:518-526 (2008b); Atteian Et al., J. Biol. Chem. 281:9909-9918 (2006)) and Clostridium pasteurianum (Weidner et al., J Bacteriol. 178:2440-2444 (1996)).

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |
| pflD | NP_070278.1 | 11499044 | Archaeglubus fulgidus |
| Pfl | CAA03993 | 2407931 | Lactococcus lactis |
| Pfl | BAA09085 | 1129082 | Streptococcus mutans |
| PFL1 | XP_001689719.1 | 159462978 | Chlamydomonas reinhardtii |
| pflA1 | XP_001700657.1 | 159485246 | Chlamydomonas reinhardtii |
| Pfl | Q46266.1 | 2500058 | Clostridium pasteurianum |
| Act | CAA63749.1 | 1072362 | Clostridium pasteurianum |

FIG. 5, Step R—Pyruvate Dehydrogenase (EFR14A), Pyruvate Ferredoxin Oxidoreductase (EFR14B), Pyruvate: NADP+ Oxidoreductase (EFR14C)

The pyruvate dehydrogenase (PDH) complex catalyzes the conversion of pyruvate to acetyl-CoA (FIG. 2H). The E. coli PDH complex is encoded by the genes aceEF and lpdA. Enzyme engineering efforts have improved the E. coli PDH enzyme activity under anaerobic conditions (Kim et al., J. Bacteriol. 190:3851-3858 (2008); Kim et al., Appl. Environ. Microbiol. 73:1766-1771 (2007); Zhou et al., Biotechnol. Lett. 30:335-342 (2008)). In contrast to the E. coli PDH, the B. subtilis complex is active and required for growth under anaerobic conditions (Nakano et al., 179:6749-6755 (1997)). The Klebsiella pneumoniae PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from Azotobacter vinelandii are available (Mattevi et al., Science. 255:1544-1550 (1992)). Some mammalian PDH enzymes complexes can react on alternate substrates such as 2-oxobutanoate. Comparative kinetics of Rattus norvegicus PDH and BCKAD indicate that BCKAD has higher activity on 2-oxobutanoate as a substrate (Paxton et al., Biochem. J. 234:295-303 (1986)). The S. cerevisiae PDH complex can-consist of an E2 (LAT1) core that binds E1 (PDA1, PDB1), E3 (LPD1), and Protein X (PDX1) components (Pronk et al., Yeast 12:1607-1633 (1996)). The PDH complex of S. cerevisiae is regulated by phosphorylation of E1 involving PKP1 (PDH kinase I), PTC5 (PDH phosphatase I), PKP2 and PTC6. Modification of these regulators may also enhance PDH activity. Coexpression of lipoyl ligase (LptA of E. coli and AIM22 in S. cerevisiae) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | Escherichia coli |
| aceF | NP_414657.1 | 16128108 | Escherichia coli |
| lpd | NP_414658.1 | 16128109 | Escherichia coli |
| lplA | NP_418803.1 | 16132203 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumoniae |
| aceF | YP_001333809.1 | 152968700 | Klebsiella pneumoniae |
| lpdA | YP_001333810.1 | 152968701 | Klebsiella pneumoniae |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| AIM22 | NP_012489.2 | 83578101 | Saccharomyces cerevisiae |

As an alternative to the large multienzyme PDH complexes described above, some organisms utilize enzymes in the 2-ketoacid oxidoreductase family (OFOR) to catalyze acylating oxidative decarboxylation of 2-keto-acids. Unlike the PDH complexes, PFOR enzymes contain iron-sulfur clusters, utilize different cofactors and use ferredoxin or flavodixin as electron acceptors in lieu of NAD(P)H. Pyruvate ferredoxin oxidoreductase (PFOR) can catalyze the oxidation of pyruvate to form acetyl-CoA (FIG. 2H). The PFOR from *Desulfovibrio africanus* has been cloned and expressed in *E. coli* resulting in an active recombinant enzyme that was stable for several days in the presence of oxygen (Pieulle et al., *J Bacteriol.* 179:5684-5692 (1997)). Oxygen stability is relatively uncommon in PFORs and is believed to be conferred by a 60 residue extension in the polypeptide chain of the *D. africanus* enzyme. The *M. thermoacetica* PFOR is also well characterized (Menon et al., *Biochemistry* 36:8484-8494 (1997)) and was even shown to have high activity in the direction of pyruvate synthesis during autotrophic growth (Furdui et al., *J Biol Chem.* 275:28494-28499 (2000)). Further, *E. coli* possesses an uncharacterized open reading frame, ydbK, that encodes a protein that is 51% identical to the *M. thermoacetica* PFOR. Evidence for pyruvate oxidoreductase activity in *E. coli* has been described (Blaschkowski et al., *Eur. J Biochem.* 123: 563-569 (1982)). Several additional PFOR enzymes are described in Ragsdale, *Chem. Rev.* 103:2333-2346 (2003). Finally, flavodoxin reductases (e.g., fqrB from *Helicobacter pylori* or *Campylobacter jejuni* (St Maurice et al., *J. Bacteriol.* 189:4764-4773 (2007))) or Rnf-type proteins (Seedorf et al., *Proc. Natl. Acad. Sci. U S.A.* 105:2128-2133 (2008); Herrmann et al., *J. Bacteriol.* 190:784-791 (2008)) provide a means to generate NADH or NADPH from the reduced ferredoxin generated by PFOR. These proteins are identified below.

| Protein | GenBank ID | GI Number | Organism |
|---|---|---|---|
| Por | CAA70873.1 | 1770208 | *Desulfovibrio africanus* |
| Por | YP_428946.1 | 83588937 | *Moorella thermoacetica* |
| ydbK | NP_415896.1 | 16129339 | *Escherichia coli* |
| fqrB | NP_207955.1 | 15645778 | *Helicobacter pylori* |
| fqrB | YP_001482096.1 | 157414840 | *Campylobacter jejuni* |
| RnfC | EDK33306.1 | 146346770 | *Clostridium kluyveri* |
| RnfD | EDK33307.1 | 146346771 | *Clostridium kluyveri* |
| RnfG | EDK33308.1 | 146346772 | *Clostridium kluyveri* |
| RnfE | EDK33309.1 | 146346773 | *Clostridium kluyveri* |
| RnfA | EDK33310.1 | 146346774 | *Clostridium kluyveri* |
| RnfB | EDK33311.1 | 146346775 | *Clostridium kluyveri* |

Pyruvate:NADP oxidoreductase (PNO) catalyzes the conversion of pyruvate to acetyl-CoA. This enzyme is encoded by a single gene and the active enzyme is a homodimer, in contrast to the multi-subunit PDH enzyme complexes described above. The enzyme from *Euglena gracilis* is stabilized by its cofactor, thiamin pyrophosphate (Nakazawan Et al, *Arch Biochem Biophys* 411:183-8 (2003)). The mitochondrial targeting sequence of this enzyme should be removed for expression in the cytosol. The PNO protein of *E. gracilis* and other NADP-dependant pyruvate:NADP+ oxidoreductase enzymes are listed in the table below.

| Protein | GenBank ID | GI Number | Organism |
|---|---|---|---|
| PNO | Q94IN5.1 | 33112418 | *Euglena gracilis* |
| cgd4_690 | XP_625673.1 | 66356990 | *Cryptosporidium parvum* Iowa II |
| TPP_PFOR_PNO | XP_002765111.11 | 294867463 | *Perkinsus marinus* ATCC 50983 |

FIG. 5, Step S—Formate Dehydrogenase (EFR15)

Formate dehydrogenase (FDH) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and hydrogenases (EC 1.1.99.33). FDH enzymes have been characterized from *Moorella thermoacetica* (Andreesen and Ljungdahl, *J Bacteriol* 116:867-873 (1973); Li et al., *J Bacteriol* 92:405-412 (1966); Yamamoto et al., *J Biol Chem.* 258:1826-1832 (1983). The loci, Moth_2312 is responsible for encoding the alpha subunit of formate dehydrogenase while the beta subunit is encoded by Moth_2314 (Pierce et al., *Environ Microbiol* (2008)). Another set of genes encoding formate dehydrogenase activity with a propensity for $CO_2$ reduction is encoded by Sfum_2703 through Sfum_2706 in *Syntrophobacter fumaroxidans* (de Bok et al., *Eur J Biochem.* 270:2476-2485 (2003)); Redan Et al., *PNAS* 105:10654-10658 (2008)). A similar set of genes presumed to carry out the same function are encoded by CHY_0731, CHY_0732, and CHY_0733 in *C. hydrogenoformans* (Wu et al., *PLoS Genet* 1:e65 (2005)). Formate dehydrogenases are also found many additional organisms including *C. carboxidivorans* P7, *Bacillus methanolicus*, *Burkholderia stabilis*, *Moorella* thermoacetica ATCC 39073, *Candida boidinii*, *Candida methylica*, and *Saccharomyces cerevisiae* S288c. The soluble formate dehydrogenase from *Ralstonian Eutropha* reduces $NAD^+$ (fdsG, -B, -A, -C, -D) (Oh and Bowien, 1998)

| Protein | GenBank ID | GI Number | Organism |
|---|---|---|---|
| Moth_2312 | YP_431142 | 148283121 | *Moorella thermoacetica* |
| Moth_2314 | YP_431144 | 83591135 | *Moorella thermoacetica* |
| Sfum_2703 | YP_846816.1 | 116750129 | *Syntrophobacter fumaroxidans* |
| Sfum_2704 | YP_846817.1 | 116750130 | *Syntrophobacter fumaroxidans* |
| Sfum_2705 | YP_846818.1 | 116750131 | *Syntrophobacter fumaroxidans* |
| Sfum_2706 | YP_846819.1 | 116750132 | *Syntrophobacter fumaroxidans* |
| CHY_0731 | YP_359585.1 | 78044572 | *Carboxydothermus hydrogenoformans* |
| CHY_0732 | YP_359586.1 | 78044500 | *Carboxydothermus hydrogenoformans* |
| CHY_0733 | YP_359587.1 | 78044647 | *Carboxydothermus hydrogenoformans* |
| CcarbDRAFT_0901 | ZP_05390901.1 | 255523938 | *Clostridium carboxidivorans* P7 |
| CcarbDRAFT_4380 | ZP_05394380.1 | 255527512 | *Clostridium carboxidivorans* P7 |
| fdhA, MGA3_06625 | EIJ82879.1 | 387590560 | *Bacillus methanolicus* MGA3 |

-continued

| Protein | GenBank ID | GI Number | Organism |
|---|---|---|---|
| fdhA, PB1_11719 | ZP_10131761.1 | 387929084 | *Bacillus methanolicus* PB1 |
| fdhD, MGA3_06630 | EIJ82880.1 | 387590561 | *Bacillus methanolicus* MGA3 |
| fdhD, PB1_11724 | ZP_10131762.1 | 387929085 | *Bacillus methanolicus* PB1 |
| fdh | ACF35003. | 194220249 | *Burkholderia stabilis* |
| FDH1 | AAC49766.1 | 2276465 | *Candida boidinii* |
| Fdh | CAA57036.1 | 1181204 | *Candida methylica* |
| FDH2 | P0CF35.1 | 294956522 | *Saccharomyces cerevisiae* S288c |
| FDH1 | NP_015033.1 | 6324964 | *Saccharomyces cerevisiae* S288c |

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A non-naturally occurring microbial organism (NNOMO) comprising:
   (A) a methanol metabolic pathway (MMP) consisting of a combination of MMP enzymes (MMPEs) selected from the group consisting of:
      (i) a methanol dehydrogenase (EM9), a methylenetetrahydrofolate dehydrogenase (EM3), a methenyltetrahydrofolate cyclohydrolase (EM4) and a formyltetrahydrofolate deformylase (EM5);
      (ii) an EM9, an EM3, an EM4, and a formyltetrahydrofolate synthetase (EM6);
      (iii) an EM9 and a formaldehyde dehydrogenase (EM11);
      (iv) an EM9, a S-(hydroxymethyl)glutathione synthase (EM12), a glutathione-dependent formaldehyde dehydrogenase (EM13), and a S-formylglutathione hydrolase (EM14);
      (v) an EM9, an EM13, and an EM14;
      (vi) an EM9, a formaldehyde activating enzyme (EM10), an EM3, an EM4, and an EM5; and
      (vii) an EM9, an EM10, an EM3, an EM4, and an EM6;
   wherein said MMPEs of said MMP are encoded by exogenous nucleic acids;
   wherein said MMP enhances the availability of reducing equivalents in the presence of methanol; and
   wherein a chemical conversion of said MMP consisting of said combination of MMPEs of group (i) or (ii) comprises spontaneous conversion of formaldehyde to methylene-THF and a chemical conversion of said MMP consisting of the combination of MMPEs of group (vii) comprises spontaneous conversion of formaldehyde to S-hydroxymethylglutathione; and
   (B) (i) an adipate pathway (AdiP),
      (ii) a 6-aminocaproate (6-ACA) pathway (6-ACAP),
      (iii) a hexamethylenediamine (HMDA) pathway (HMDAP), or
      (iv) a caprolactam pathway (CapP).

2. The NNOMO of claim 1, wherein
   (a) said NNOMO comprises an AdiP, and wherein
      (1) said NNOMO comprises at least two exogenous nucleic acids each encoding an AdiP enzyme (AdiPE) expressed in a sufficient amount to produce adipate, wherein said AdiP comprises (i) a 3-oxoadipyl-CoA thiolase (EA1); (ii) a 3-oxoadipyl-CoA reductase (EA2); (iii) a 3-hydroxyadipyl-CoA dehydratase (EA3); (iv) a 5-carboxy-2-pentenoyl-CoA reductase (EA4); and (v) an adipyl-CoA hydrolase (EA11A), an adipyl-CoA ligase (EA11B), an adipyl-CoA transferase (EA11C) or a phosphotransadipylase/adipate kinase (EA11D),
      (2) said NNOMO comprises three, four or five exogenous nucleic acids, each encoding an AdiPE; and/or
      (3) said at least one exogenous nucleic acid encoding an AdiPE is a heterologous nucleic acid;
   (b) said NNOMO comprises a 6-ACAP, and wherein
      (1) said NNOMO comprises at least two exogenous nucleic acids each encoding a 6-ACAP enzyme (6-ACAPE) expressed in a sufficient amount to produce 6-ACA, wherein said 6-ACAP comprises (i) an EA1; (ii) an EA2; (iii) an EA3; (iv) an EA4; (v) adipyl-CoA reductase (aldehyde forming) (EA5); and (vi) a 6-ACA transaminase (EA6A) or a 6-ACA dehydrogenase (EA6B);
      (2) said NNOMO comprises three, four, five or six exogenous nucleic acids, each encoding a 6-ACAPE; and/or
      (3) said at least one exogenous nucleic acid encoding a 6-ACAPE is a heterologous nucleic acid;
   (c) said NNOMO comprises a HMDAP, and wherein
      (1) said NNOMO comprises at least two exogenous nucleic acids each encoding a HMDA pathway enzyme (HMDAPE) expressed in a sufficient amount to produce HMDA, wherein said HMDAP comprises (i) an EA1; (ii) an EA2; (iii) an EA3; (iv) an EA4; (v) an EA5; (vi) an EA6A or an EA6B; (vii) a 6-aminocaproyl-CoA/acyl-CoA transferase (EA7A) or 6-aminocaproyl-CoA synthase (EA7B); (viii) a 6-aminocaproyl-CoA reductase (aldehyde forming) (EA9); and (ix) a HMDA transaminase (EA10A) or a HMDA dehydrogenase (EA10B);
      (2) said NNOMO comprises three, four, five, six, seven, eight or nine exogenous nucleic acids, each encoding a HMDAPE; and/or
      (3) said at least one exogenous nucleic acid encoding a HMDAPE is a heterologous nucleic acid; or
   (d) said NNOMO comprise a CapP, and wherein
      (1) said NNOMO comprises at least two exogenous nucleic acids each encoding a CapP enzyme (CapPE) expressed in a sufficient amount to produce caprolactam, wherein said CapP comprises:
         (a) (i) an EA1; (ii) an EA2; (iii) an EA3; (iv) an EA4; (v) an EA5; (vi) an EA6A or an EA6B; and (vii) EA7A or EA7B; or
         (b) (i) an EA1; (ii) an EA2; (iii) an EA3; (iv) an EA4; (v) an EA5; (vi) an EA6A or an EA6B; and (vii) an amidohydrolase (EA8);

wherein said CapP optionally further comprises a spontaneous cyclization, which converts a 6-aminocaproyl-CoA to caprolactam;
(2) said NNOMO comprises three, four, five, six or seven exogenous nucleic acids, each encoding a CapPE; and/or
(3) said at least one exogenous nucleic acid encoding a CapPE is a heterologous nucleic acid.

3. The NNOMO of claim 1 further comprising (i) a formate dehydrogenase (EM8); (ii) a formate hydrogen lyase (EM15); or (iii) an EM15 and a hydrogenase (EM16).

4. The NNOMO of claim 1, wherein:
(a) at least one of said exogenous nucleic acids encoding said MMPEs is a heterologous nucleic acid;
(b) said NNOMO comprises one or more gene disruptions, wherein said one or more gene disruptions occur in one or more endogenous genes encoding protein(s) or enzyme(s) involved in native production of ethanol, glycerol, acetate, lactate, formate, $CO_2$, and/or amino acids, by said microbial organism, and wherein said one or more gene disruptions confers increased production of adipate, 6-ACA, HMDA or caprolactam in said NNOMO; and/or
(c) one or more endogenous enzymes involved in: native production of ethanol, glycerol, acetate, lactate, formate, $CO_2$ and/or amino acids by said NNOMO, has attenuated enzyme activity or expression levels.

5. The NNOMO of claim 1, further comprising a formaldehyde assimilation pathway (FAP), wherein said NNOMO comprises at least one exogenous nucleic acid encoding a FAP enzyme (FAPE) expressed in a sufficient amount to produce an intermediate of glycolysis and/or a metabolic pathway that can be used in the formation of biomass, and wherein
(A) (i) said FAP comprises a hexulose-6-phosphate (H6P) synthase (EF1) and a 6-phospho-3-hexuloisomerase (EF2);
(ii) said FAP comprises a dihydroxyacetone (DHA) synthase (EF3), and optionally further comprises a DHA kinase (EF4); or
(iii) said FAP comprises an EF1, an EF2, an EF3, and optionally further an EF4; and/or
(B) said intermediate optionally is (i) a H6P, a fructose-6-phosphate (F6P), or a combination thereof; or (ii) a DHA, a DHA phosphate (DHAP), or a combination thereof; and/or
(C) said NNOMO optionally comprises two exogenous nucleic acids, each encoding a FAPE.

6. The NNOMO of claim 1, wherein
(a) at least one of said exogenous nucleic acids encoding said MMPEs is a heterologous nucleic acid;
(b) said NNOMO is in a substantially anaerobic culture medium; and/or
(c) said NNOMO is a species of bacteria, yeast, or fungus.

7. A method for producing adipate, 6-ACA, HMDA or caprolactam, comprising culturing the NNOMO of claim 1 under conditions and for a sufficient period of time to produce adipate, 6-ACA, HMDA or caprolactam.

8. The NNOMO of claim 1, wherein said AdiP, 6-ACAP, HMDAP or CapP further comprises (i) a PEP carboxylase (EFR16A) or PEP carboxykinase (EFR16B); (ii) a pyruvate carboxylase (EFR17); (iii) a malate dehydrogenase (EFR18); (iv) a malic enzyme (EFR19); and/or (v) a fumarase (EFR20A), fumarate reductase (EFR20B), succinyl-CoA synthetase (EFR20C), succinyl-CoA ligase (EFR20D), or succinyl-CoA transferase (EFR20E);
wherein optionally said AdiP, 6-ACAP, HMDAP or CapP comprises (1) (i) EFR16A or EF16B, (ii) EFR18, and (iii) EFR20A, EFR20B, EFR20C, EFR20D, or EFR20E; (2) (i) EFR17, (ii) EFR18 and (iii) EFR20A, EFR20B, EFR20C, EFR20D, or EFR20E; or (3) (i) EFR19 and (ii) EFR20A, EFR20B, EFR20C, EFR20D, or EFR20E.

9. The NNOMO of claim 1, further comprising a formate reutilization pathway (FRP), and wherein:
said NNOMO comprises at least one exogenous nucleic acid encoding a FRP enzyme (FRPE) expressed in a sufficient amount to produce formaldehyde, pyruvate or acetyl-CoA, wherein said FRP comprises: (1) a formate reductase (EFR1); (2) (i) a formate ligase (EFR2A), a formate transferase (EFR2B), or a formate synthetase (EFR2C), and (ii) a formyl-CoA reductase (EFR3); (3) (i) a formyltetrahydrofolate synthetase (EFR4), (ii) a methenyltetrahydrofolate cyclohydrolase (EFR5), (iii) a methylenetetrahydrofolate dehydrogenase (EFR6) and (iv) a formaldehyde-forming enzyme (EFR7) or spontaneous; (6) (i) an EFR4, (ii) an EFR5, (iii) an EFR6, (iv) a glycine cleavage system (EFR8), (v) a serine hydroxymethyltransferase (EFR9), and (vi) a serine deaminase (EFR10); (7) (i) an EFR1, (ii) an EFR4, (iii) an EFR5, (iv) an EFR6, (v) an EFR8, (vi) an EFR9, and (vii) an EFR10; (8) (i) an EFR2A, an EFR2B or an EFR2C, (ii) an EFR3, (iii) an EFR4, (iv) an EFR5, (v) an EFR6, (vi) an EFR8, (vii) an EFR9, and (viii) an EFR10; (9) (i) an EFR7 or spontaneous, (ii) an EFR4, (iii) an EFR5, (iv) an EFR6, (v) an EFR8, (vi) an EFR9, and (vii) an EFR10; and (10) (i) an EFR4, (ii) an EFR5, (iii) an EFR6, (iv) a methylenetetrahydrofolate reductase (EFR11), and (v) an acetyl-CoA synthase (EFR12);
(ii) the NNOMO comprises two, three, four, five, six, seven or eight exogenous nucleic acids, each encoding a FRPE; and/or
(iii) said at least one exogenous nucleic acid encoding a FRPE is a heterologous nucleic acid;
wherein optionally the FRP further comprises (i) a pyruvate formate lyase (EFR13); (ii) a pyruvate dehydrogenase (EFR14A), a pyruvate ferredoxin oxidoreductase (EFR14B), or a pyruvate:NADP+ oxidoreductase (EFR14C); (iii) a formate dehydrogenase (EFR15); or (iv) an EFR14A, EFR14B, or EFR14C; and an EFR15.

10. The NNOMO of claim 1, wherein said combination of MMPEs is an EM9, an EM3, an EM4, and an EM5, and wherein said chemical conversion of said MMP comprises spontaneous conversion of formaldehyde to methylene-THF.

11. The NNOMO of claim 1, wherein said combination of MMPEs is EM9, an EM3, an EM4, and an EM6, and wherein said chemical conversion of said MMP comprises spontaneous conversion of formaldehyde to methylene-THF.

12. The NNOMO of claim 1, wherein said combination of MMPEs is an EM9 and an EM11.

13. The NNOMO of claim 1, wherein said combination of MMPEs is an EM9, an EM12, an EM13, and an EM14.

14. The NNOMO of claim 1, wherein said combination of MMPEs is an EM9, an EM13, and an EM14, and wherein said chemical conversion of said MMP comprises spontaneous conversion of formaldehyde to S-hydroxymethylglutathione.

15. The NNOMO of claim 1, wherein said combination of MMPEs is an EM9, an EM10, an EM3, an EM4, and an EM5.

16. The NNOMO of claim 1, wherein said combination of MMPEs is an EM9, an EM10, an EM3, an EM4, and an EM6.

17. The method of claim 7, wherein said method further comprises separating the adipate, 6-ACA, HMDA or caprolactam from other components in the culture.

18. The method of claim 17, wherein the separation comprises extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, or ultrafiltration.

19. The method of claim 7, wherein the NNOMO is a Crabtree positive, eukaryotic organism.

20. The method of claim 19, wherein the organism is cultured in a culture medium comprising glucose.

* * * * *